(12) United States Patent
Lunyak et al.

(10) Patent No.: US 11,291,689 B2
(45) Date of Patent: Apr. 5, 2022

(54) METHODS AND DEVICES FOR THE PRODUCTION AND DELIVERY OF BENEFICIAL FACTORS FROM ADIPOSE-DERIVED STEM CELLS

(71) Applicant: Aelan Cell Technologies, Inc., San Francisco, CA (US)

(72) Inventors: Victoria Lunyak, San Anselmo, CA (US); Meenakshi Gaur, San Francisco, CA (US)

(73) Assignee: AELAN CELL TECHNOLOGIES, INC., San Francisco, CA (US)

( * ) Notice: Subject to any disclaimer, the term of this patent is extended or adjusted under 35 U.S.C. 154(b) by 1044 days.

(21) Appl. No.: 15/579,184

(22) PCT Filed: Jun. 2, 2016

(86) PCT No.: PCT/US2016/035487
§ 371 (c)(1),
(2) Date: Oct. 9, 2018

(87) PCT Pub. No.: WO2016/196774
PCT Pub. Date: Dec. 8, 2016

(65) Prior Publication Data
US 2018/0161373 A1 Jun. 14, 2018

Related U.S. Application Data

(60) Provisional application No. 61/175,203, filed on Jun. 12, 2015, provisional application No. 62/170,619, filed on Jun. 3, 2015, provisional application No. 62/170,604, filed on Jun. 3, 2015.

(51) Int. Cl.
| | | |
|---|---|---|
| *A61K 35/28* | (2015.01) | |
| *A61K 38/43* | (2006.01) | |
| *C12N 5/0775* | (2010.01) | |
| *C07K 16/24* | (2006.01) | |
| *C12N 5/00* | (2006.01) | |
| *A61P 35/00* | (2006.01) | |
| *A61K 38/20* | (2006.01) | |
| *C12Q 1/6886* | (2018.01) | |
| *G01N 33/574* | (2006.01) | |

(52) U.S. Cl.
CPC .......... *A61K 35/28* (2013.01); *A61K 38/2013* (2013.01); *A61K 38/43* (2013.01); *A61P 35/00* (2018.01); *C07K 16/246* (2013.01); *C12N 5/0018* (2013.01); *C12N 5/0663* (2013.01); *C12N 5/0667* (2013.01); *C12Q 1/6886* (2013.01); *G01N 33/574* (2013.01); *C12N 2501/2302* (2013.01); *C12N 2501/65* (2013.01); *C12Q 2600/158* (2013.01); *G01N 2333/4703* (2013.01); *G01N 2333/475* (2013.01); *G01N 2333/495* (2013.01); *G01N 2333/55* (2013.01); *G01N 2333/705* (2013.01); *G01N 2333/91205* (2013.01); *G01N 2333/96466* (2013.01); *G01N 2333/96486* (2013.01)

(58) Field of Classification Search
CPC ...... A61K 35/28; A61K 38/43; C07K 16/246; C12N 5/0018; C12N 5/0663
See application file for complete search history.

(56) References Cited

U.S. PATENT DOCUMENTS

| | | | |
|---|---|---|---|
| 4,929,354 | A | 5/1990 | Meyering et al. |
| 5,270,192 | A | 12/1993 | Li et al. |
| 6,582,955 | B2 | 6/2003 | Martinez et al. |
| 6,759,245 | B1 | 7/2004 | Toner et al. |
| 6,858,146 | B1 | 2/2005 | Myers et al. |
| 7,160,719 | B2 | 1/2007 | Nyberg |
| 8,172,784 | B2 | 5/2012 | Yarmush et al. |
| 9,074,172 | B2 | 7/2015 | Johnson |
| 10,921,324 | B2 | 2/2021 | Lunyak et al. |
| 2004/0033589 | A1 | 2/2004 | O'Brien |
| 2011/0003008 | A1 | 1/2011 | Lim |
| 2012/0165216 | A1 | 6/2012 | Rodriguez et al. |
| 2013/0251670 | A1 | 9/2013 | Riordan et al. |
| 2014/0205563 | A1 | 7/2014 | Maguire et al. |

(Continued)

FOREIGN PATENT DOCUMENTS

| | | |
|---|---|---|
| WO | WO-2011/048222 A1 | 4/2011 |
| WO | WO-2012/058097 A1 | 5/2012 |

(Continued)

OTHER PUBLICATIONS

Aggarwal et al., Blood. 2005;105:1815-1822.*
Zhou et al., Cytotherapy, 15: 434-448, 2013.*
Watson et al. Advances in Wound Care 3(3): 219-228, 2014.*
Beane, O. S. et al., "Impact of Aging on the Regenerative Properties of Bone Marrow-, Muscle-, and Adipose-Derived Mesenchymal Stem/Stromal Cells", Plos One, Dec. 26, 2014; 9(12): 1-22.
Blaber, S. P. et al., "Analysis of in vitro secretion profiles from adipose-derived cell populations", J Transl Med. Aug. 22, 2012; 10:172.
Deenick, E. K. et al. "Stochastic model of T cell proliferation: a calculus revealing IL-2 regulation of precursor frequencies, cell cycle time, and survival", J. Immunol May 15, 2003 [Retrieved from the Internet Jun. 27, 2019]; 170(10):4963-72.

(Continued)

*Primary Examiner* — Thaian N. Ton
(74) *Attorney, Agent, or Firm* — Cooley LLP

(57) ABSTRACT

Provided herein are methods and devices related to inducing a population of self-renewing or senescent stem cells, to produce one or more beneficial factors for the treatment of a disease or disorder in an individual. Also provided are compositions and methods for inducing senescence, useful for inducing senescence in a population of stem cells, in order to produce one or more beneficial factors for the treatment of a disease or disorder in an individual. Methods and devices to control and customize the production of the beneficial factors for the requirements of a disease or disorder being treated are described. Also provided are factor production units for the production of the beneficial factors, and devices for the delivery of the beneficial factors to an individual in need.

3 Claims, 130 Drawing Sheets

Specification includes a Sequence Listing.

(56) References Cited

U.S. PATENT DOCUMENTS

2019/0241958 A1  8/2019  Lunyak et al.
2019/0322729 A1  10/2019  Lunyak et al.

FOREIGN PATENT DOCUMENTS

| WO | WO-2013/078392 A1 | 5/2013 |
| WO | WO-2013/126565 A1 | 8/2013 |
| WO | WO-2014/054004 A1 | 4/2014 |
| WO | WO-2014/128634 A1 | 8/2014 |
| WO | WO-2015/153011 A | 10/2015 |
| WO | WO-2017/160880 A1 | 9/2017 |
| WO | WO-2017/184873 A2 | 10/2017 |
| WO | WO-2017/184895 A2 | 10/2017 |

OTHER PUBLICATIONS

Dixit, V. et al. "The bioartificial liver: state-of-the-art", Eur. J. Surg. Suppl. 1998; 582:71-6.

Dominici, M. et al. "Minimal criteria for defining multipotent mesenchymal stromal cells. The International Society for Cellular Therapy position statement", Cytotherapy. 2006; 8(4): 315-7.

Extended European Search Report dated Oct. 25, 2018 for EP Application No. 16804422.0, 11 pages.

Fan, H. et al. "Comparative study of regulatory T cells expanded ex vivo from cord blood and adult peripheral blood", Immunology. Jun. 2012; 136(2): 218-30.

Feng, J. et al. "GFOLD: a generalized fold change for ranking differentially expressed genes from RNA-seq data", Bioinformatics. Nov. 1, 2012 [retrieved from the Internet Jun. 27, 2019]; 28(21):2782-8. Epub Aug. 24, 2012.

Glenn J. D. et al. "Mesenchymal stem cells: Emerging mechanisms of immunomodulation and therapy", World J Stem Cells. Nov. 26, 2014; 6(5): 526-39. Published online Nov. 26, 2014.

International Search Report dated Nov. 7, 2016 for PCT Application No. PCT/US2016/035487 filed Jun. 2, 2016, 6 pages.

Jin, H. J. et al. "Comparative analysis of human mesenchymal stem cells from bone marrow, adipose tissue, and umbilical cord blood as sources of cell therapy", Int. J. Mol. Sci. Sep. 3, 2013; 14(9):17986-8001.

Legallais, C. et al. "Bioartifical livers (BAL): current technological aspects and future developments", J. Membr. Sci. 2001; 181:81-95.

Li, X. et al. "Comprehensive characterization of four different populations of human mesenchymal stem cells as regards their immune properties, proliferation and differentiation", Int J Mol Med. Sep. 2014; 34(3):695-704. Epub Jun. 25, 2014.

Niu, D. G. et al. "Morphine promotes cancer stem cell properties, contributing to chemoresistance in breast cancer", Oncotarget. Feb. 28, 2015; 6(6):3963-76.

Niu, P. et al., "Transcriptional profiling of interleukin-2-primed human adipose derived mesenchymal stem cells revealed dramatic changes in stem cells response imposed by replicative senescence", Oncotarget. Jul. 20, 2015; 6(20): 17938-57.

Perez, L. M. et al. "Obese-derived ASCs show impaired migration and angiogenesis properties", Arch Physiol Biochem. Dec. 11, 2013; 119(5): 195-201. Epub May 14, 2013.

Smigiel, K. S. et al. "Regulatory T-cell homeostasis: steady-state maintenance and modulation during inflammation", Immunol Rev. May 2014; 259(1):40-59.

Tollervey, J. et al. "Epigenetics: Judge, jury and executioner of stem cell fate", Epigenetics. Aug. 1, 2012; 7(8): 823-840.

U.S. Appl. No. 16/164,676, filed Oct. 18, 2018, for Lunyak et al.
U.S. Appl. No. 16/164,701, filed Oct. 18, 2018, for Lunyak et al.

Wang J. et al. "Primate-specific endogenous retrovirus-driven transcription defines naive-like stem cells", Nature. Dec. 18, 2014; 516(7531):405-9. Epub Oct. 15, 2014.

Wang, J. et al., "Inhibition of activated pericentromeric SINE/Alu repeat transcription in senescent human adult stem cells reinstates self-renewal", Cell Cycle. Sep. 1, 2011; 10(17):3016-30. Epub Sep. 1, 2011.

Written Opinion dated Nov. 7, 2016 for PCT Application No. PCT/US2016/035487 filed Jun. 2, 2016, 10 pages.

\* cited by examiner

Specialized Expression of the Factors

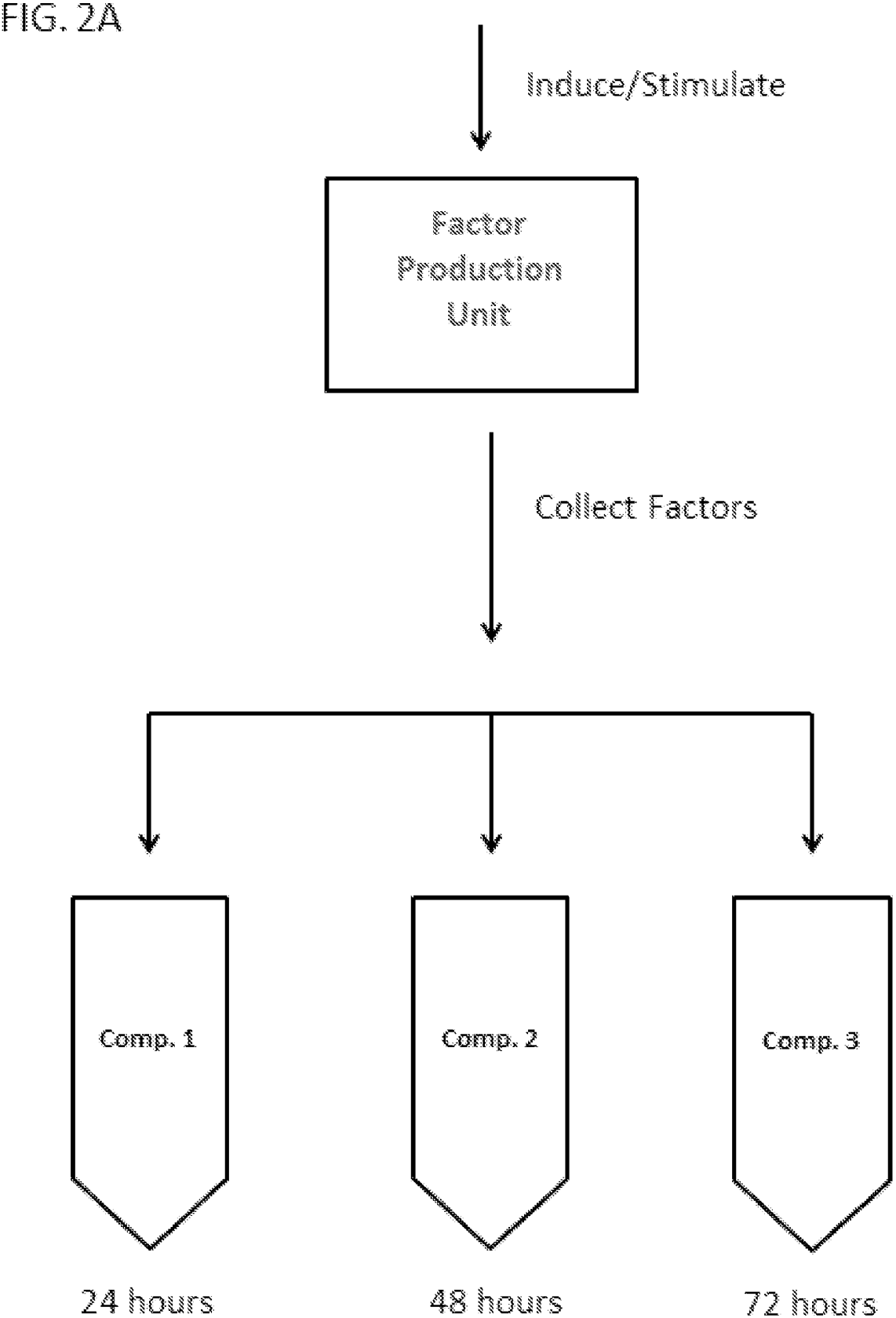

FIG. 2B    Factor Production Units A-E
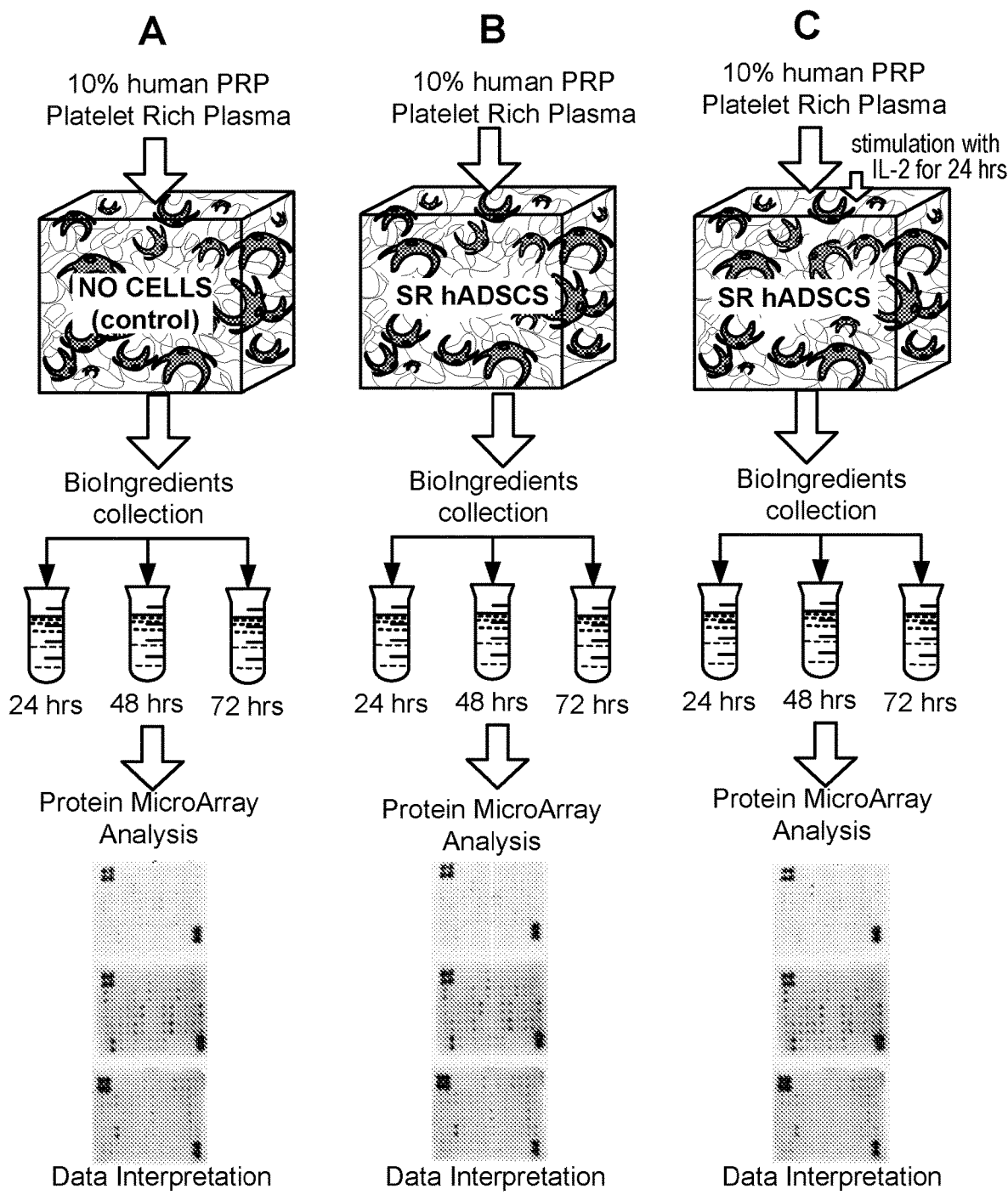

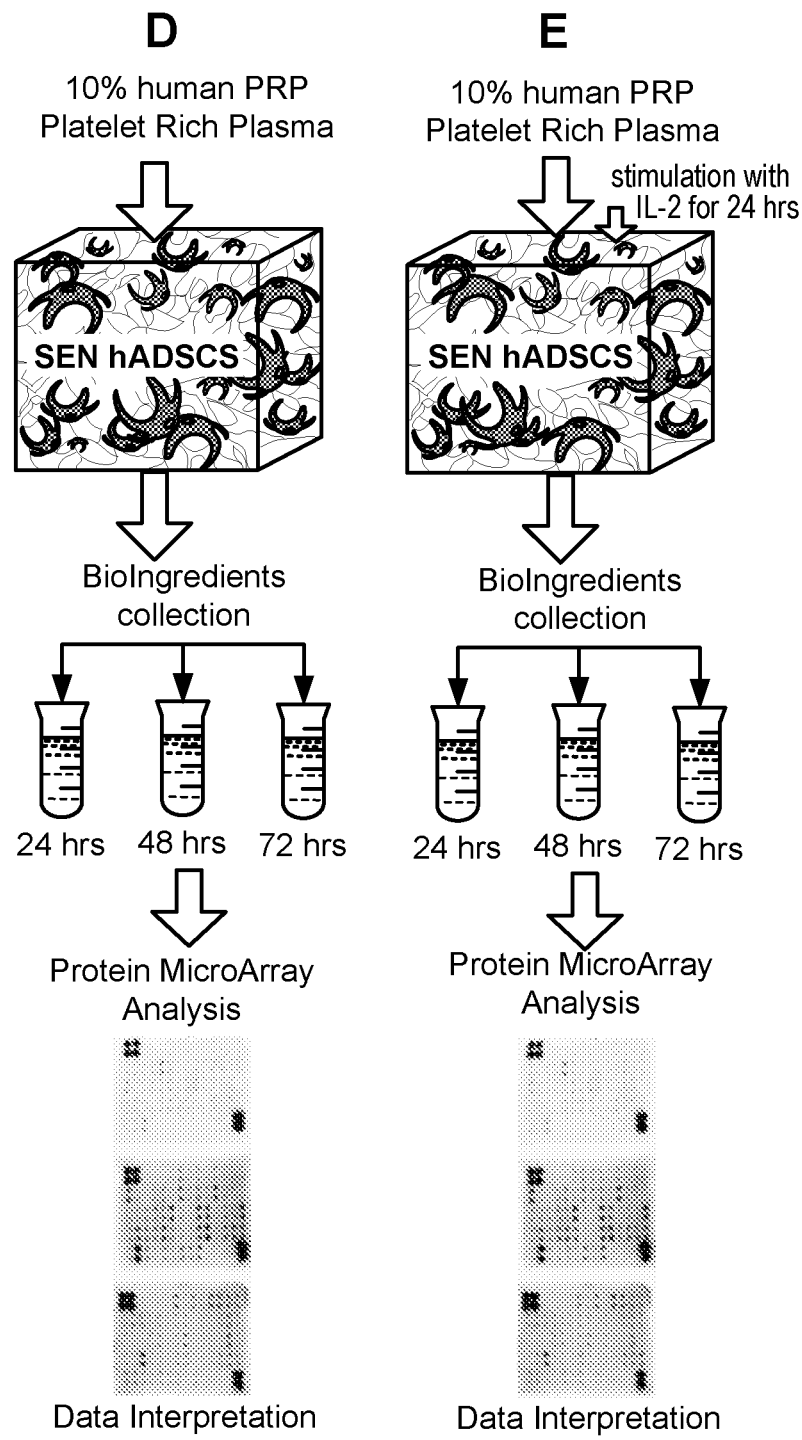
FIG. 2B (Continued) Factor Production Units A-E

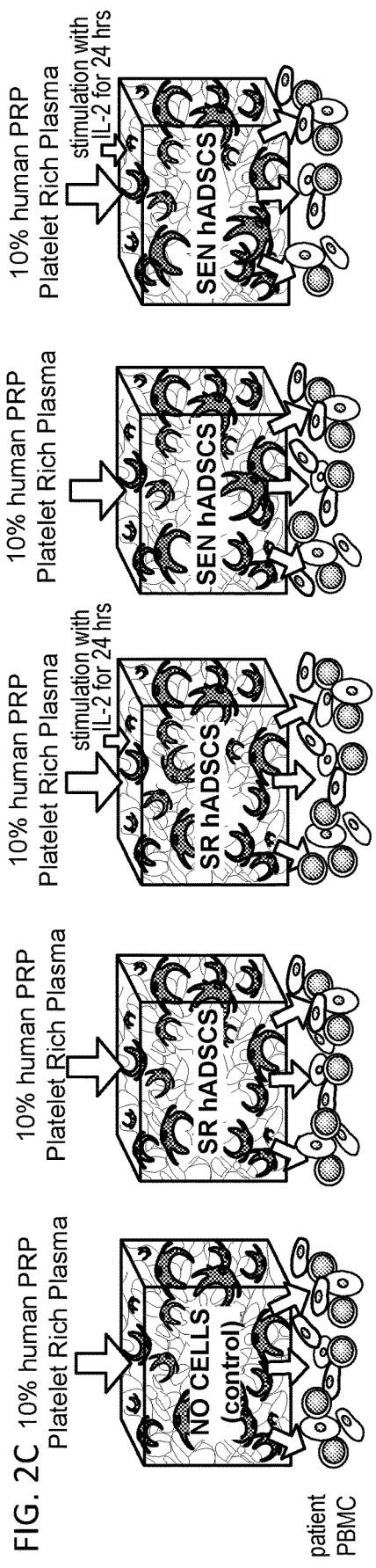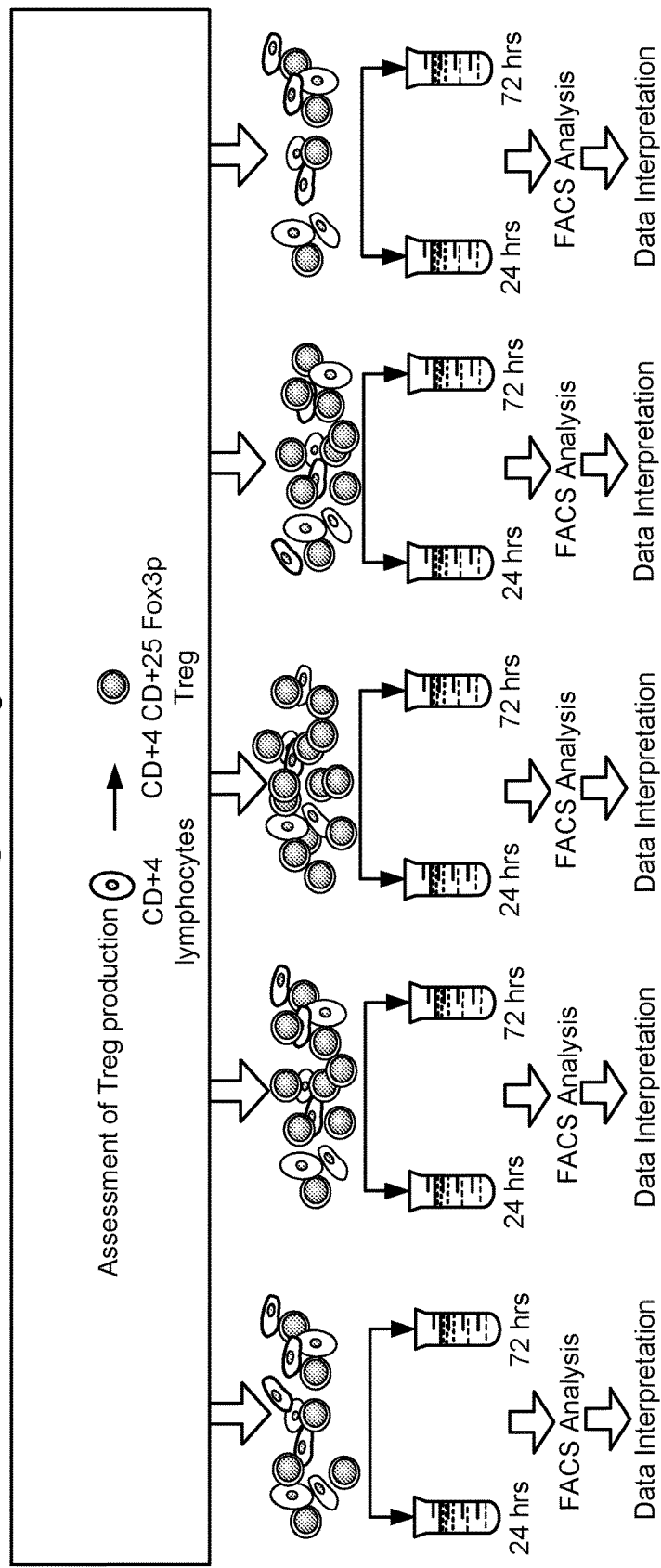
FIG. 2C

Senescence-associated β-galactosidase

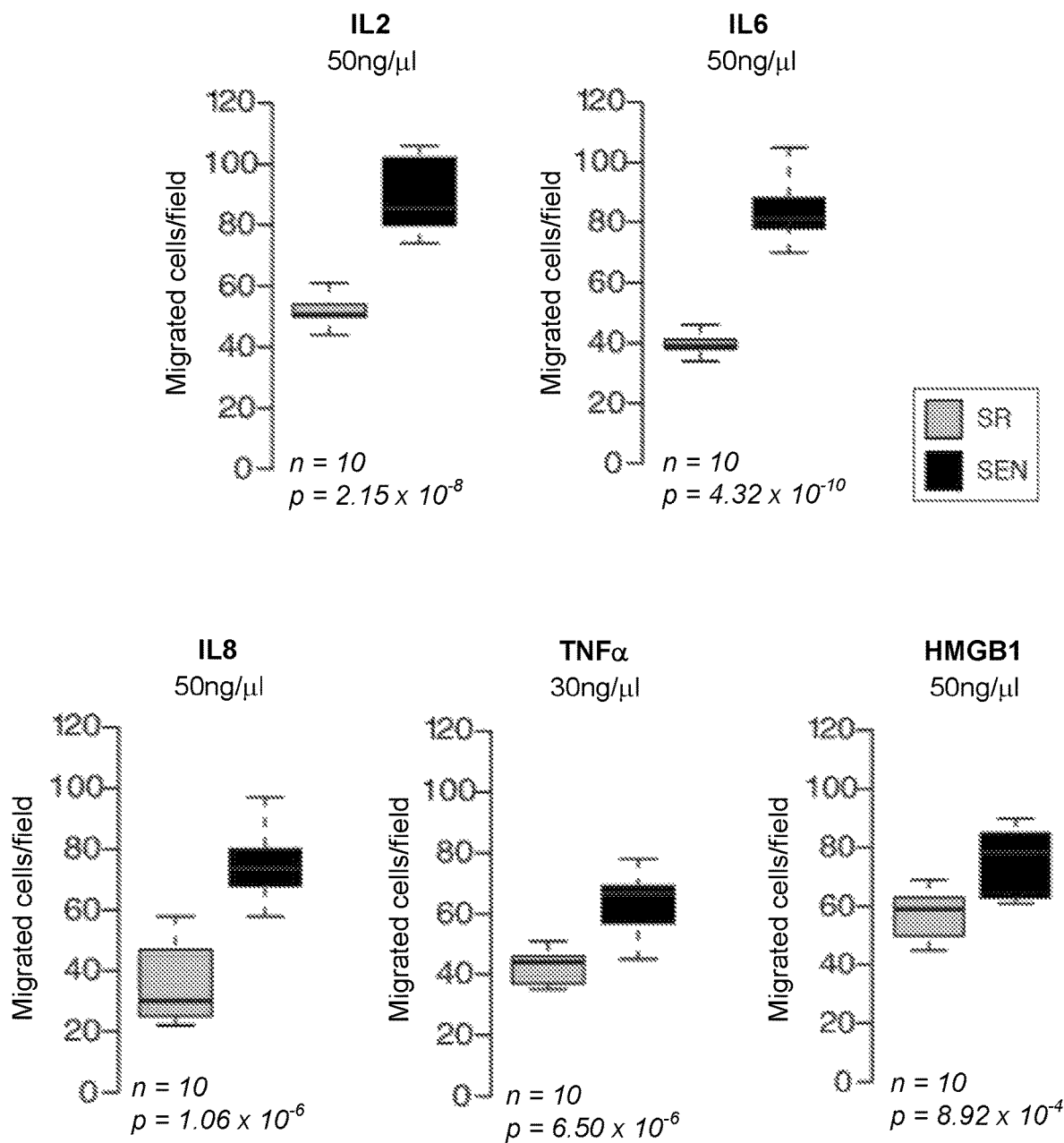
FIG. 3D  Migration in prescence of various cytokines

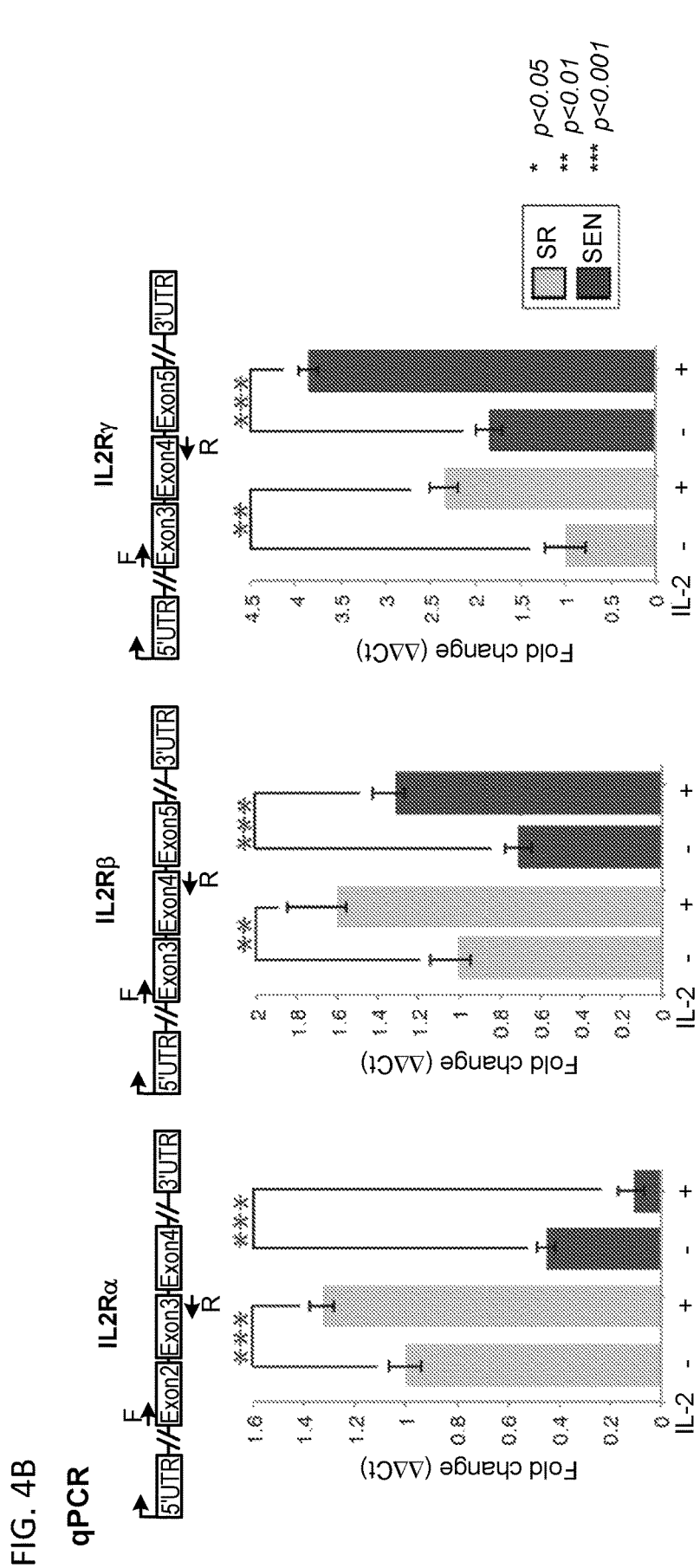

FIG. 4C
ELISA
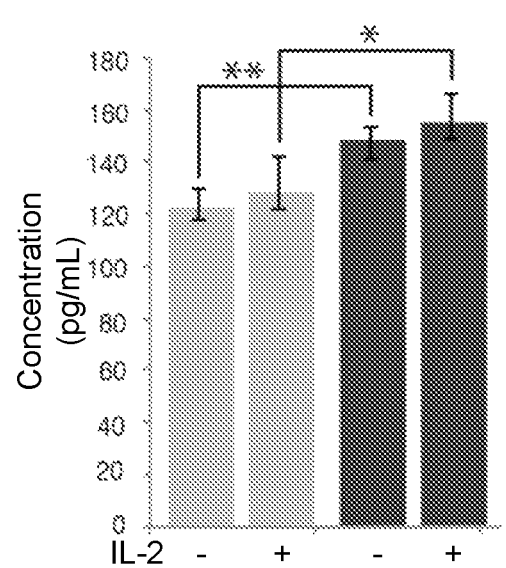
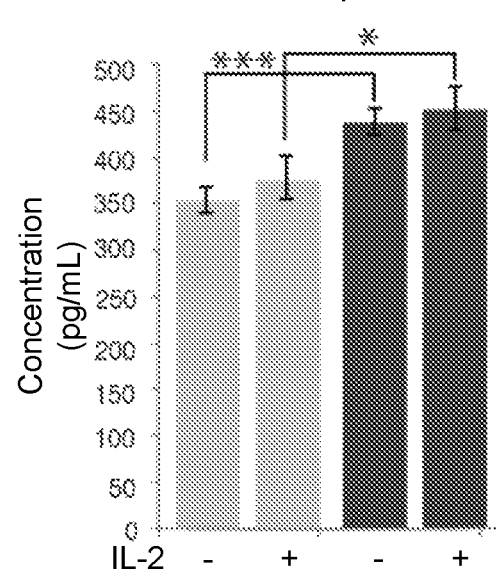
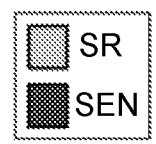
SR
SEN
\* $p<0.05$
\*\* $p<0.01$
\*\*\* $p<0.001$ FIG. 5
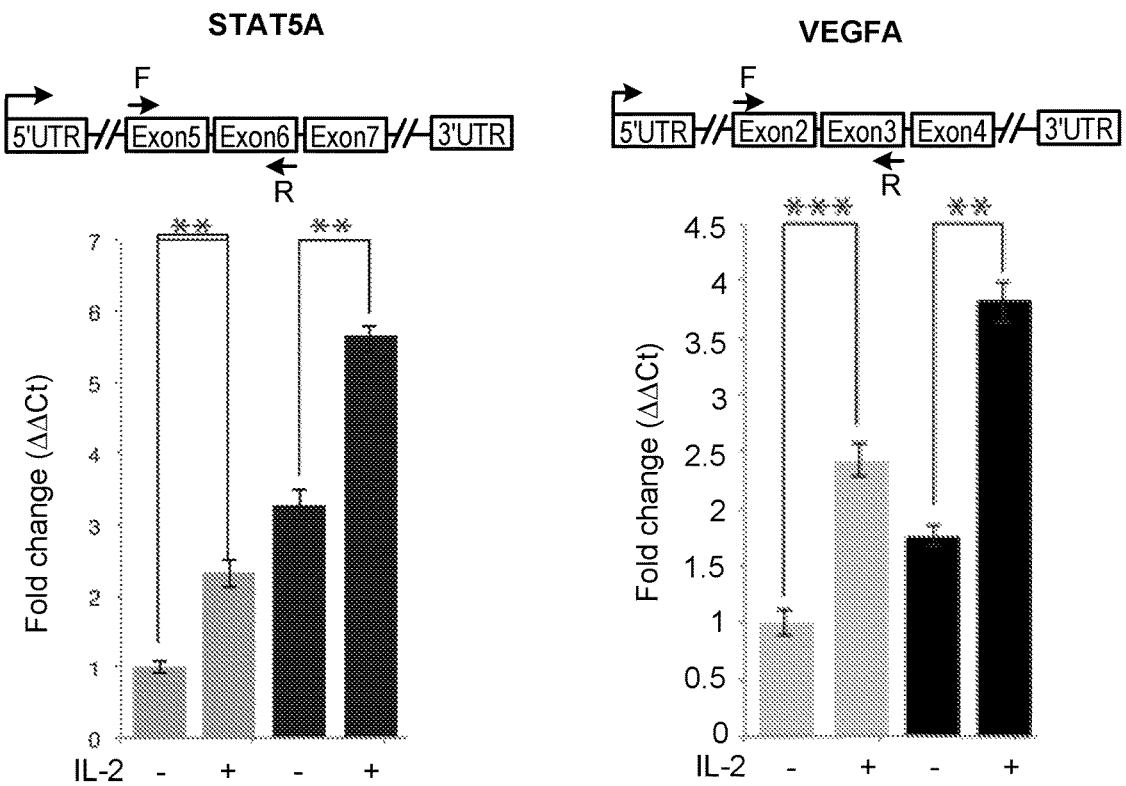
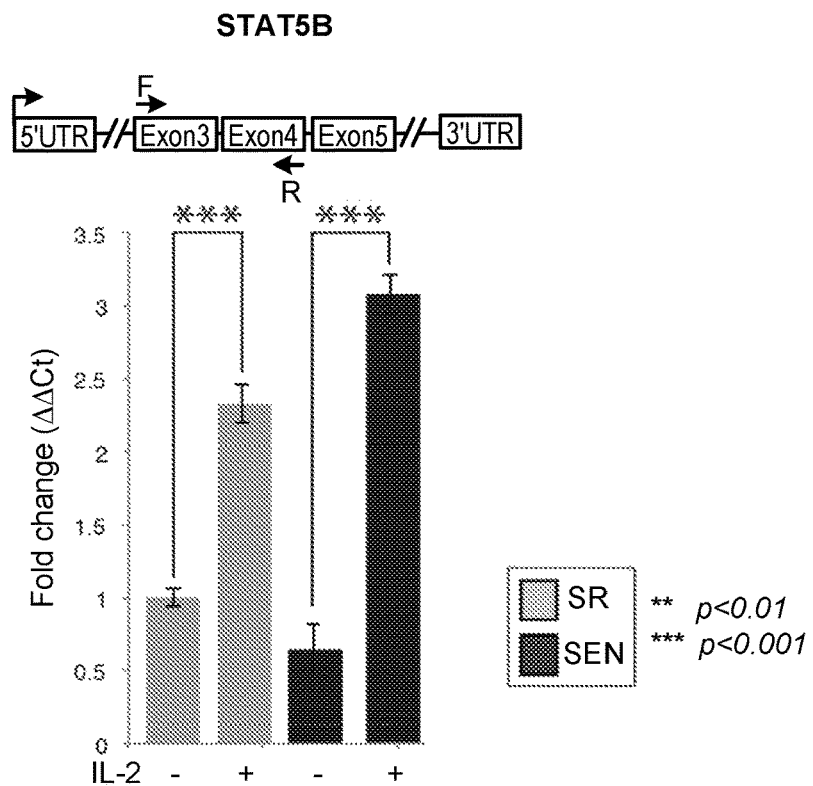

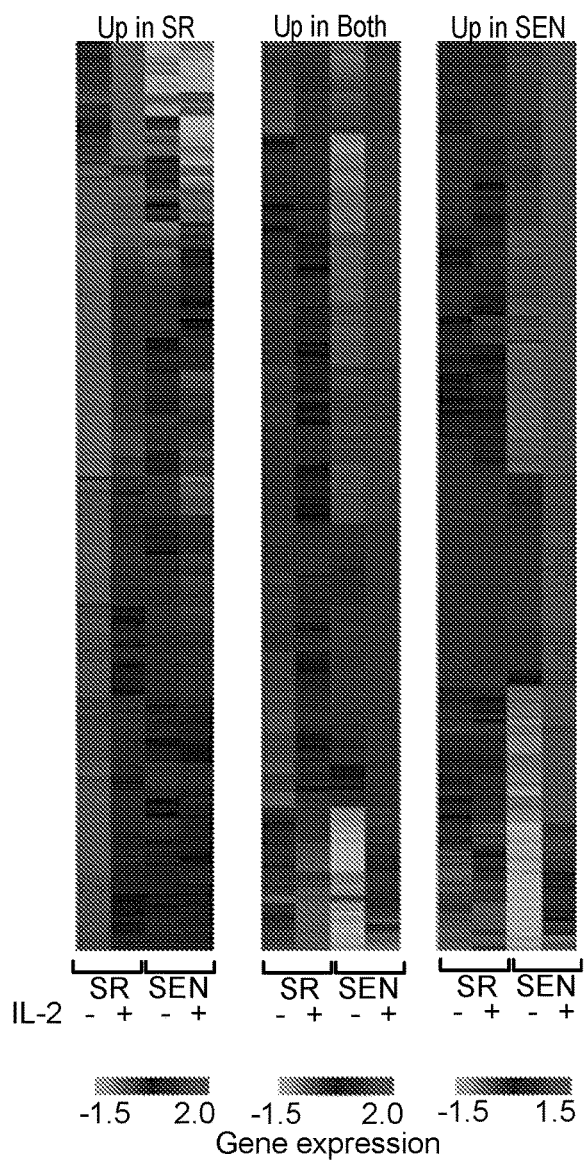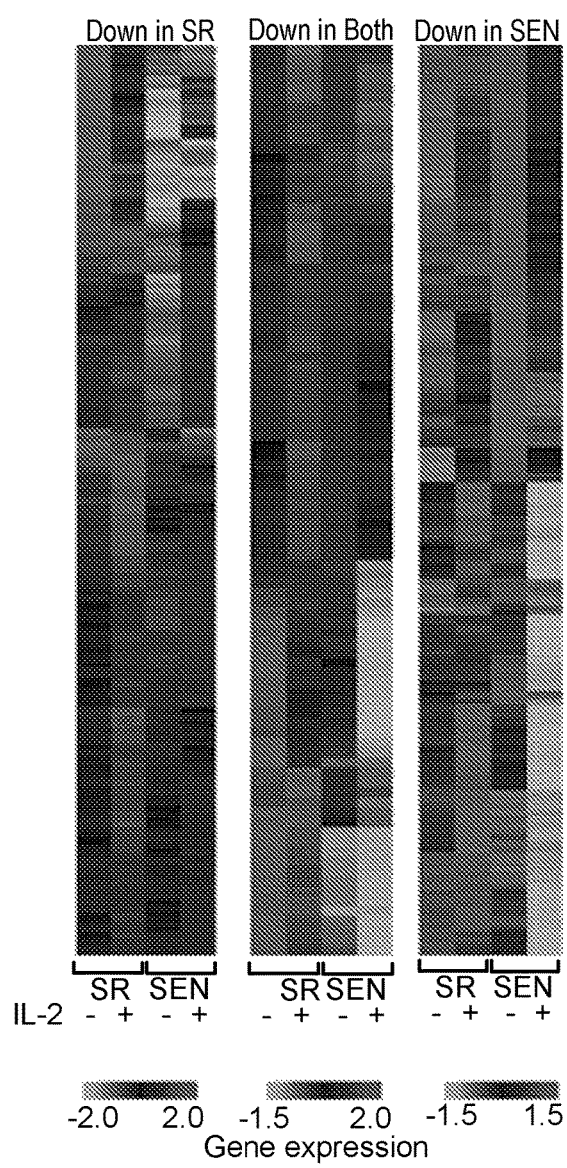

Trophic factors

Anti-inflammatory and immunomodulatory

Anti-appoptotic and metastasis promoting

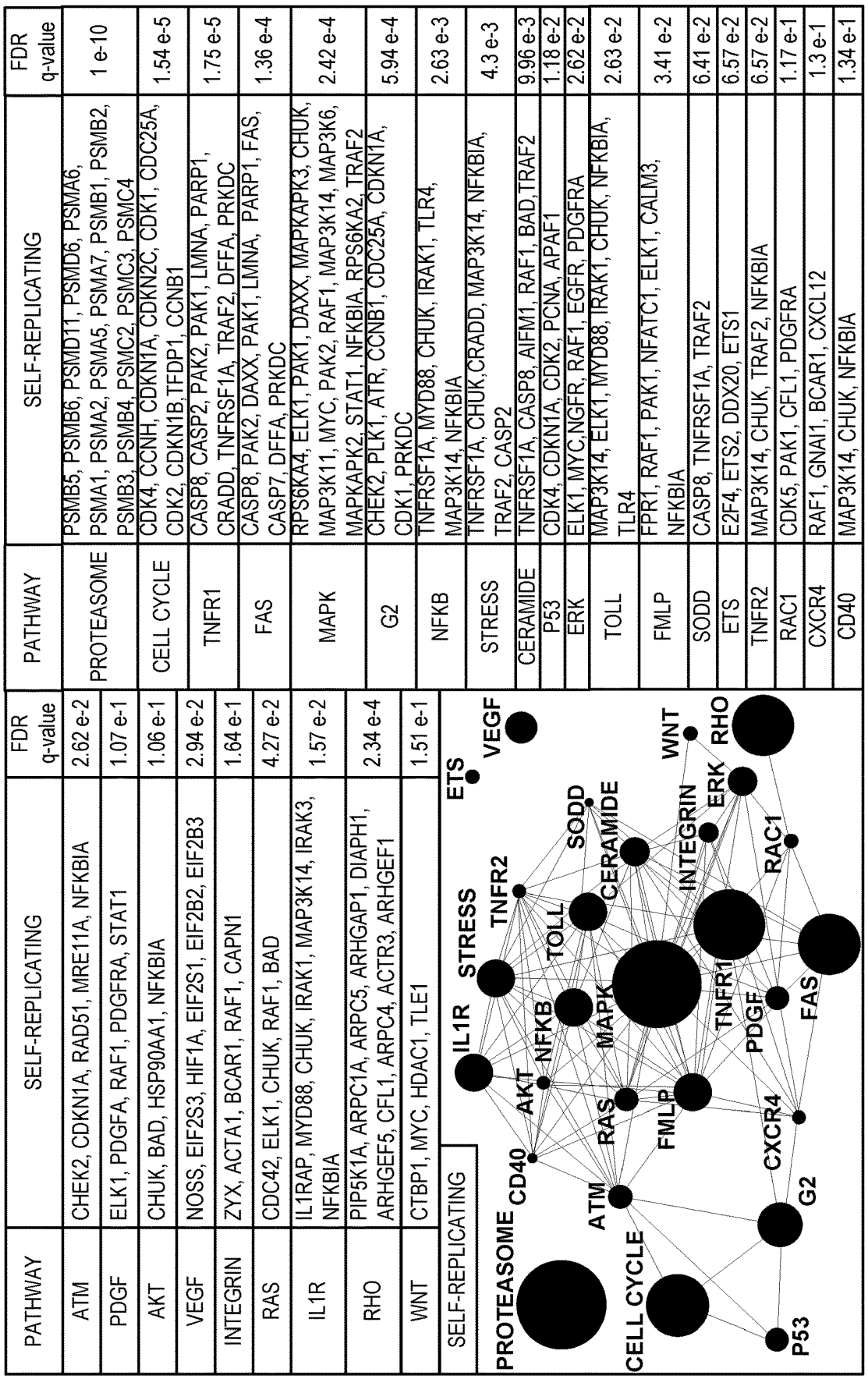
FIG. 10A  BIOLOGICAL PATHWAYS UPREGULATED UPON IL-2 TREATMENT

FIG. 10A (Continued)

| PATHWAY | SENESCENT | FDR q-value |
|---|---|---|
| ATM | JUN, GADD45A, MDM2, NBN, MAPK8, ATM, RBBP8, ABL1, RAD50 | 8.15 e-5 |
| PDGF | RASA1, JUN, FOS, PRKCA, PIK3CA, MAPK8, STAT5A, HRAS, STAT4 | 6.86 e-4 |
| AKT | FOXO4, CASP9, PIK3CA, AKT1, PDPK1, FOXO1, FOXO3 | 1.6 e-3 |
| VEGF | VEGFA, EIF2S2, EIF1AX, PRKCA, PIK3CA, EIF2B4, HRAS | 5.24 e-3 |
| INTEGRIN | JUN, RAP1A, MAPK8, ROCK1, CSK, HRAS, SRC, PPP1R12B | 5.55 e-3 |
| RAS | RALA, FOXO4, CASP9, PIK3CA, AKT1, HRAS | 6.57 e-3 |
| IL1R | JUN, IL1RN, IRAK2, TRAF6, MAPK8, IL6 | 2.51 e-2 |
| RHO | ARHGAP5, BAIAP2, ROCK1, SRC, PPP1R12B, OPHN1 | 2.34 e-2 |
| WNT | GSK3B, BTRC, SMAD4, APC, AXIN1 | 3.37 e-2 |
| EGF | RASA1, JUN, FOS, EGF, PRKCA, PIK3CA, MAPK8, STAT5A, HRAS, STAT4 | 2.33 e-4 |
| LONGEVITY | SOD2, IGF1R, PIK3CA, AKT1, SOD1, FOXO3, HRAS | 2.53 e-4 |
| IL2 | JUN, FOS, JAK3, MAPK8, STAT5A, HRAS | 5.55 e-3 |
| IL6 | JUN, CEBPB, FOS, JAK3, IL6, HRAS | 5.55 e-3 |
| IL7 | PTK2B, JAK3, EP300, PIK3CA, STAT5A | 8.47 e-3 |
| TGFB | TGFBR1, SKIL, EP300, SMAD4, APC | 1.25 e-2 |
| IL2RB | FOS, JAK3, PIK3CA, STAT5A, AKT1, CBL, HRAS | 1.51 e-2 |
| B-CELL SURVIVAL | FOS, PIK3CA, XIAP, AKT1 | 2.76 e-2 |
| LEPTIN | LEP, PRKAB2, PRKAA2 | 5.08 e-2 |
| IL12 | JUN, ETV5, MAPK8, STAT4 | 7.39 e-2 |
| NOS1 | PRKACB, GRIN2D, PRKCA, DLG4 | 8.32 e-2 |

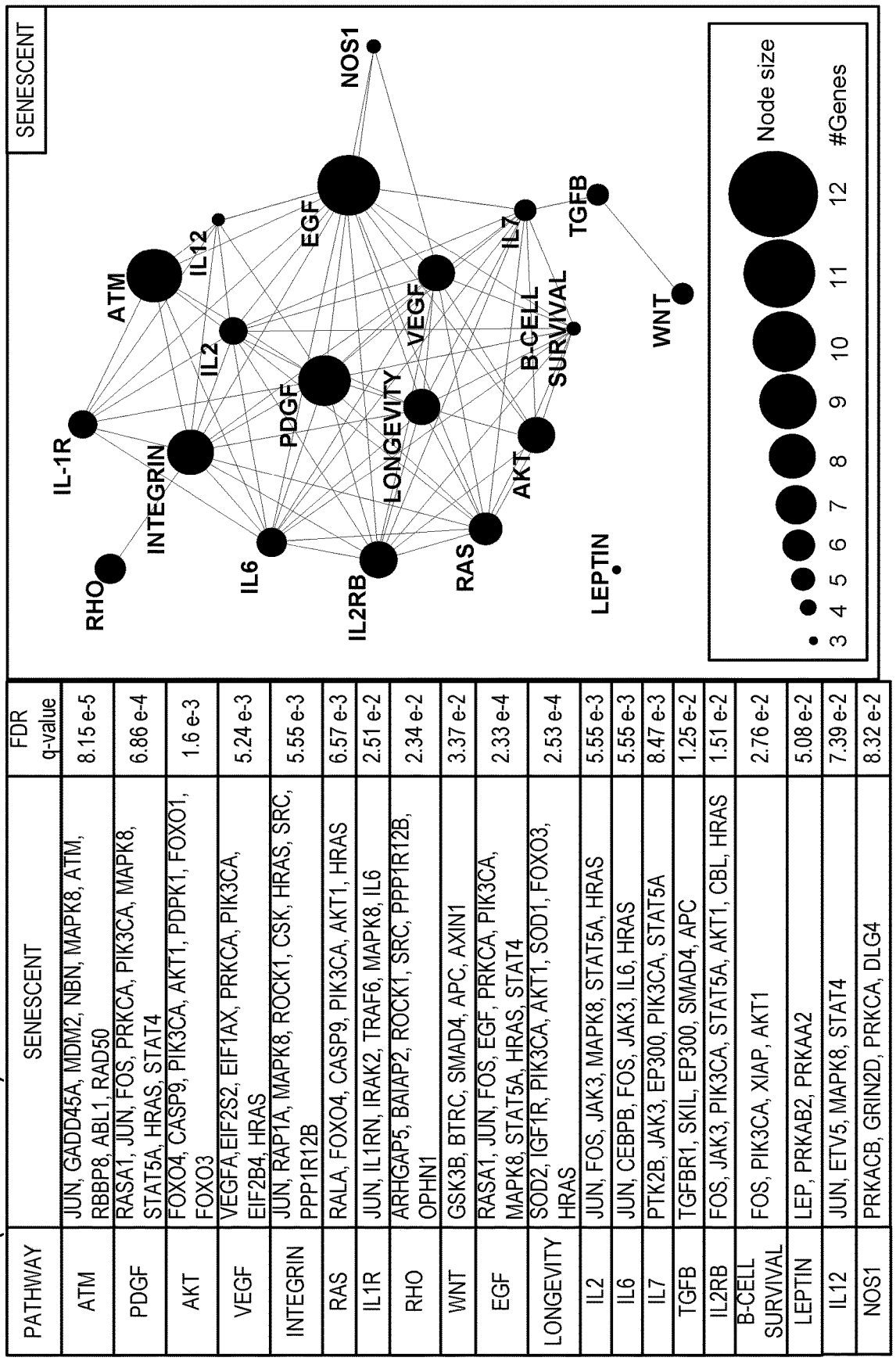

FIG. 10B BIOLOGICAL PATHWAYS DOWNREGULATED UPON IL-2 TREATMENT

| PATHWAY | SELF-REPLICATING | FDR q-value |
|---|---|---|
| G2 | GADD45A, CDKN2D | 5.35 e-1 |
| P53 | GADD45A, BAX | 5.35 e-1 |
| MTOR | EIF3A, FKBP1A | 5.35 e-1 |
| ETS | NCOR2, CSF1R | 5.35 e-1 |

FIG. 10B
(Continued)

| PATHWAY | SENESCENT | FDR q-value | PATHWAY | SENESCENT | FDR q-value |
|---|---|---|---|---|---|
| G2 | PRKDC, CDK1, CDKN1A, CCNB1, CHEK1, CDC25C, CDC25B, PLK1 | 3.06 e-5 | PDGF | MAP3K1, STAT1, SRF, PDGFRA, PDGFA | 3.28 e-2 |
|  |  |  | CERAMIDE | CASP8, MAP3K1, TRAF2, CYCS | 3.92 e-2 |
| P53 | CDK2, CDKN1A, CDK4, PCNA | 1.86 e-2 | NFKB | MAP3K1, MAP3K14, TNFRSF1B, IL1R1 | 4.25 e-2 |
|  |  |  | RAC1 | MAP3K1, PDGFRA, CFL1, CHN1 | 4.25 e-2 |
| MTOR | EIF4A1, PRS6, TSC1 | 1.59 e-1 | CD40 | IKBKAP, MAP3K1, MAP3K14 | 6.79 e-2 |
|  |  |  | B-CELL SURVIVAL | BIRC5, CCT4, ITGA1 | 7.61 e-2 |
| MCM | CDK2, KITLG, ORC6, ORC3, MCM2, MCM3, MCM4, MCM5, MCM7, CDT1 | 1.62 e-8 | CDC42RAC | ARPC4, CDC42, PDGFRA | 7.61 e-2 |
| PROTEA-SOME | PSMA7, PSMA5, PSMA6, PSMB3, PSMB5, PSMB6, PSMB7, PSMC2, PSMC3 | 2.17 e-5 | IL-10 | BLVRA, BLVRB, STAT1 | 8.64 e-2 |
|  |  |  | EGF | EGFR, MAP3K1, SRF, STAT1 | 9.19 e-2 |
| HIV-I NEF | PRKDC, CASP8, LMNA, PARP1, LMNB1, LMNB2, MAP3K1, TRAF2, CYCS, MAP3K14, TNFRSF1B, ACTG1 | 2.52 e-5 | RHO | ARHGAP1, ARPC4, CFL1, PIP5K1A | 1 e-1 |
|  |  |  | IL-1R | IL1R1, IRAK3, MAP3K1, MAP3K14 | 1.09 e-1 |
| CELL CYCLE | CDK2, CDK1, CDKN1A, CCNB1, CDK4, TFDP1, CDKN2C, CCND3 | 2.52 e-5 | mCALPAIN | ACTA1, EGFR, ITGA1 | 1.79 e-1 |
|  |  |  | STRESS | MAP3K1, MAP3K14, TRAF2 | 1.79 e-1 |
| RB | CDK2, CDK1, CDK4, CHEK1, CDC25C, CDC25B | 6.97 e-5 | TALL1 | MAP3K14, TRAF2 | 2.81 e-1 |
|  |  |  | NO1 | ACTA1, CALM3, FLT1 | 2.97 e-1 |
| TNFR1 | PRKDC, CASP8, LMNA, PARP1, LMNB1, LMNB2, MAP3K1, TRAF2 | 1.02 e-4 | 4-1BB | MAP3K1, TRAF2 | 3.21 e-1 |
| FAS | PRKDC, CASP8, LMNA, PARP1, LMNB1, LMNB2, MAP3K1, TRAF2 | 1.1 e-3 | LAIR | C5, ITGA4 | 3.21 e-1 |
|  |  |  | ETS | E2F4, ETS1 | 3.4 e-1 |
| TNFR2 | MAP3K1, TRAF2, MAP3K14, TNFRSF1B, IKBKAP | 4.02 e-3 | FMLP | CALM3, CAMK1G, MAP3K1 | 3.8 e-1 |
| NFAT | ACTA1, MEF2C, CALM3, CAMK1G, CTF1, FGF2, HAND2 | 2.9 e-2 | CCR5 | CALM3, CCL2 | 3.8 e-1 |
|  |  |  | ERK | EGFR, PDGFRA | 5.82 e-1 |
| SODD | CASP8, TRAF2, TNFRSF1B | 3.24 e-2 | TOLL | MAP3K1, MAP3K14 | 8.06 e-1 |
| ATM | CDKN1A, CHEK1, MRE11A, RAD51 | 3.28 e-2 | INTEGRIN | ACTA1, ITGA1 | 8.25 e-1 |

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
No IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

FIG. 54
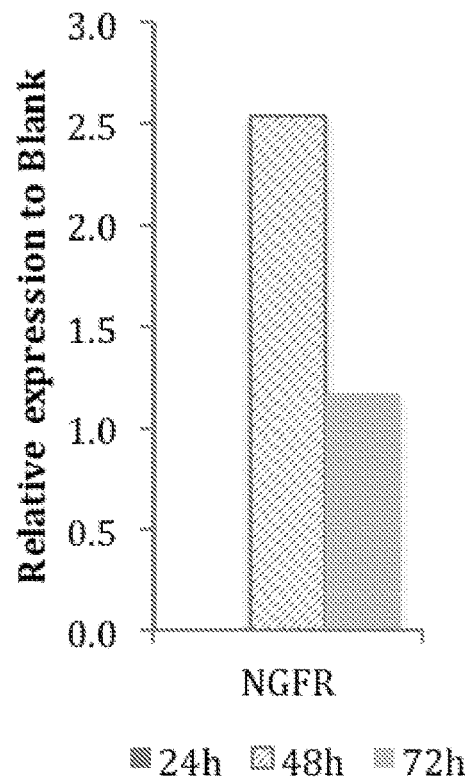
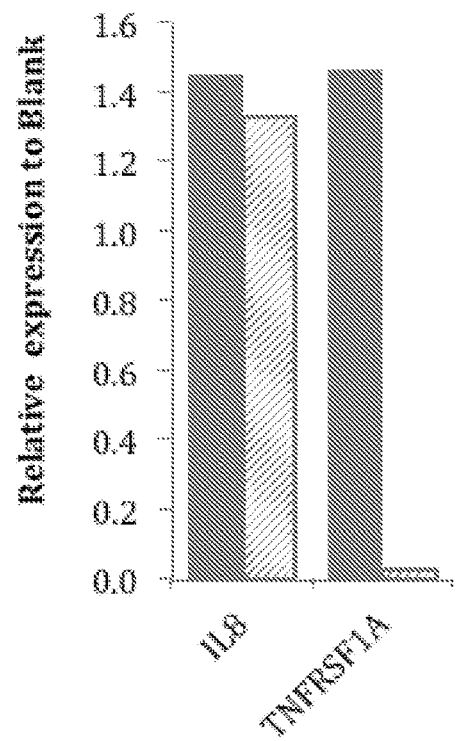
SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SR-MSCs in a FPU
+ IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
No IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

SEN-MSCs in a FPU
+ IL-2 Stimulation

FIG. 91

Interleukins

*10% PRP*

| | |
|---|---|
| IL 1b | Interleukin 1 beta |
| IL3 | Interleukin 3 |
| IL5 | Interleukin 5 |
| IL6 | Interleukin 6 |
| IL6ST | Interleukin 6ST |
| IL9 | Interleukin 9 |
| IL11 | Interleukin 11 |
| IL12a | Interleukin 12 alpha |
| IL12b | Interleukin 12 beta |
| IL17 | Interleukin 17 |

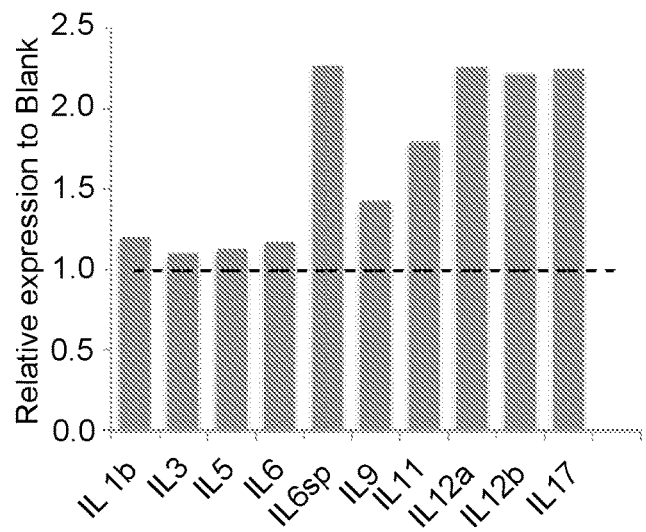

Interleukins Receptors

*10% PRP*

| | |
|---|---|
| IL1Ra | Interleukin 1 receptor alpha |
| IL1R1 | Interleukin 1 receptor |
| IL1R2 | Interleukin 1 receptor 2 |
| IL1R4 | Interleukin 1 receptor 4 |
| IL2Ra | Interleukin 2 receptor alpha |
| IL5Ra | Interleukin 5 receptor alpha |
| IL6R | Interleukin 6 receptor |
| IL10Rb | Interleukin 10 receptor beta |
| IL13Ra | Interleukin 13 receptor alpha |
| IL18Rb | Interleukin 18 receptor b |
| IL21R | Interleukin 21 receptor |

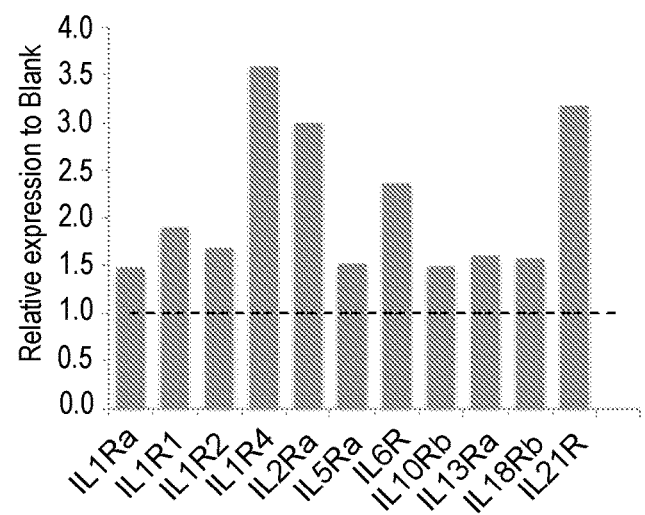

FIG. 92

Growth factors

*10% PRP*

| | |
|---|---|
| bFGF | Basic fibroblast growth factor 2 |
| bNGF | Beta-nerve growth factor |
| FGF4 | Fibroblast growth factor 4 |
| FGF6 | Fibroblast growth factor 6 |
| FGF9 | Fibroblast growth factor 9 |
| HGF like | Hepatocyte growth factor like |
| IGF1 | Insulin growth factor 1 |
| IGF2 | Insulin growth factor 2 |
| IGFBP3 | Insulin growth factor binding protein 3 |
| IGFBP6 | Insulin growth factor binding protein 6 |
| LAP | Transforming growth factor like |
| PDGFAA | Placenta derived growth factor A alpha |
| PDGFAB | Placenta derived growth factor A beta |
| PDGFBB | Placenta derived growth factor B beta |
| PLGF | Placenta growth factor |
| TGF b1 | Transforming growth factor beta 1 |
| TGF b2 | Transforming growth factor beta 2 |
| TGF b3 | Transforming growth factor beta 3 |
| VEGF | Vascular endothelial growth factor |
| VEGFD | Vascular endothelial growth factor D |

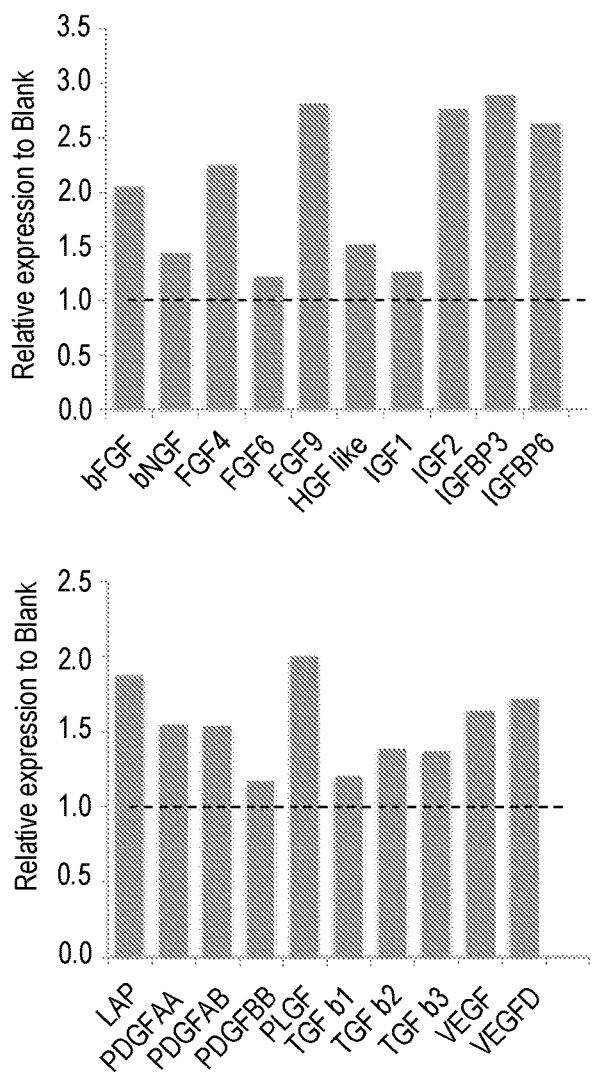

FIG. 93

Growth factor Receptors

*10% PRP*

| | |
|---|---|
| EGFR | Epithelial growth factor receptor |
| IGF1 sR | Interleukin 1 receptor 2 |
| VEGFR2 | Interleukin 1 receptor 4 |
| VEGFR3 | Interleukin 2 receptor alpha |

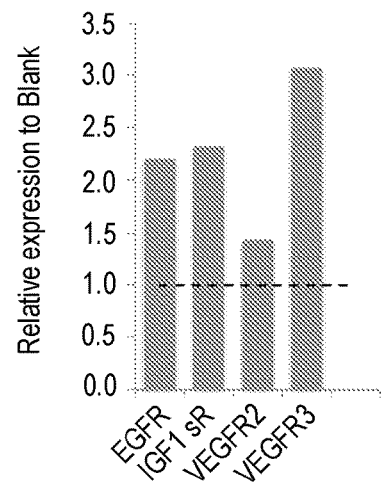

Adhesion and proliferation

*10% PRP*

| | |
|---|---|
| ALCAM | Activated leukocyte cell adhesion molecule |
| BMP 5 | Bone morphogenic protein 5 |
| BMP 7 | Bone morphogenic protein 7 |
| E selectin | Endothelial leukocyte adhesion molecule |
| ICAM-1 | Intracellular adhesion molecule 1 |
| ICAM2 | Intracellular adhesion molecule 2 |
| ICAM-3 | Intracellular adhesion molecule 3 |
| L Selectin | Lymphocytes adhesion molecule |
| MMP 1 | Matrix metalloproteinase 1 |
| MMP 3 | Matrix metalloproteinase 3 |
| MMP 9 | Matrix metalloproteinase 9 |
| MMP 13 | Matrix metalloproteinase 13 |
| PECAM 1 | Platelet endothelial cell adhesion molecule |
| TIMP1 | Metallopeptidase inhibitor 1 |
| TIMP2 | Metallopeptidase inhibitor 2 |

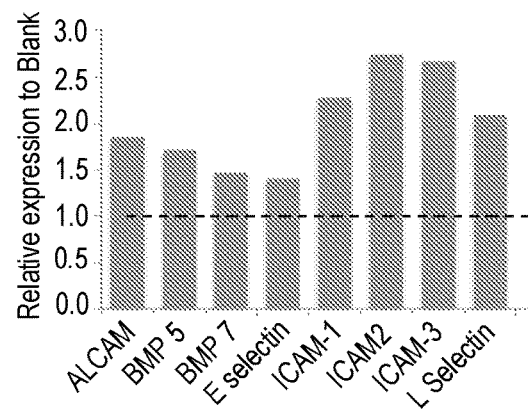

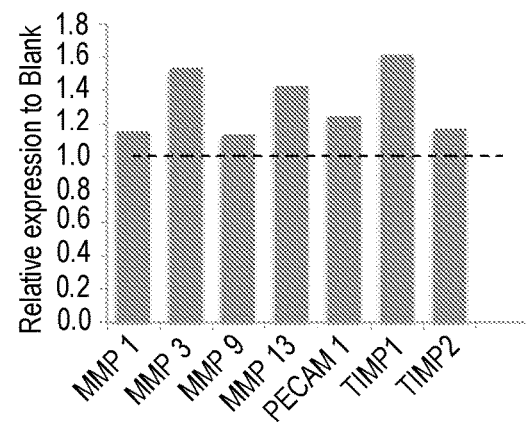

Necrosis and neurotrophic factors

*10% PRP*

| | |
|---|---|
| GDNF | Glial derived neurotrophic factor |
| GITR | TNF receptor family 18 |
| GITR LG | TNF family 18 |
| TNFa | Tumor necrosis factor alpha |
| TNFb | Tumor necrosis factor beta |
| TNFRSF10C | TNF receptor family 10C |
| TNFRSF10D | TNF receptor family 10D |
| TNFRSF6 | TNF receptor family 6 |
| TNFSF14 | TNF family 14 |
| TNFSF6 | TNF family 6 |
| TNFSRF1A | TNF receptor family 1A |

FIG. 95

Chemokines

*10% PRP*

| | |
|---|---|
| CCL2 | Chemokine ligand 2 |
| CCL3 | Chemokine ligand 3 |
| CCL4 | Chemokine ligand 4 |
| CCL5 | Chemokine ligand 5 |
| CCL7 | Chemokine ligand 7 |
| CCL8 | Chemokine ligand 8 |
| CCL13 | Chemokine ligand 13 |
| CCL15 | Chemokine ligand 15 |
| CCL16 | Chemokine ligand 16 |
| CCL17 | Chemokine ligand 17 |
| CCL18 | Chemokine ligand 18 |
| CCL19 | Chemokine ligand 19 |
| CCL20 | Chemokine ligand 20 |
| CCL22 | Chemokine ligand 22 |
| CCL24 | Chemokine ligand 24 |
| CCL25 | Chemokine ligand 25 |
| CCL26 | Chemokine ligand 26 |
| CCL27 | Chemokine ligand 27 |
| CXCL1 | Chemokine ligand 1 |
| CXCL1/2/3 | Chemokine ligand 1/2/3 |
| CXCL5 | Chemokine ligand 5 |
| CXCL9 | Chemokine ligand 9 |
| CXCL10 | Chemokine ligand 10 |
| CXCL11 | Chemokine ligand 11 |

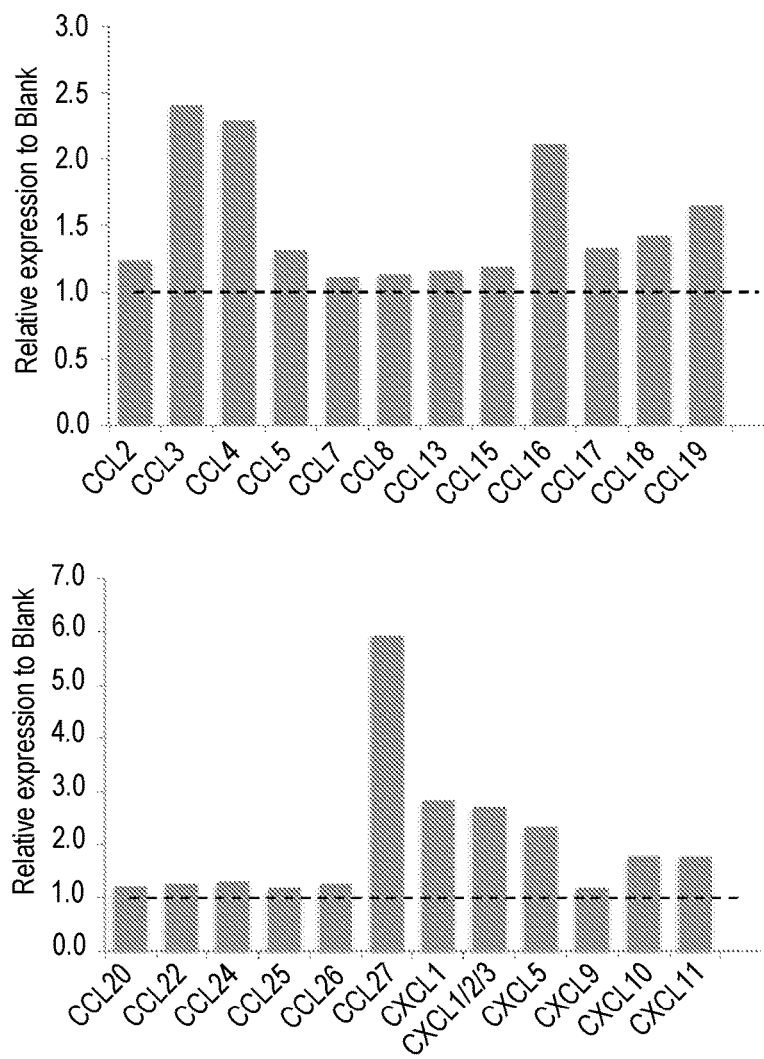

FIG. 96

Other factors

*10% PRP*

| | |
|---|---|
| Activin A | Activin A |
| Adipoq | Adiponectin |
| AgRP | Agouti related protein |
| ANGPT2 | Agiopoietin-2 |
| AREG | Amphiregulin |
| Axl | Tyrosine-protein kinase receptor UFO |
| BTC | Betacellulin |
| CD14 | Monocyte differentiation antigen |
| CD80 | Monocyte differentiation antigen |
| CT-1 | Cardiotropin-1 |
| Dtk | Tyrosine-protein kinase receptor TYRO3 |
| ENG | Endoglin |
| ErbB3 | Receptor tyrosine-protein kinase erB-3 |
| LEP | Leptin |
| LEPR | Leptin Receptor |
| LIF | Leukemia inhibitor factor |
| MIF | Macrophage migration inhibitory factor |
| NT-3 | Neutrophin-3 |
| NT-4 | Neutrophin-4 |
| OPG | Osteoprotegerin |
| OSM | Oncostatin M |
| PPBP | Platelet basic protein |
| PRL | Prolactin |
| SCF | Stem cell factor |
| SCF R | Stem cell factor receptor |
| SDF1a | Stromal derived factor 1 alpha |
| SDF1b | Stromal derived factor 1 beta |
| THPO | Thrombopoietin |
| TIE-1 | Angiopoietin 1 receptor |
| TIE-2 | Angiopoietin 1 receptor |

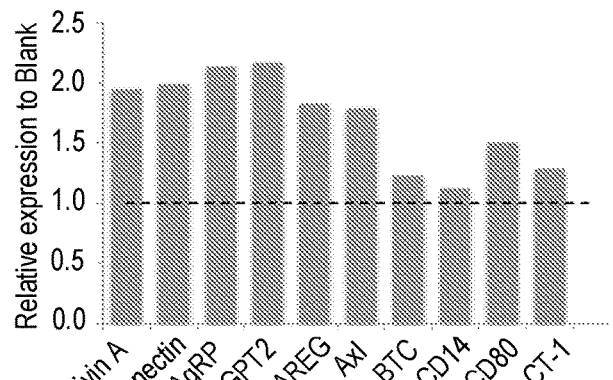
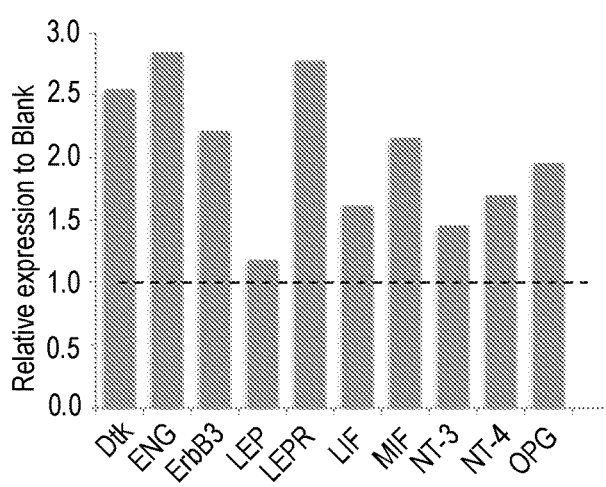
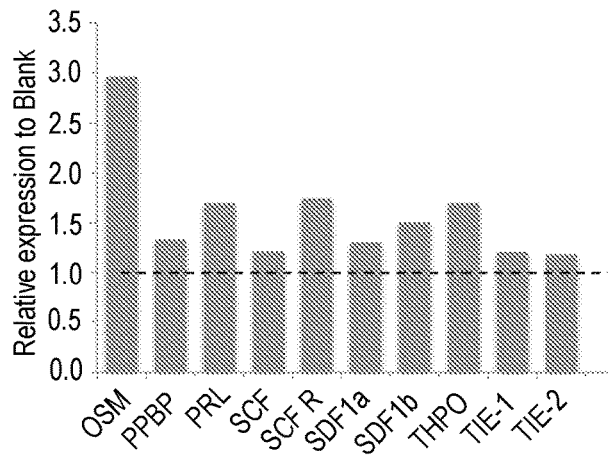

FIG. 97    Transrepresentation of IL-2R alpha (CD25)
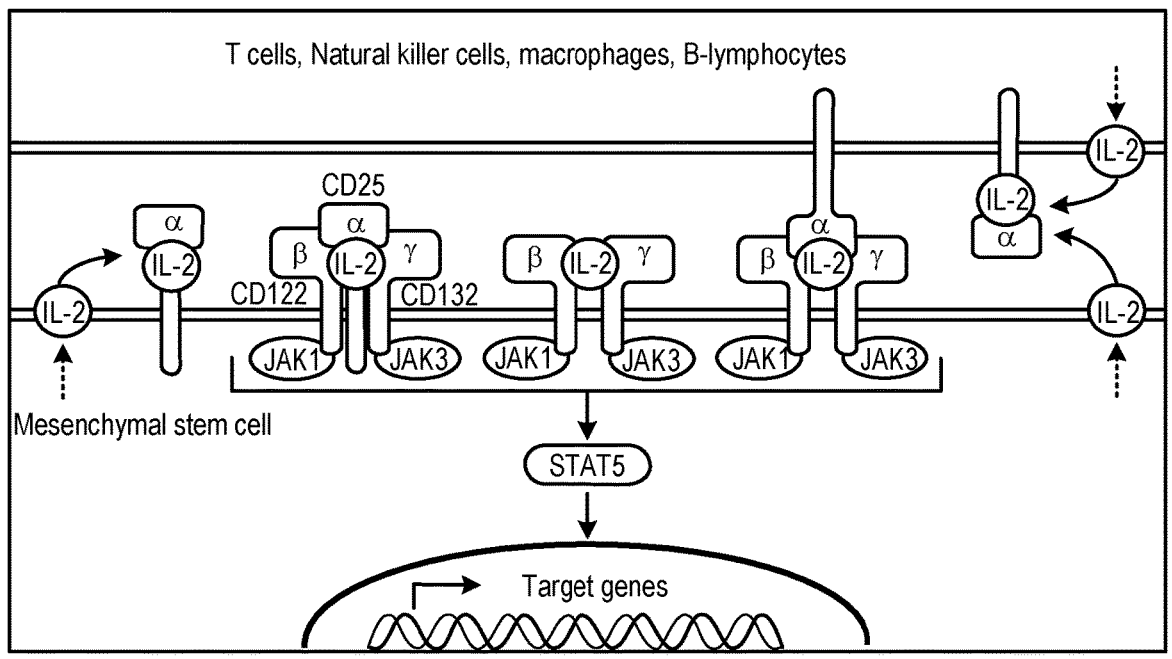
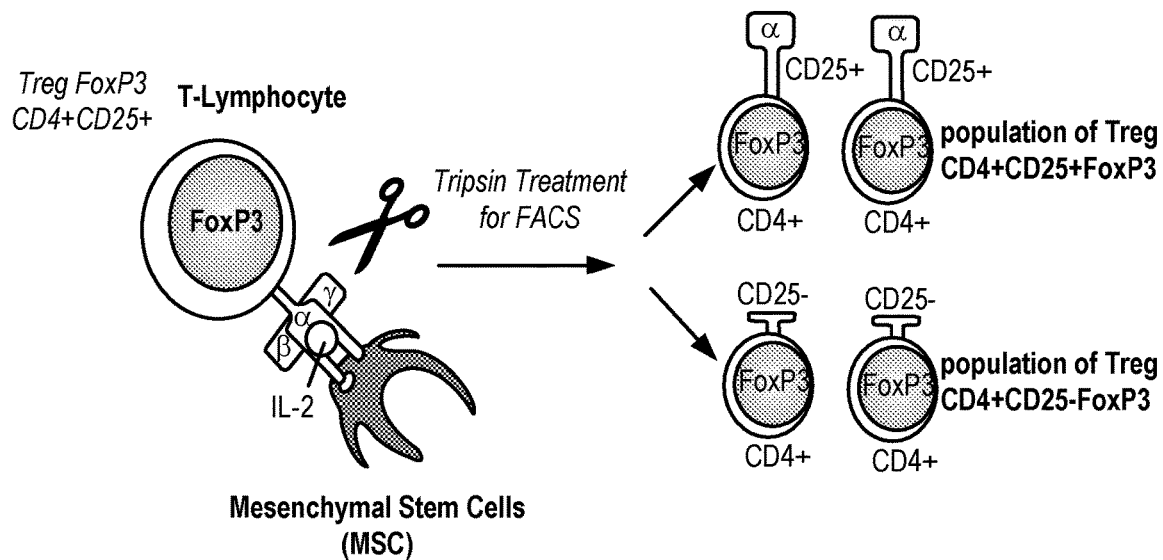

FIG. 108
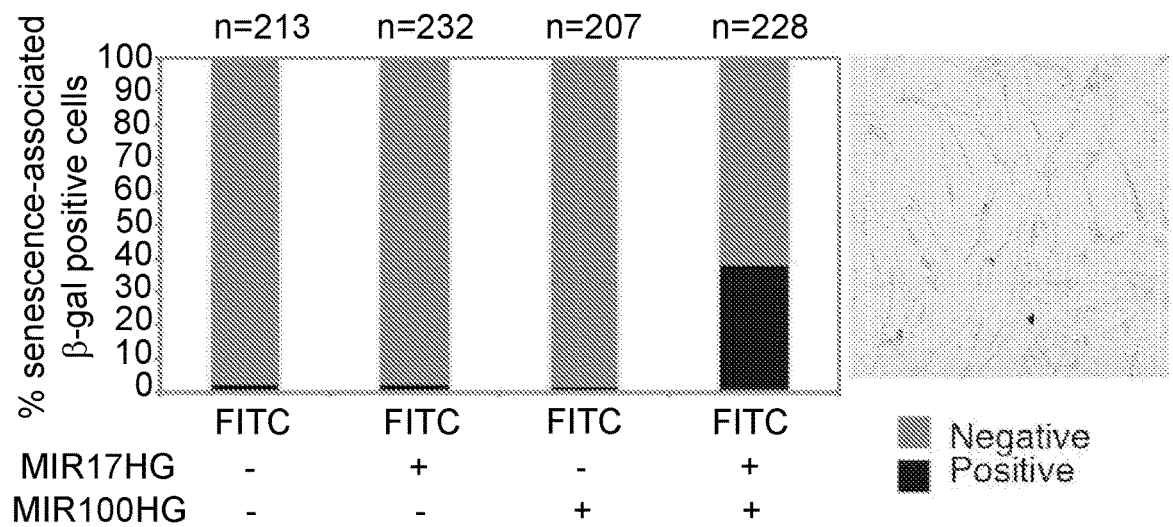
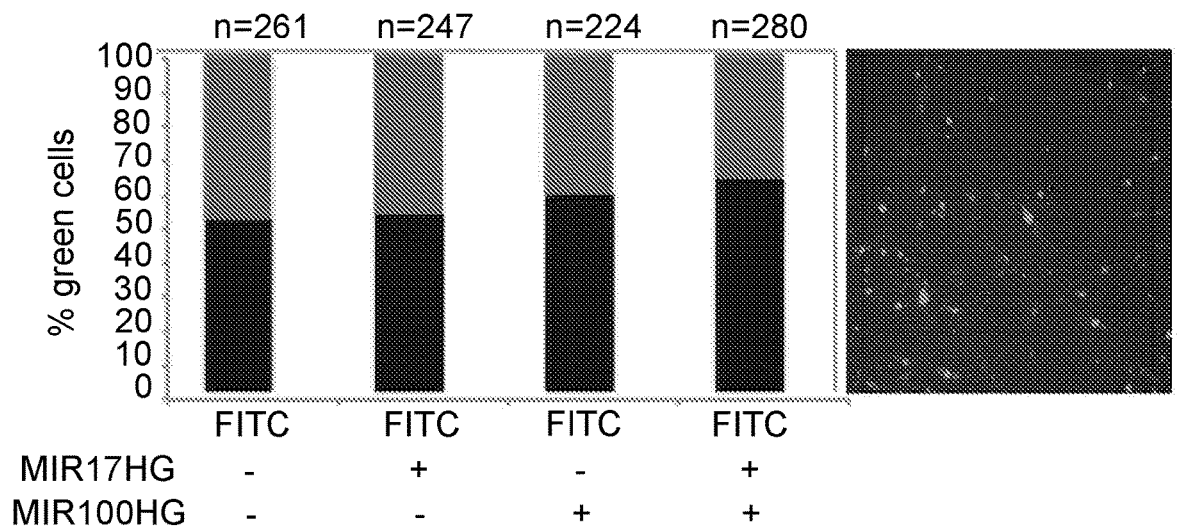

METHODS AND DEVICES FOR THE PRODUCTION AND DELIVERY OF BENEFICIAL FACTORS FROM ADIPOSE-DERIVED STEM CELLS

CROSS-REFERENCE TO RELATED APPLICATIONS

This application is a U.S. National Stage Application under 35 U.S.C. § 371 of International Application No. PCT/US2016/035487, filed on Jun. 2, 2016, which claims priority to U.S. Provisional Application Ser. No. 62/170,604, filed on Jun. 3, 2015, U.S. Provisional Application Ser. No. 62/170,619, filed Jun. 3, 2015, and U.S. Provisional Application Ser. No. 62/175,203, filed Jun. 12, 2015, each of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALNC_001_01US_SeqList_ST25.txt, date recorded: Oct. 9, 2021, file size~7.97 kilobytes).

BACKGROUND OF THE INVENTION

Adult stem cells, for example, adult mesenchymal stem cells (MSCs), generate differentiated cell types within many organs throughout the lifespan of an organism and are thus ultimately responsible for the longevity of multicellular organisms. Stem cells possess three important properties: (1) they self-renew, allowing the maintenance of the original stem cell population; (2) they differentiate into multiple types of mature cells in order to replace the mature cells that turn over in adult tissues; and (3) they maintain the stability stem cell pool through the life (Tollervey and Lunyak, 2011). Utilizing these properties in the clinical setting, stem cell transplantation-based therapies have, for example, been shown to: restore neuronal integrity by stimulating the release of neurotrophic factors by neighboring cells, prevent cognitive decline caused by aging, facilitate nerve recovery after injury both in the CNS and in the periphery; stimulate remyelination processes and glial regenerative support to neurons; prevent retinal damage and maintain retinal barrier properties; impede oxidative insults, produce strong suppression of inflammation and autoimmune response, provide immunomodulation, guide angiogenesis and create microenvironment conducive to regeneration or organ and tissue repair.

Human adipose derived mesenchymal stem cells (hADSCs or hAMSCs) are currently one of the primary sources of stem cells with direct clinical relevance. Transplanted mesenchymal stem cells, however, pose problems such as oncogenic potential, and poor retention upon implantation.

While it is known that stem cells possess signaling capabilities and are able to produce and secrete factors, such production cannot be controlled with transplantation. Thus there remains a need to control and customize the production of, produce, and deliver therapeutic factors from stem cells to individuals in need. Provided herein are methods and devices that address this need.

BRIEF SUMMARY OF THE INVENTION

Provided herein are methods and devices related to inducing a population of self-renewing (SR) or senescent (SEN) stem cells, to produce one or more beneficial factors for the treatment of a disease or disorder in an individual. Also provided are compositions and methods for inducing senescence, useful for inducing senescence in a population of stem cells, in order to produce one or more beneficial factors for the treatment of a disease or disorder in an individual. Methods and devices to customize the production of the beneficial factors for the requirements of the disease or disorder being treated are also described. Also provided are factor production units (FPUs) for the production of the beneficial factors, and delivery of the beneficial factors to individual in need.

In one aspect of the invention, provided herein is a method of treating a disease or disorder in an individual comprising delivering one or more factors produced by a population of stem cells to the individual or to a biological fluid from the individual. In one variation, the stem cells comprise mesenchymal stem cells (MSCs). In some variations, the stem cells comprise SR and SEN cells. In some particular variations, the population of stem cells comprises at least 50% SR cells, or comprises at least 50% SEN cells. In some variations, the stem cells have been induced to produce the factors upon exposure to an inducing agent. In a particular variation, the exposure of the population of cells to the inducing agent is for about 24 hours. In some variations, the inducing agent comprises IL-2. In some variations, the stem cells comprise at least 50% SR cells, whereas in other variations, the stem cells comprise at least 50% SEN cells. In some variations, the factors are secreted from the cells. As the invention also contemplates delivery, in some variations, the factors are delivered 24, 48 or 72 hours post-induction. In some variations, the delivery comprises use of a transdermal patch, a plasmapheresis system, a microneedle-based system, a cream, or a dermaroller. In some variations, the disease or disorder is cancer, an autoimmune disease, a cardiovascular disease, diabetes, a skin disease, a neurodegenerative disease, osteoporosis, osteoarthritis, a spinal cord injury, a disease of the liver, a disease of the kidney, an age-related pathology, hair loss, a burn, a condition in need of a skin graft, or a skin lesion. In some variations, the stem cells are adipose derived stem cells (ADSCs). In some variations, the stem cells are from a vesicular stromal fraction. In some variations, the factors are autologous to the individual, whereas in other variations, the factors are allogeneic to the individual. In some variations, the factors are produced in a factor production unit. In some variations, the factors comprise Interleukin 1 beta (IL1b), Interleukin 3 (IL3), Interleukin-13 Receptor subunit alpha-2 (IL13Rα2), Interleukin 1 receptor alpha (IL1Rα), Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, platelet-derived growth factor B beta (PDGF BB), Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), insulin-like growth factor-binding protein-4 (IGFBP4), Stem cell factor/c-kit ligand (SCF), Stromal Cell-Derived Factor-1 alpha (SDF1a), Stromal Cell-Derived Factor-1 beta (SDF1b), Angiotensin (ANG), colony stimulating factor 2 (CSF2), Transforming growth factor beta 1 (TGFb1), Transforming growth factor beta 3 (TGFb3), tumor necrosis factor superfamily member 14 (TNFSF14), Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), Chemokine (C-C motif)

ligand 11 (CCL11), Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), CXC Chemokine ligand 10 (CXCL10), Chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1). In some variations, the factors are delivered to a biological fluid from the individual. In some variations, the factors are delivered to plasma from the individual. In some variations, the delivery of the factors to the plasma induces production of regulatory T cells in the blood. In some variations, the delivery of the factors further comprises introducing the blood back into the individual.

In another aspect of the invention, provided herein is a method of producing one or more factors in a factor production unit comprising adding an inducing agent to a population of stem cells in the factor production unit to induce the production of factors, whereby producing the one or more factors. The factors can be isolated from the factor production unit. In one variation, the stem cells in the factor production unit comprise mesenchymal stem cells (MSCs). In another variation, the stem cells in the factor production unit comprise adipose derived stem cells (ADSCs). In another variation, the stem cells in the factor production unit are from a vesicular stromal fraction. The stem cells in the factor production unit can comprise SR and SEN cells. In one variation, the population of stem cells comprises at least 50% SR cells; in another variation, population of stem cells comprise at least 50% SEN cells. In some variations, the stem cells in the factor production unit have been induced to produce the factors upon exposure to an inducing agent. The inducing agent can be protein, a small molecule, or a gene-based inducing agent. In one variation, the inducing agent comprises IL-2. In some variations, the factors are secreted from the cells. In some variations, the factors are obtained, and can be obtained 24, 48 or 72 hours post-induction. In some variations, the population of stem cells is from a single individual; in other variations, the population of stem cells is from a plurality of individuals. In a particular variations, a collection of factors is produced and comprises Interleukin 1 beta (IL1b), Interleukin 3 (IL3), Interleukin-13 Receptor subunit alpha-2 (IL13Rα2), Interleukin 1 receptor alpha (IL1Rα), Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, platelet-derived growth factor B beta (PDGF BB), Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), insulin-like growth factor-binding protein-4 (IGFBP4), Stem cell factor/c-kit ligand (SCF), Stromal Cell-Derived Factor-1 alpha (SDF1a), Stromal Cell-Derived Factor-1 beta (SDF1b), Angiotensin (ANG), colony stimulating factor 2 (CSF2), Transforming growth factor beta 1 (TGFb1), Transforming growth factor beta 3 (TGFb3), tumor necrosis factor superfamily member 14 (TNFSF14), Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), Chemokine (C-C motif) ligand 11 (CCL11), Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), CXC Chemokine ligand 10 (CXCL10), Chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1). In several variations, the factors are useful for the treatment of cancer, an autoimmune disease, a cardiovascular disease, diabetes, a skin disease, a neurodegenerative disease, osteoporosis, osteoarthritis, a spinal cord injury, a disease of the liver, a disease of the kidney, an age-related pathology, hair loss, a burn, a condition in need of a skin graft, or a skin lesion. In a particular variation, the factors are useful for derma-cosmetic applications.

In another aspect of the invention, provided herein is a method of producing one or more factors suitable for derma-cosmetic applications comprising, incubating a population of stem cells with 10% PRP, whereby producing one or more factors suitable for derma-cosmetic applications.

In another aspect of the invention, provided herein is a method of increasing the number of regulatory T cells in a sample, the method comprising contacting a sample comprising T cells with a factor composition, wherein the factor composition comprises factors collected from SR-hADSCs 72 hours following incubation with IL-2. In some variations, the sample contacted with the factor composition is blood. In other variations, the sample contacted with the factor composition is plasma.

In another aspect of the invention, provided herein is a factor production unit comprising a substrate and a population of input stem cells. In some variations of the invention, the substrate is a 3-dimensional substrate. The substrate of the factor production unit can comprises a polymer material, for example in some variations the polymer material comprises a biodegradable polymer; whereas in other variations, the polymer material comprises a non-biodegradable polymer. In some variations, the polymer material comprises a polyethylene terephthalate, a polyester, a polymethylmethacrylate, polyacrylonitrile, a silicone, a polyurethane, a polycarbonate, a polyether ketone ketone, a polyether ether ketone, a polyether imide, a polyamide, a polystyrene, a polyether sulfone, a polysulfone, a polycaprolactone (PCL), a polylactic acid (PLA), a polyglycolic acid (PGA), a polyglycerol sebacic, a polydiol citrate, a polyhydroxy butyrate, a polyether amide, a polydiaxanone, fibronectin, collagen, gelatin, hyaluronic acid, chitosan, and combinations, blends, or copolymers thereof. In other variations, the substrate comprises a plurality of electrospun nanofibers or 3-D printed nanofibers. In a particular variation, the nanofibers are electrospun with the stem cells. In some variations, the plurality of electrospun fibers are configured as an artificial extracellular matrix. In some variations, the population of stem cells is disposed on a surface of the substrate, whereas in some variations, the population of stem cells is disposed within a polymer material of the substrate. In some variations, the stem cells SR and SEN stem cells, for example SR-MSCs and SEN-MSCs. In some variations, the population of stem cells comprise at least 50% SR cells—in some variations the SR cells are induced SR cells. In some variations, the population of stem cells comprises at least 50% SEN cells—in some variations the SEN cells are induced SEN cells. In some variations, the factor production unit is part of an aphereisis system. In a particular variation, the apheresis system is a plasmapheresis system. In some variations, the factors are produced from the factor production unit and the factors are used for modulation of immune cells. In some variations, the factors are produced and used to increase production of regulatory T cells. In some variations, the factors are produced and the factors are used for treatment of autoimmune diseases, cancer, diabetes, a skin disease, a neurodegenerative disease, osteoporosis, osteoarthritis, a disease of the liver, a disease of the kidney, an age-related pathology, a condition in need of a skin graft, or a skin lesion.

In another aspect of the invention, provided herein are particular factor compositions for use in the treatment of various diseases and disorders. In one variation, a factor composition of the invention comprises factors collected from SR-hADSCs 72 hours following incubation with IL-2. In another variation, a factor composition of the invention comprises Interleukin 1 beta (IL1b), Interleukin 3 (IL3), Interleukin-13 Receptor subunit alpha-2 (IL13Rα2), Interleukin 1 receptor alpha (IL1Rα), Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, platelet-derived growth factor B beta (PDGF BB), Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), insulin-like growth factor-binding protein-4 (IGFBP4), Stem cell factor/c-kit ligand (SCF), Stromal Cell-Derived Factor-1 alpha (SDF1a), Stromal Cell-Derived Factor-1 beta (SDF1b), Angiotensin (ANG), colony stimulating factor 2 (CSF2), Transforming growth factor beta 1 (TGFb1), Transforming growth factor beta 3 (TGFb3), tumor necrosis factor superfamily member 14 (TNFSF14), Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), Chemokine (C-C motif) ligand 11 (CCL11), Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), CXC Chemokine ligand 10 (CXCL10), Chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1). In some variations, the factor compositions of the invention can be further formulated in the form of a cream or lotion. In other variations, a factor composition of the invention is further formulated on a patch comprising microneedles. In other variations, the factor compositions of the invention are further formulated to be combined with a dermaroller-based delivery system. In another aspect of the invention, provided herein are kits comprising any one of the factor compositions of the invention.

In another aspect of the invention, provided herein is a method of inducing senescence in a SR-stem cell, for example for the purpose of inducing a certain group of factors, the method comprising transfecting into the cell one or microRNAs (miRNAs) selected from the group consisting of miR-17-5p, miR-18a-5p, miR-20a-5p, mir-92a1-5p, mir-19a-3p, mir-125b1-5p, mir100-5p, and mir-let7a-2-3p. In one variation, the SR-stem cell is a SR-hADSC.

It is to be understood that one, some, or all of the properties of the various variations described herein may be combined to form other variations of the present invention. These and other aspects of the invention will become apparent to one of skill in the art.

BRIEF DESCRIPTION OF THE DRAWINGS

FIGS. 2A and 2B show exemplary methods for producing factors and factor compositions, and practicing an aspect of the invention as described herein.

FIG. 2C illustrates one exemplary method for practicing an aspect of the invention as described herein, for exemplary use of the factors for immunomodulation to influence regulatory T-cell (Treg) production.

FIGS. 3A-3D illustrate how replicative senescence (SEN) impairs the migratory properties of the human adipose derived mesenchymal stem cells (hADSCs, also referred to herein interchangeably hADSCs). FIG. 3A shows a growth curve of hADSCs and is represented as cumulative population doubling over day in culture. FIG. 3B shows detection of senescence-associated β-galactosidase. FIG. 3C shows ex vivo migration assays for SR (left) and SEN (right) hADSCs. FIG. 3D shows the migration of SR-hADSCs (left) and SEN-hADSCs (right).

FIGS. 4A-4C illustrate the gene expression of IL-2 receptor isoforms and their association with membrane in SR-hADSCs and SEN-hADSCs induced with IL-2. FIG. 4A shows a schematic representation of IL-2 receptor composition. FIG. 4B shows IL-2 receptors α, β, and γ assessed by quantitative PCR (qPCR) SR and SEN-hADSC, either, in the presence or absence of IL-2. FIG. 4C shows the cellular membrane-associated protein levels of IL-2Rα and IL-2Rβ.

FIG. 5 illustrates the effect of stimulation of the SR and SEN-hADSCs with IL-2. STAT5A, STAT5B and VEGFA mRNA expression was assessed by quantitative RT-PCR.

FIGS. 6A-6D show a comparison of gene expression levels between SR and SEN cells upon IL-2 treatment.

FIG. 8A provides a schematic representation of the RNA-seq analysis design. FIG. 8B shows the distributions of the gene-specific RNA-seq read counts for each condition prior to ACTB normalization. FIG. 8C shows the condition-specific RNA-seq read counts for ACTB that were used for normalization. FIG. 8D shows distributions of the gene specific RNA-seq read counts for each condition after ACTB normalization.

FIGS. 10A-10B represent tables of the genes differentially expressed upon IL-2 treatment in SEN-hADSCs (senescent hADSCs) and SR-hADSCs (self-renewing hADSCs). FIG. 10A shows biological pathways enriched for genes up-regulated upon IL-2 treatment in SR and SENhADSCs. FIG. 10B shows biological pathways enriched for genes down-regulated upon IL-2 treatment in SR and SEN-hADSCs.

FIGS. 91-96 illustrate the presence of the particular named factors basally present in the 10% platelet rich plasma (PRP) used as culturing media for hADCSs.

FIG. 106A shows the factor production unit comprising a cartridge formed by a plurality of hollow polymeric fibers (tubes). FIG. 106B provides a cross-sectional view of one of the hollow polymeric tubes in FIG. 106A showing stem cells entrapped within the fiber walls.

FIG. 108 illustrates that senescence associated-miRNAs (SA-miRNAs) function to establish the hADSC senescent phenotype.

DETAILED DESCRIPTION OF THE INVENTION

Figure 1A:
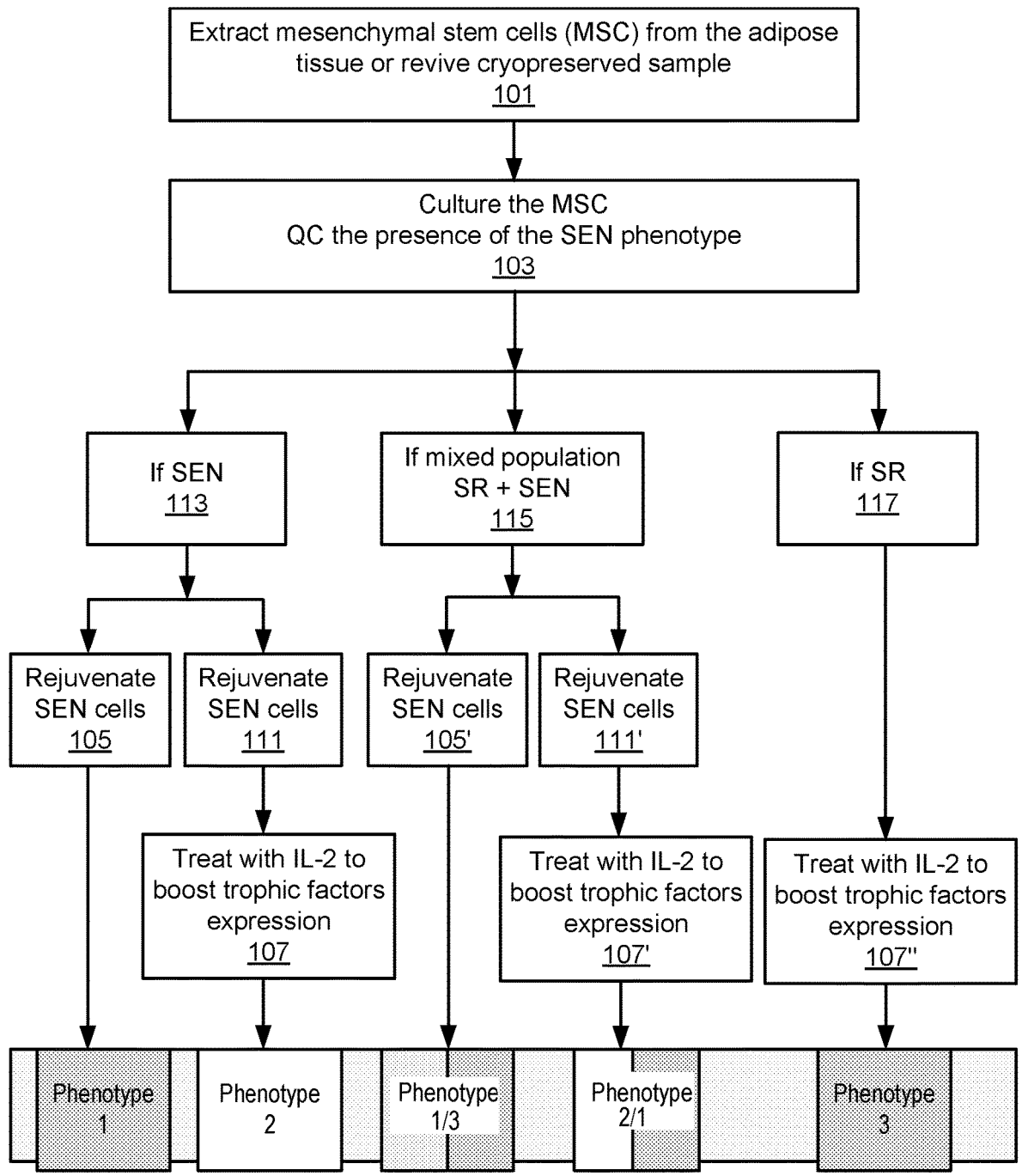
FIG. 1A illustrates an exemplary method for practicing an aspect of the invention described herein.

Described herein are methods and compositions related to inducing a population of stem cells (SCs), for example mesenchymal stem cells (MSCs), to produce one or more beneficial factors for the treatment of a disease or disorder in an individual, where such production is customized for the requirements of the disease or disorder being treated. Also provided are compositions and methods for inducing senescence, useful for inducing senescence in a population of stem cells, in order to produce one or more beneficial factors for the treatment of a disease or disorder in an individual. Also provided is a factor production unit for the production of the beneficial factors along with methods of making and using thereof.

I. Production of Factors

A. Background and Overall System

The invention described herein provides compositions, apparatuses, and methods for: the production of one or more beneficial factors by induced stem cells, and for the delivery and administration of such factors to an individual in need. The production system is customizable, tailored to produce factors beneficial for the particular clinical need. The factors can be produced using an individual's own cells (an autologous system) or using cells from another individual (an allogeneic system). Delivery can entail acute or chronic administration paradigms, and virtually any delivery system can be utilized.

Beneficial factors as provided herein can be polypeptides (full length proteins and peptides) and include wound healing factors, apoptotic factors, anti-apoptotic factors, anti-inflammatory factors, immunomodulatory factors, angiogenic factors, chemokines factors, cytokines factors, interleukins, interleukin receptors, growth factors, growth factor receptors, hormones, adhesion promoting factors, proliferation inducing factors, signal-transduction stimulators and their receptors, neurotrophic factors, regenerative factors, and repair triggering factors. Beneficial factors are not limited to proteins, however, and also include small molecules and metabolites.

B. Input Cells

As provided herein, populations of mammalian cells comprising stem cells are induced to produce one or more desired beneficial factors. The cell populations used for production (i.e. the input cells) need not be comprised purely of stem cells. One or more cell types can be included in the input cell populations as long as the input cells comprise a suitable type of stem cell that can be induced or generically modified to secrete a factor. Exemplary stem cells include without limitation, embryonic stem (ES) cells, adult stem cells, induced pluripotent stem cells (iPSCs), and SEN cells induced to be SR using a variety of methods. More particularly the adult stem cells include without limitation hematopoietic stem cells (HSCs) and mesenchymal stem cells (MSCs). Other types of cells that may be employed are stromal vesicular fraction, plasma cells, cord blood cells, placental cells, bone marrow derived cells, epithelial cells, endothelial cells, immune cells, fibroblasts, chondrocytes, hepatocytes, antigen presenting cells, mast cells, muscular cells, antibody producing cells, neurons, and glial cells.

In one exemplary variation, MSCs are induced for the production of one or more beneficial factors. The use of MSCs in the cell population may be beneficial. MSCs are a subset of non-hematopoietic adult stem cells that originate from the mesoderm and typically possess self-renewal ability and multilineage differentiation into not only mesoderm lineages, such as chondrocytes, osteocytes, adipocytes, and muscle cells, but also ectodermic cells and endodermic cells. MSCs exist in almost all tissues.

MSCs may be derived from any suitable tissue. In one variation, the MSCs are derived from adipose tissue (ADSCs), and in particular, the stromal vascular fraction (SVF) obtained from digested or mechanically separated adipose tissue. As used herein, the term "adipose" refers to any fat tissue and the adipose tissue may be from any organism having fat tissue. The adipose tissue may be brown or white adipose tissue, derived from subcutaneous, omental/visceral, mammary, gonadal, or other adipose tissue sites in a mammal. In certain variations, the adipose is subcutaneous white adipose tissue, visceral adipose tissue, or a lipoaspirate sample. A convenient source of adipose tissue is from liposuction surgery, however, the source of adipose tissue need not be so limited. The adipose tissue may be digested with any suitable enzyme (e.g. collagenase) to yield MSCs or may be mechanically separated. In some variations, the MSCs human are adipose derived MSCs (hADMCs or hADSCs or hADMSCs). In other variations, the MSCs are from non-human mammalian adipose tissue.

The input cells may be autologous (cells from the individual who receives the factors) or allogeneic (cells not from the individual who receives the factors). The input cells may comprise cells from a single individual, or alternatively comprise a mixture of cells from more than one individual. The cells may be purely ADSCs, or may be a heterogeneous mix of cells. It is understood that a skilled artisan will have the ability to customize the input cells in order to control the subsequent factor production.

In some variations, the input cell comprise stem cells, wherein the stem cells are at least 20%, 30%, 40%, 50%, 60%, 70%, 80%, or even 90% SR stem cells (e.g. SR-ADSCs, or SR-hADSCs). In an exemplary variation the input cells are MSCs and comprise at least 50% SR MSCs. The SR stem cells can be defined in regards their morphology, proliferation index and one or many markers.

In some variations, the input cell comprise stem cells, wherein the stem cells are at least 20%, 30%, 40%, 50%, 60%, 70%, 80%, or even 90% SEN stem cells (e.g. SEN-ADSCs, or SEN-hADSCs). In an exemplary variation the input cells are MSCs and comprise at least 50% SEN MSCs. The SEN stem cells can be defined in regards their morphology, proliferation index and one or many markers.

1. Induction of Senescence

In some variations, to achieve the production of a particular set of desired factors, it is desirable to utilize stem cells that are senescent or are nearing senescence (collectively referred to as SEN). As used herein SEN stem cells are those cells that are replicatively senescent. Replicative senescence is characterized by growth arrest, apoptosis resistance, high levels of metabolic activities, morphological and cell-size changes, high levels of expression of the tumor suppressors P16, P21, P53 and/or RB, increased activity of senescence associated beta galactosidase (SA-β-gal) and the loss of the ability to synthesize and repair DNA. The replicative aging of stem cells can influence their biological properties.

In particular variations, the stem cells are SEN-ADSCs, for example SEN-hADSCs. Stem cells may be naturally SEN or they may be induced to undergo senescence. When referring to SEN cells throughout, it is to be understood that this term encompasses both naturally occurring SEN stem cells as well as those stem cells induced to be SEN. Exemplary methods to induce stem cells to undergo senescence include, but are not limited to, delivery of noncoding miRNAs (described below), delivery of senescence-inducers such as those described in WO2013/078392, including, but not limited to exposure to a genotoxin, radiation, ultraviolet light, a tumor suppressor inducer, a mitotic inhibitor, a nucleic acid damaging agent, an antitumor antibiotic, a topoisomerase inhibitor, a hormone inhibitor, a growth factor inhibitor, or a PARP inhibitor.

In one variation, a method of inducing senescence comprises transfection of senescence-associated miRNA mimics into a population of SR cells or a population of stem cells comprising at least some SR cells in need of induction to achieve a SEN state. In this variation, SR-ADSCs are transfected with a miRNA selected from miR-17-5p, miR-18a-5p, miR-20a-5p, mir-92a1-5p, mir-19a-3p, mir-125b1-5p, mir100-5p, and mir-let7a-2-3p, as described in Example 10 and FIGS. 108-112.

2. Induction of Stemness (Rejuvenation)

In other variations, to achieve the production of a particular set of desired factors, it is desirable to utilize stem cells that are SR and exhibit a high degree of stemness. In particular variations, the stem cells are SR-ADSCs, for example SR-hADSCs. The stem cells can be naturally SR, or they may rejuvenated to be SR. When referring to SR cells throughout, it is to be understood that this term encompasses both naturally occurring SR stem cells as well as those stem cells induced to be SR. Exemplary methods to induce stem cells to undergo rejuvenation include, but are not limited to those described in WO2012058097 and WO2013126565 (reducing the level or activity of SINE/ALU retrotransposon transcripts in a population of stem cells).

In one variation, an exemplary method comprises isolation of a sample comprising stem cells. The sample is assayed to determine if it is SEN or SR, by looking at particular characteristics as described above. If SEN, cells may be rejuvenated to be SR as provided above. The factors released by rejuvenated SEN stem cells may be the same or different from SR stem cells.

In one variation, rejuvenating a SEN stem cell involves reducing the level or activity of SINE/ALU retrotransposon. Reduction may include introducing into said cell any construct that comprises or encodes a small interfering RNA (siRNA or shRNA) molecule that targets SINE/ALU retrotransposon transcripts. For example, a small interfering RNA can comprise a molecule selected from the group consisting of a single strand RNA, a paired double strand RNA (dsRNA), a small hairpin RNA (shRNA), and a PIWI RNA (piRNA). The construct may produce a stable down-regulation of SINE/ALU transcripts, or in some variations a temporary down-regulation. For example, the construct may comprise a vector, such as a plasmid vector or a viral vector. For example, a viral vector may be selected from the group consisting of a retroviral vector, a lentiviral vector, an adenoviral vector, and an adeno-associated vector.

Any appropriate mechanism for introducing the construct may be used, for example, transformation, transduction, transfection, or infection. In some variations, the method may include via a lipid or liposome. In addition, the delivery of the Synthetic piRNA that targets SINE/ALU retrotransposons can be accomplished by use of any type of biolistic device that provides a physical method of transfecting cells with DNA and is not dependent on specific ligand-receptors or any biochemical features (see, e.g., US20040033589).

In one variation, rejuvenation may be achieved by those methods described in Wang et al. (Nature. 2014 Dec. 18; 516(7531):405-9), with delivery of HERVH to drive HERVH-based transcription; or to drive LBP9 transcription factor-driven rejuvenation of adult stem cells.

In some variations, the step of reducing the level or activity of SINE/ALU retrotransposon transcripts in a population of input stem cells in an amount sufficient to induce or restore proliferative capacity is performed only in cells first identified as SEN. For example, cells (fresh or cryo-preserved) may be screened by quality control (QC) techniques as described herein to identify SEN cells, and these cells may be targeted for rejuvenation. Thus, any of the methods described herein may include a QC step to identify the senescent state of the cells prior to rejuvenation and/or induction. Alternatively, in some variations all of the cells in a mixed population of SEN and SR stem cells may be treated for rejuvenation using any of the methods described herein for rejuvenation. Once rejuvenated, the factors of a population of just formerly SEN rejuvenated cells, or a mixed population of SR/rejuvenated SEN may be used directly from these cells (e.g., without induction). Alternatively or additionally a population of rejuvenated SEN cells, a mixed population of rejuvenated SEN and SR cells, or a population of just SR cells may be induced to produce factors, and their resulting factors used as described herein. In some variations, factors (and/or the cells themselves) from induced and non-induced populations may be combined, or used separately. In some variations, extracts from induced or non-induced populations are administered. This is schematically described in FIG. 1A.

The use of rejuvenated stem cells may be particularly important in situations where cryopreserved or other storage methods are used. Prolonged passage or revival of the stem cells from cryopreservation generally reduces the capacity of stem cells to divide, when compared to freshly isolated stem cells, which may be in a SR state.

C. Induction of Stem Cells and the Production of Factors

As provided herein, the production of factors from SEN and SR stem cells is customizable for the treatment of a broad range of diseases and disorders. In response to inducing agents, under particularized sets of conditions, stem cells can be induced to produce or secrete particular combinations of factors. Contributing to the particular combinations of factors produced include which type of stem cells are induced, characterization of the stem cell population as SR or SEN, the inducing agent selected for use, the duration of induction, and the time interval post-induction.

In variations provided herein, collections of factors can be characterized generally to be, for example, collections of a plurality of factors, where one or more of the factors are wound healing factors, apoptotic factors, anti-apoptotic factors, anti-inflammatory factors, immunomodulatory factors, angiogenic factors, chemokines factors, cytokines factors, interleukins, interleukin receptors, growth factors, growth factor receptors, hormones, adhesion promoting factors, proliferation inducing factors, signal-transduction stimulators and their receptors, neurotrophic factors, regenerative factors, and repair triggering factors.

1. Inducing Agents and Conditions

The stem cells of the invention are placed in contact with (e.g. combined with) an inducing agent of the invention. As used herein, an inducing agent can be any molecule or genetic modification capable of interacting with or influencing a stem cell (e.g. bind a receptor, specifically or non-specifically; induce transcription and translation), produce inducing factors by integrating into the genome of stem cells or express them ectopically, influencing or inducing a stem cell's gene expression, influencing a stem cell's signal transduction, and/or influencing a stem cell's transcriptional, translational, or post-translational machinery to induce the production and secretion of one or more factors.

Non-limiting examples of inducing agents include small molecules, proteins, peptides, antibodies, oligonucleotides, aptamers, factors encoded by a nucleic acid molecule, as well as RNAi, miRNA, or long ncRNA.

Representative examples of virus vectors used for gene introduction include an adenovirus vector, an adeno-associated virus vector, and a retrovirus vector. A target gene may be introduced into a cell by introducing a target gene into a DNA or RNA virus, such as a detoxicated retrovirus, herpes virus, vaccinia virus, poxvirus, poliovirus, Sindbis virus, Sendai virus, SV40, or human immunodeficiency virus (HIV), and infecting the cell with such recombinant virus, or with the use of CRISPR technology.

In one variation, the inducing agent comprises a cytokine, for example IL-2, retinoid acid and its derivatives, chemotactic factors, chemokines, hormones, growth factors, leukotrienes, prostaglandins, thromboxanes and platelet activating factor (PAF), and mediators secreted by cells exemplified but not limited to Mast cell secreted mediators.

In one exemplary variation, the inducing agent is IL-2, or an isoform of IL-2.

Induction factors may be combined with the cells in any type of media, or delivered by the means of genetic engineering (e.g. if the inducing factor is encoded by a nucleic acid molecule), as well as delivered as RNAi, miRNA, long ncRNA.

The media comprising the factors produced/secreted upon induction may be referred to herein as "conditioned media."

In one exemplary variation, the cells are cultured in a media comprising platelet rich plasma (PRP, for example 10% PRP) and the inducing agent is mixed with the media.

In another variation the cell are cultured in plasma, serum, umbilical cord blood serum, and platelet derivatives like platelet lysate. In one variation, the SVF is cultured using human platelet lysate. In other variations, platelet-rich plasma is included in the SVF culture medium In another exemplary variation, when a stromal vesicular fraction is used for factor production, fetal bovine serum (FBS) and fibroblast growth factor (FGF)-2 are substances that can be used in the culture medium.

In another variation, the cells are cultured in a serum free media. The serum free media may comprise components such as the elements provided in standard serum-free media formulations, including an energy source such as glucose, inorganic salts, fat soluble components, a nitrogen source and vitamins or lipid compositions.

In general, inducing the stem cells include exposing the stem cells to the inducing agent (interchangeably referred to herein throughout as exposing the stem cells to an inducing agent/priming with an inducing agent/contacting with an inducing agent/inducing with an inducing agent/incubating with an inducing agent/stimulating with an inducing agent), for a predetermined amount of time, such as longer than 5 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 30 hours, 36 hours, 42 hours, 48 hours, 3 days, 4 days, or even longer than 5 days. The cells may be exposed to a constant level of the inducing agent or to a varying level (e.g., initial higher, then followed with lower-levels, increasing levels over the time of exposure, decreasing levels over the time of exposure, random levels over the time of exposure, etc.). Following exposure, the cells may be washed or otherwise treated to remove the inducing agent, prior to using the factors produced by the cells. Varying incubation times influence the production of the factors and thus can be varied in order to customize the production for a particular downstream clinical application. In some variations, factors are collected immediately after the removal of the inducing agent; in some variations, the factors are collected/removed/delivered/used 5 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 30 hours, 36 hours, 42 hours, 48 hours, 3 days, 4 days, or even longer than 5 days after removal of the induction agent. In some exemplary variations, the factors are collected/removed/delivered/used 24, 48, or 72 hours following removal of the inducing agent. In other exemplary variations, the cells are combined with the induction agent for a prescribed period of time as above, the induction agent is removed (e.g. media is replaced) and the cells are allowed to recover for a predetermined time period post-induction ranging from one (1) hour, six (6) hours, 12 hours, 24 hours, 36 hours, 48 hours, 60 hours, or 72 hours, or any combination of these time periods post-induction.

2. Induction of Factor Production

The induction and production can be tailored to produce specific factors. This may be achieved in various ways, e.g., by selecting a certain cell population, by adjusting the composition of the cell culturing media, or by selecting a particular induction agent. As provided herein, and described below, the production of factors take place in any one of the factor production units provided herein. A factor production unit comprises a population of input stem cells and a substrate that provides support for the cell population.

The duration of culturing (e.g., post induction) may be adjusted or controlled to customize factor production by the factor production unit. Factors can be collected at predetermined times ranging from 5 minutes to 5 days post induction, and is described above.

Factors which may beneficial in the methods described herein include without limitation, interleukins that are involved in skin regeneration/rejuvenation pathways, interleukin receptors and binding proteins, growth factors, growth factor receptors, chemokines, cytokines, chemotactic factors, molecules that provide cell adhesion, factors that may promote cell proliferation, neurotrophic factors, factors that may promote skin regeneration, factors that may promote or suppress wound healing, factors that may promote hyaluronic acid synthesis, factors that may promote skin elasticity, factors that suppress malignancy formation, factors related to inhibition of UV-induced skin damage and pigmentation, and factors that stimulate hair growth, factors that stimulate metabolism, endocrine functions and improve insulin sensitivity, factors that promote nitric oxide production, anti-apoptotic factors, pro-apoptotic factors, anti-necrotic, anti-inflammatory factors and factors useful to suppress asthma and allergic reactions, immunomodulatory, angiogenic, immunomodulators, signal transduction ligands and receptors, neurotrophic factors suppressing brain inflammation, brain trauma and neuromuscular disease aspects, factors suppressing abnormalities in neurocrest development, factors potentiating reversal of degeneration of spinal cord motor neurons axons, and stimulating neurogenesis and neuronal survival, factors promoting restoration of extacellular matrix (ECM) by production of collagen, elastin and hyaluronan, bactericidal, anti-microbial, anti-fungal activities, and factors promoting cell survival, tissue repair, regeneration and cell differentiation.

Figure 11:
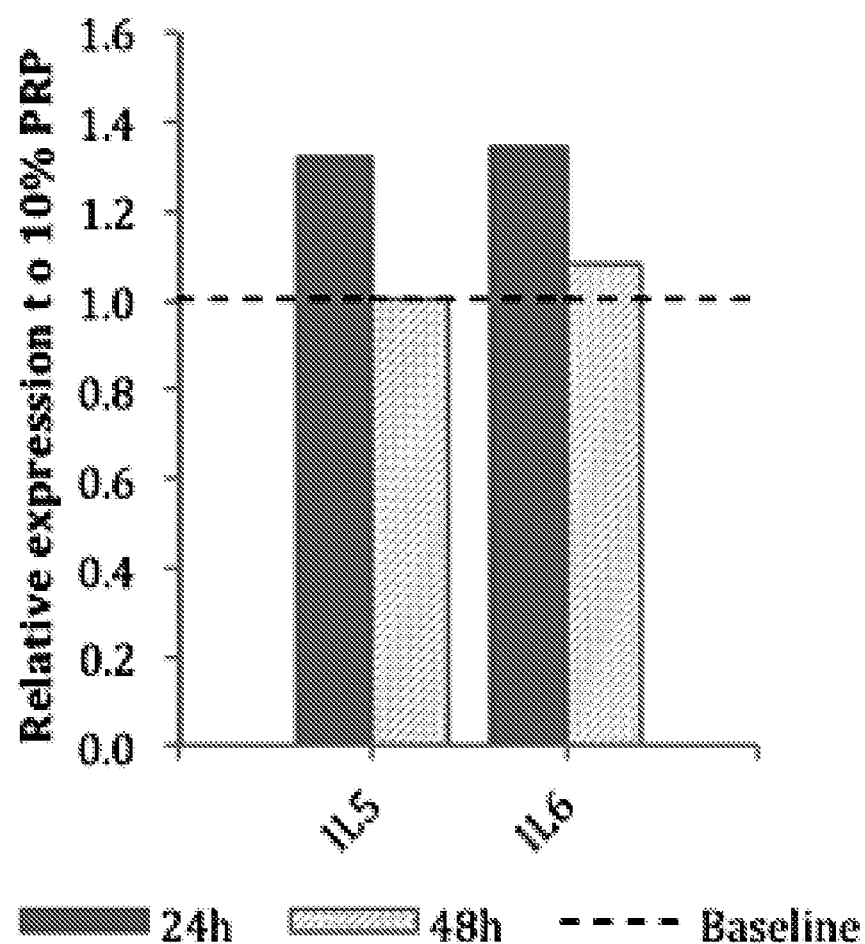
FIGS. 11-90 illustrate the increase in secretion of the named proteins (factors) from SR-hADSCs or SEN-hADSCs maintained in a factor production unit, following incubation media alone (no IL-2 stimulation) or following stimulation with IL-2.

FIGS. 11-17 show the increase in secretion of the below named proteins (factors) from SR-hADSCs maintained in a factor production unit of the invention, 24 hours post incubation with media containing 10% PRP (platelet-rich plasma) alone (no IL-2 stimulation). Secretion levels are shown relative to the amount of the corresponding protein present at basal levels in the 10% PRP containing media, used for hADSC support. The factors produced from the factor production unit are beneficial and can provide therapeutic benefits for: stimulation of immunoresponse in burns and diseases leading to inflammation upon tissue damage, such as wound healing, Inflammatory Bowel Disease (IBD) such as Crohn's disease (CD) and ulcerative colitis, Rheumatoid arthritis (RA), Sjogren's syndrome, polymyositis, dermatomyositis and scleroderma, derma-cosmetic applications related to aged and photo-damaged skin, and for treatments required antimicrobial protein with bactericidal and antifungal activity, FIG. 11 shows the increase in secretion of Interleukin 5 (IL5) and Interleukin 6 (IL6). Controlled production and delivery of IL-6 may be desirable for delivery for anti-inflammatory conditions, osteoporosis, and for improvement of sleep-associate conditions. Controlled production and delivery of IL-5 may be desirable for enhancing immunity, such as increase in production of Th1 cells, macrophages, IFN-gamma, and dendritic cells.

Figure 12:
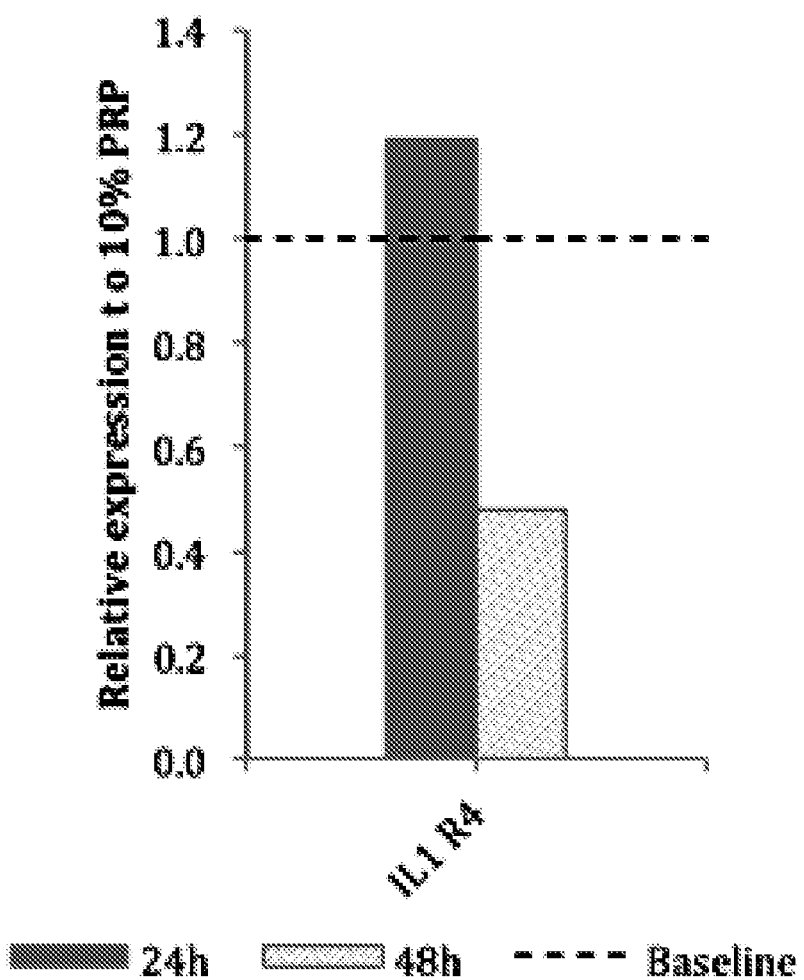
Figure 13:
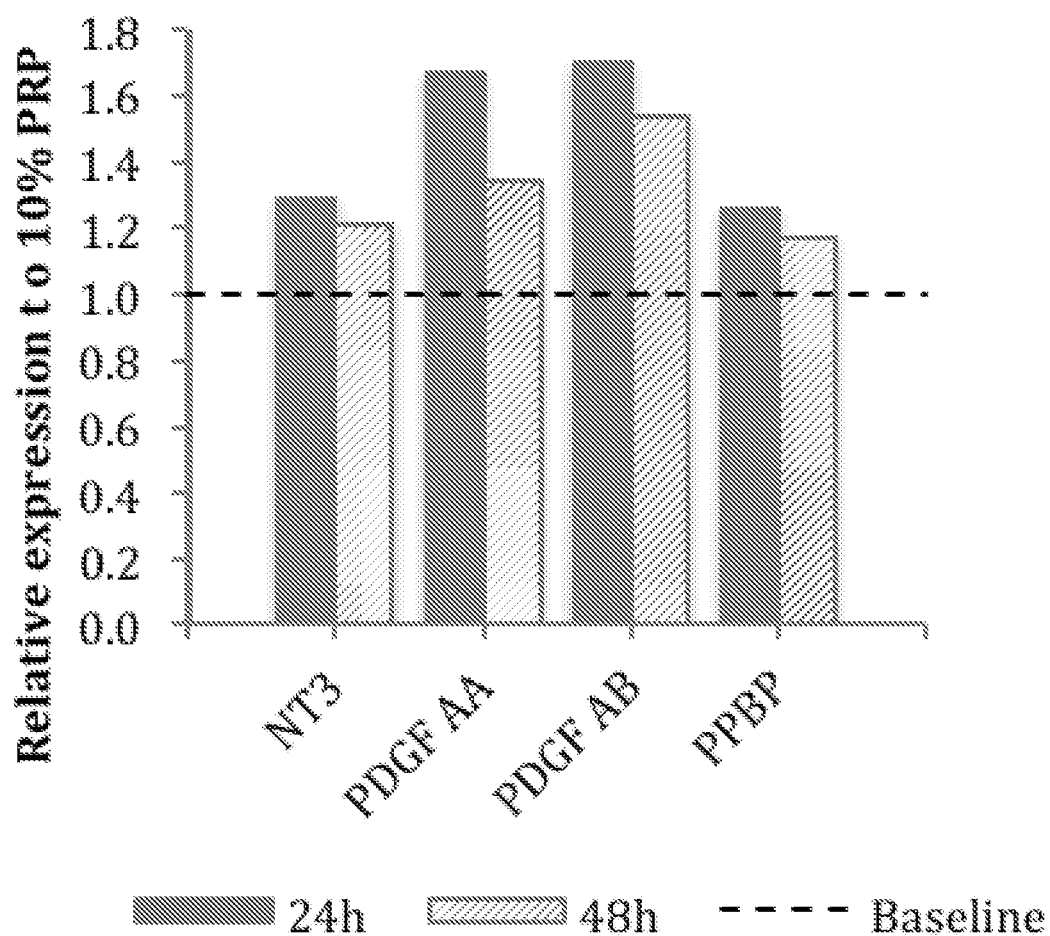
Figure 14:
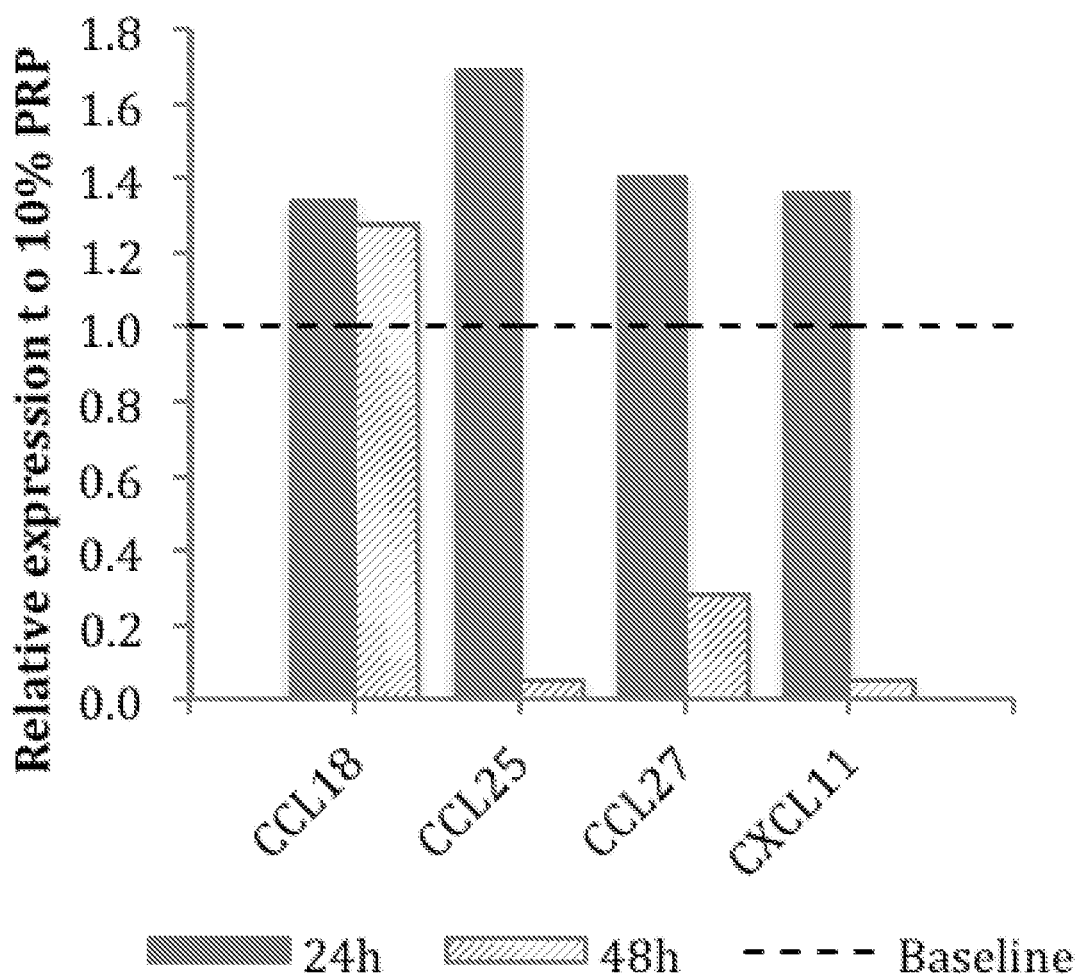
Figure 15:
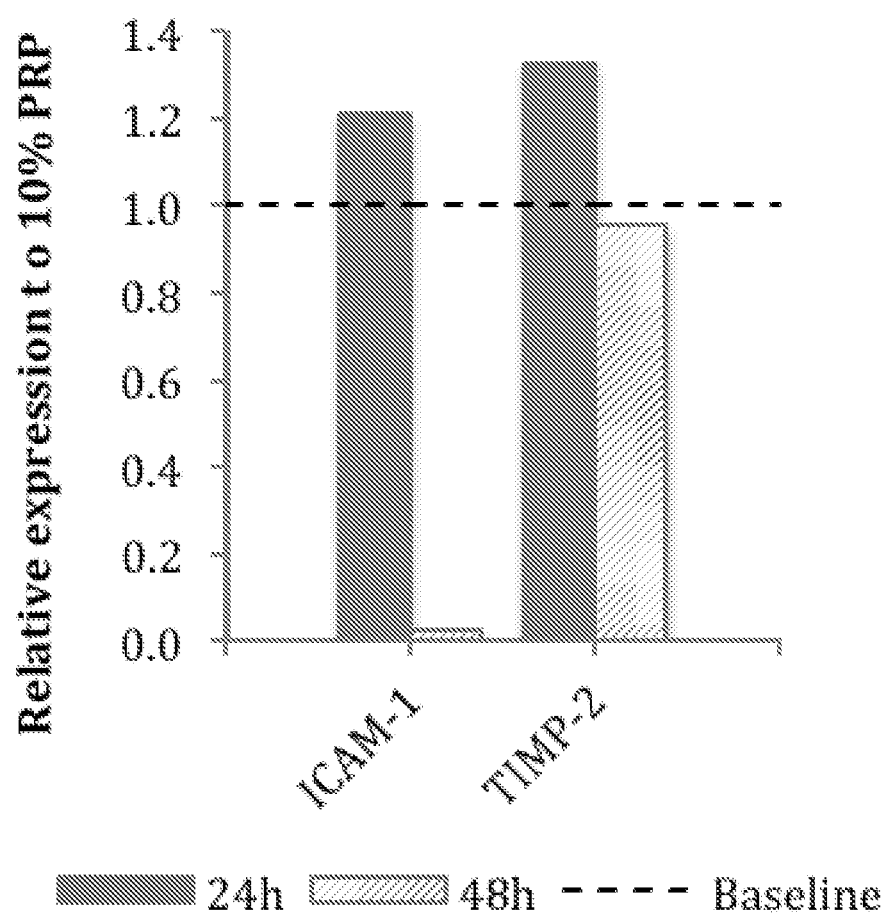
Figure 16:
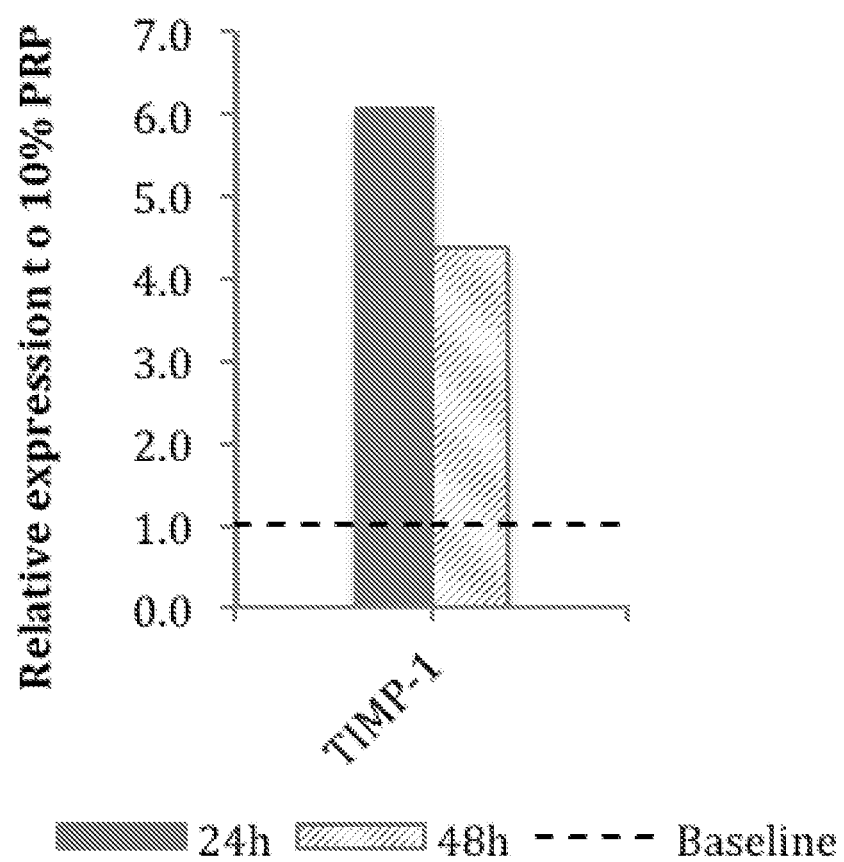
Figure 17:
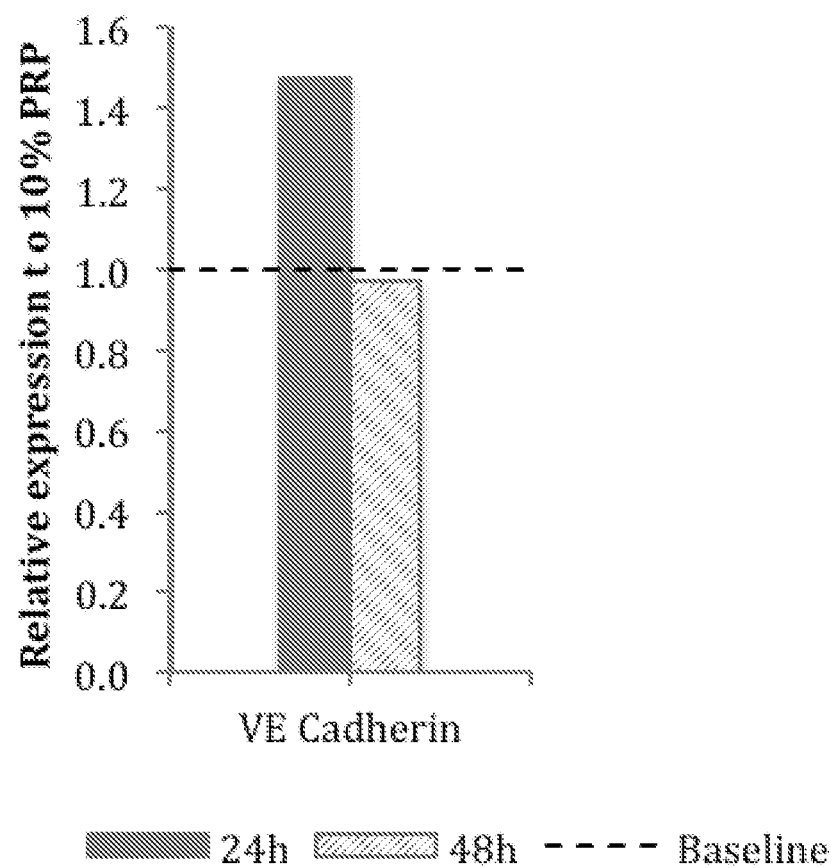

FIG. 12 shows the increase in secretion of Interleukin 1 receptor 4 (IL1R4). FIG. 13 shows the increase in secretion of Neurotrophin 3 (NT3), platelet derived growth factor A alpha (PDGF AA), platelet derived growth factor A beta (PDGF AB), and pro-platelet basic protein (PPBP). FIG. 14 shows the increase in secretion of Chemokine (C-C motif) ligand 18 (CCL18), Chemokine (C-Cmotif) ligand 25 (CCL25), Chemokine (C-C motif) ligand 27 (CCL27), and CXC chemokine ligand 11 (CXCL11). FIG. 15 shows the increase in secretion of Intercellular Adhesion Molecule 1 (ICAM-1) and Metalloproteinase inhibitor 2 (TIMP-2). FIG. 16 shows the increase in secretion of Metalloproteinase inhibitor 1 (TIMP-1). FIG. 17 shows the increase in secretion of vascular epithelium (VE) Cadherin (calcium dependent cell adhesion protein).

Figure 18:
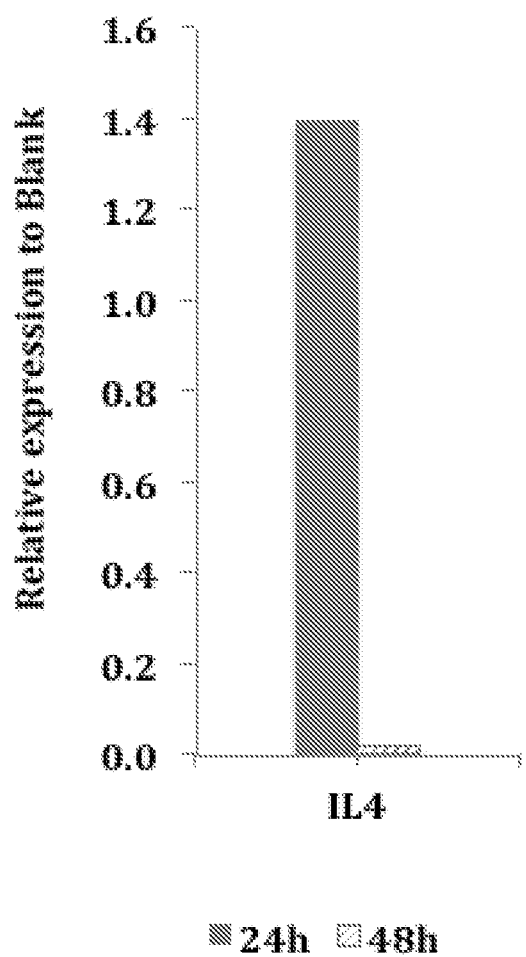
Figure 19:
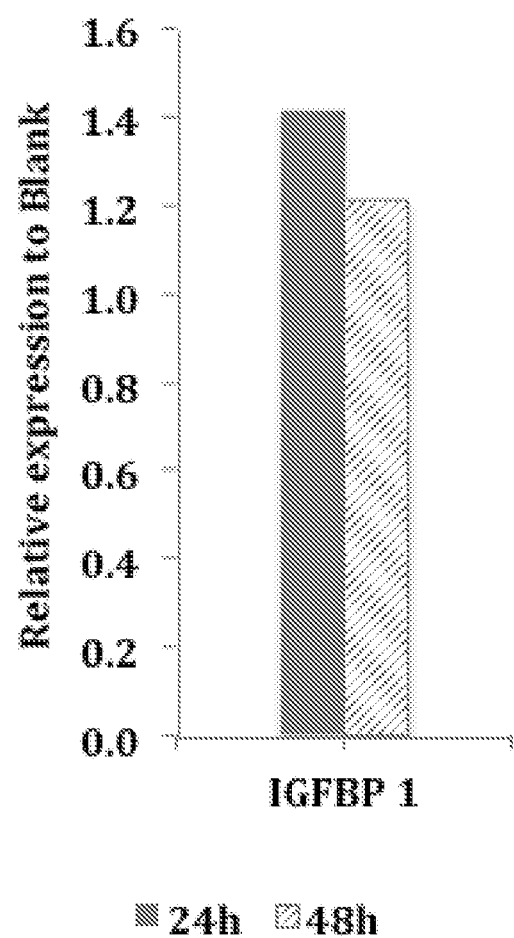

FIGS. 18-19 show the increase in secretion of the below named proteins (factors) from SR-hADSCs, 24 hours post incubation with 10% PRP alone (no IL-2 stimulation). These proteins were found to not be present in PRP. FIG. 18 shows the increase in secretion of Interleukin 4 (ILA). FIG. 19 shows the increase in secretion of insulin-like growth factor-binding protein-1 (IGFBP1).

The factors produced by this factor production unit (FIGS. 18-19) can provide therapeutic benefits for stimulation of activated B-cell and T-cell proliferation, and the differentiation of B cells into plasma cells. IL-4 induces B-cell class switching to IgE, and upregulates MHC class II production. IL-4 decreases the production of Th1 cells, macrophages, IFN-gamma, and dendritic cell. The presence of IL-4 in extravascular tissues promotes alternative activation of macrophages into M2 cells and inhibits classical activation of macrophages into M1 cells. IGFBP1 and 2 and their proteolytic fragments have been shown to improve tissue repair under inflammatory conditions, through effects on proliferation and migration of human gingival fibroblasts.

FIGS. 20-31 show an increase in the below named proteins (factors) from SR-hADSCs maintained in a factor production unit of the invention, 48 hours post incubation with 10% PRP alone (no IL-2 stimulation). Secretion levels are shown relative to the amount of the corresponding protein present at basal levels in the 10% PRP containing media, used for hADSC support.

The factors produced from the factor production unit under these conditions may provide therapeutic benefits for: hair growth and morphogenesis, cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, ulceration, a pathological condition characterized by initial injury inducing inflammation and immune dysregulation leading to chronic tissue remodeling including fibrosis and loss of function, skin defense against infection, new synthesis of collagen, elastin and hyaluronan, inhibition of melanoma growth, diabetic ulcers, myocardial infraction, atherosclerosis, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, and chronic inflammation resulting from chronic viral or bacterial infections, chronic liver fibrosis, cirrhosis, fulminant hepatic failure, allergic airway inflammation, acute lung injuries, myocardial infarction, fetal maternal tolerance, osteoarthritis, GVHD, treatment of neurodegenerative pathologies, such as for example Parkinson's disease, Alzheimer's disease, progressive supranuclear palsy, multiple system atrophy, amyotrophic lateral sclerosis, Huntington's chorea or following trauma such as stroke and cerebral or spinal traumas.

Figure 20:
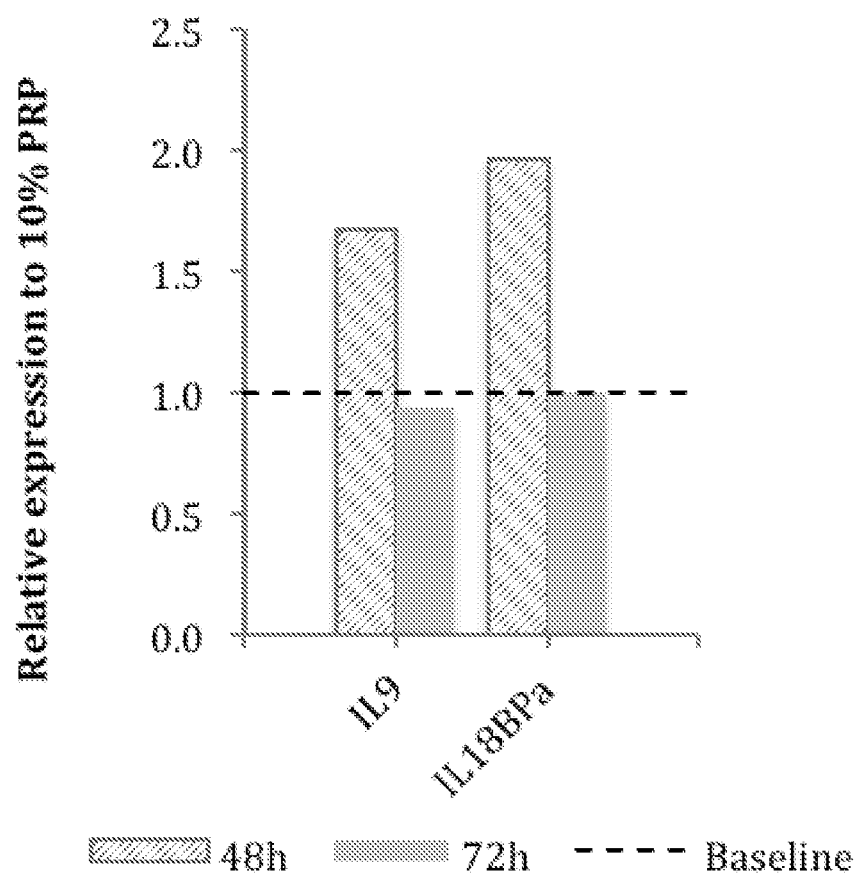
Figure 21:
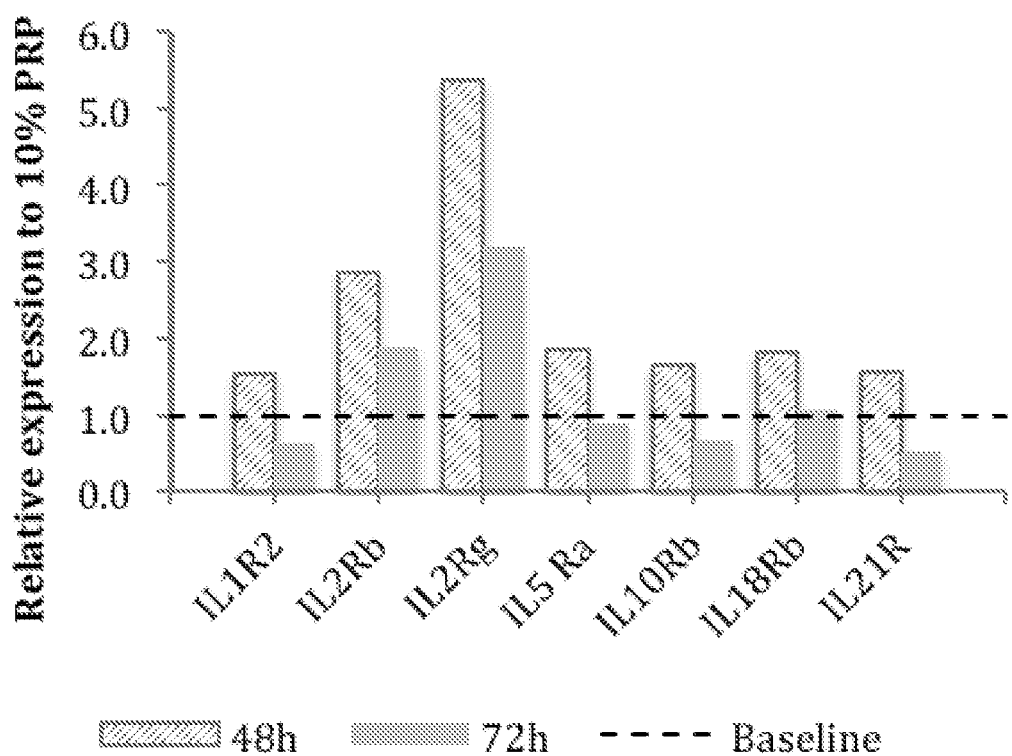
Figure 22:
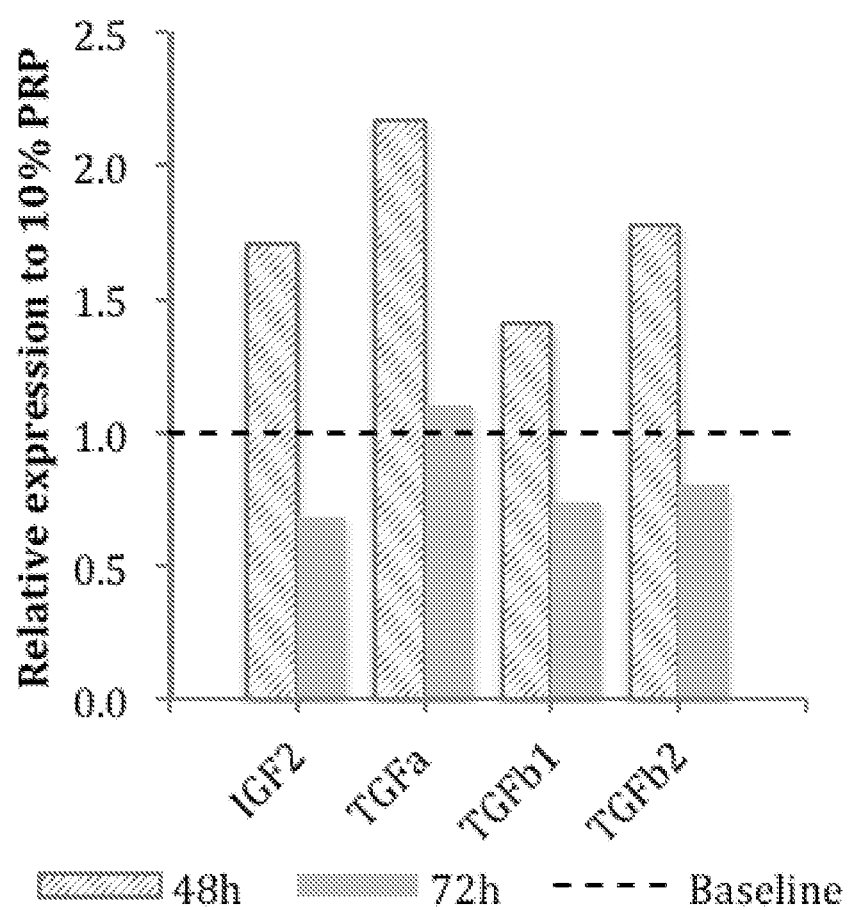
Figure 23:
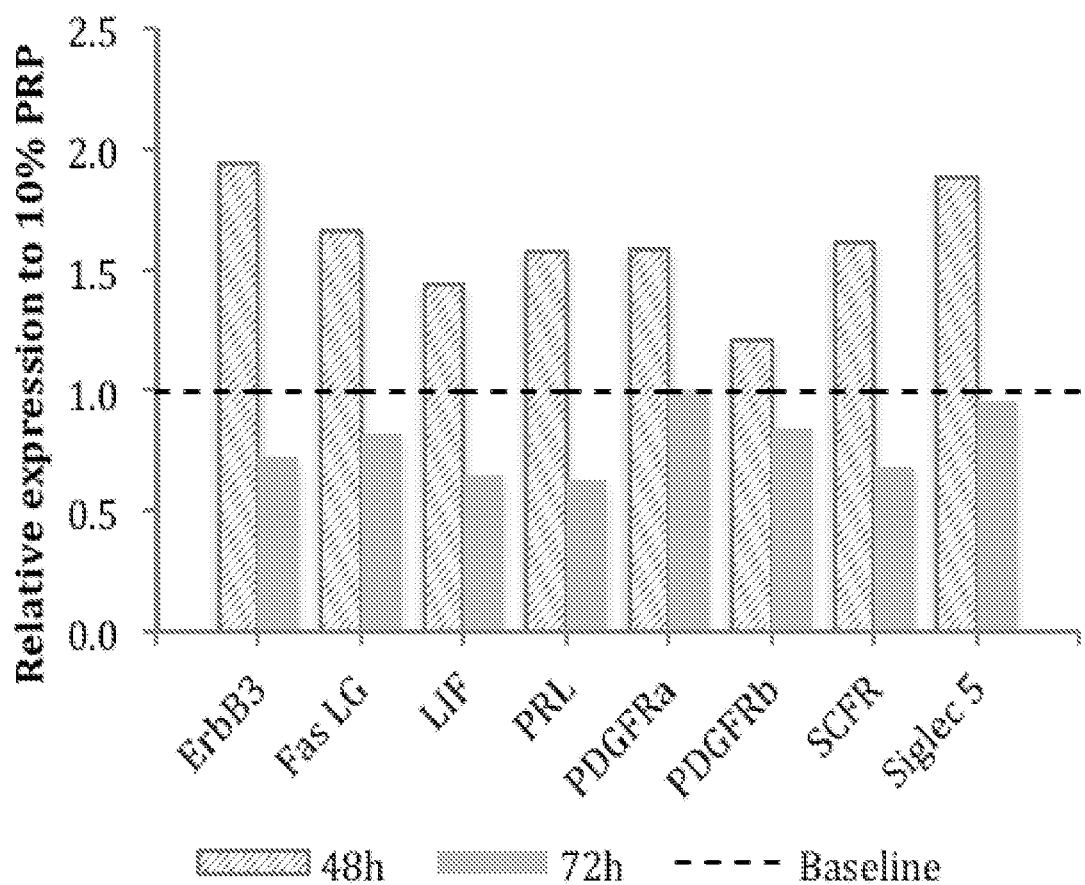
Figure 24:
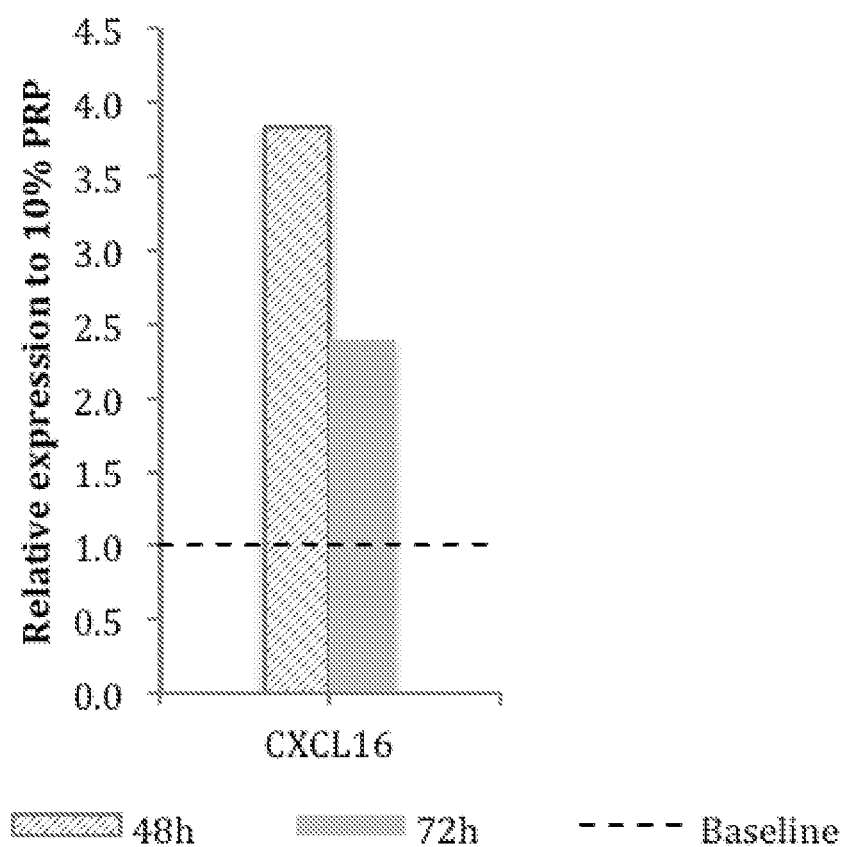
Figure 25:
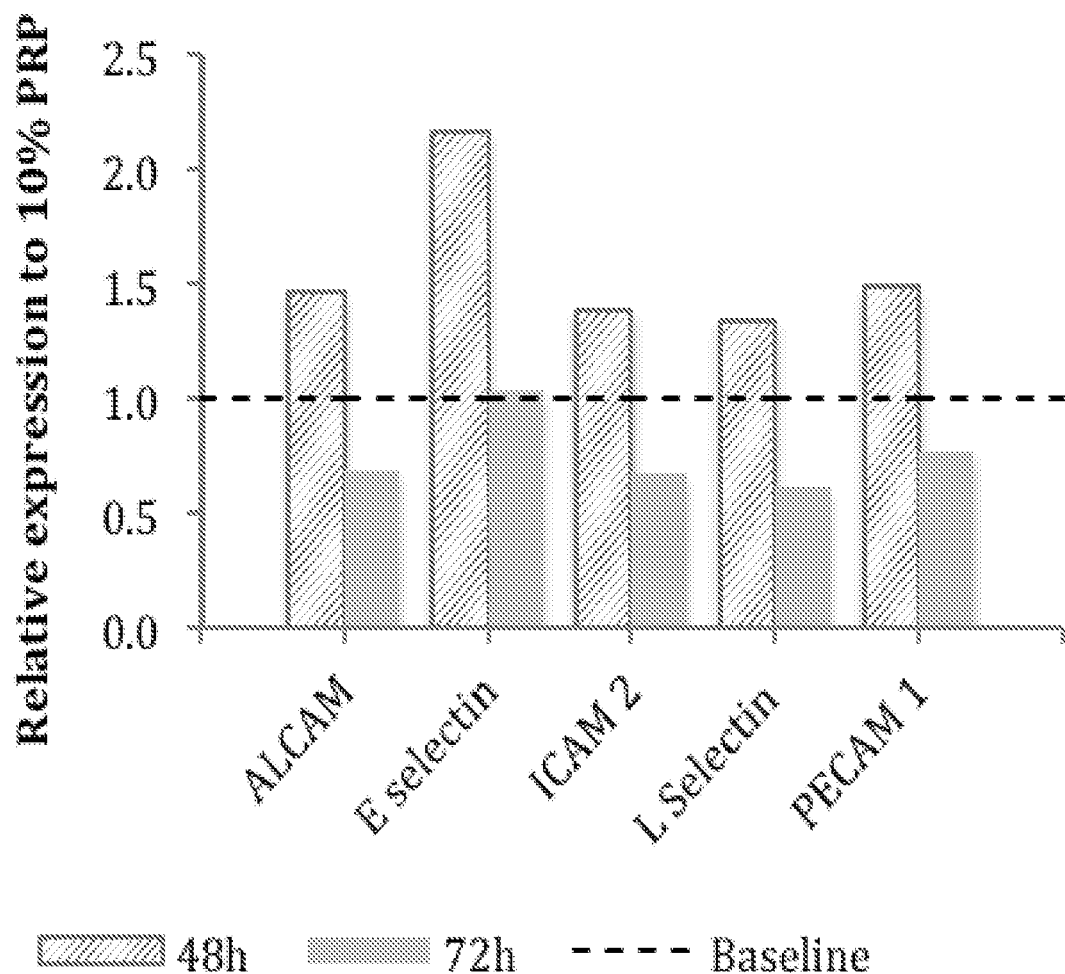
Figure 26:
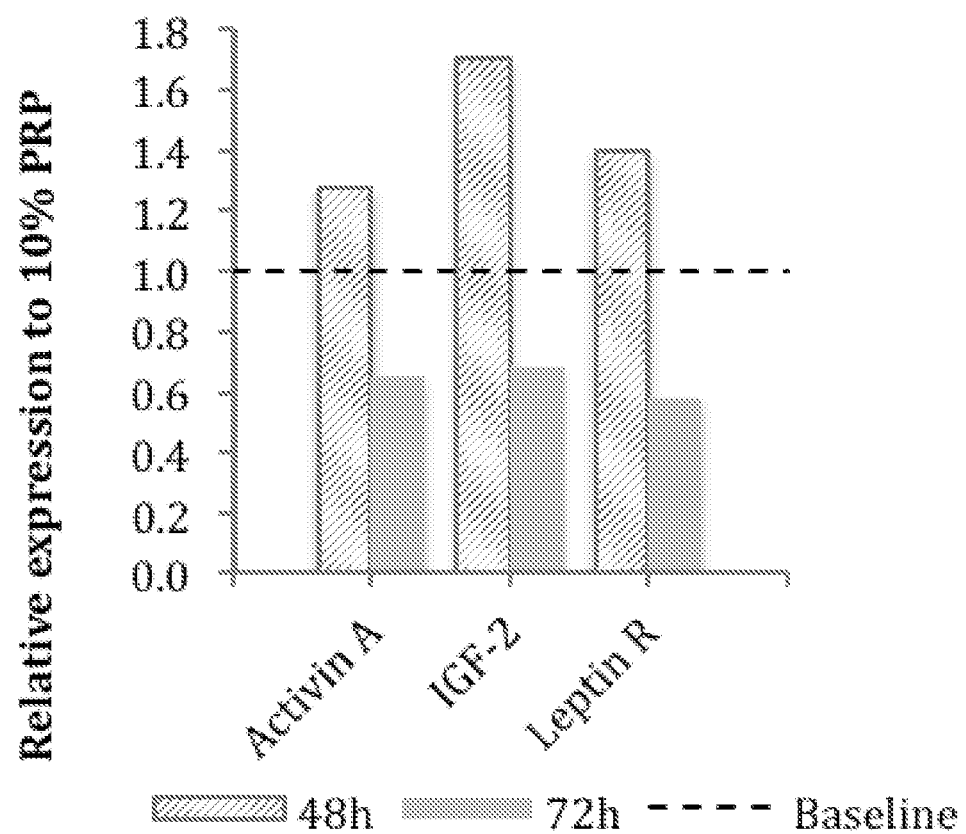
Figure 27:
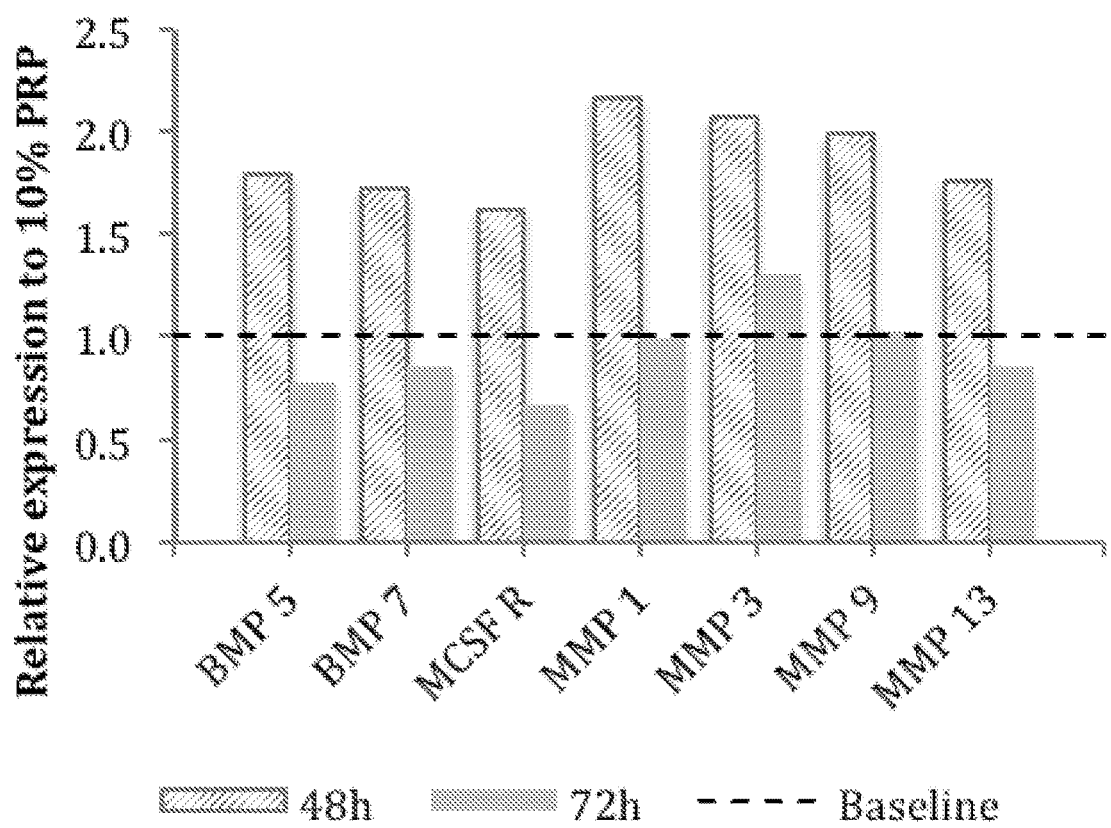
Figure 28:
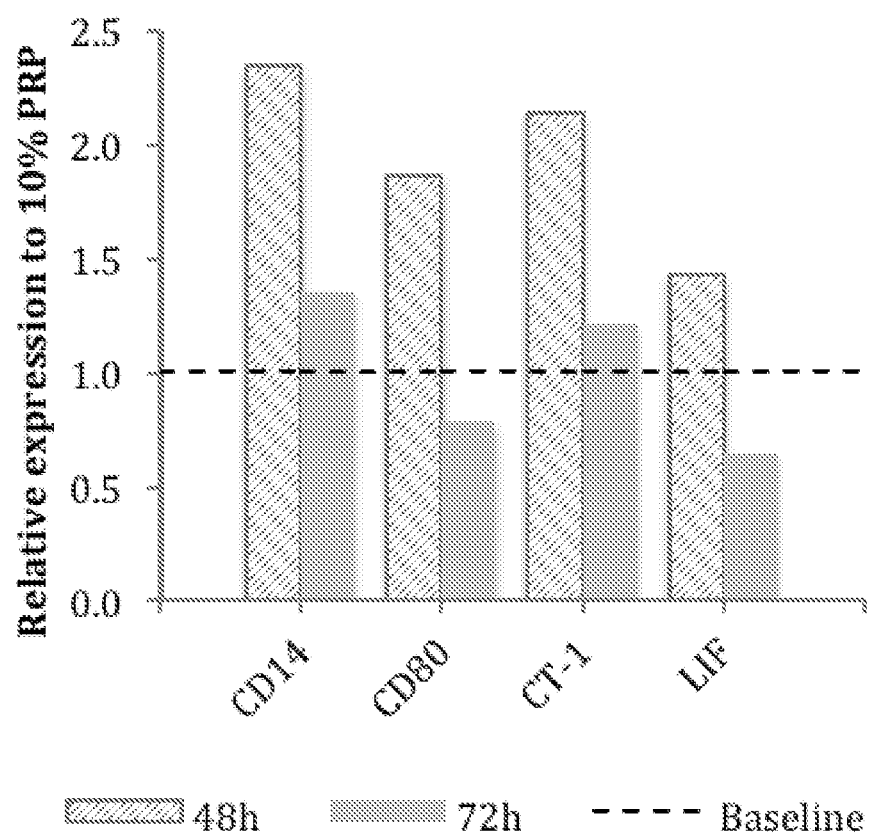
Figure 29:
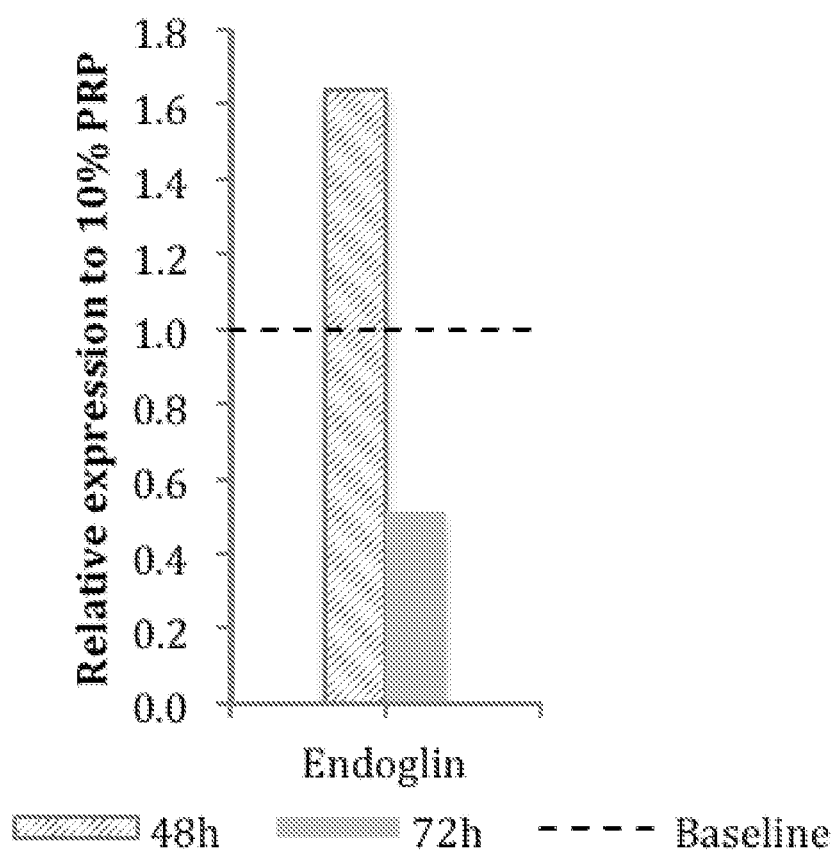
Figure 30:
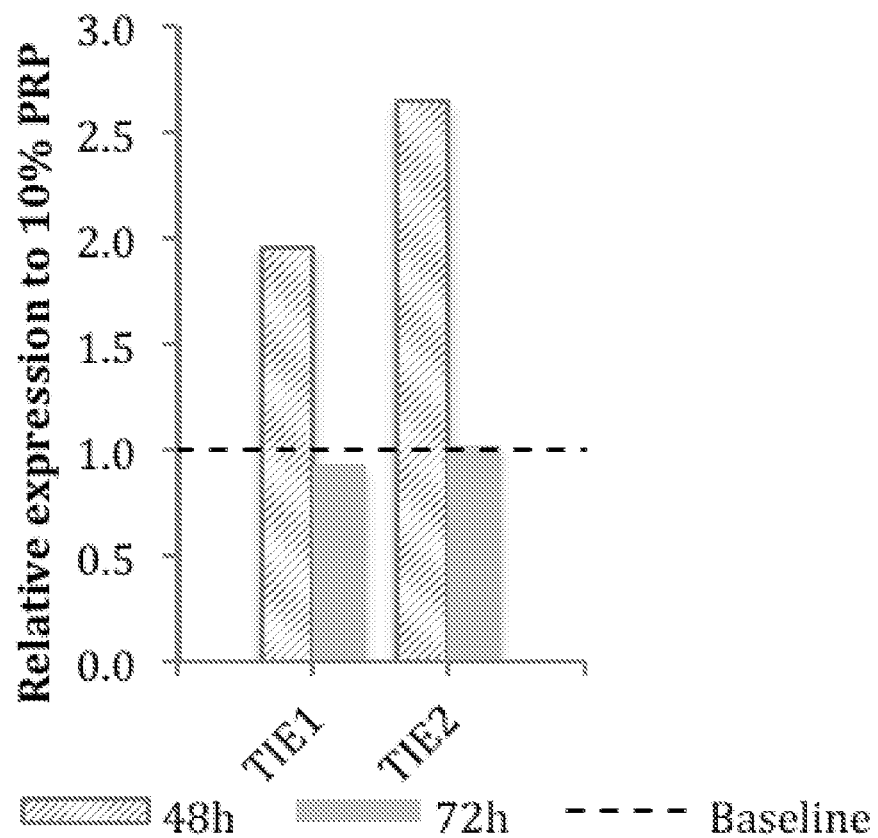
Figure 31:
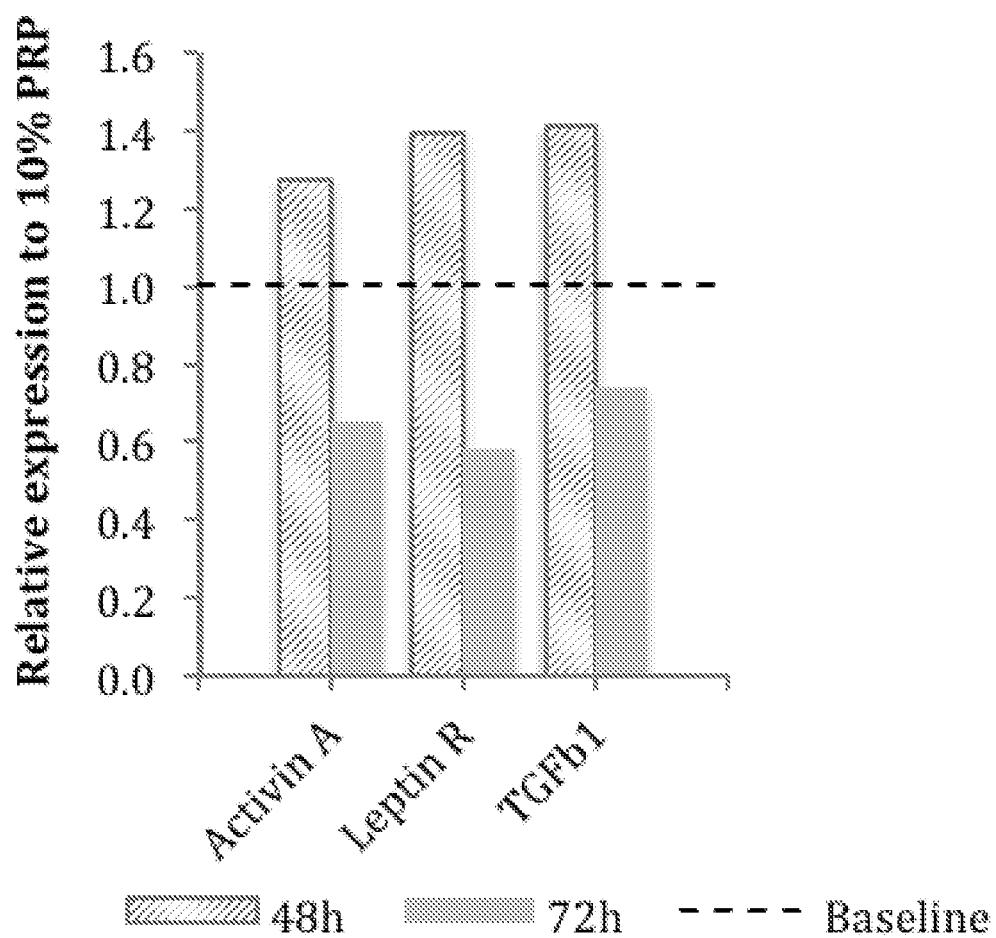

FIG. 20 shows the increase in secretion of Interleukin 9 (IL9) and Interleukin 18 binding protein alpha (IL18BPa). FIG. 21 shows the increase in secretion of Interleukin 1 receptor type II (IL1R2), Interleukin 2 receptor beta (IL-2Rb), Interleukin 2 receptor gamma (IL-2Rg), Interleukin 5 receptor alpha (IL5Ra), Interleukin 10 receptor beta (IL10Rb), Interleukin 18 receptor accessory protein (IL18Rb), and Interleukin 21 receptor (IL-21R). FIG. 22 shows the increase in secretion of Insulin-like growth factor 2 (IGF2), Transforming growth factor alpha (TGFa), Transforming growth factor beta 1/latency-associated peptide (LAP) (TGFb1), and Transforming growth factor beta 2 (TGFb2). FIG. 23 shows the increase in secretion of Receptor tyrosine-protein kinase ErbB-3 (ErbB3), Fas ligand (Fas LG), Leukemia inhibitory factor (LIF), Prolactin (PRL) factor, platelet-derived growth factor receptor alpha (PDGFRa), platelet-derived growth factor receptor beta (PDGFRb), Stem cell factor kit receptor (SCFR), and Sialic acid-binding Ig-like Lectin 5 (Siglec 5). FIG. 24 shows the increase in secretion of CXC chemokine ligand 16 (CXCL16). FIG. 25 shows the increase in secretion of activated leukocyte cell adhesion molecule (ALCAM), E selectin (cell surface glycoprotein in immune-adhesion), Intercellular adhesion molecule 2 (ICAM2), L selectin (Lymphocyte adhesion molecule), and Platelet endothelial cell adhesion molecule (PECAM 1). FIG. 26 shows the increase in secretion of Activin A (INHBA), Insulin-like growth factor 2 (IGF-2), and Leptin Receptor (LEPR). FIG. 27 shows the increase in secretion of Bone morphogenetic protein 5 (BMP5), Bone morphogenetic protein 7 (BMP7), Macrophage colony-stimulating factor 1 receptor (MCSFR), matrix metalloproteinase 1 (MMP1), matrix metalloproteinase 3 (MMP3), matrix metalloproteinase 9 (MMP9), and matrix metalloproteinase 13 (MMP13). FIG. 28 shows the increase in secretion of monocyte differentiation antigen (CD14), cell differentiation antigen (CD80), Cardiotrophin-1 (CT-1), and Leukemia inhibitory factor (LIF). FIG. 29 shows the increase in secretion of Endoglin (ENG). FIG. 30 shows the increase in secretion of Tyrosine kinase with immunoglobulin-like and EGF-like domains 1 (TIE1) and Tyrosine kinase with immunoglobulin-like and EGF-like domains 2 (TIE2). FIG. 31 shows the increase in secretion of Activin A (Inhibin beta A, INHBA), Leptin Receptor (Leptin R), and Transforming growth factor beta 1 (TGFb1).

Figure 32:
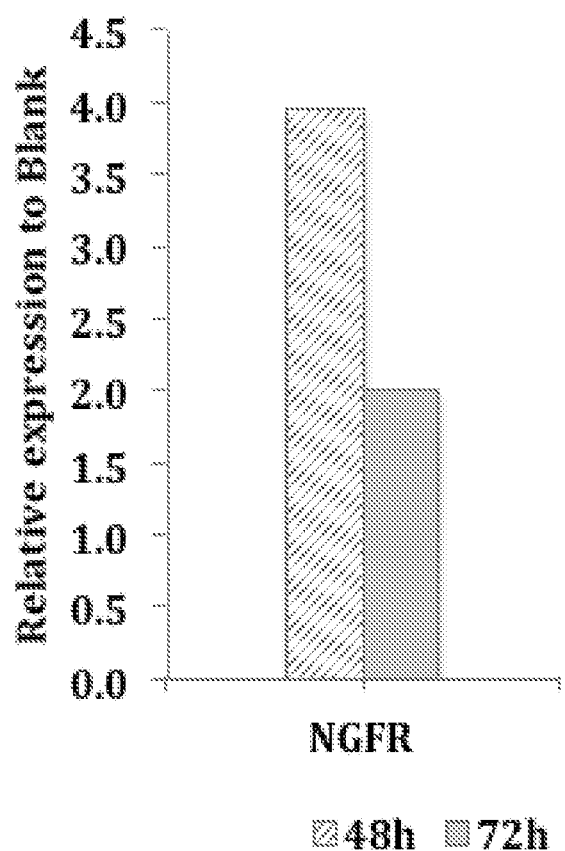

FIG. 32 shows the increase in secretion of Nerve growth factor receptor (NGFR) from SR-MSCs maintained in a factor production unit of the invention, 48 hours post incubation with 10% PRP alone (no IL-2 stimulation). NGFR was found to not be present in in PRP. The factors produced from the factor production unit under these conditions can provide therapeutic benefits for treatment of neurodegenerative pathologies, such as for example Parkinson's disease, Alzheimer's disease, progressive supranuclear palsy, multiple system atrophy, amyotrophic lateral sclerosis, Huntington's chorea or following trauma such as stroke and cerebral or spinal traumas and stand alone or combinational treatments for conditions requiring musculoskeletal and cardiac repair.

FIGS. 33-39 show the increase in secretion of the below named proteins (factors) from SR-hADSCs maintained in a factor production unit of the invention, 72 hours post incubation with 10% PRP alone (no IL-2 stimulation). The factors produced from the factor production unit may provide therapeutic benefits for treatment of neurodegenerative pathologies, such as for example Parkinson's disease, Alzheimer's disease, progressive supranuclear palsy, multiple system atrophy, amyotrophic lateral sclerosis, Huntington's chorea or following trauma such as stroke and cerebral or spinal traumas and stand alone or combinational treatments for conditions requiring musculoskeletal and cardiac repair. cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, ulceration, a pathological condition characterized by initial injury inducing inflammation and immune dysregulation leading to chronic tissue remodeling including fibrosis and loss of function, skin defense against infection, new synthesis of collagen, elastin and hyaluronan, inhibition of melanoma growth, diabetic ulcers, myocardial infraction, atherosclerosis, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, and chronic inflammation resulting from chronic viral or bacteria infections, chronic liver fibrosis, cirrhosis, fulminant hepatic failure, allergic airway inflammation, acute lung injuries, myocardial infarction, fetal maternal tolerance, osteoarthritis, GVHD.

Figure 33:
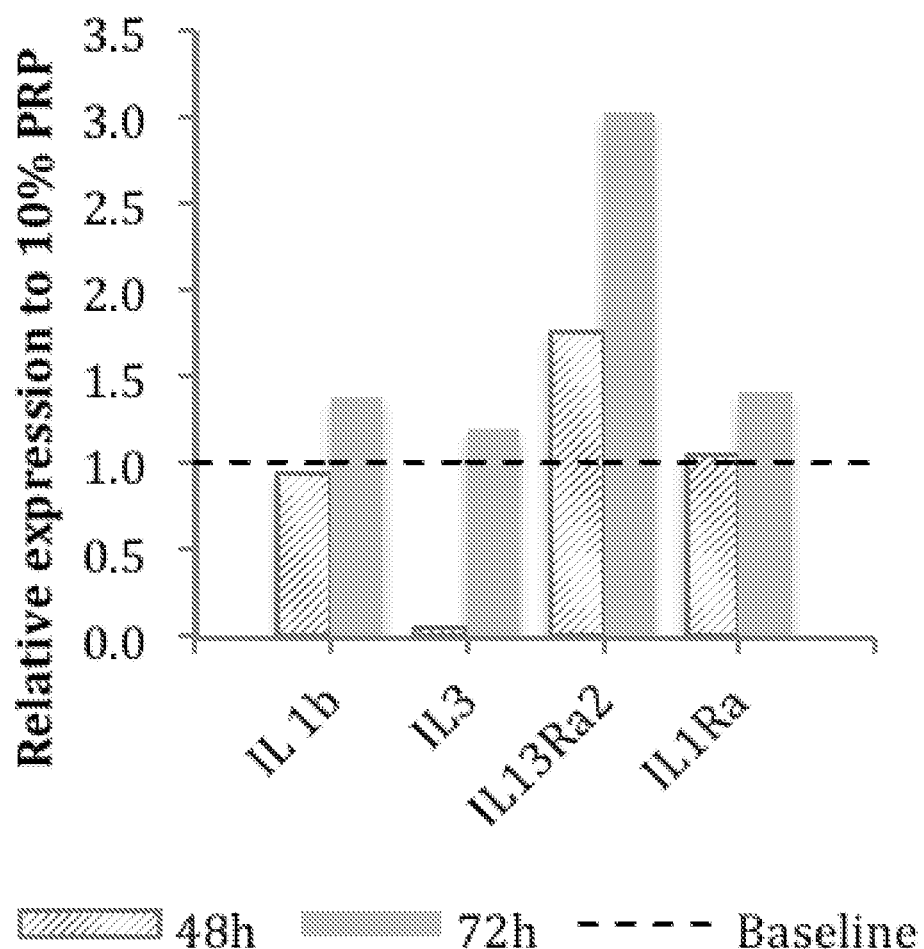
Figure 34:
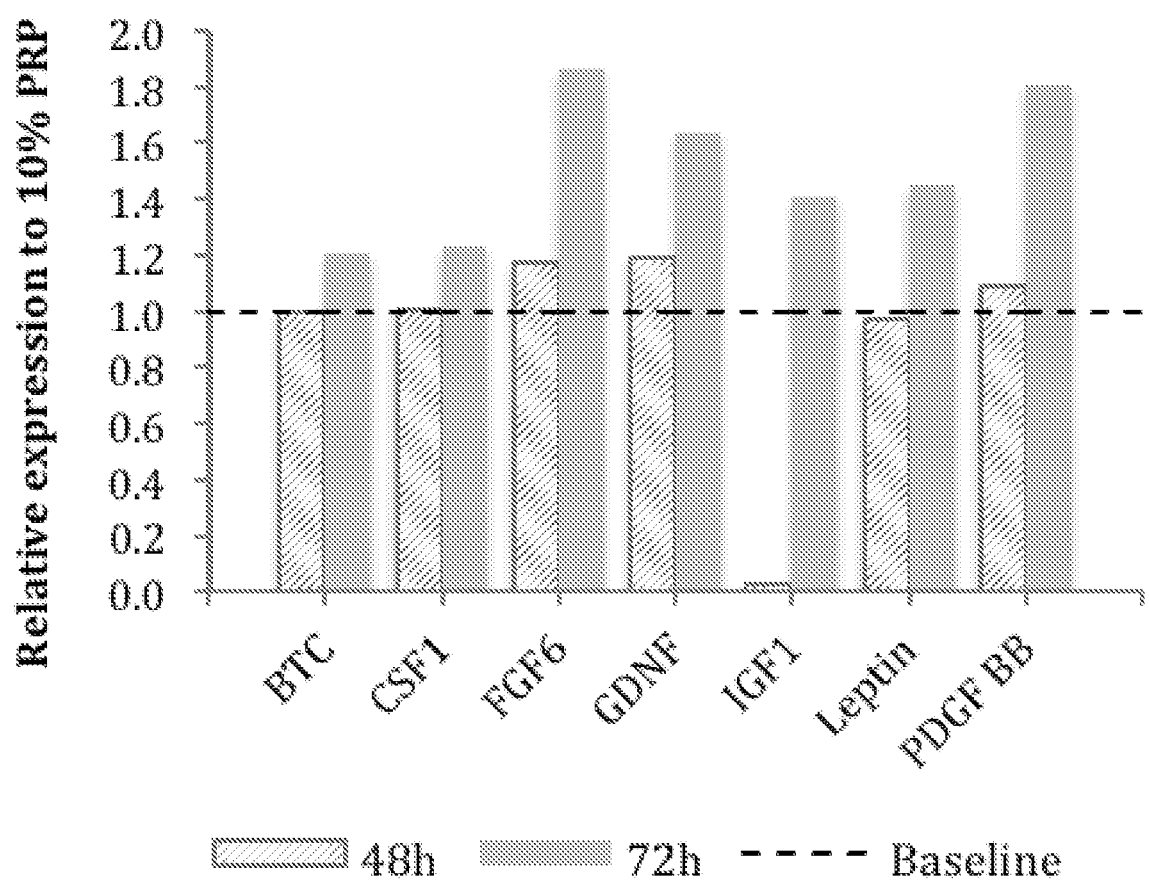
Figure 35:
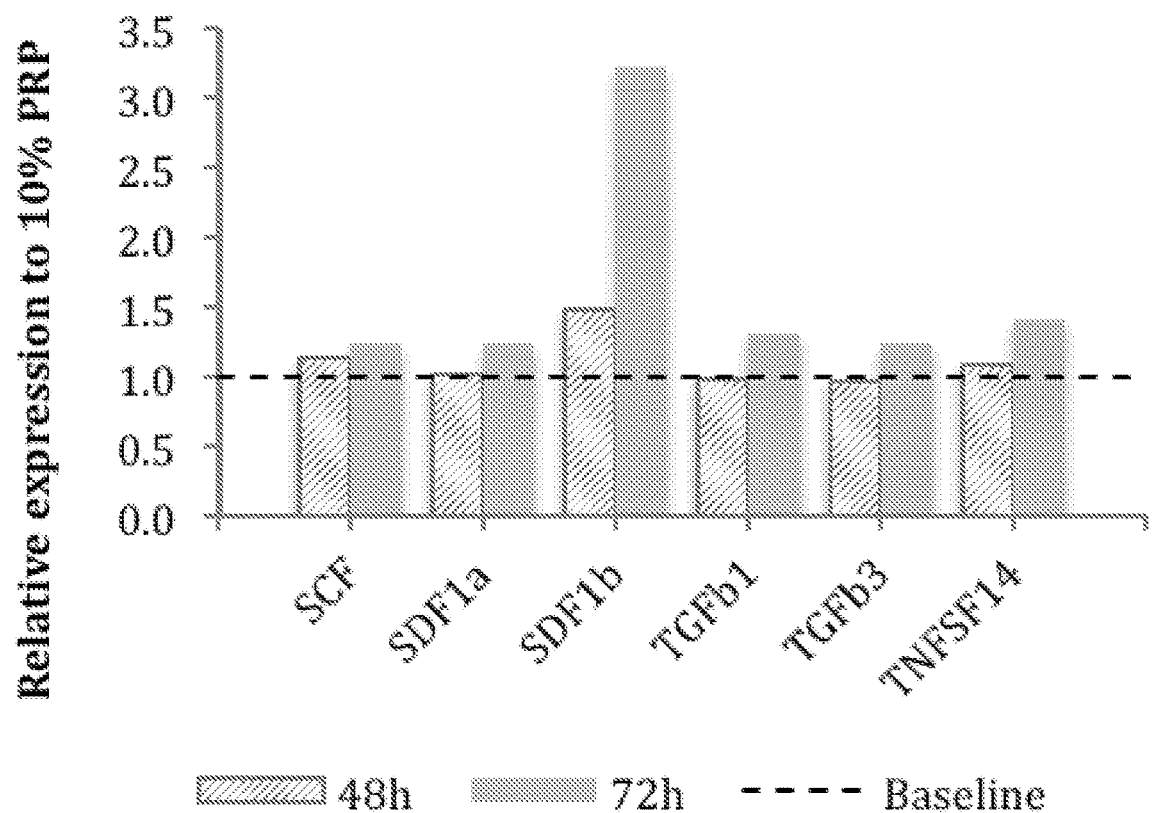
Figure 36:
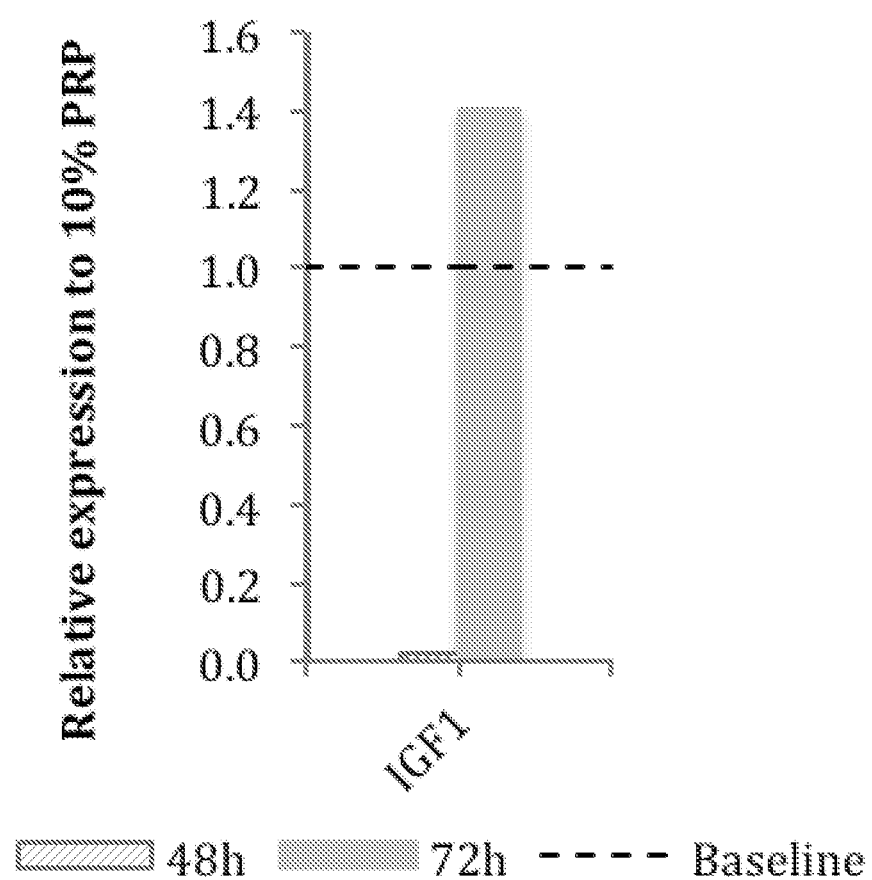
Figure 37:
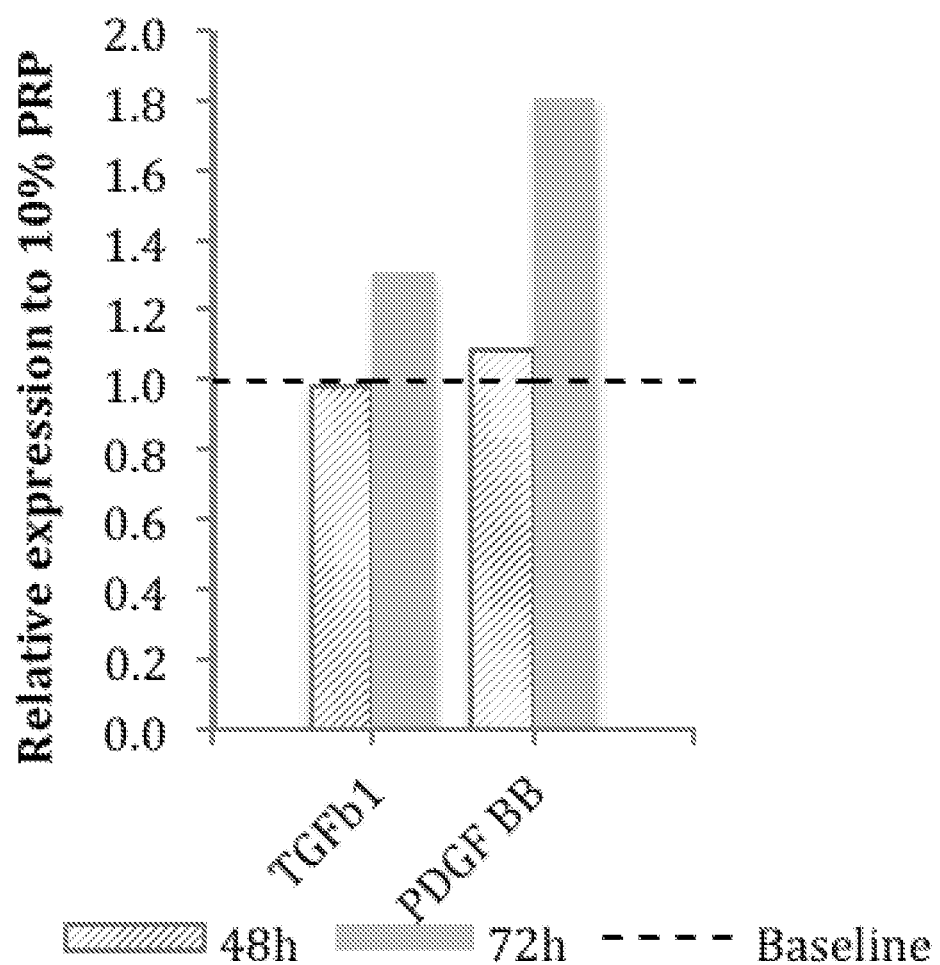
Figure 38:
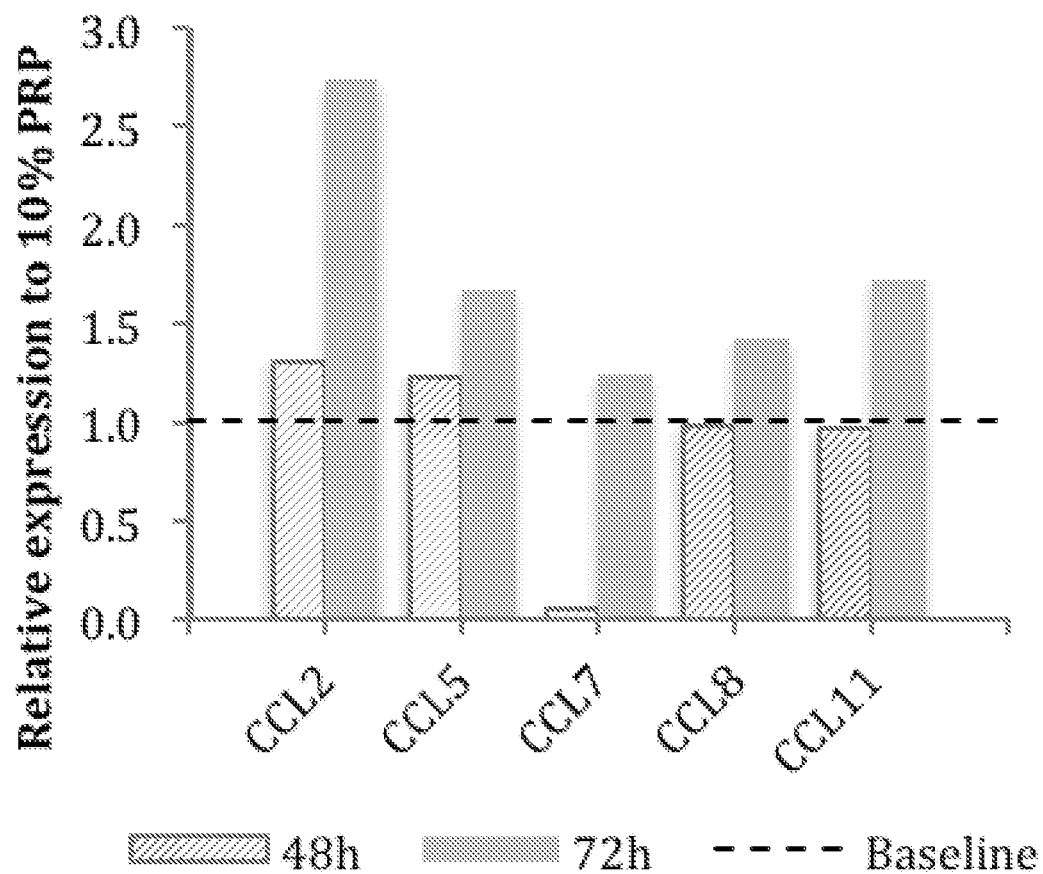
Figure 39:
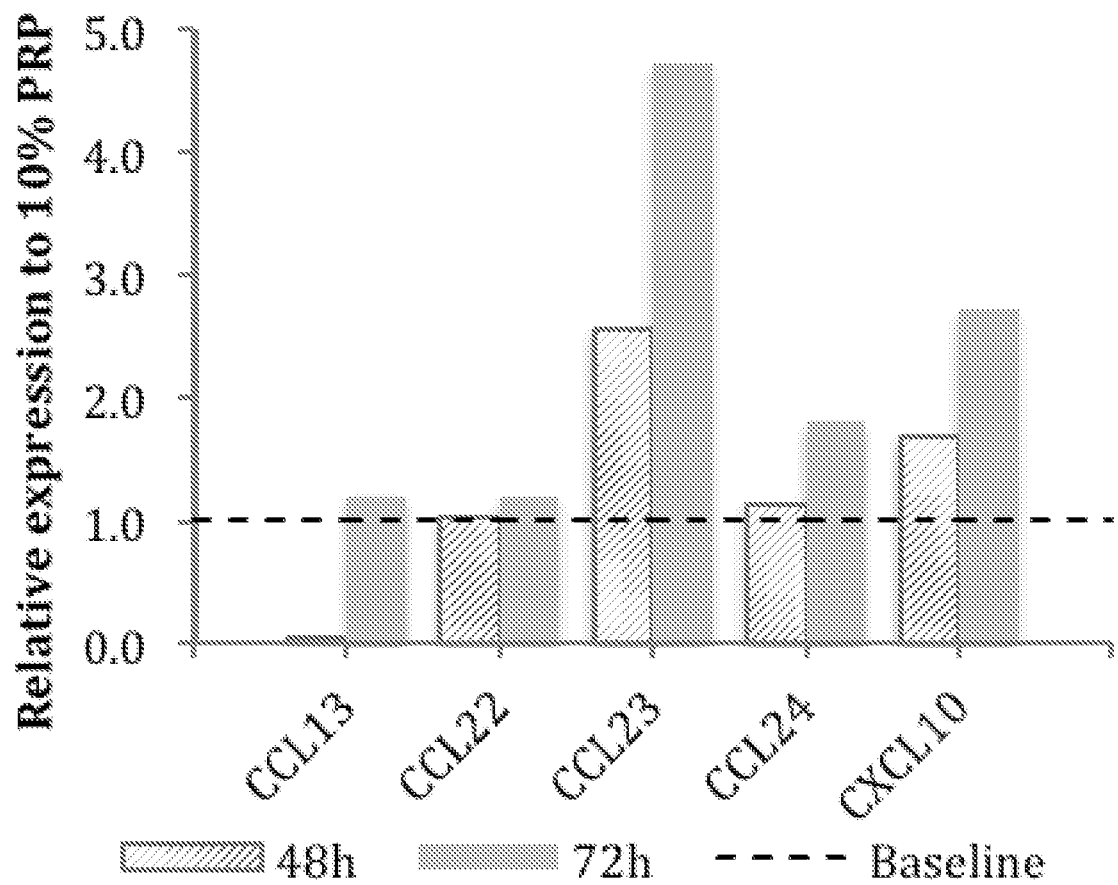

In FIGS. 33-39, secretion levels are shown relative to the amount of the corresponding protein present at basal levels in the 10% PRP containing media, used for hADSC support. FIG. 33 shows the increase in secretion of Interleukin 1 beta (IL1b), Interleukin 3 (IL3), Interleukin-13 Receptor subunit alpha-2 (IL13Rα2), and Interleukin 1 receptor alpha (IL1Rα). FIG. 34 shows the increase in secretion of Pro-betacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, and platelet-derived growth factor B beta (PDGF BB). FIG. 35 shows the increase in secretion of stem cell factor/c-kit ligand (SCF), Stromal Cell-Derived Factor-1 alpha (SDF1a), Stromal Cell-Derived Factor-1 beta (SDF1b), Transforming growth factor beta 1 (TGFb1), Transforming growth factor beta 3 (TGFb3), and tumor necrosis factor superfamily member 14 (TNFSF14). FIG. 36 shows the increase in secretion of Insulin-like growth factor 1 (IGF1). FIG. 37 shows the increase in secretion of Transforming growth factor beta 1 (TGFb1) and platelet-derived growth factor B beta (PDGF BB). FIG. 38 shows the increase in secretion of Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), and Chemokine (C-C motif) ligand 11 (CCL11). FIG. 39 shows the increase in secretion of Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), and CXC Chemokine ligand 10 (CXCL10).

Figure 40:
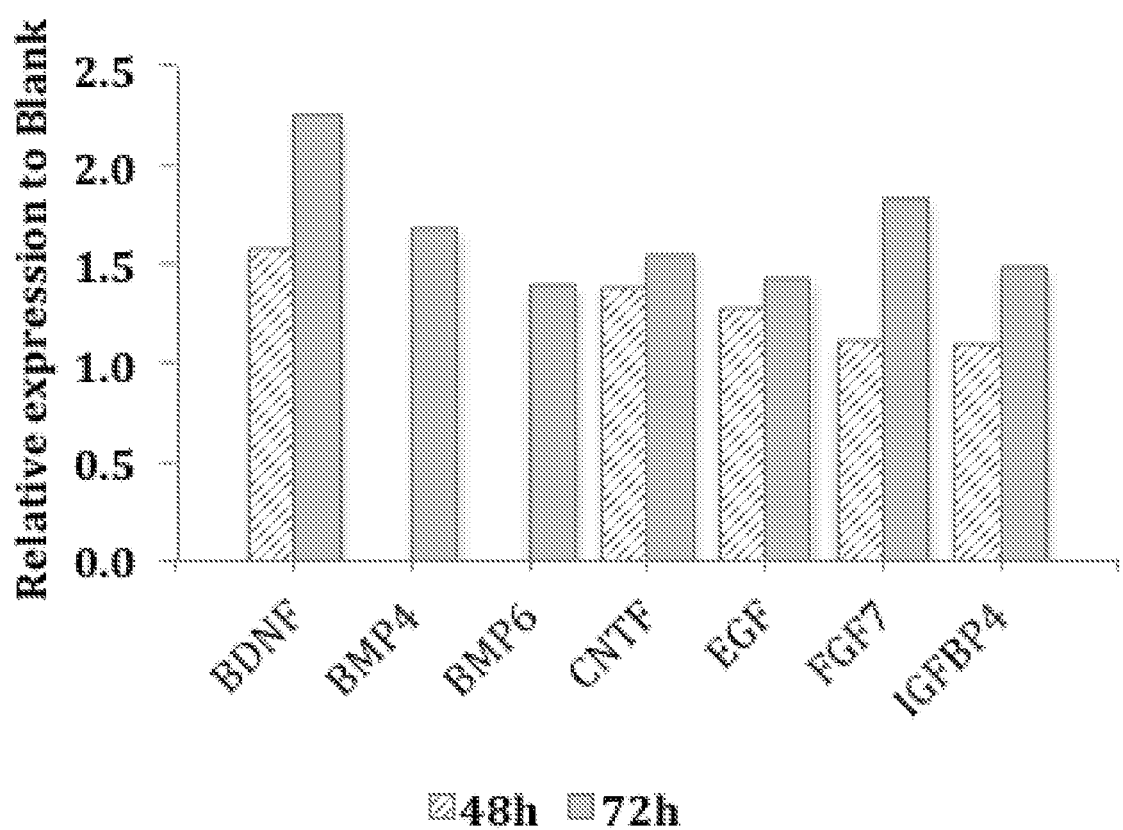
Figure 41:
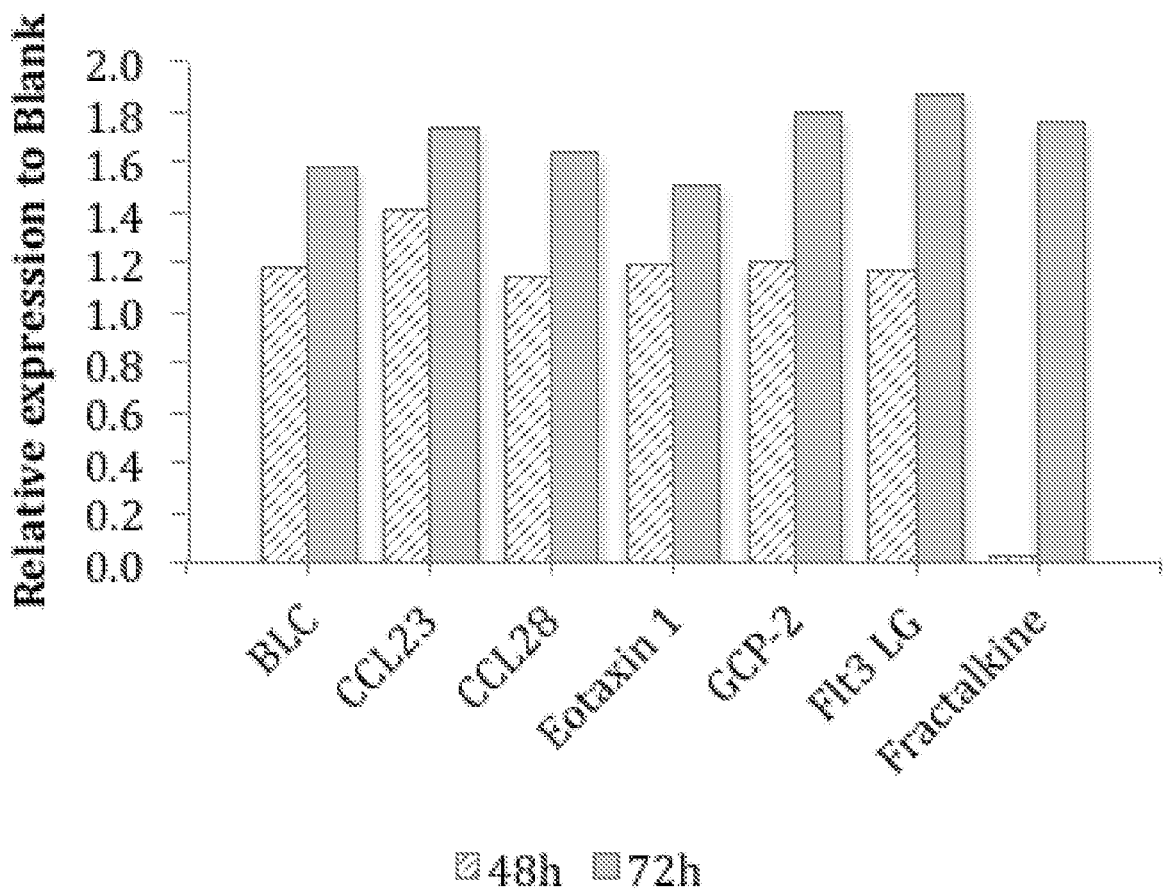
Figure 42:
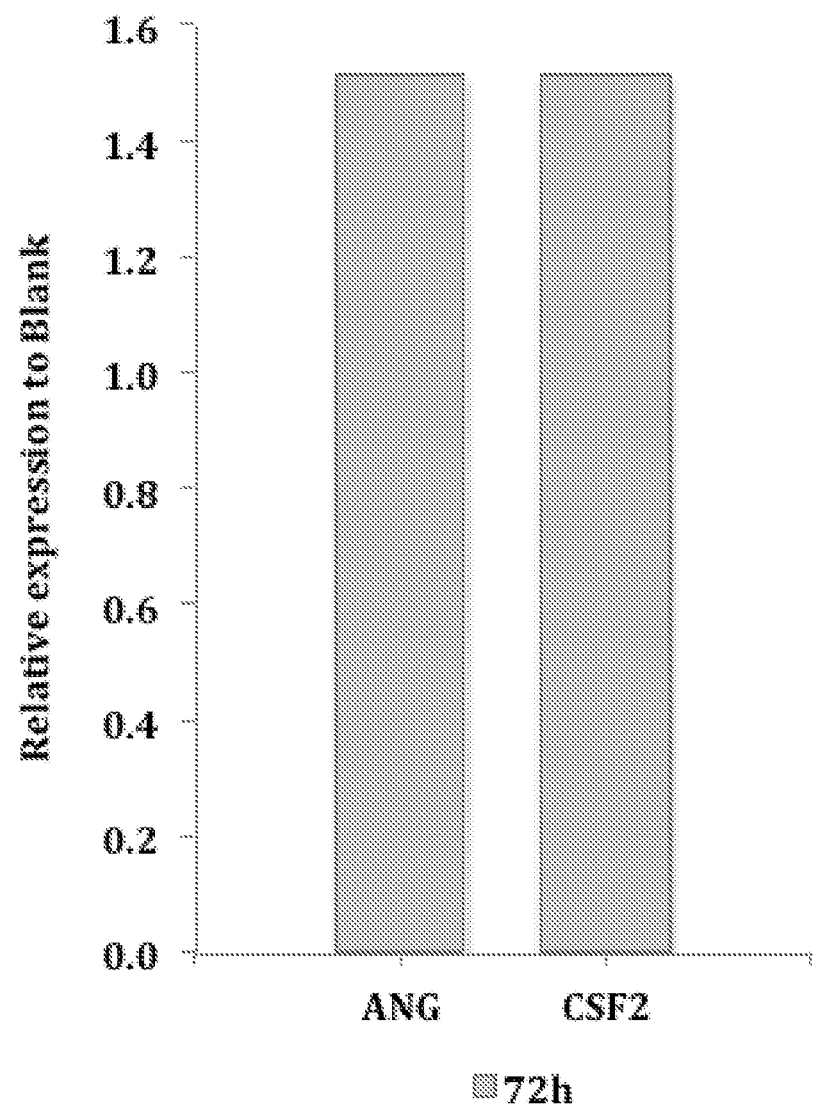

FIGS. 40-42 show the increase in secretion of the below named proteins (factors) from SR-hADSCs maintained in a factor production unit of the invention, 72 hours post incubation with 10% PRP alone (no IL-2 stimulation). These factors were found to not be present in PRP. FIGS. 40-42 show the increase in secretion of the below named proteins (factors) from SR-hADSCs maintained in a factor production unit of the invention, 72 hours post incubation with 10% PRP alone (no IL-2 stimulation). These factors were found to not be present in PRP. The factors produced from the factor production unit under these conditions may provide therapeutic benefits for treatment of neurodegenerative pathologies, such as for example Parkinson's disease, Alzheimer's disease, progressive supranuclear palsy, multiple system atrophy, amyotrophic lateral sclerosis, Huntington's chorea or following trauma such as stroke and cerebral or spinal traumas, condyloma, verruca, hemangioma, keloid, skin cancer, retinoditis pigmentosa, idiopathic pulmonary fibrosis, chronic liver fibrosis, cirrhosis, fulminant hepatic failure, allergic airway inflammation, acute lung injuries atopic dermatitis, Behcet disease, chronic granulomatous disease, cutaneous T cell lymphoma, ulceration, a pathological condition characterized by initial injury inducing inflammation and immune dysregulation leading to chronic tissue remodeling including fibrosis and loss of function, renal ischemic injury, cystic fibrosis, sinusitis and rhinitis or an orthopaedic disease, autoimmune hepatitis and stand alone or combinational treatments for conditions requiring musculoskeletal and cardiac repair.

FIG. 40 shows the increase in secretion of Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), and insulin-like growth factor-binding protein-4 (IGFBP4). FIG. 41 shows the increase in secretion of chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1). FIG. 42 shows the increase in secretion of Angiotensin (ANG) and colony stimulating factor 2 (CSF2). Eotaxin 1 works as a drug against asthma and allergic reactions. Flt3 LG stimulates proliferation and differentiation of hematopoietic cells progenitors, Fractalkine modulates cytotoxic effector T cells, induced migration T & B cell lymphocytes, NK cells and monocytes, BLC controls organization of B-cells in lymphoid tissue. CCL23 is associated with immunomodulation in lung and liver tissue, ANG signaling is associated with protective effects in cardiovascular diseases, CSF2 is used as a potential to therapy for rheumatoid arthritis and stimulates macrophages. In addition, stimulates production of white blood cells and prevents neutropenia post chemotherapy. It is approved for treatment in Non-Hodgkins lymphoma, acute lymphocutic leukemia, fungal infection and Hodgkins disease.

Figure 43:
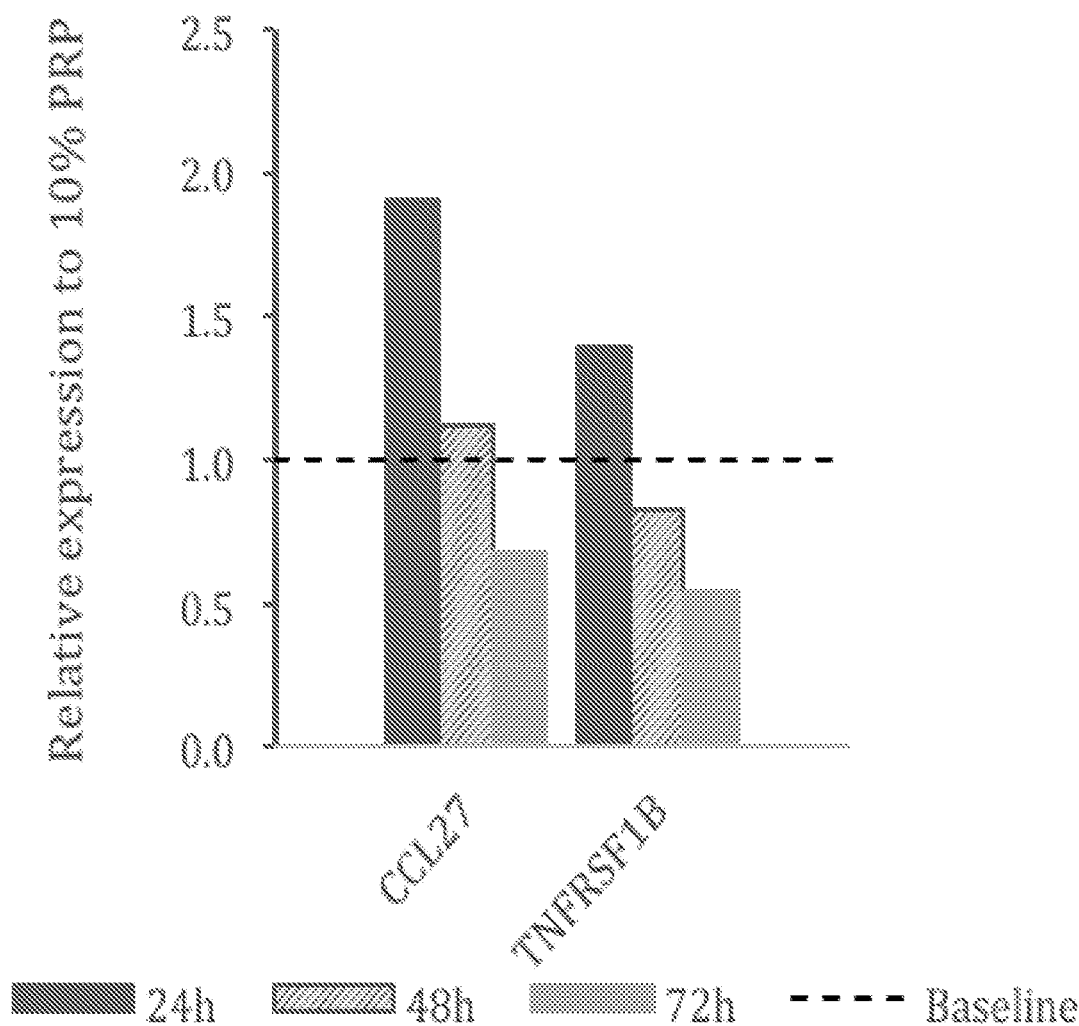

FIG. 43 shows the increase in secretion of Chemokine (C-C motif) ligand 27 (CCL27) and TNFRSF1B (Tumor Necrosis Factor Receptor Superfamily, Member 1B) from SR-hADSCs maintained in a factor production unit of the invention, 24 hours post stimulation with IL-2. Secretion levels are shown relative to the amount of the corresponding protein present at basal levels in the 10% PRP containing media, used for hADSC support.

FIGS. 44-53 show the increase of the below named proteins (factors) from SR-hADSCs maintained in a factor production unit of the invention, 48 hours post stimulation with IL-2. Secretion levels are shown relative to the amount of the corresponding protein present at basal levels in the 10% PRP containing media, used for hADSC support.

FIGS. 44-53 show the increase of the below named proteins (factors) from SR-hADSCs maintained in a factor production unit of the invention, 48 hours post stimulation with IL-2. Secretion levels are shown relative to the amount of the corresponding protein present at basal levels in the 10% PRP containing media, used for hADSC support. The factors produced from the factor production unit under these conditions may provide therapeutic benefits for treatment of autoimmune diseases. As referred to herein, "autoimmune diseases" refer to a condition in a subject characterized by cellular, tissue and/or organ injury caused by an immunological reaction of the subject to its own cells, tissues and/or organs. Illustrative, non-limiting examples of autoimmune diseases which can be treated with the immunomodulatory cells of the invention include alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type I or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, Psoriasis, etc. as well diseases and conditions required enhancing of angiogenesis.

Figure 44:
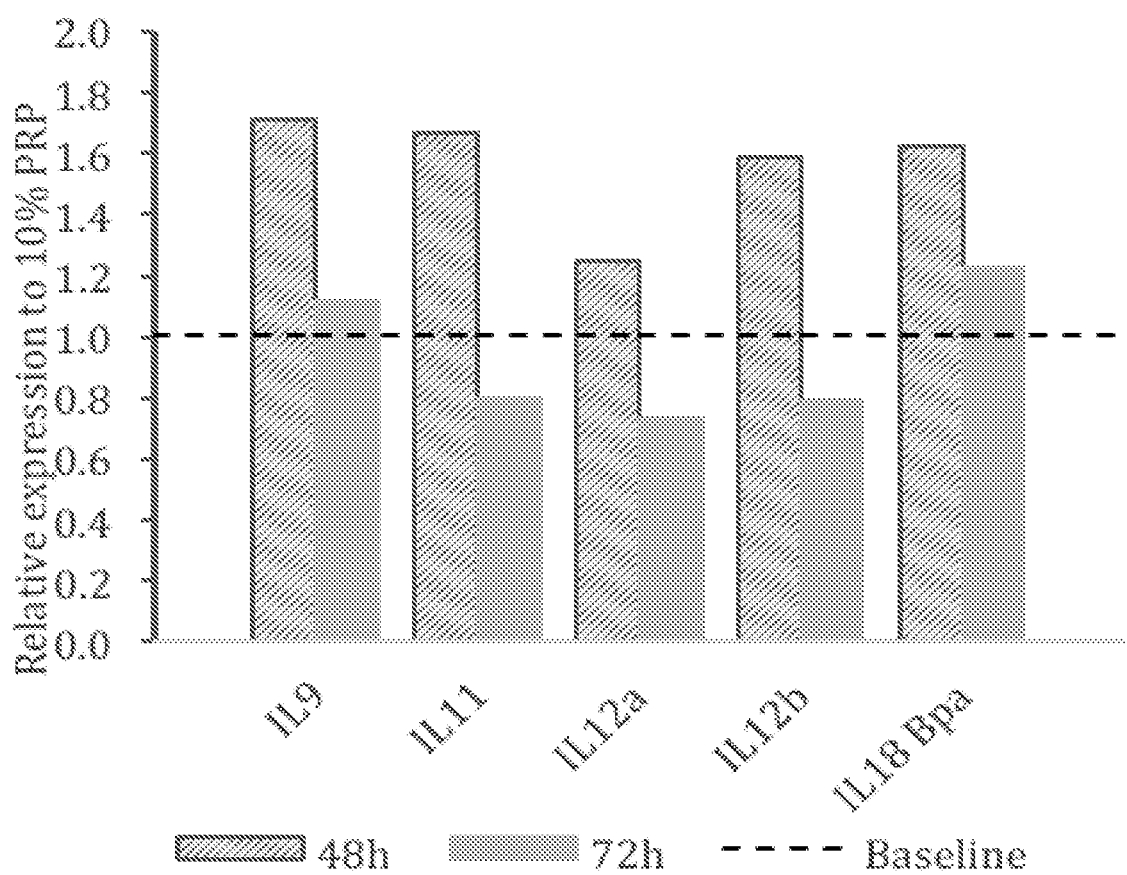
Figure 45:
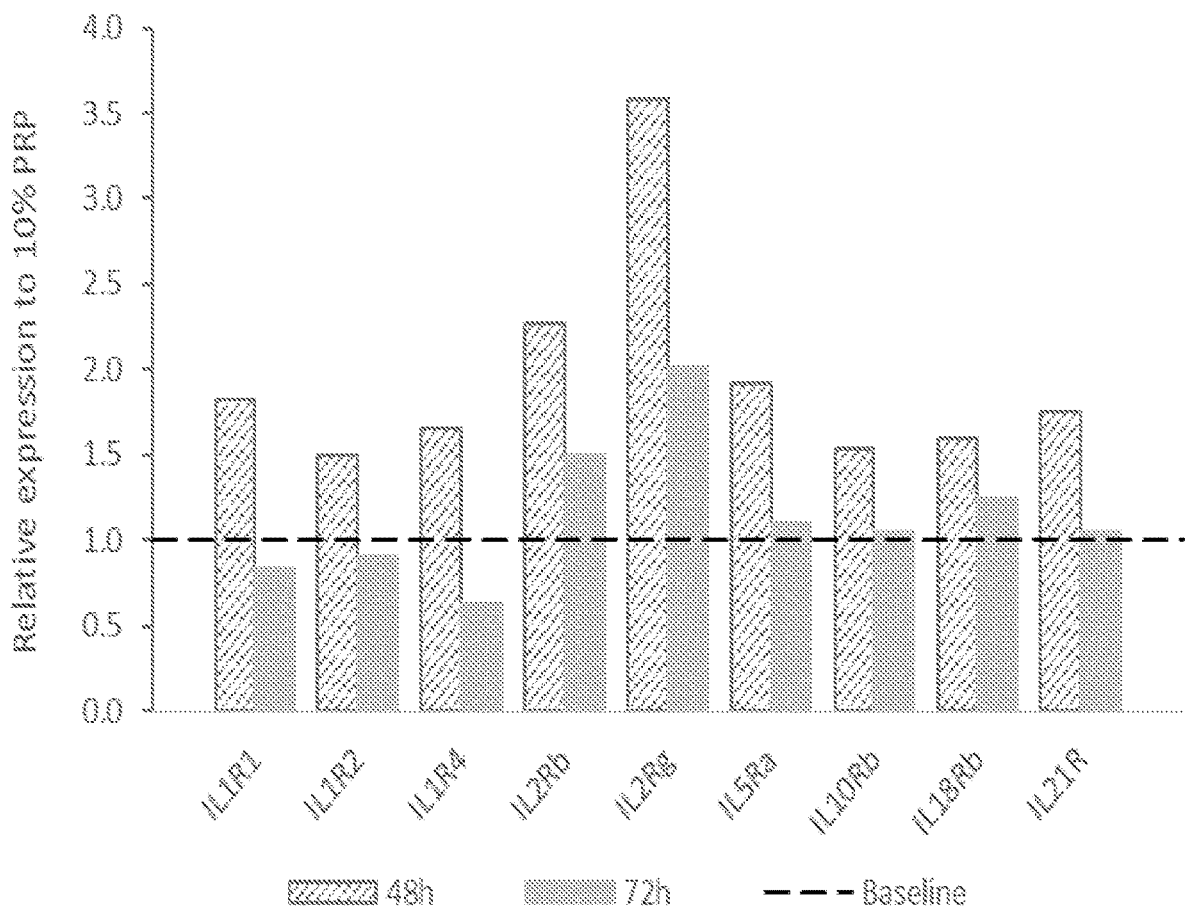
Figure 46:
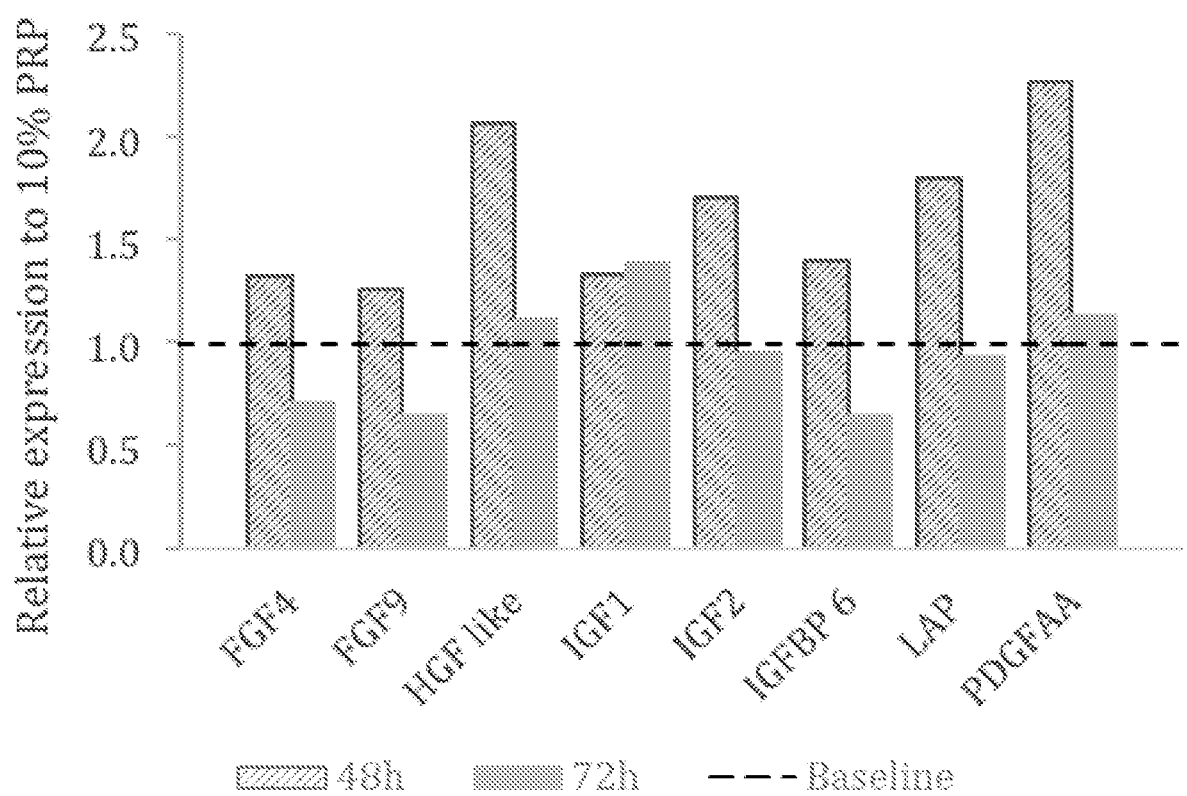
Figure 47:
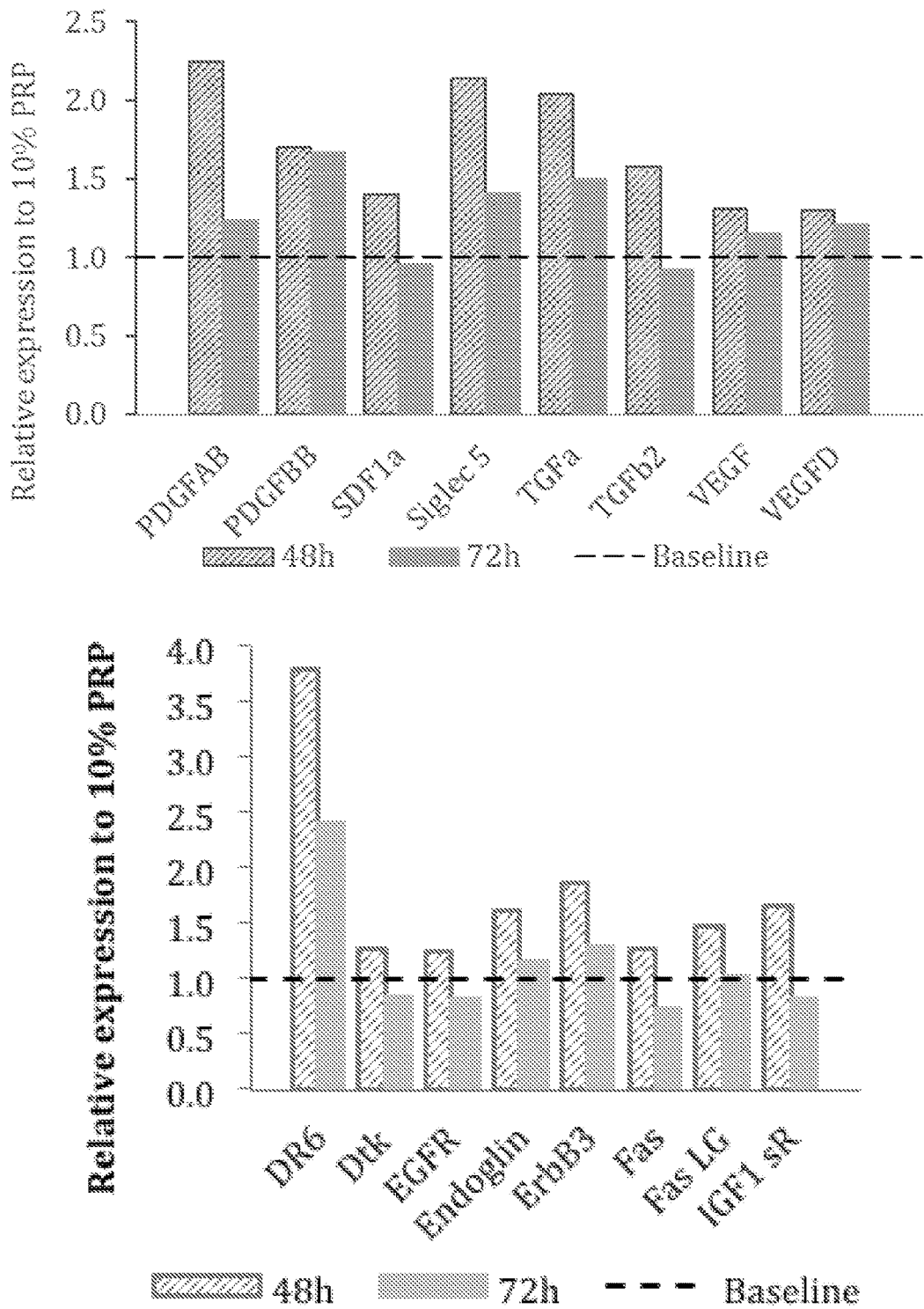
Figure 48:
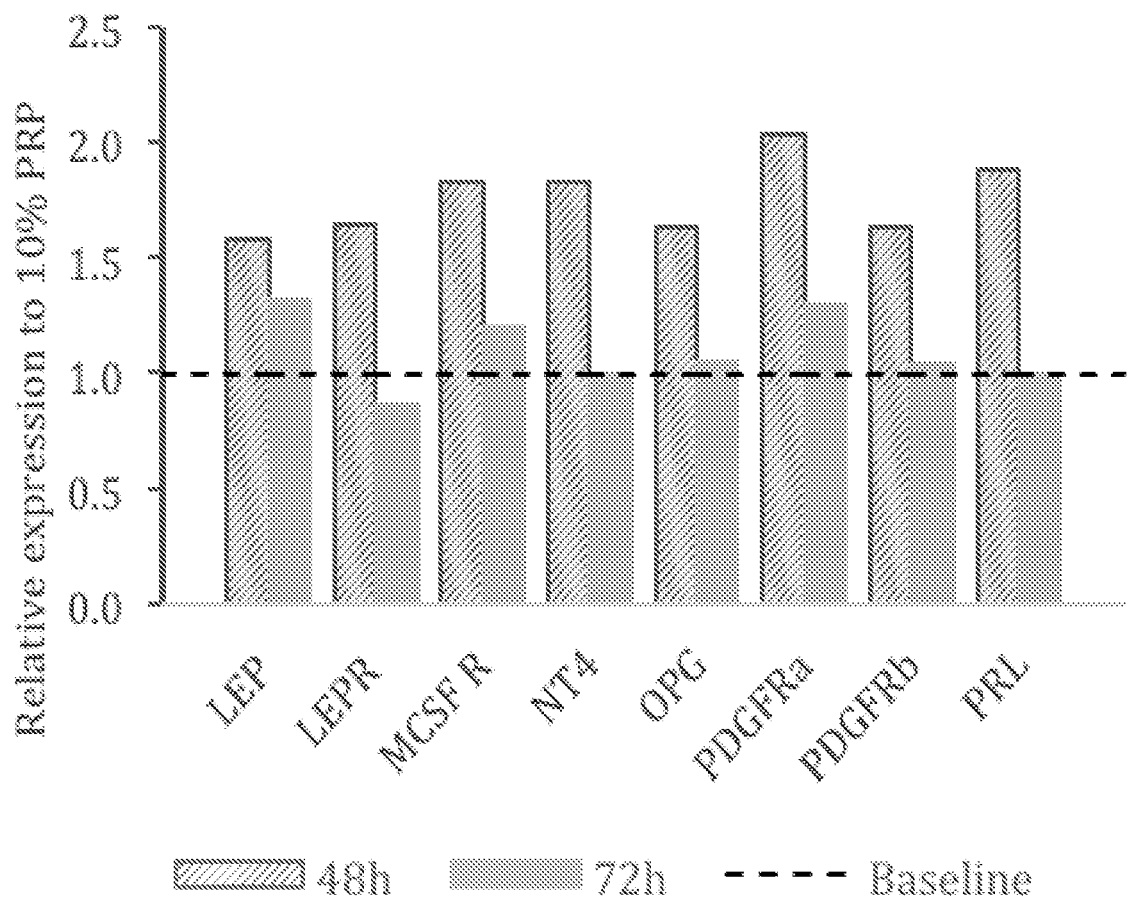
Figure 49:
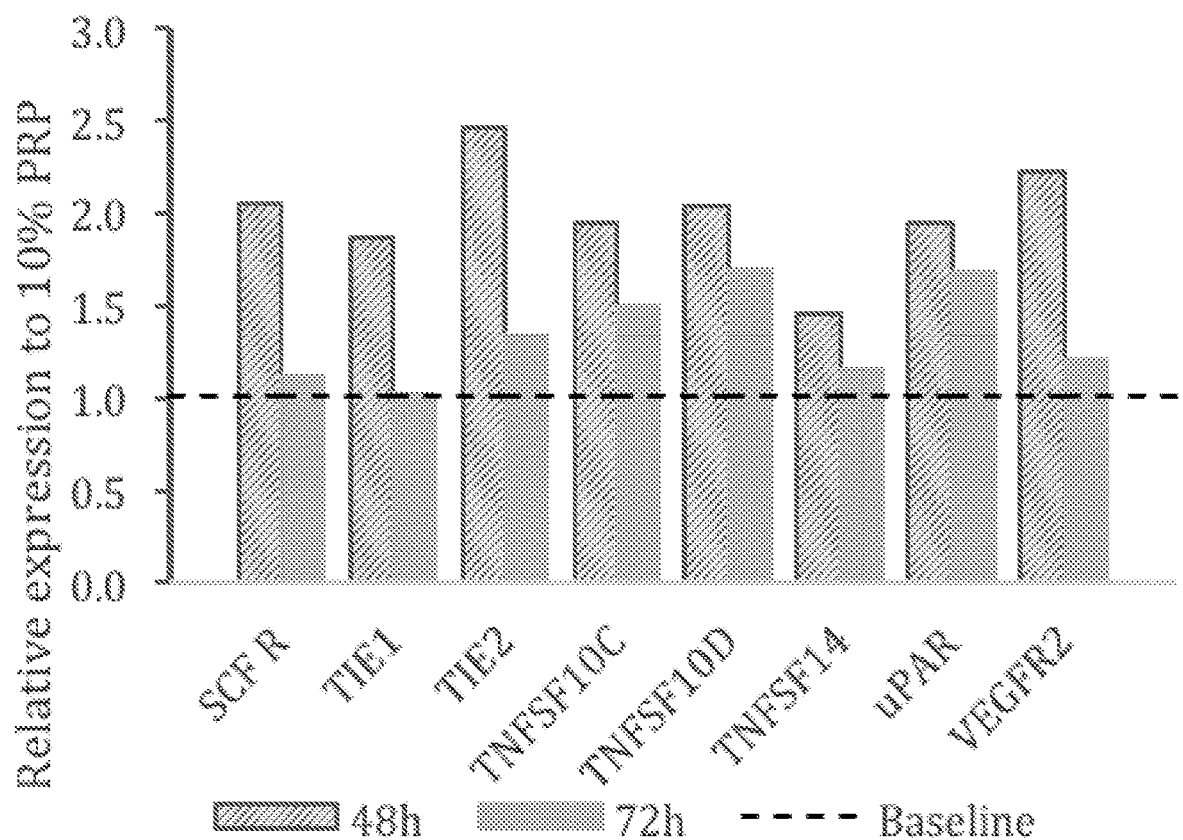
Figure 50:
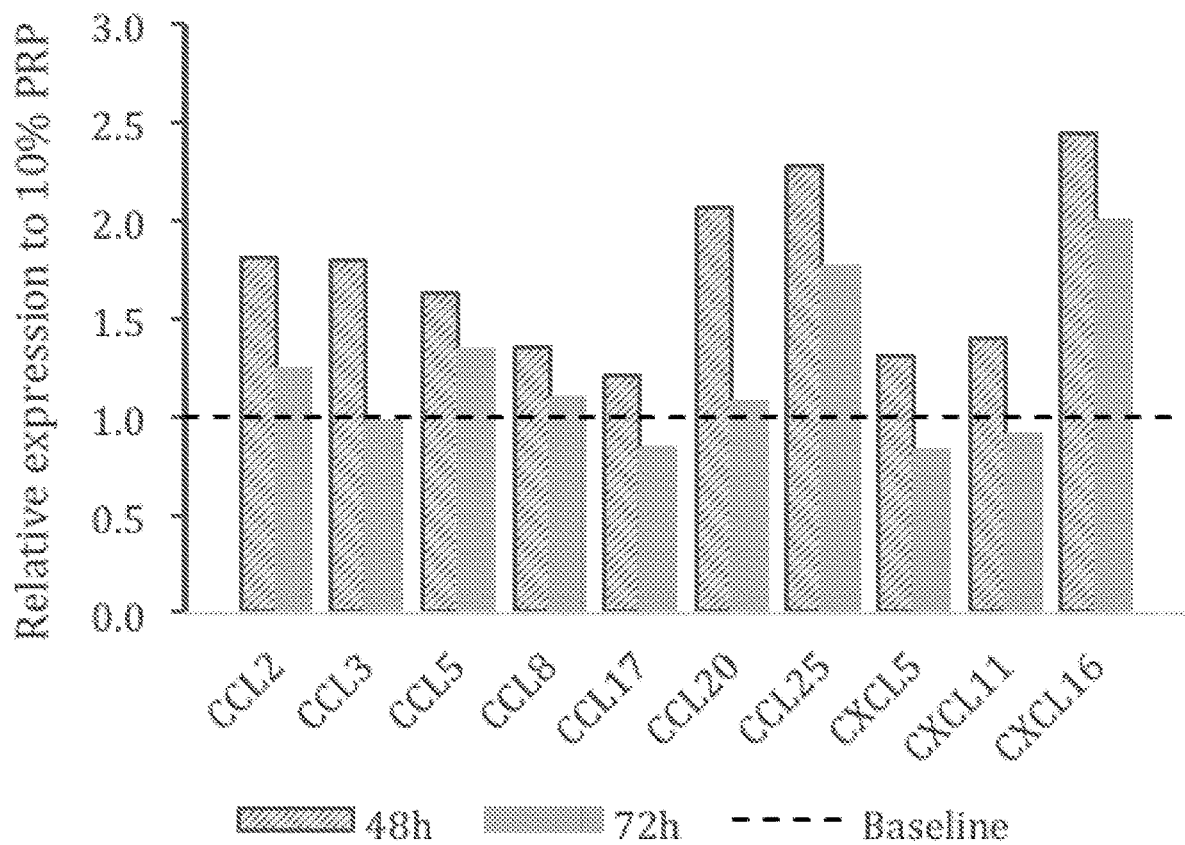
Figure 51:
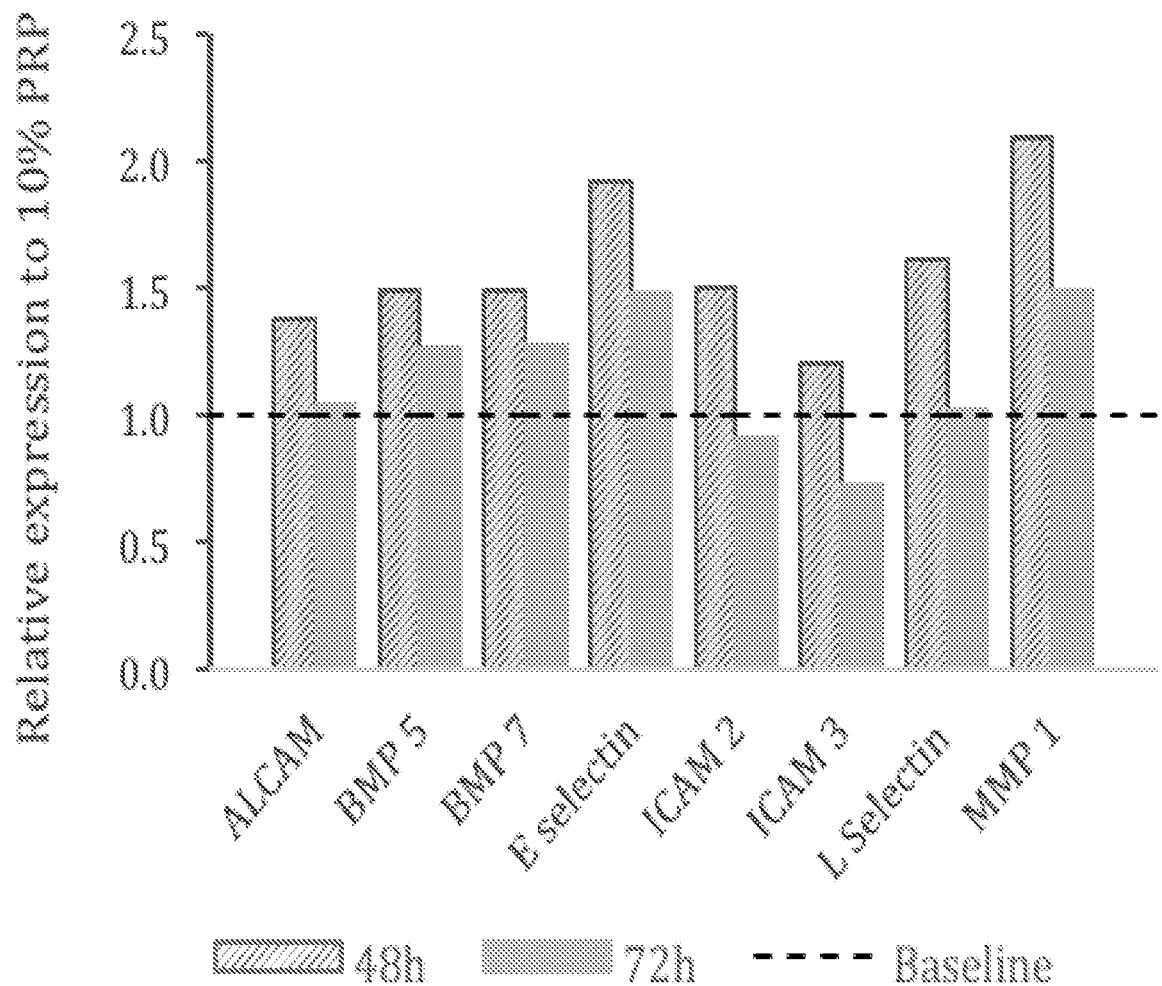
Figure 52:
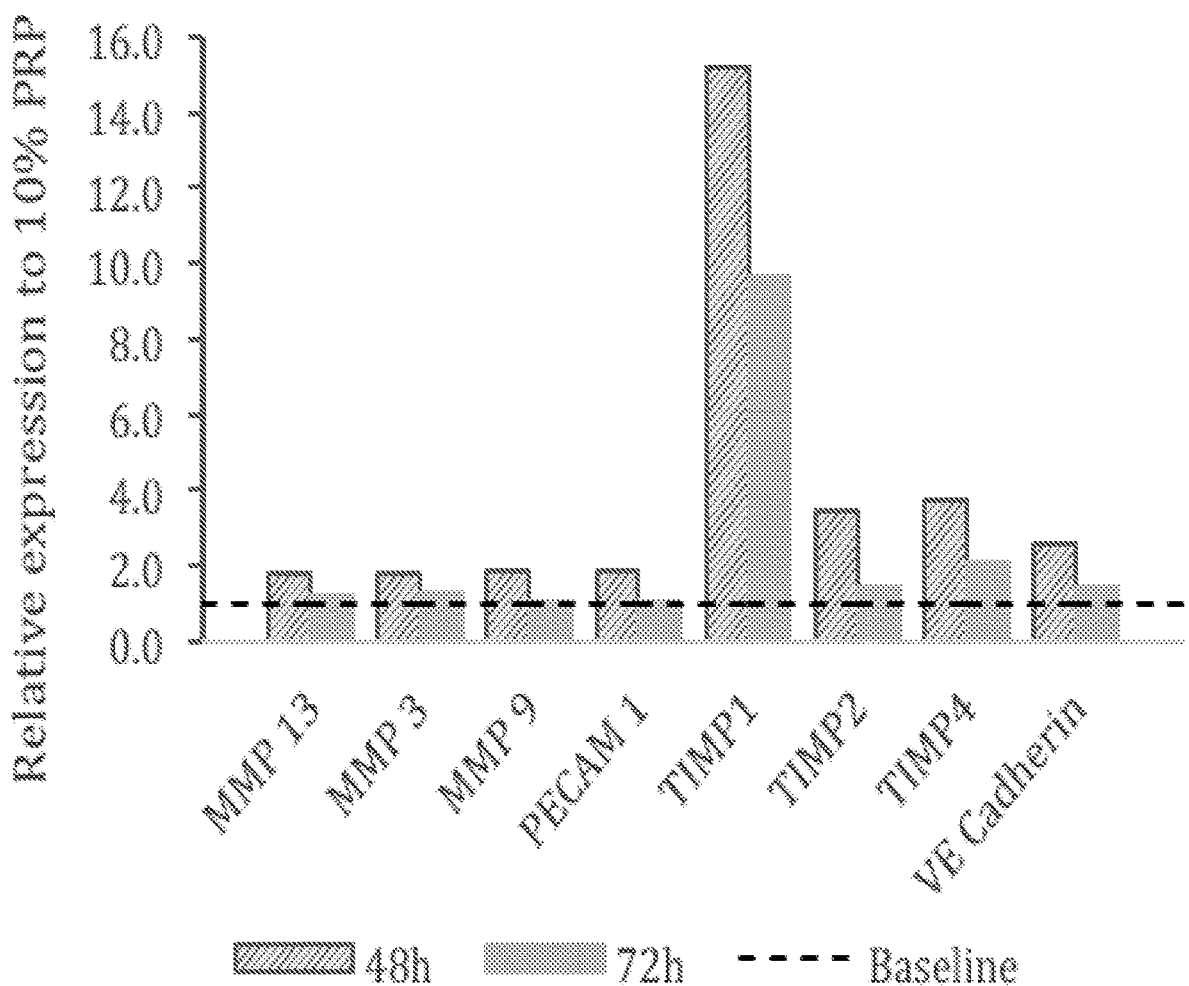
Figure 53:
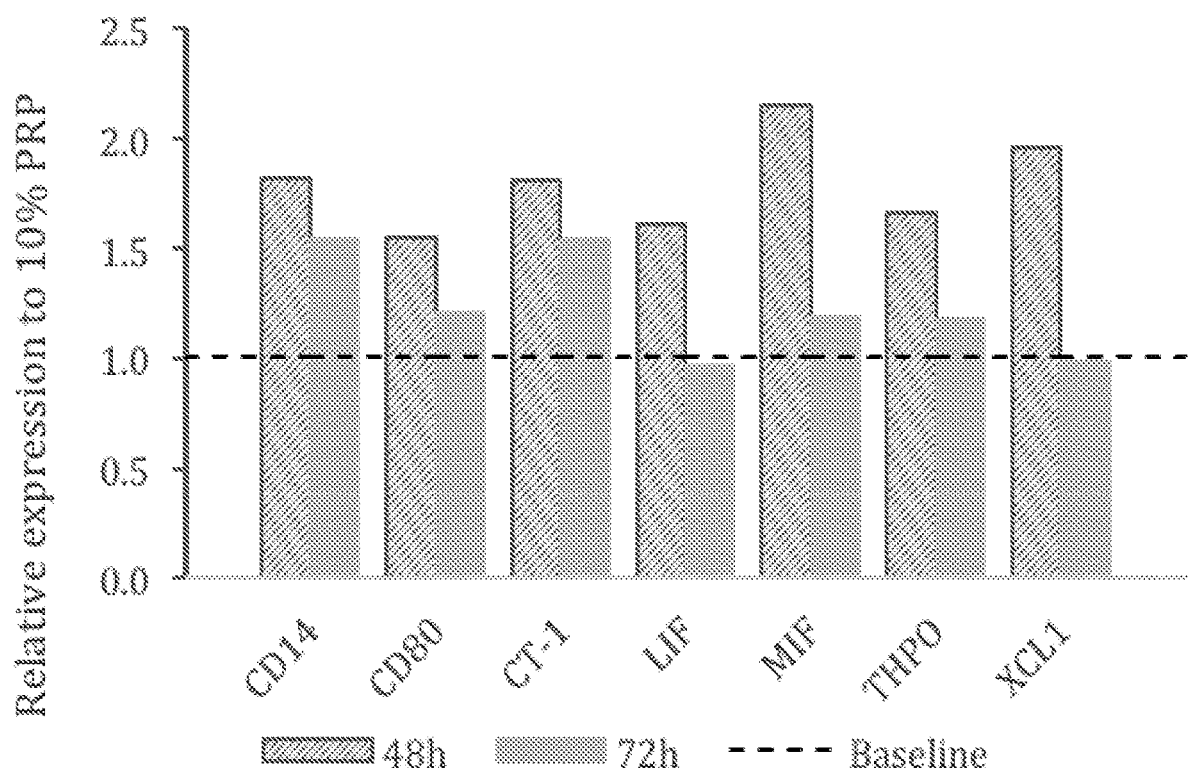

FIG. 44 shows the increase in secretion of Interleukin 9 (IL9), Interleukin 11 (IL 11), Interleukin 12 alpha (IL12a), Interleukin 12 beta (IL12b), and Interleukin 18 binding protein alpha (IL18BPa). FIG. 45 shows the increase in secretion of Interleukin 1 receptor type I (IL1R1), Interleukin 1 receptor type II (IL1R2), Interleukin 1 receptor type IV (IL1R4), Interleukin 2 receptor beta (IL-2Rb), Interleukin 2 receptor gamma (IL-2Rg), Interleukin 5 receptor alpha (IL5Ra) Interleukin 10 receptor beta (IL10Rb), Interleukin 18 receptor beta (IL18Rb), and Interleukin 21 receptor (IL-21R). FIG. 46 shows the increase in secretion of Fibroblast growth factor 4 (FGF4), FGF9, MSP alpha/HGF like factor (HGF like), Insulin-like growth factor 1 (IGF1), IGF2, insulin-like growth factor-binding protein-6 (IGFBP6), LAP (TGF beta family), and platelet derived growth factor A alpha (PDGFAA). FIG. 47 shows the increase in secretion of platelet derived growth factor A beta (PDGFAB), platelet derived growth factor B beta (PDGFBB), Stromal Cell-Derived Factor-1 alpha (SDF1a), Sialic acid-binding Ig-like Lectin 5 (Siglec 5), Transforming growth factor alpha (TGFa), Transforming growth factor beta 2 (TGFb2), Vascular endothelial growth factor (VEGF), and Vascular endothelial growth factor D (VEGFD). FIG. 47 also shows the increase in secretion of DR6, Dtk, EGFR, Endoglin, ErbB3, Fas, Fas LG, and IGF1 sR. FIG. 48 shows the increase in secretion of Leptin (LEP), Leptin Receptor (LEPR), Macrophage colony-stimulating factor 1 receptor (MCSFR), Neurotrophin 4 (NT4), Osteoprotegerin (OPG), platelet-derived growth factor receptor alpha (PDGFRa), platelet-derived growth factor receptor beta (PDGFRb), and Prolactin (PRL). FIG. 49 shows the increase in secretion of Stem cell factor receptor (SCFR), Angiopoietin 1 receptor (TIE1), Angiopoietin 1 receptor (TIE2), TNF superfamily member 10C (TNFSF10C), TNF superfamily member 10D (TNFSF10D), TNF superfamily member 14 (TNFSF14), urokinase plasminogen activator receptor (uPAR), and Vascular endothelial growth factor receptor-2 (VEGFR2). FIG. 50 shows the increase in secretion of Chemokine (C-C motif) ligand 2 (CCL2), CCL3, CCL5, CCL8, CCL17, CCL20, CCL25, CXC chemokine ligand 5 (CXCL5), CXCL11, and CXCL16. FIG. 51 shows the increase in secretion of activated leukocyte cell adhesion molecule (ALCAM), Bone morphogenetic protein 5 (BMP5), BMP7, E selectin (endothelial cell adhesion molecule), Intercellular adhesion molecule 2 (ICAM2), ICAM3, L selectin (Lymphocyte adhesion molecule), and matrix metalloproteinase 1 (MMP1). FIG. 52 shows the increase in secretion of matrix metalloproteinase 13 (MMP13), MMP3, MMP9, Platelet endothelial cell adhesion molecule (PECAM 1), Metalloproteinase inhibitors TIMP 1, TIMP 2, TIMP 4, and vascular epithelium (VE) Cadherin (calcium dependent cell adhesion protein). FIG. 53 shows the increase in secretion of monocyte differentiation antigen (CD14), cell differentiation antigen (CD80), Cardiotrophin-1 (CT-1), Leukemia inhibitory factor (LIF), Macrophage migration inhibitory factor (MIF), Thrombopoietin (THPO), and Lymphotactin (XCL1).

As shown in FIG. 44, certain factors are increased. IL18BPa can block interleukins IL18 induced interferon gamma production and is associated with suppression of inflammatory responses initiated by infections, trauma and allergies. IL9 prevents apoptosis and inhibition of melanoma. IL11 is associated with adipogenesis inhibitory factor, improves platelet recovery after chemotherapy and modulates Ag/Ab responses. IL9 participates in bone-cell proliferation differentiation. IL12 induces interferon gamma, stimulates differentiation of Th1 and Th2, potent immunomodulators.

FIG. 54 shows the increase in secretion of Nerve growth factor receptor (NGFR) from SR-hADSCs maintained in a factor production unit of the invention, 48 hours post stimulation with IL-2. FIG. 54 also shows increase in the secretion of IL8 and TNFRSF1A with IL-2 at 24h post-IL-2 stimulation. NGFR, IL8 and TNFRSF1A were found to not be present in PRP.

Figure 55:
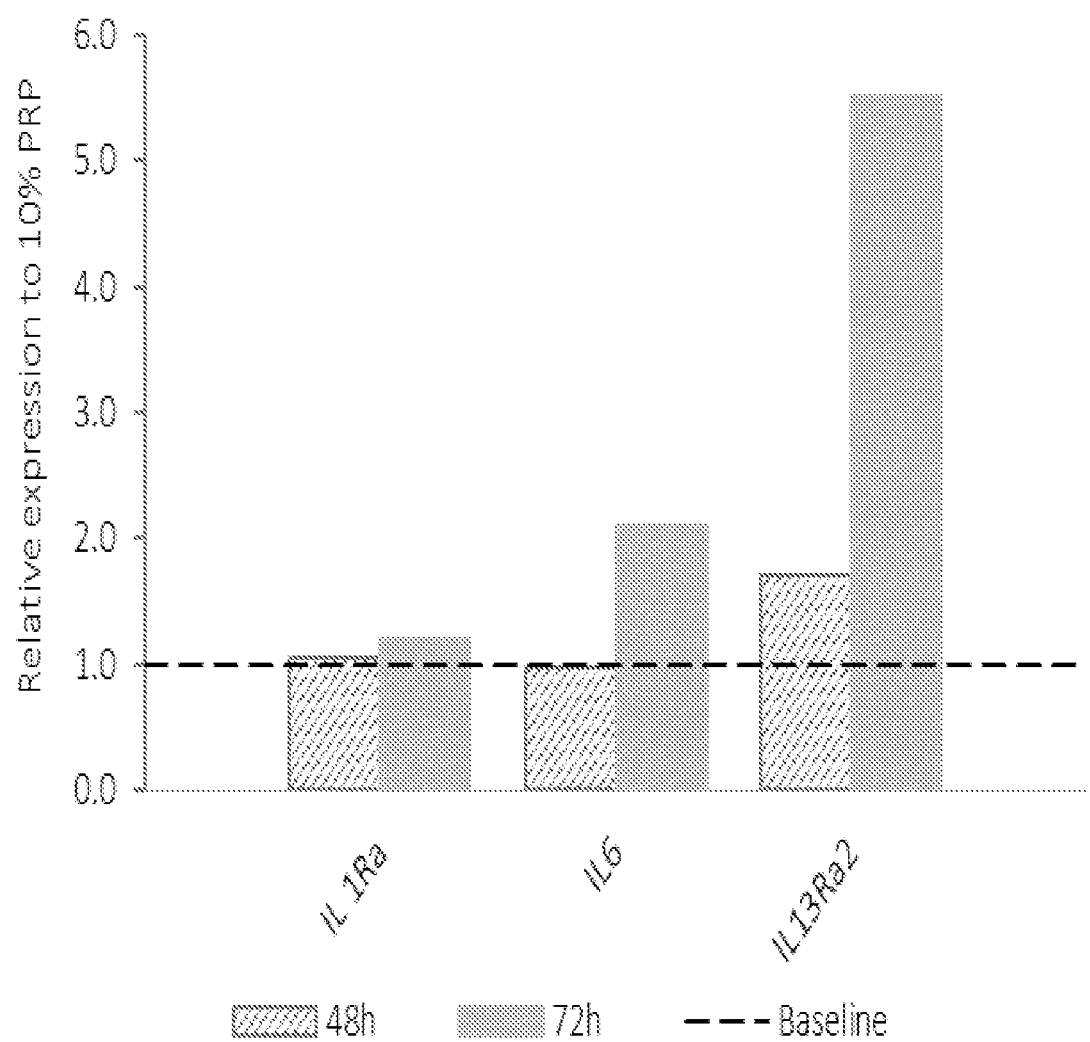
Figure 56:
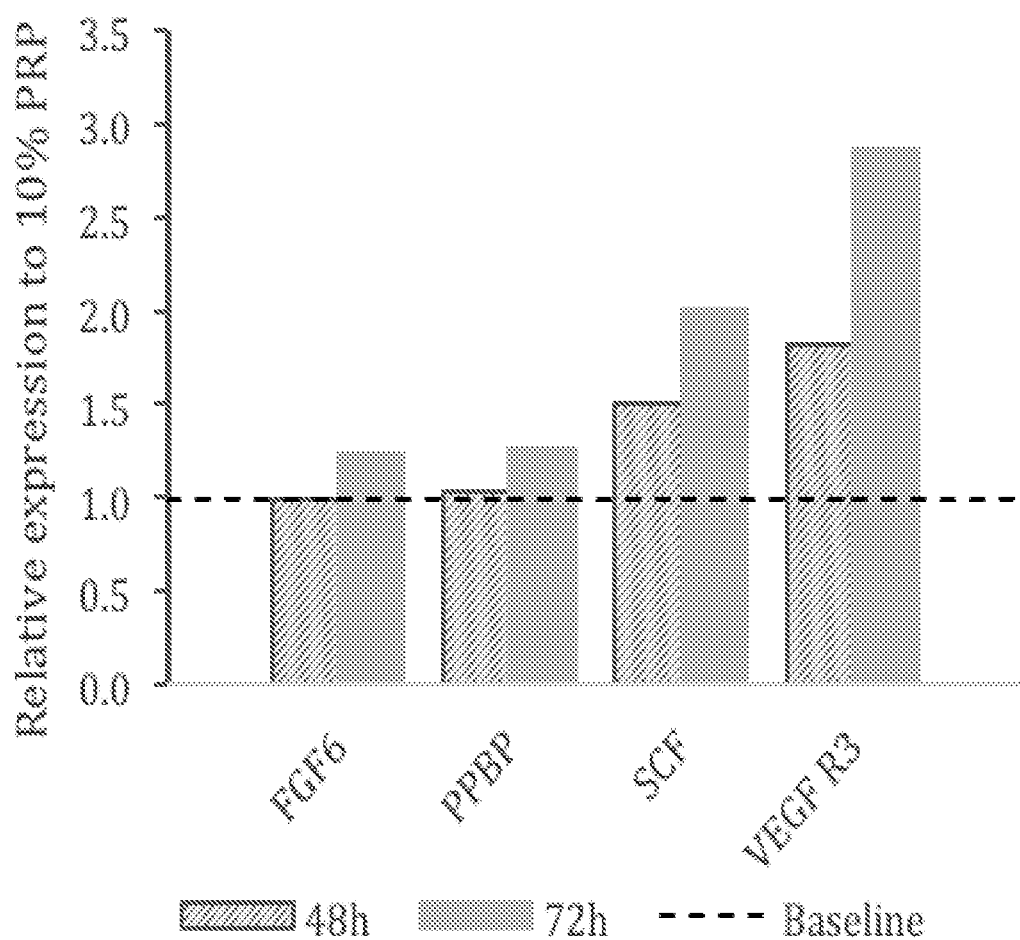
Figure 57:
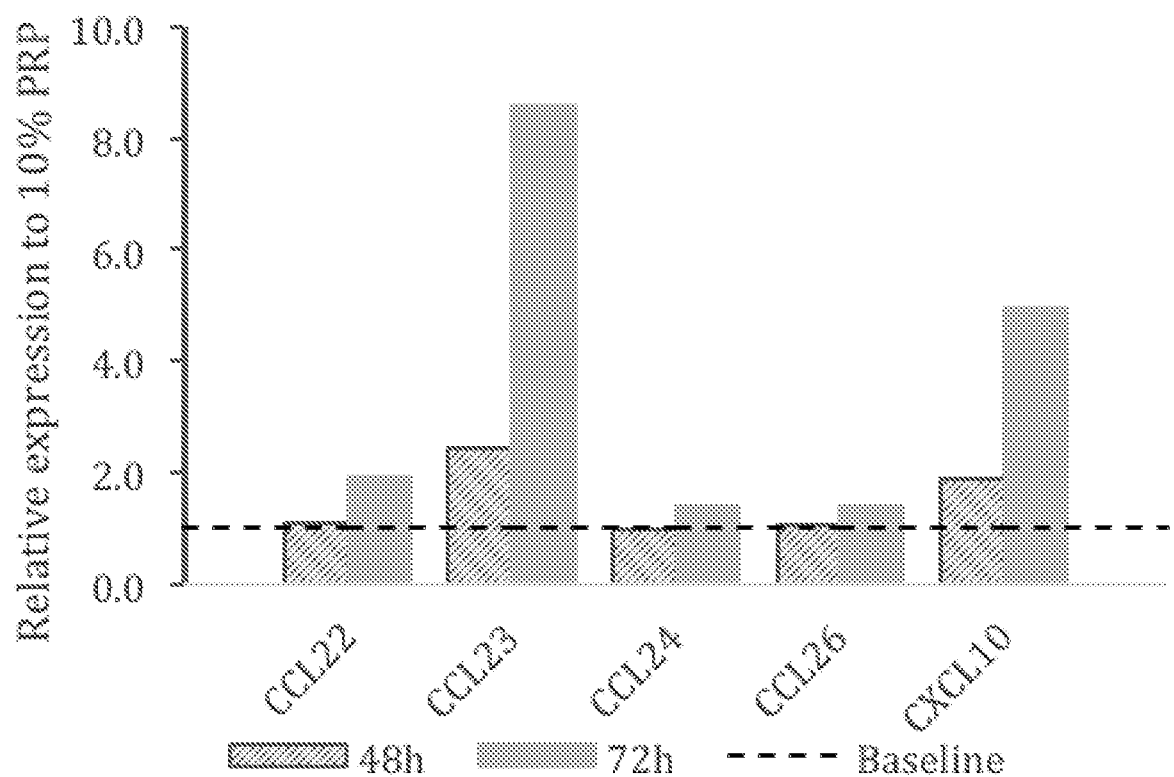

FIGS. 55-57 show the increase in the secretion of the below named proteins (factors) from SR-hADSCs maintained in a factor production unit of the invention, 72 hours post stimulation with IL-2. Secretion levels are shown relative to the amount of the corresponding protein present at basal levels in the 10% PRP containing media, used for hADSC support. FIG. 55 shows the increase in secretion of Interleukin 1 receptor alpha (IL1Ra), Interleukin 6 (IL6), and Interleukin-13 receptor subunit alpha-2 (IL13Ra2). FIG. 56 shows the increase in secretion of Fibroblast growth factor 6 (FGF6), pro-platelet basic protein (PPBP), stem cell factor (SCF), and Vascular endothelial growth factor receptor-3 (VEGFR3). FIG. 57 shows the increase in secretion of Chemokine (C-C motif) ligand 22 (CCL22), CCL23, CCL24, CCL26, and CXC chemokine ligand 10 (CXCL10).

Figure 58:
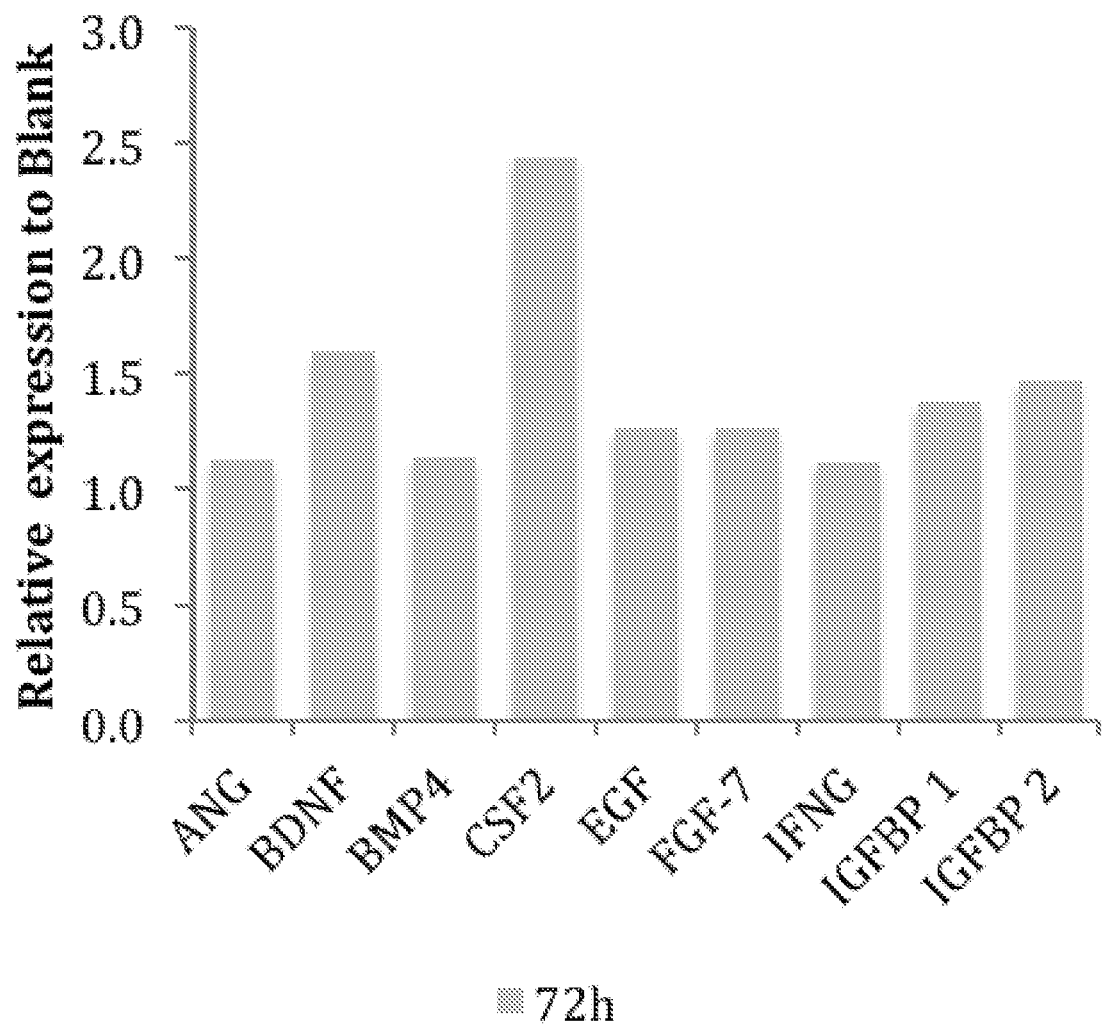

FIG. 58 shows the increase in secretion of Angiotensin (ANG), Brain-derived neurotrophic factor (BDNF), Bone morphogenetic protein 4 (BMP4), colony stimulating factor 2 (CSF2), Epidermal growth factor (EGF), Fibroblast growth factor 7 (FGF-7), Interferon gamma (IFNγ), insulin-like growth factor-binding protein-1 (IGFBP 1), and IGFBP 2 from SR-hADSCs maintained in a factor production unit of the invention, 72 hours post stimulation with IL-2. These factors were found to not be present in PRP.

Figure 59:
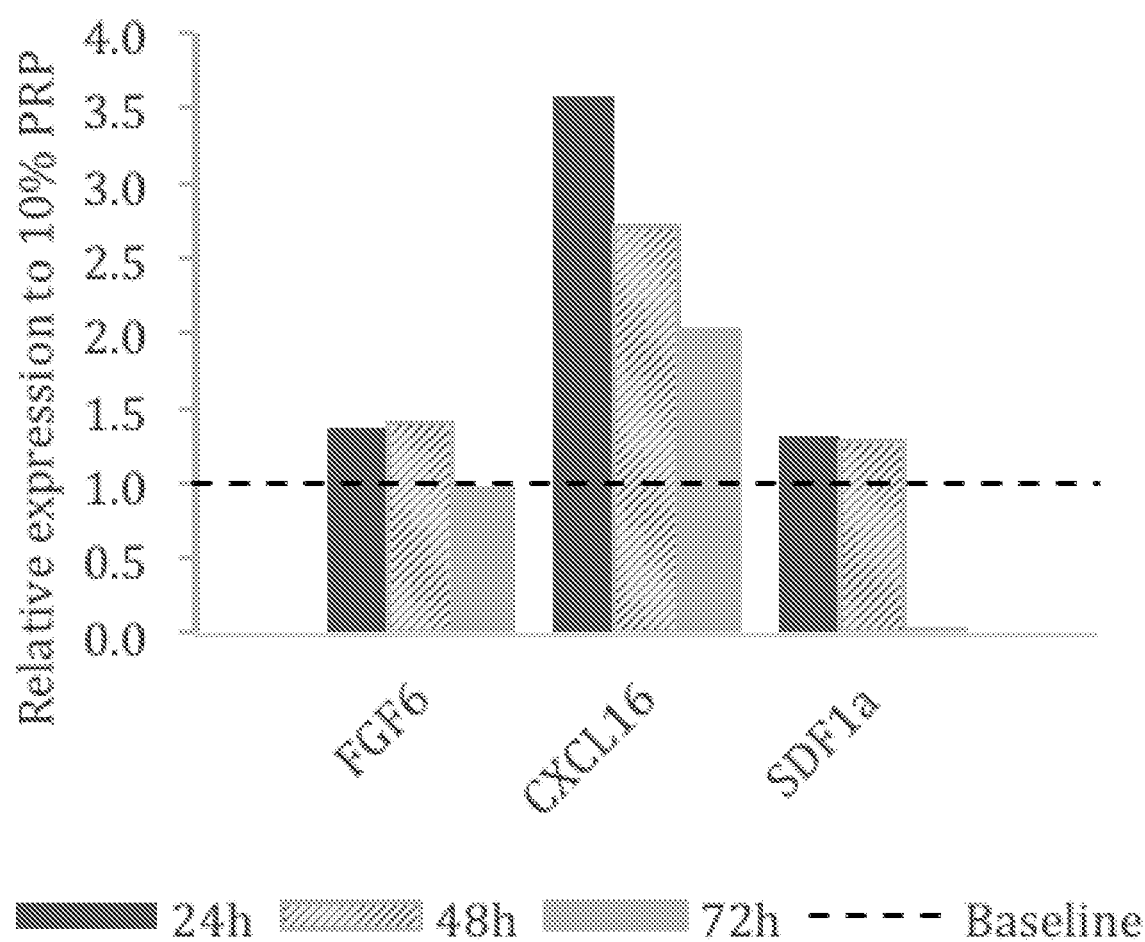

FIG. 59 shows the increase in secretion of Fibroblast growth factor 6 (FGF6), CXC chemokine ligand 16 (CXCL16), and Stromal Cell-Derived Factor-1 alpha (SDF1a) from SEN-hADSCs maintained in a factor production unit of the invention, 24 hours post incubation with 10% PRP alone (no IL-2 stimulation). Secretion levels are shown relative to the amount of the corresponding protein present at basal levels in the 10% PRP containing media, used for hADSC support.

Figure 60:
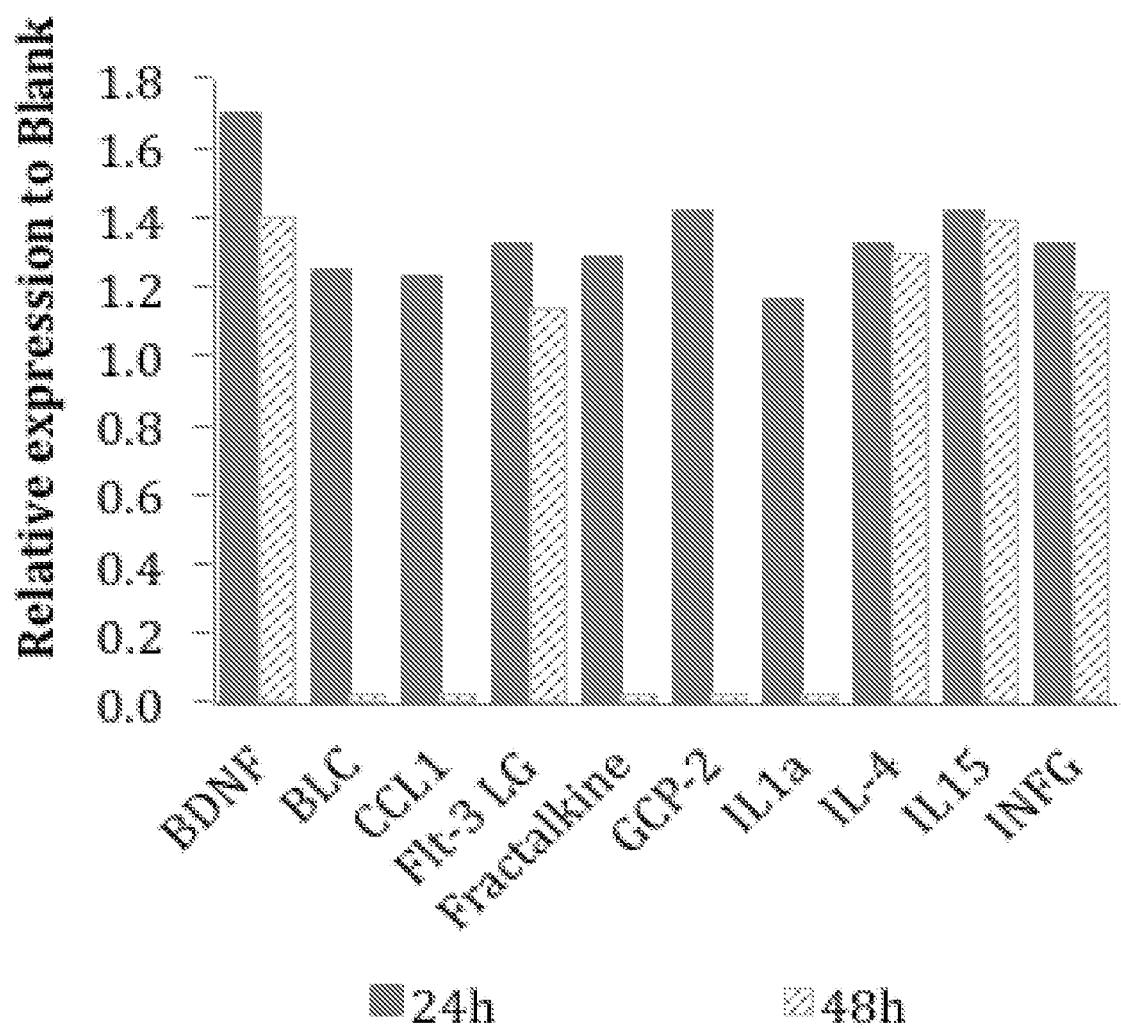

FIG. 60 shows the increase in secretion of Brain-derived neurotrophic factor (BDNF), B lymphocyte chemokine (CXCL13; BLC), Chemokine (C-C motif) ligand 1 (CCL1), Flt-3 LG (Fms-Related Tyrosine Kinase 3 Ligand), Fractalkine (T-cell chemokine CX3CL1), granulocyte chemotactic protein 2 (GCP-2)/CXCL6, Interleukin 1 alpha (IL1a), Interleukin 4 (IL4), IL15, and Interferon gamma (IFNγ) from SEN-hADSCs maintained in a factor production unit of the invention, 24 hours post incubation with 10% PRP alone (no IL-2 stimulation). These factors were found to not be present in PRP.

Figure 61:
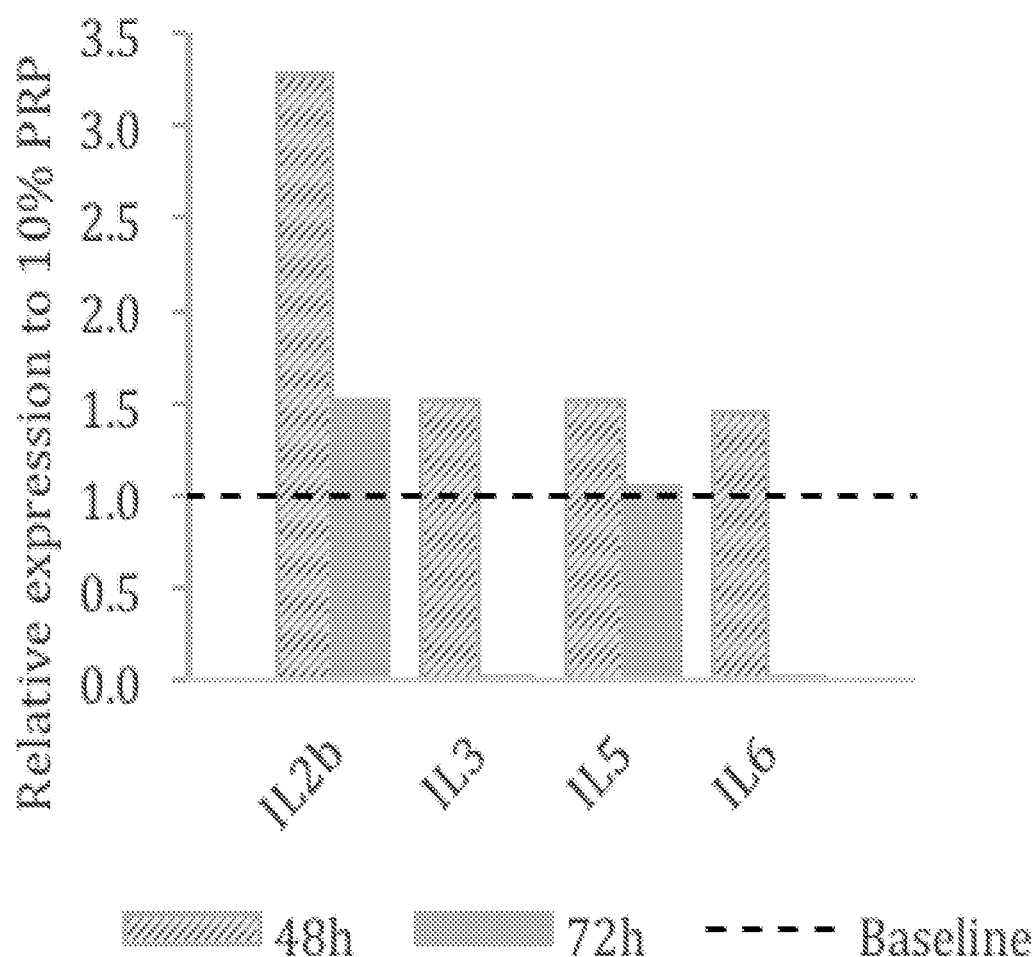
Figure 62:
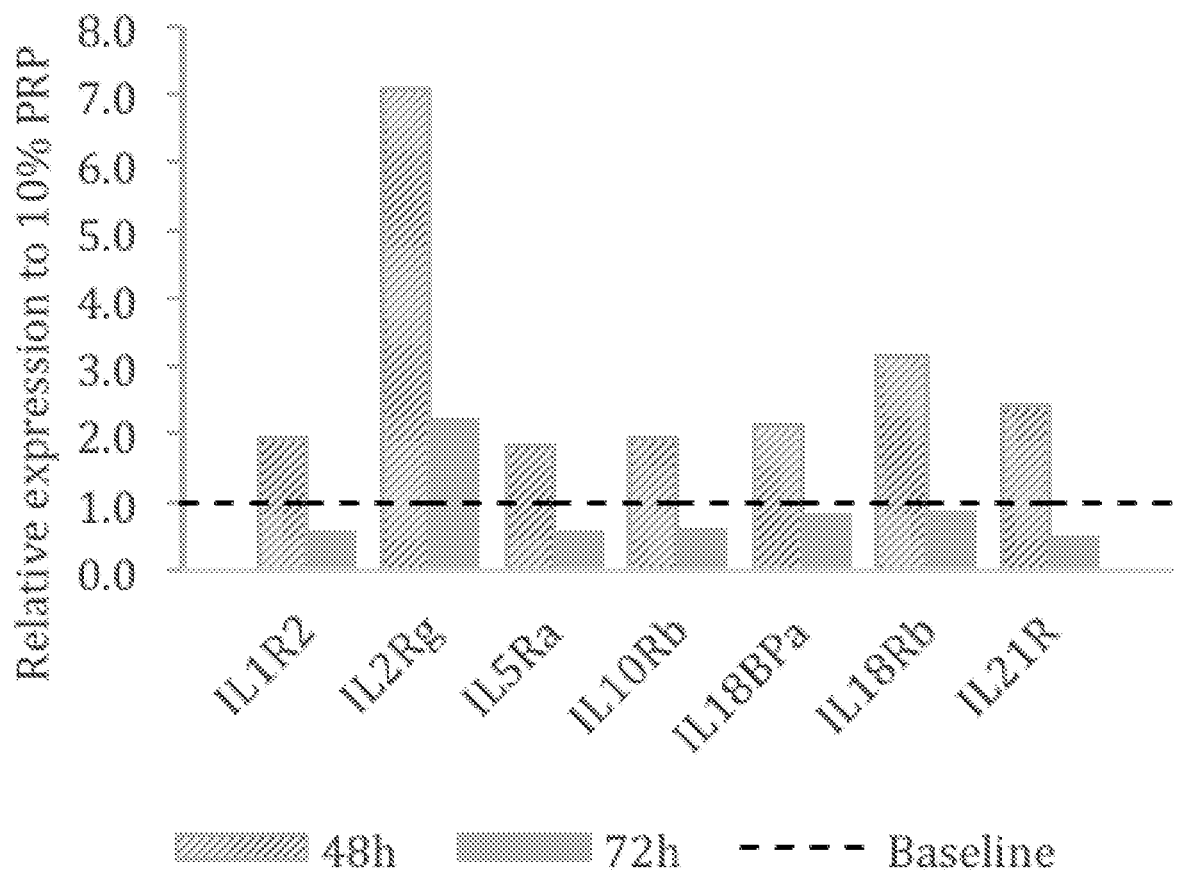
Figure 63:
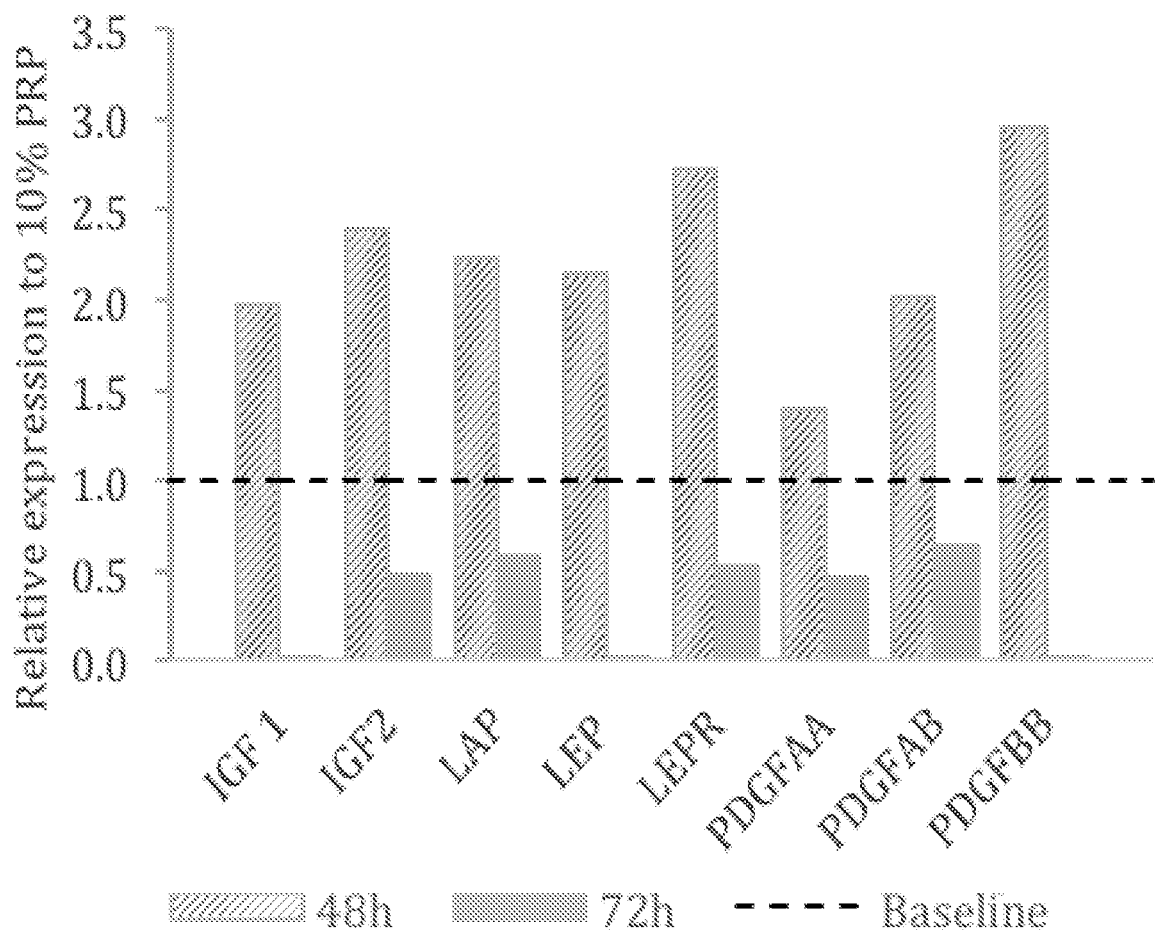
Figure 64:
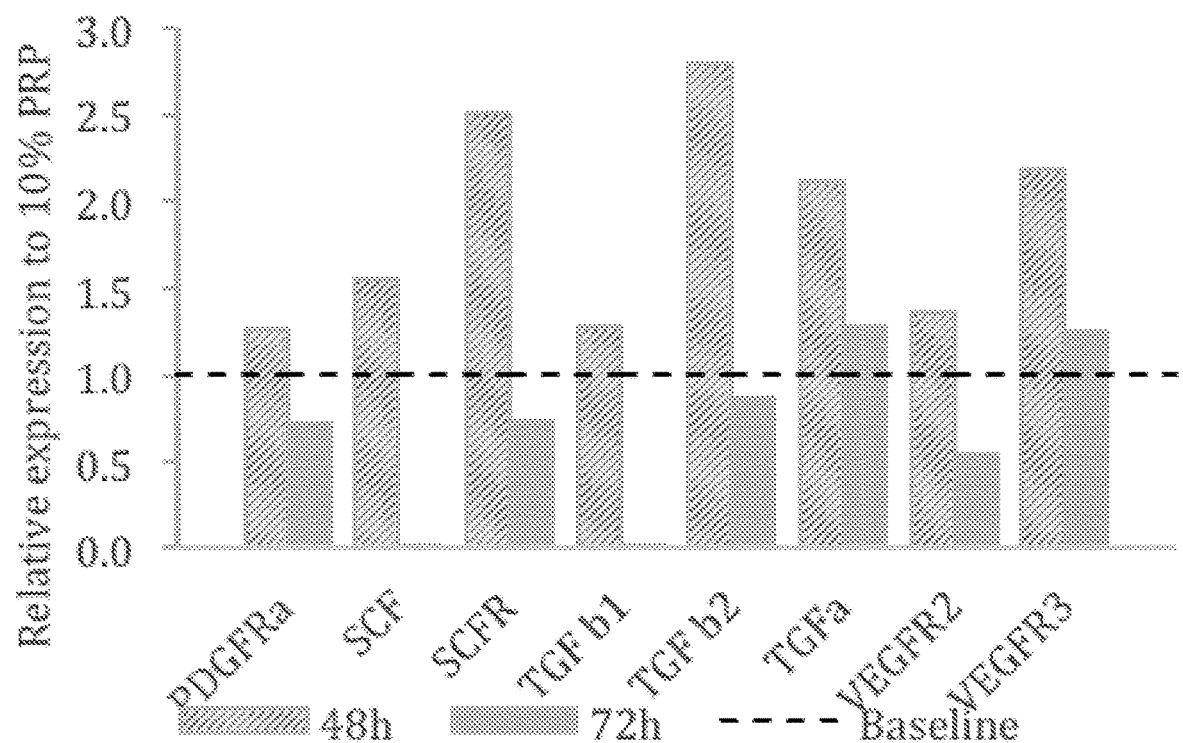
Figure 65:
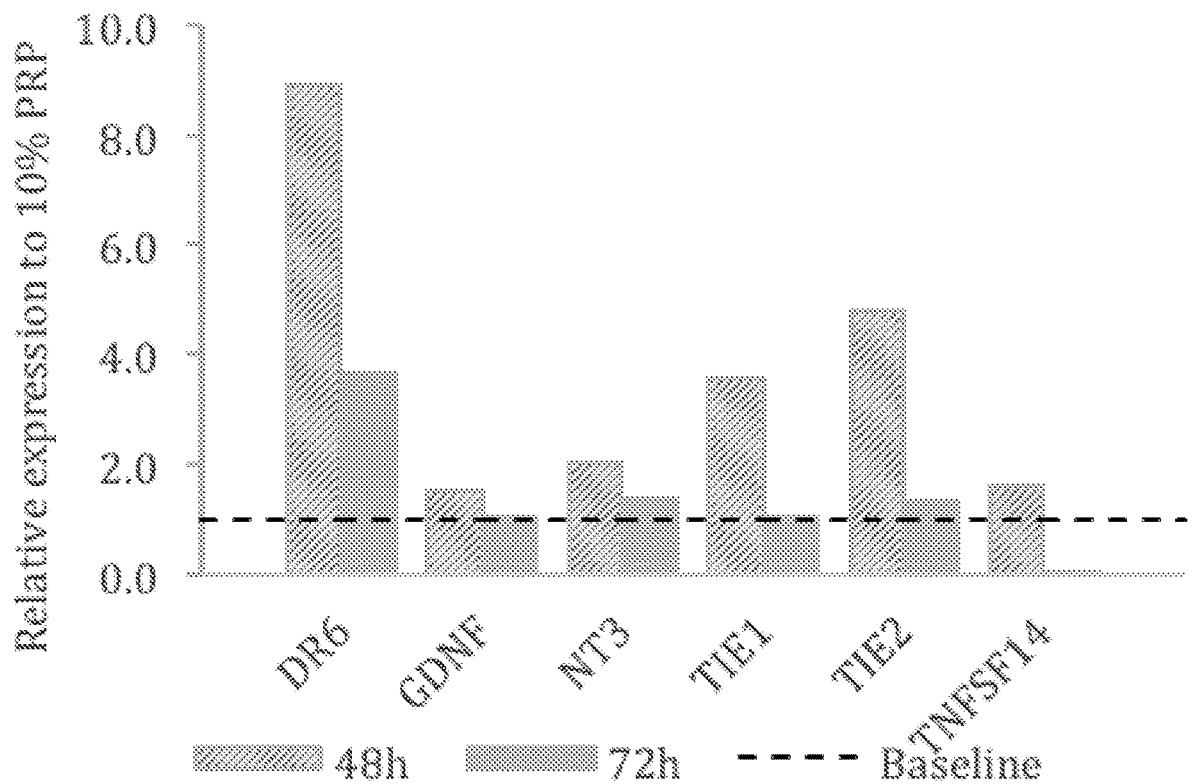
Figure 66:
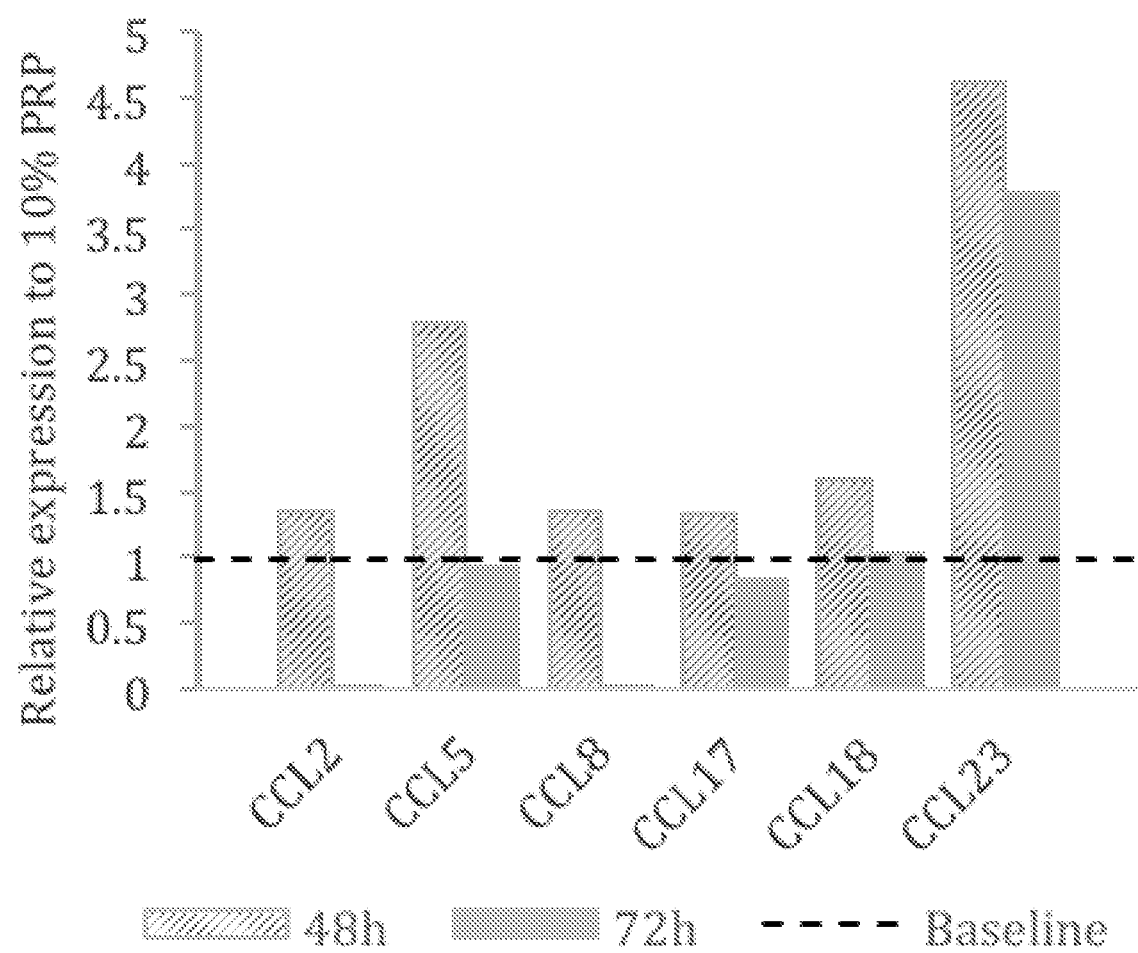
Figure 67:
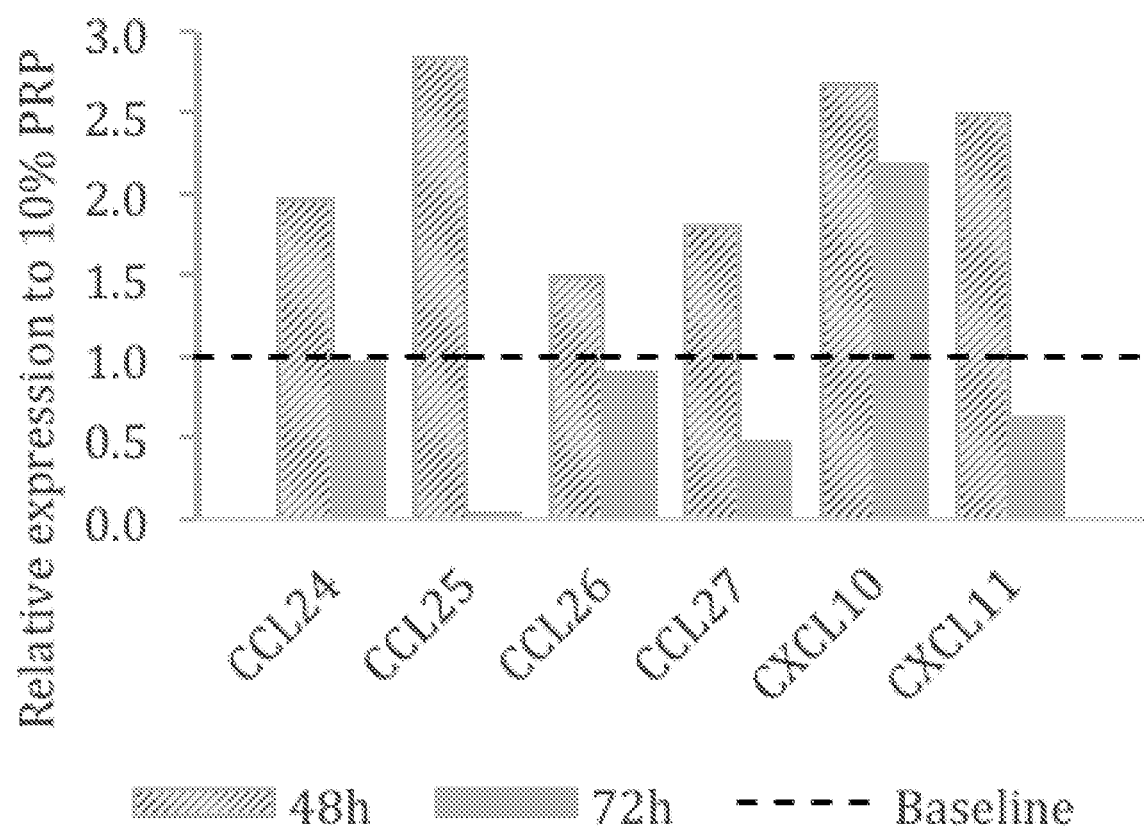
Figure 68:
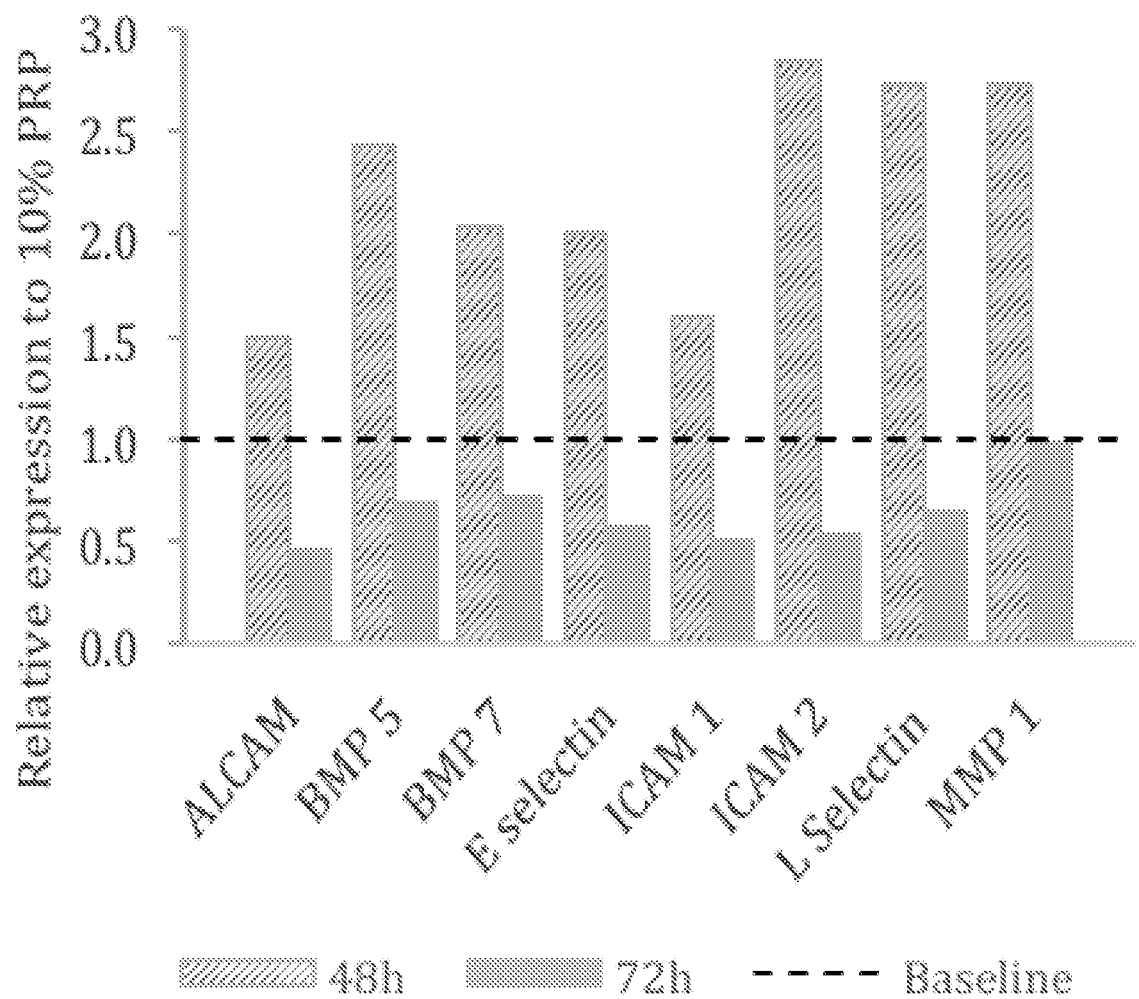
Figure 69:
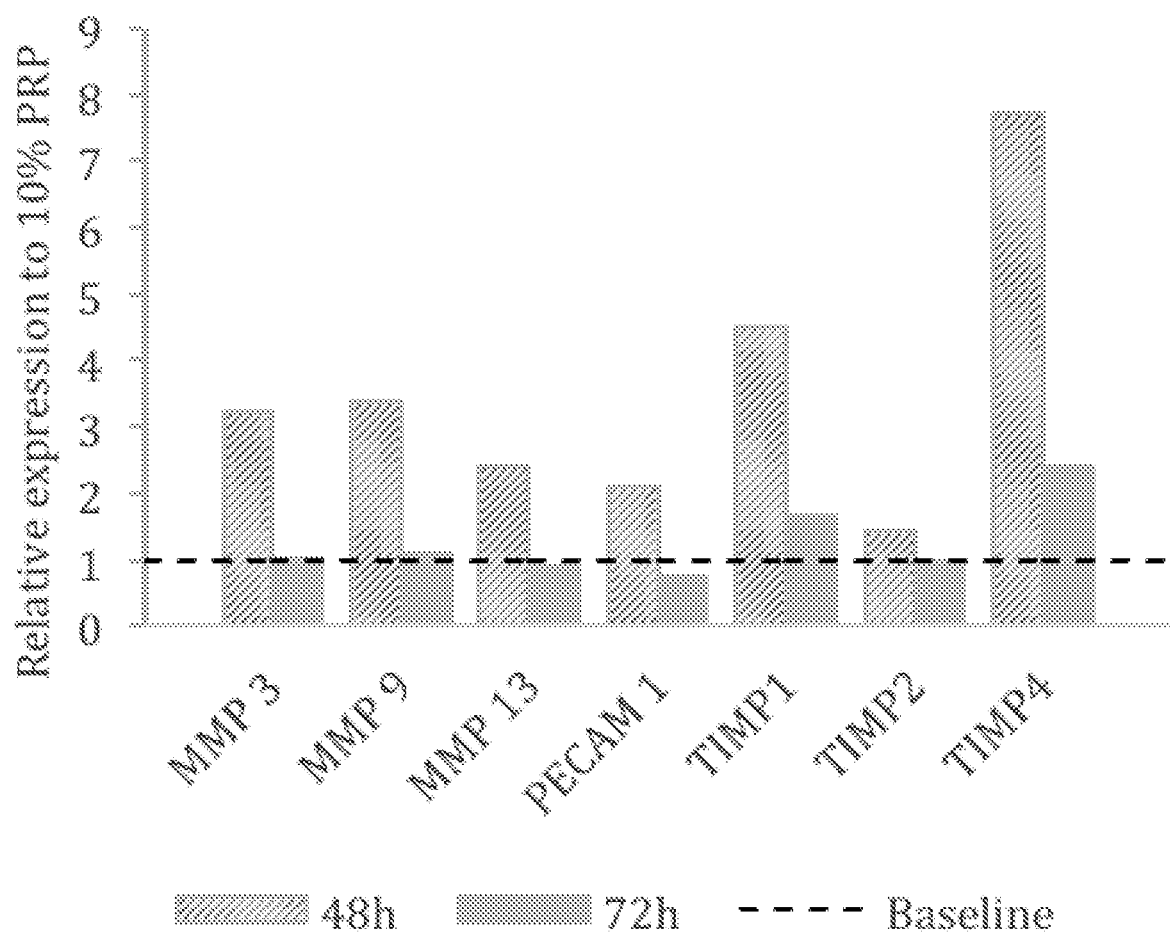
Figure 70:
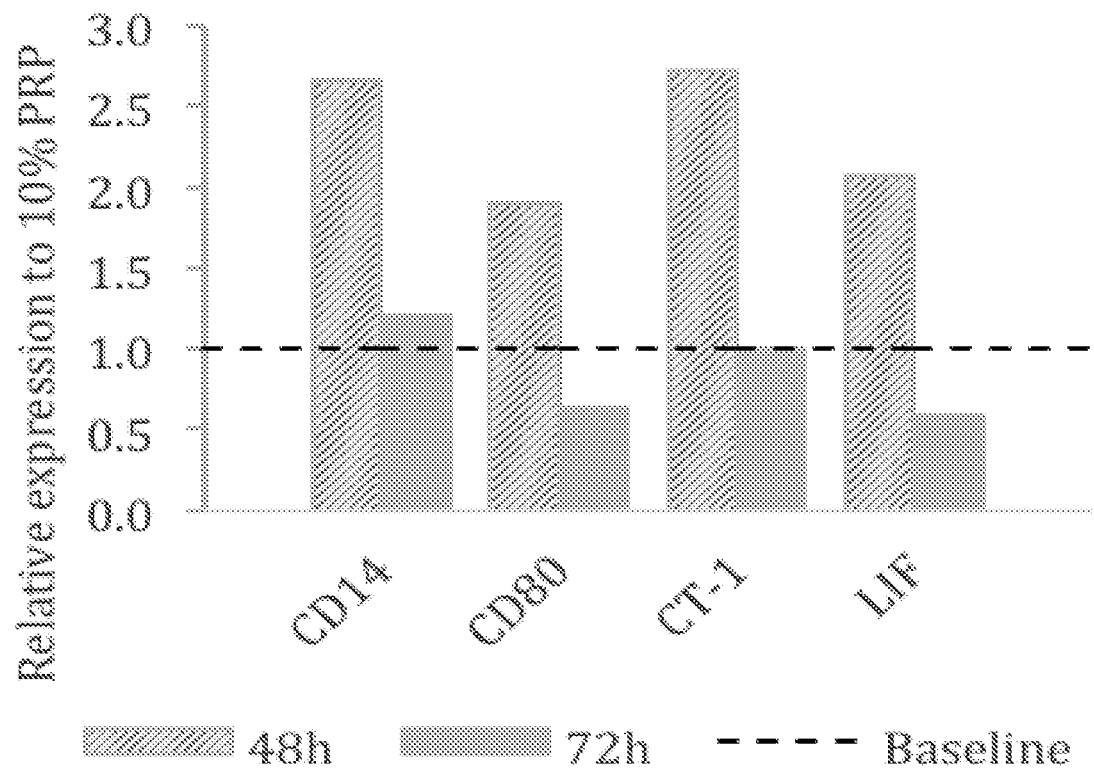

FIGS. 61-70 show the increase in the secretion of the below named proteins (factors) from SEN-hADSCs maintained in a factor production unit of the invention, 48 hours post incubation with 10% PRP alone (no IL-2 stimulation). Secretion levels are shown relative to the amount of the corresponding protein present at basal levels in the 10% PRP containing media, used for hADSC support. FIG. 61 shows the increase in secretion of Interleukin 2 beta (IL-2b), IL3, IL5, and IL6. FIG. 62 shows the increase in secretion of Interleukin 1 receptor type II (IL1R2), Interleukin 2 receptor gamma (IL-2Rg), Interleukin 5 receptor alpha (IL5Ra), Interleukin 10 receptor beta (IL10Rb), Interleukin 18 receptor binding protein alpha (IL18BPa), Interleukin 18 receptor beta (IL18Rb), and Interleukin 21 receptor (IL-21R). FIG. 63 shows the increase in secretion of Insulin-like growth factor 1 (IGF1), IGF2, LAP (TGF beta family), Leptin (LEP), Leptin Receptor (LEPR), platelet derived growth factor A alpha (PDGFAA), platelet derived growth factor A beta (PDGFAB), and platelet derived growth factor B beta (PDGFBB). FIG. 64 shows the increase in secretion of platelet-derived growth factor receptor alpha (PDGFRa), Stem cell factor (SCF), Stem cell factor receptor (SCFR), Transforming growth factor beta 1 (TGF b1), Transforming growth factor beta 2 (TGF b2), Transforming growth factor alpha (TGFa), Vascular endothelial growth factor receptor-2 (VEGFR2), and VEGFR3. FIG. 65 shows the increase in secretion of Death receptor 6 (DR6; TNF receptor superfamily member 21), Glial cell line-derived neurotrophic factor (GDNF), Neurotrophin 3 (NT3), Tyrosine kinase with immunoglobulin-like and EGF-like domains 1 (TIE1), TIE2, and TNF superfamily member 14 (TNFSF14). FIG. 66 shows the increase in secretion of Chemokine (C-C motif) ligand 2 (CCL2), CCL5, CCL8, CCL17, CCL18, and CCL23. FIG. 67 shows the increase in secretion of Chemokine (C-C motif) ligand 24 (CCL24), CCL25, CCL26, CCL27, CXC Chemokine ligand 10 (CXCL10), and CXCL11. FIG. 68 shows the increase in secretion of activated leukocyte cell adhesion molecule (ALCAM), Bone morphogenetic protein 5 (BMP5), BMP7, E selectin (endothelial cell adhesion molecule), Intercellular adhesion molecule 1 (ICAM1), ICAM2, L selectin (Lymphocyte adhesion molecule), and matrix metalloproteinase 1 (MMP1). FIG. 69 shows the increase in secretion of matrix metalloproteinase 3 (MMP3), MMP9, MMP13, Platelet endothelial cell adhesion molecule (PECAM 1), Metalloproteinase inhibitors TIMP 1, TIMP 2, and TIMP 4. FIG. 70 shows the increase in secretion of monocyte differentiation antigen (CD14), monocyte differentiation antigen (CD80), Cardiotrophin-1 (CT-1), and Leukemia inhibitory factor (LIF). CT-1 has a broad spectrum of biological activities in vivo such; it can reduce nephrotoxicity, can prevent neuronal death upon injury and imposes protection on neuromuscular degeneration in amyotrophic lateral sclerosis (ALS).

Figure 71:
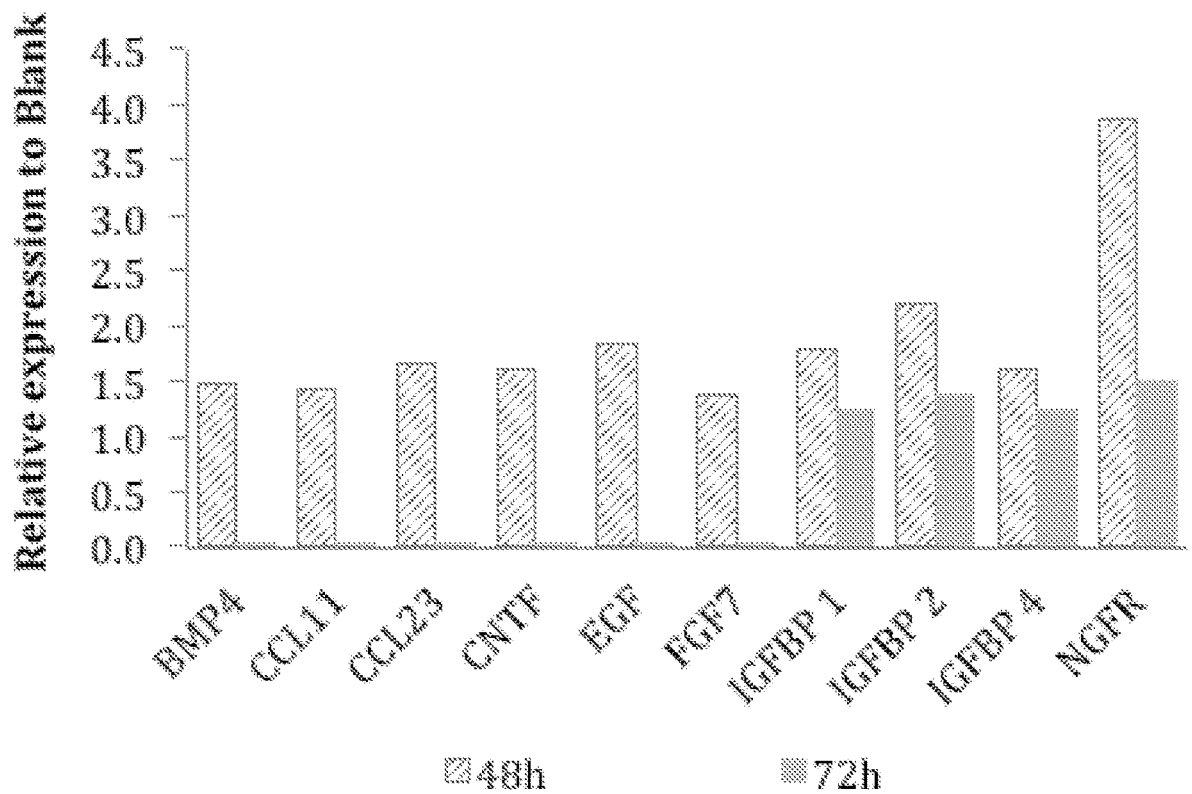
Figure 72:
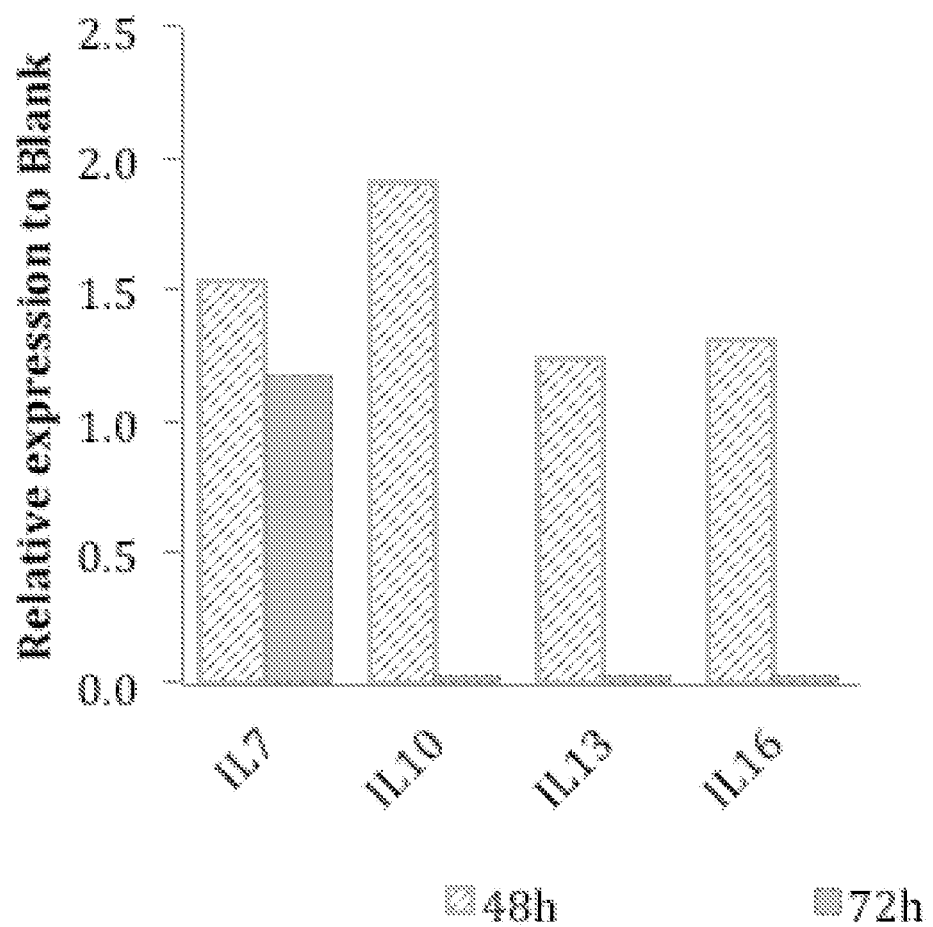

FIGS. 71-72 show the increase in the secretion the below named proteins (factors) from SEN-hADSCs maintained in a factor production unit of the invention, 48 hours post incubation with 10% PRP alone (no IL-2 stimulation). These factors were found to not be present in PRP. FIG. 71 shows the increase in secretion of Bone morphogenetic protein 4 (BMP4), Chemokine (C-C motif) ligand 11 (CCL11), CCL23, Ciliary neurotrophic factor (CNTF), Epidermal growth factor (EGF), Fibroblast growth factor 7 (FGF7), insulin-like growth factor-binding protein-1 (IGFBP1), IGFBP2, IGFBP4, and Nerve growth factor receptor (NGFR). FIG. 72 shows the increase in secretion of Interleukin 7 (IL7), IL10, IL13, and IL16.

Figure 73:
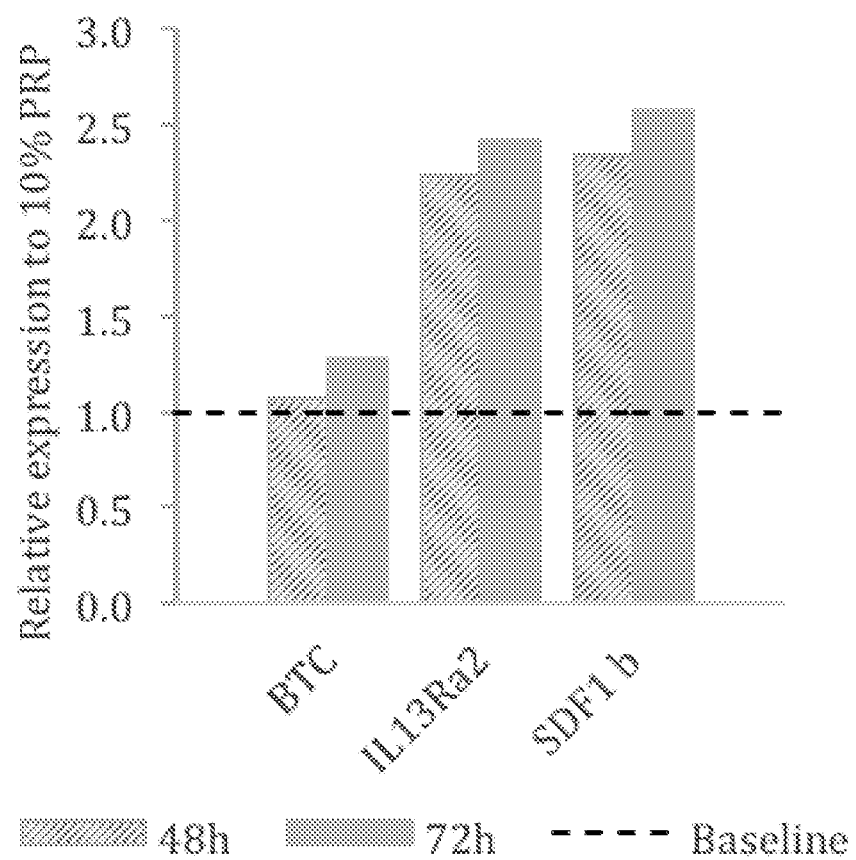

FIG. 73 shows the increase in secretion of Probetacellulin (BTC), Interleukin-13 receptor subunit alpha-2 (IL13Ra2), and Stromal Cell-Derived Factor-1 beta (SDF1b) from SEN-hADSCs maintained in a factor production unit of the invention, 72 hours post incubation with 10% PRP alone (no IL-2 stimulation). Secretion levels are shown relative to the amount of the corresponding protein present at basal levels in the 10% PRP containing media, used for hADSC support.

Figure 74:
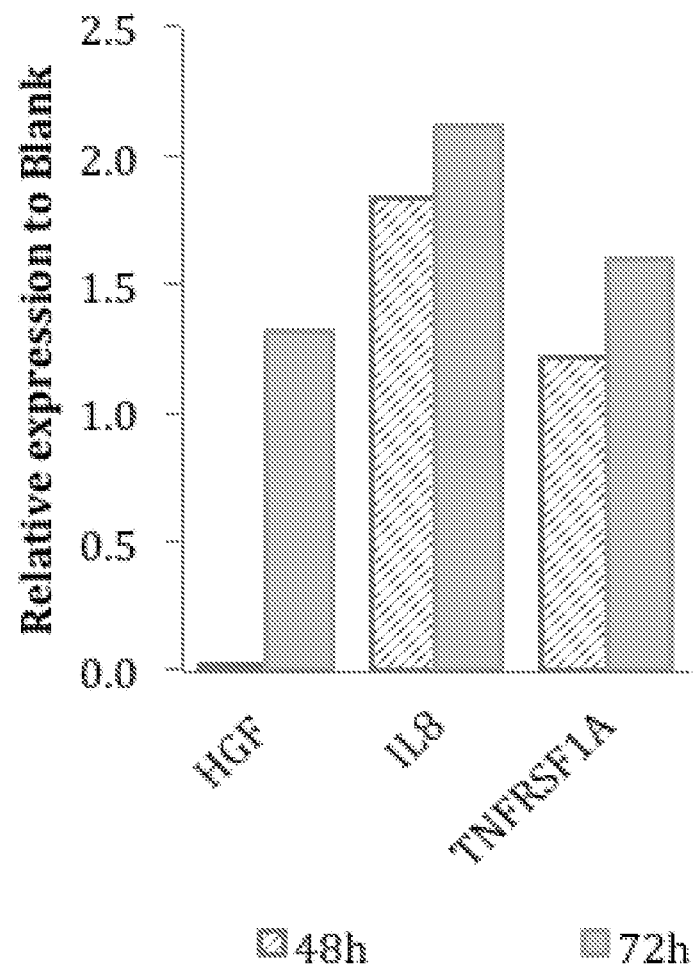

FIG. 74 shows the increase in secretion of Hepatocyte growth factor (HGF), Interleukin 8 (IL8), and TNFRSF1A (Tumor Necrosis Factor Receptor Superfamily, member 1A) from SEN-hADSCs maintained in a factor production unit of the invention, 72 hours post incubation with 10% PRP alone (no IL-2 stimulation). These factors were found to not be present in PRP.

Figure 75:
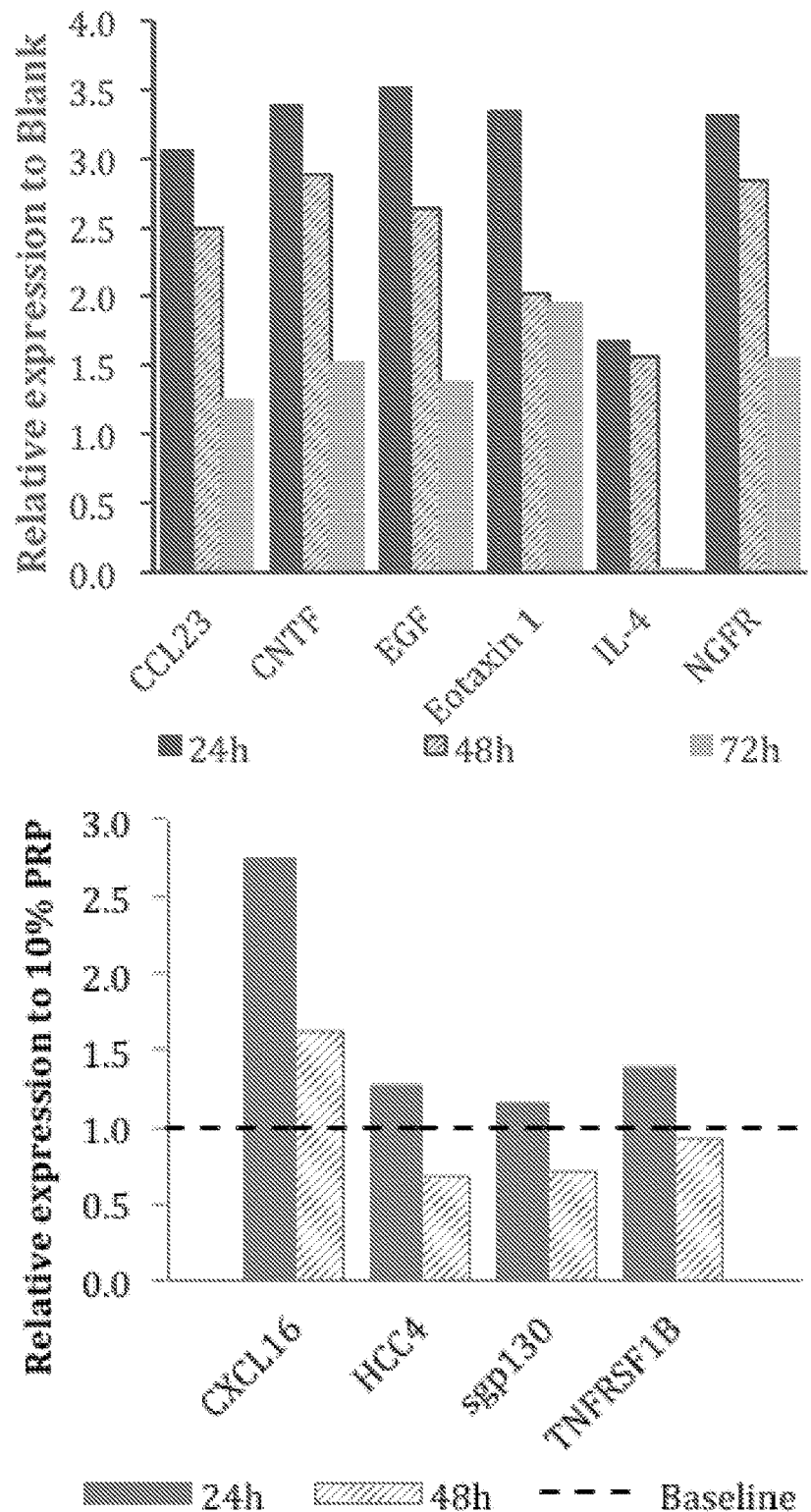

FIG. 75 shows the increase in secretion of Chemokine (C-C motif) ligand 23 (CCL23), Ciliary neurotrophic factor (CNTF), Epidermal growth factor (EGF), CCL11 (Eotaxin 1), ILA, and Nerve growth factor receptor (NGFR) from SEN-hADSCs maintained in a factor production unit of the invention, 24 hours post stimulation with IL-2. These factors were found to not be present in PRP.

FIG. 75 also shows the increase in secretion of CXCL16, HCC4, sgp130, and TNFRSF1B at 24 h post IL-2 stimulation. Secretion levels are shown relative to the amount of the corresponding protein present at basal levels in the 10% PRP containing media.

Figure 76:
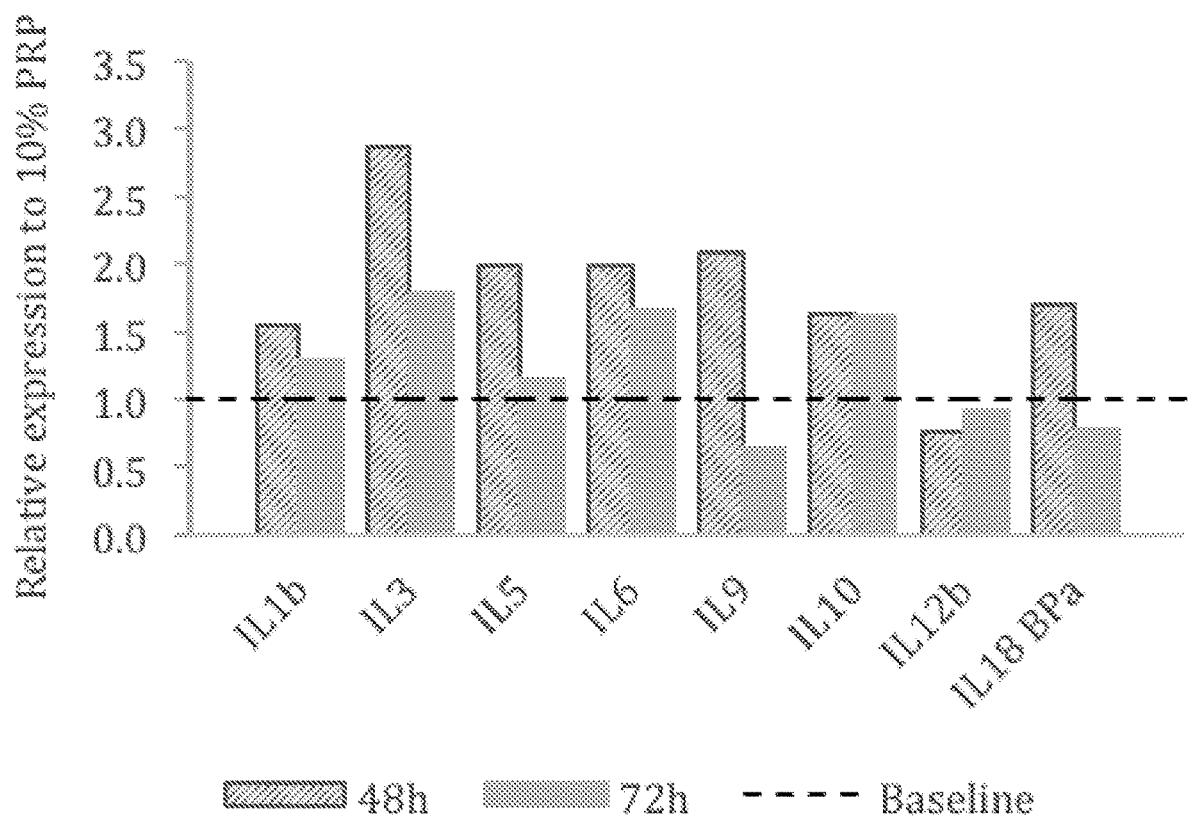
Figure 77:
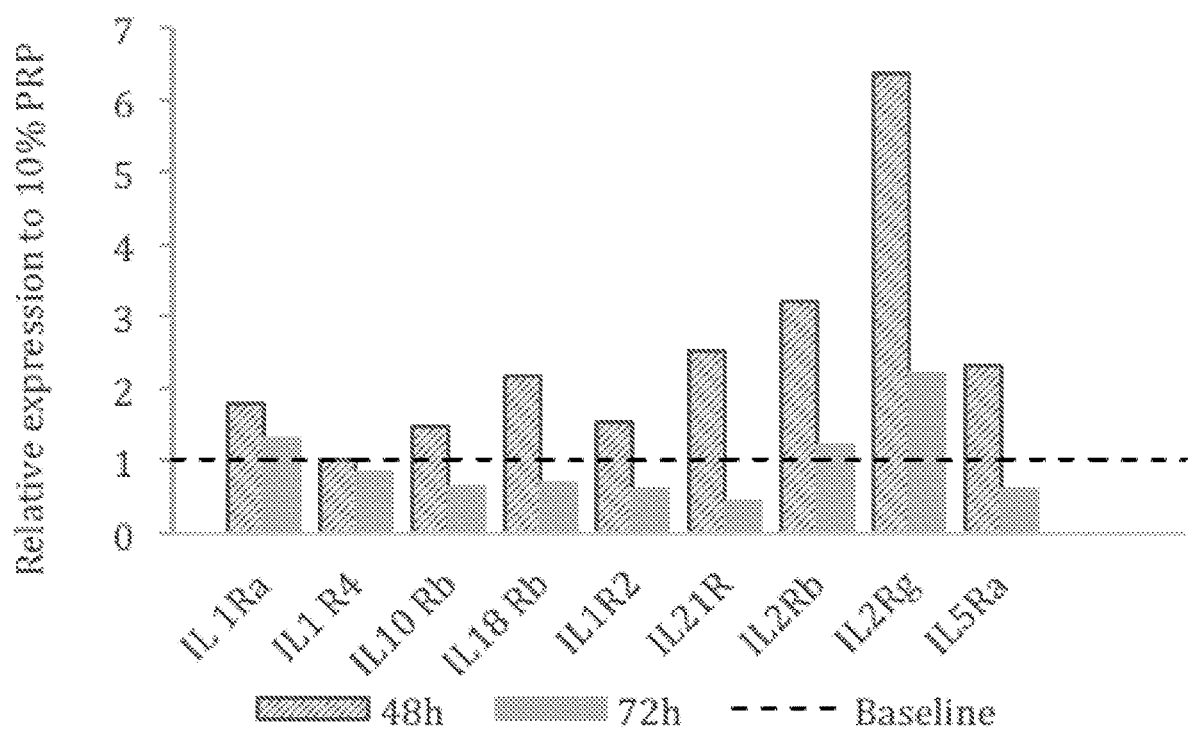
Figure 78:
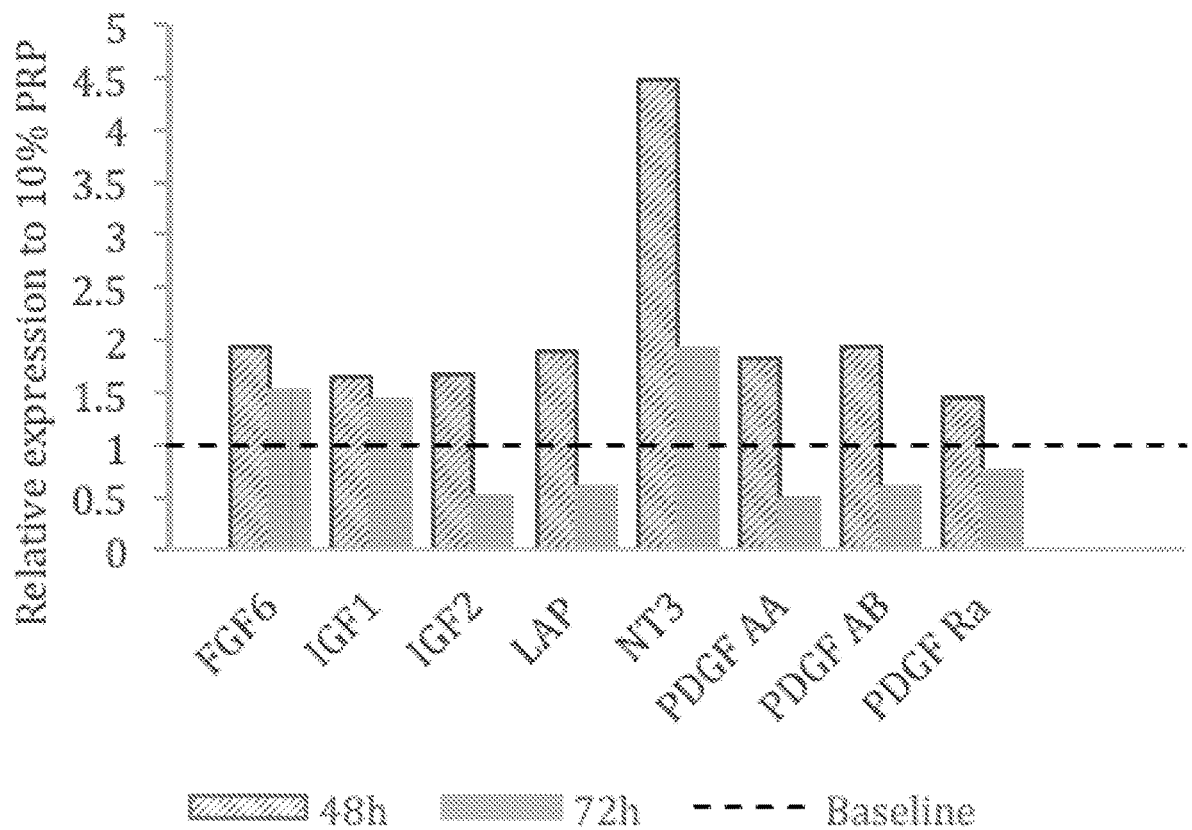
Figure 79:
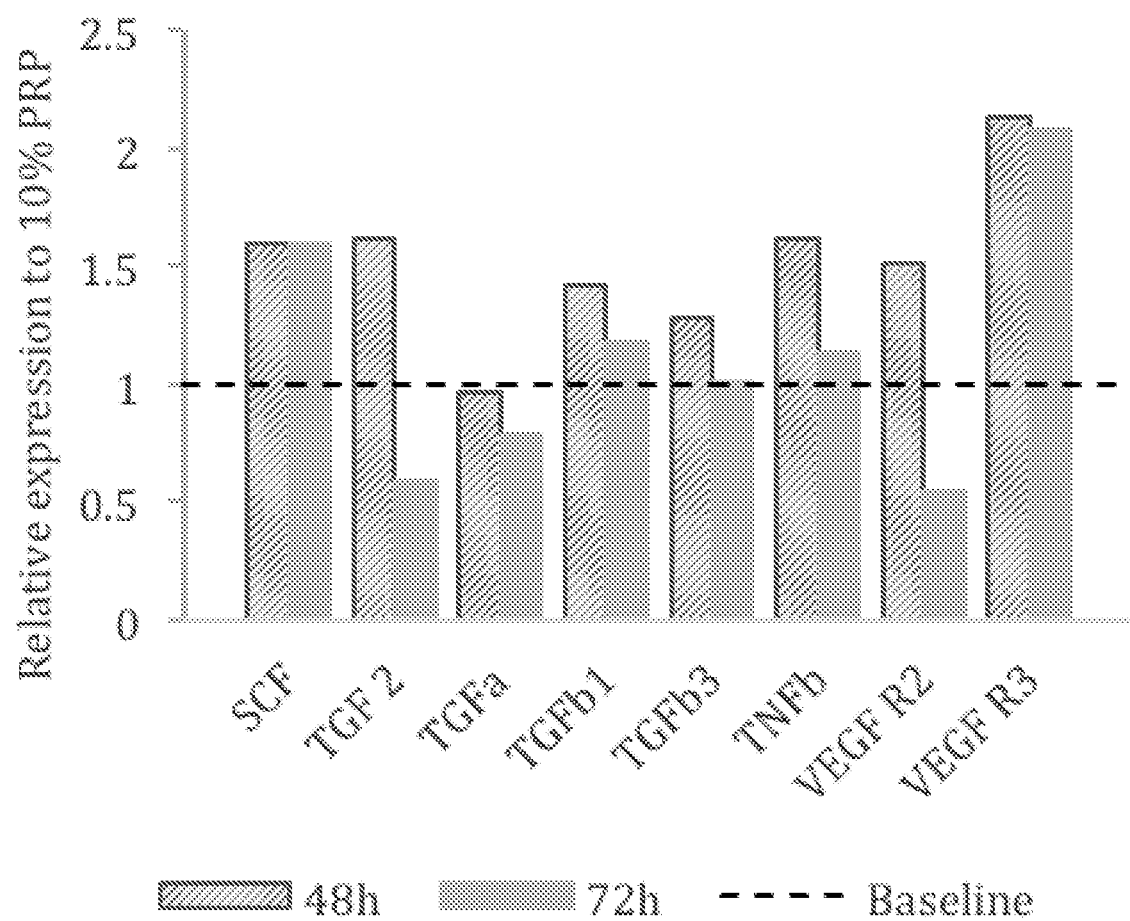
Figure 80:
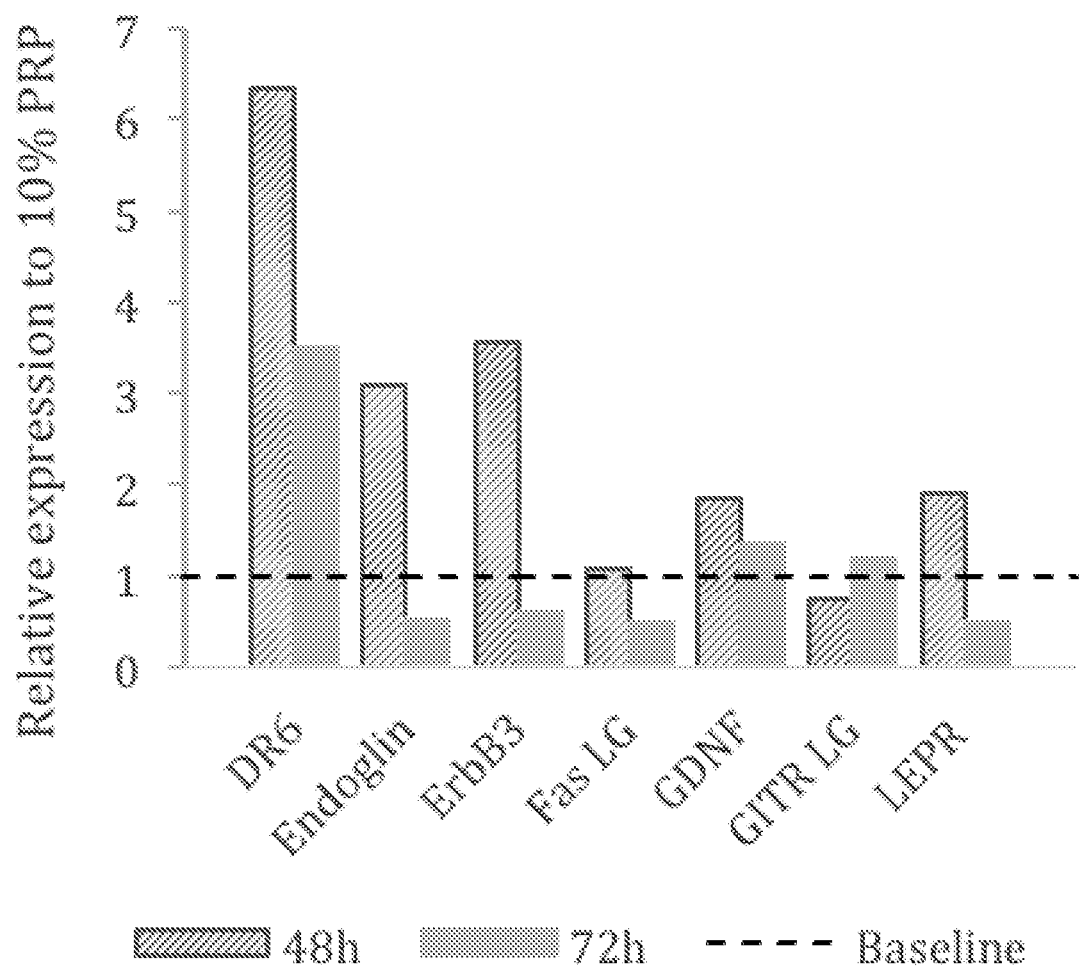
Figure 81:
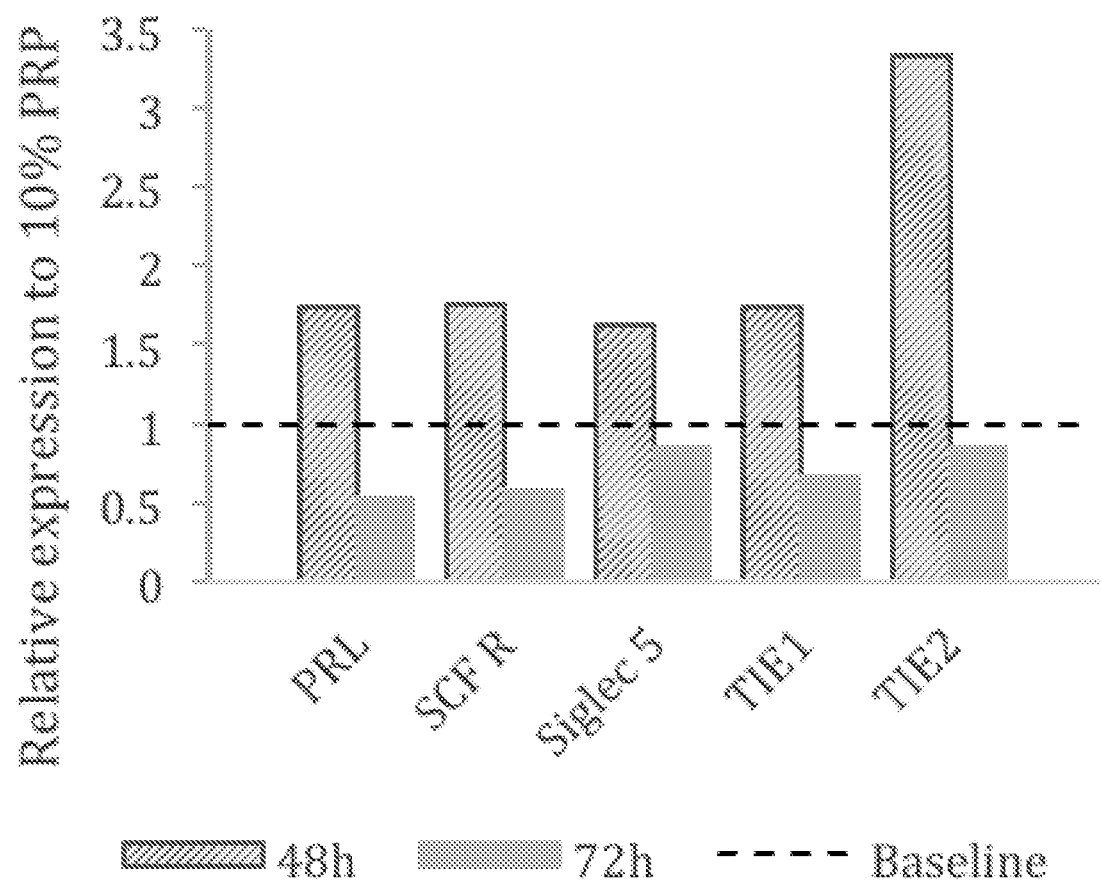
Figure 82:
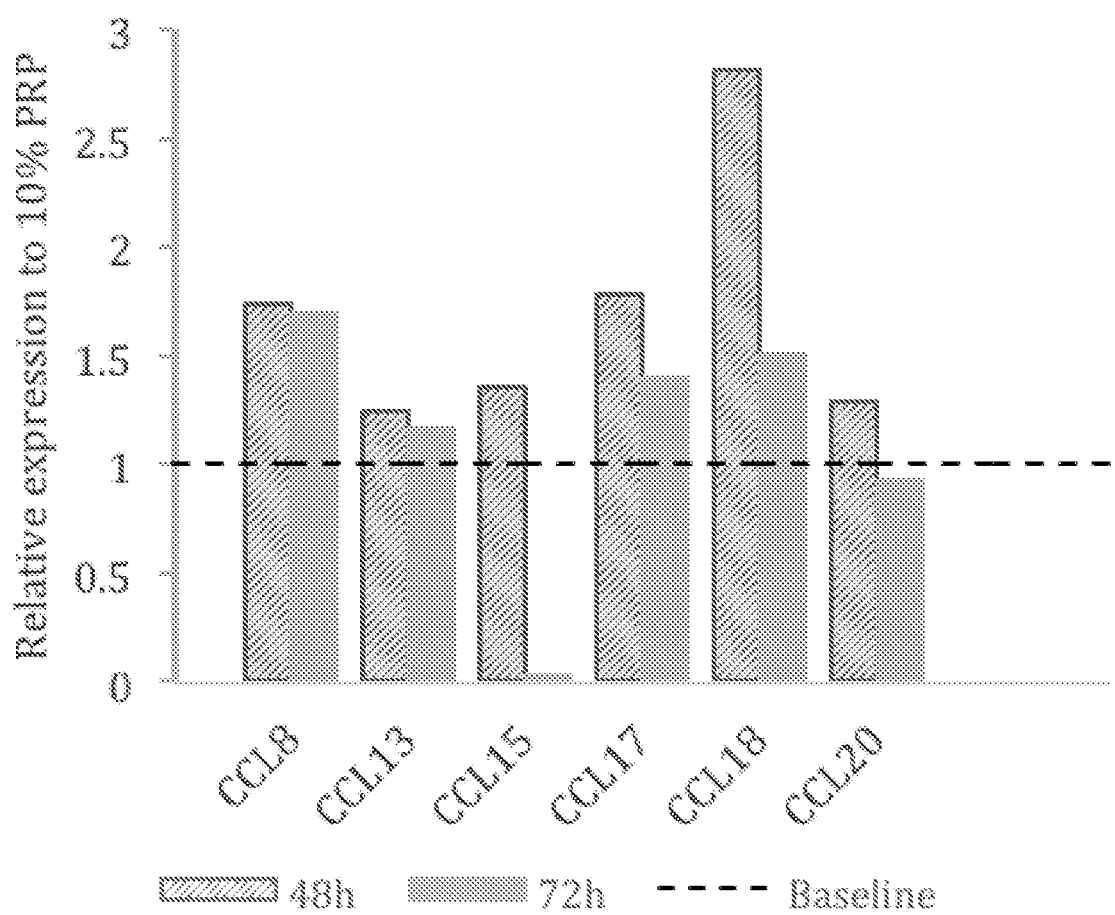
Figure 83:
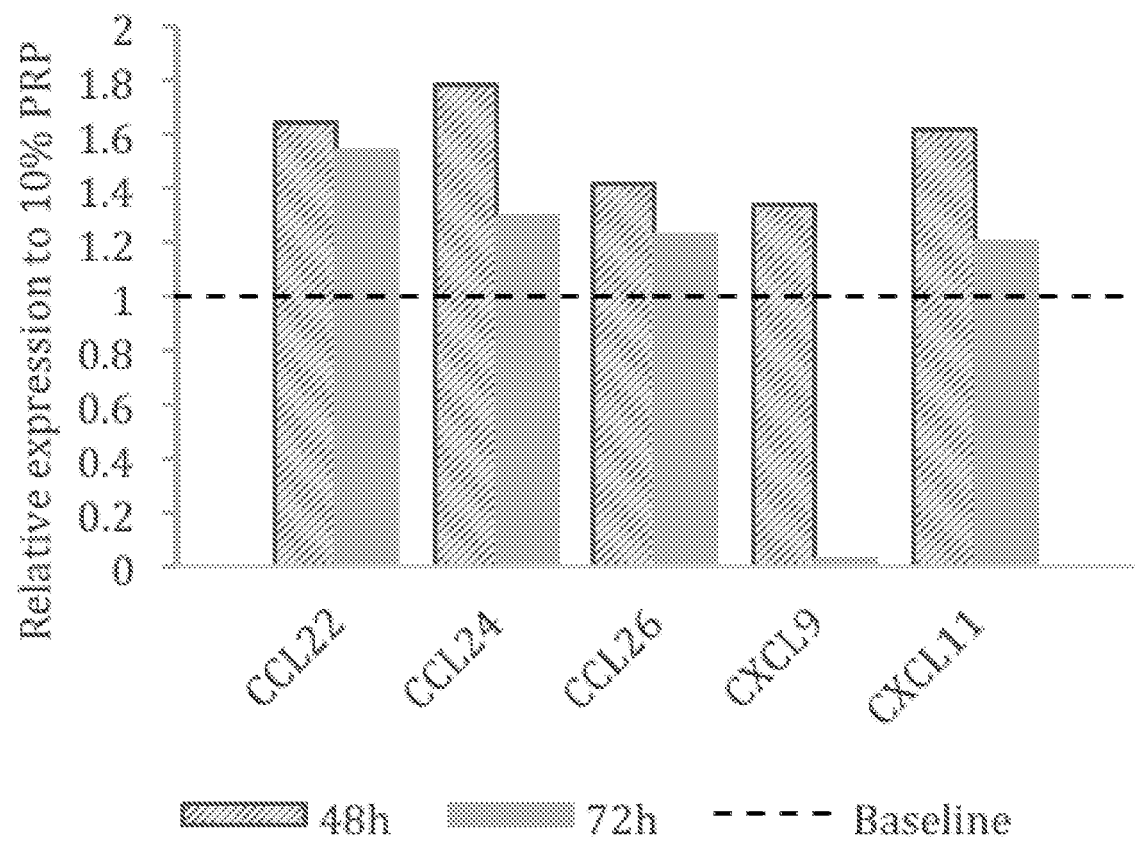
Figure 84:
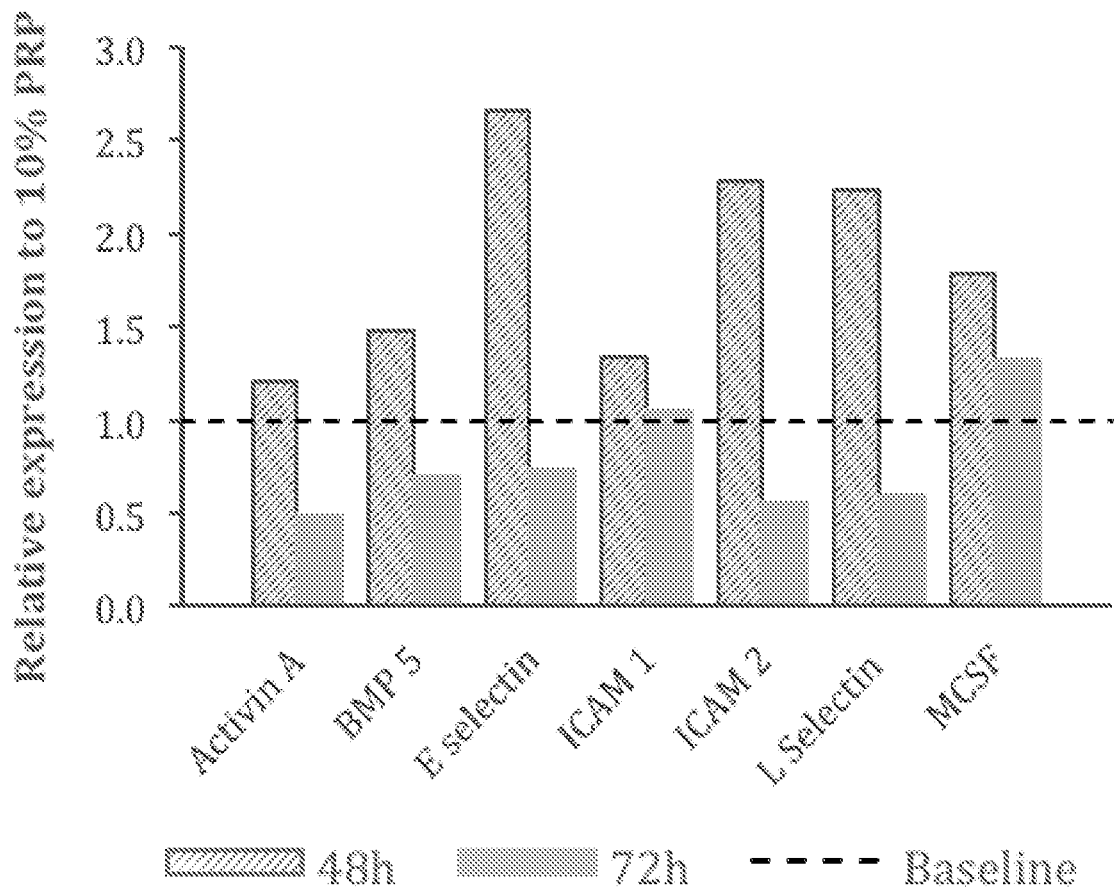
Figure 85:
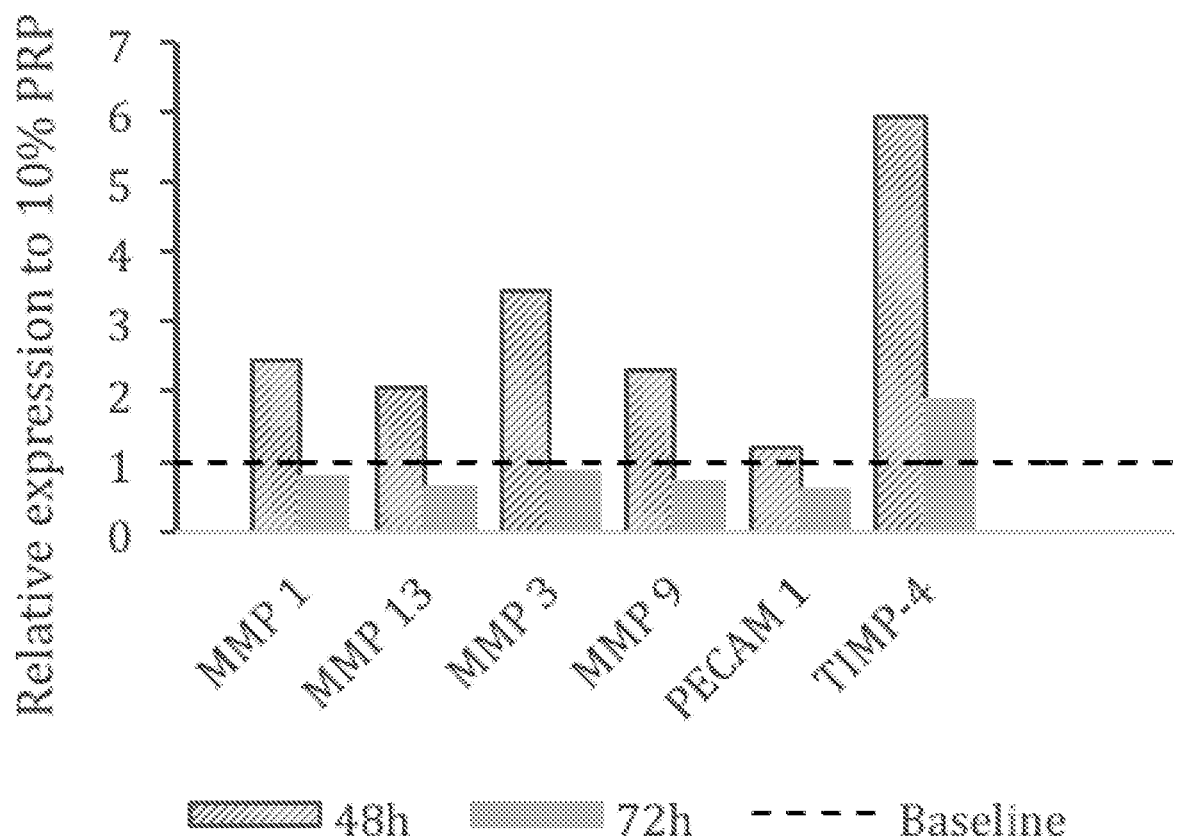
Figure 86:
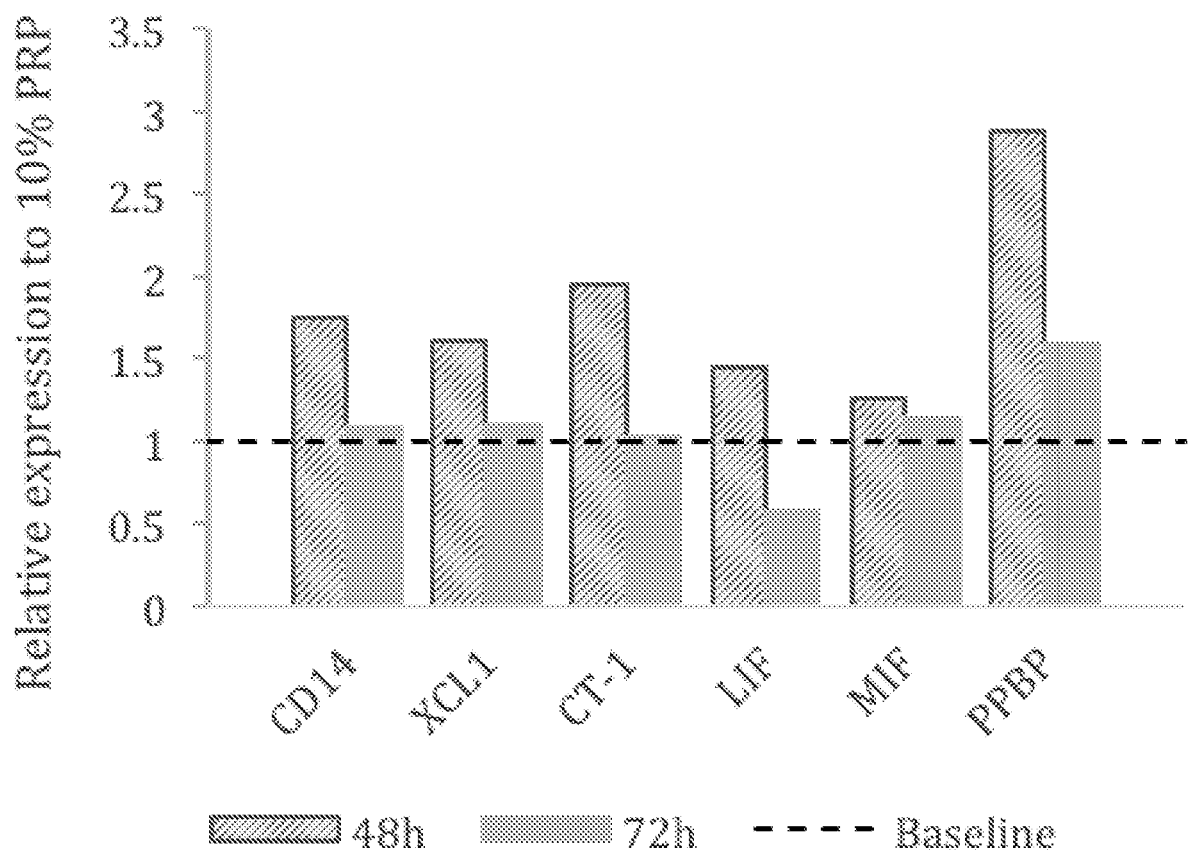

FIGS. 76-86 show the increase in the secretion of the below named proteins (factors) from SEN-hADSCs, 48 hours post stimulation with IL-2. Secretion levels are shown relative to the amount of the corresponding protein present at basal levels in the 10% PRP containing media, used for hADSC support. FIG. 76 shows the increase in secretion of Interleukin 1 beta (IL1b), IL3, IL5, IL6, IL9, IL10, IL12b, and Interleukin 18 binding protein alpha (IL18BPa). FIG. 77 shows the increase in secretion of Interleukin 1 receptor alpha (IL1Ra), IL1R4, IL10Rb, IL18Rb, IL1R2, IL-21R, IL-2Rb, IL-2Rg, and IL5Ra. FIG. 78 shows the increase in secretion of Fibroblast growth factor 6 (FGF6), insulin-like growth factors IGF1 and IGF2, LAP (TGF beta family), Neurotrophin 3 (NT3), platelet derived growth factor A alpha (PDGFAA), platelet derived growth factor A beta (PDGFAB), and platelet-derived growth factor receptor alpha (PDGFRa). FIG. 79 shows the increase in secretion of Stem cell factor (SCF), Transforming growth factor 2 (TGF2), TGFa, TGFb1, TGFb3, Tumor necrosis factor beta (TNFb), Vascular endothelial growth factor receptor-2 (VEGF R2), and VEGF R3. FIG. 80 shows the increase in secretion of DR6 (TNF receptor superfamily member 21), Endoglin (ENG), Receptor tyrosine-protein kinase erbB-3 (ErbB3), Fas ligand (Fas LG), Glial cell line-derived neurotrophic factor (GDNF), GITR ligand (GITR LG), and Leptin receptor (LEPR). FIG. 81 shows the increase in secretion of Prolactin (PRL), Stem cell factor receptor (SCFR), Sialic acid-binding Ig-like Lectin 5 (Siglec 5), Angiopoietin 1 receptor (TIE1), and Angiopoietin 1 receptor (TIE2). FIG. 82 shows the increase in secretion of Chemokine (C-C motif) ligand 8 (CCL8), CCL13, CCL15, CCL17, CCL18, and CCL20. FIG. 83 shows the increase in secretion of Chemokine (C-C motif) ligand 22 (CCL22), CCL24, CCL26, CXC chemokine ligand 9 (CXCL9), and CXCL11. FIG. 84 shows the increase in secretion of Activin A (INHBA), Bone morphogenetic protein 5 (BMP5), E selectin (endothelial cell adhesion molecule), Intercellular adhesion molecule 1 (ICAM 1), ICAM 2, L selectin (Lymphocyte adhesion molecule), and Macrophage colony-stimulating factor (MCSF). FIG. 85 shows the increase in secretion of matrix metalloproteinase 1 (MMP1), MMP13, MMP3, MMP9, Platelet endothelial cell adhesion molecule (PE-CAM 1), and Metalloproteinase inhibitor 4 (TIMP-4). FIG. 86 shows the increase in secretion of monocyte differentiation antigen (CD14), Lymphotactin (XCL1), Cardiotrophin-1 (CT-1), Leukemia inhibitory factor (LIF), Macrophage Migration Inhibitory Factor (MIF), and pro-platelet basic protein (PPBP).

Figure 87:
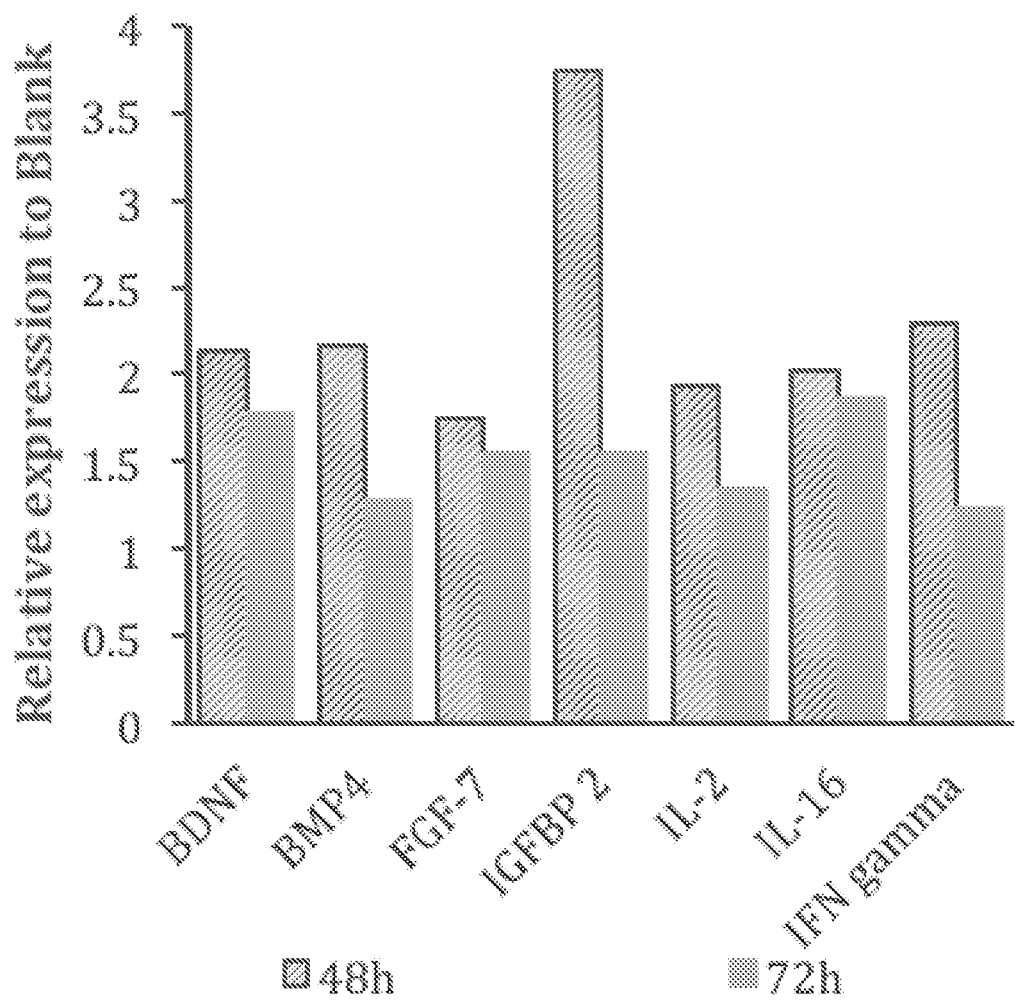

FIG. 87 shows the increase in secretion of Brain-derived neurotrophic factor (BDNF), Bone morphogenetic protein 4 (BMP4), Fibroblast growth factor 7 (FGF7), insulin-like growth factor-binding protein-2 (IGFBP2), IL-2, IL16, and Interferon gamma (INF gamma) from SEN-hADSCs maintained in a factor production unit of the invention, 48 hours post stimulation with IL-2. These factors were found to not be present in PRP.

Figure 88:
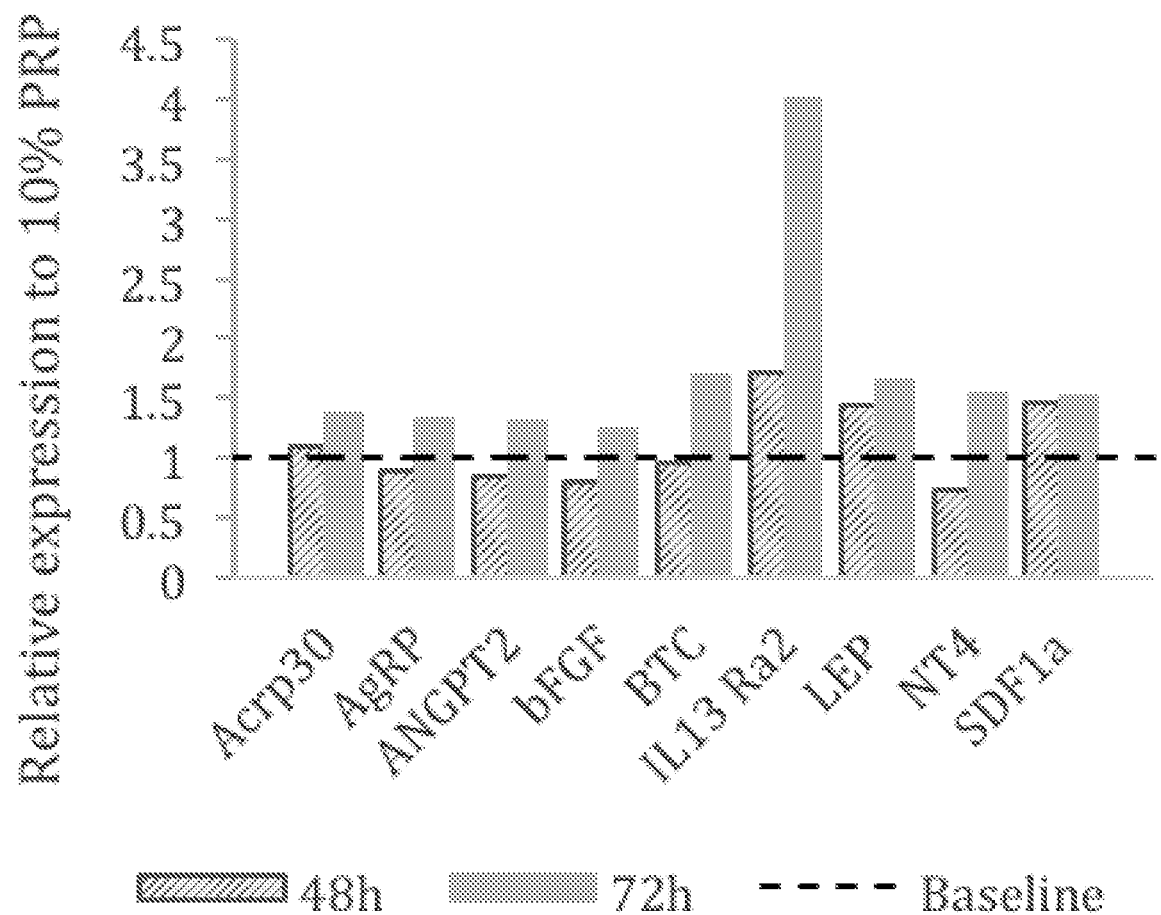
Figure 89:
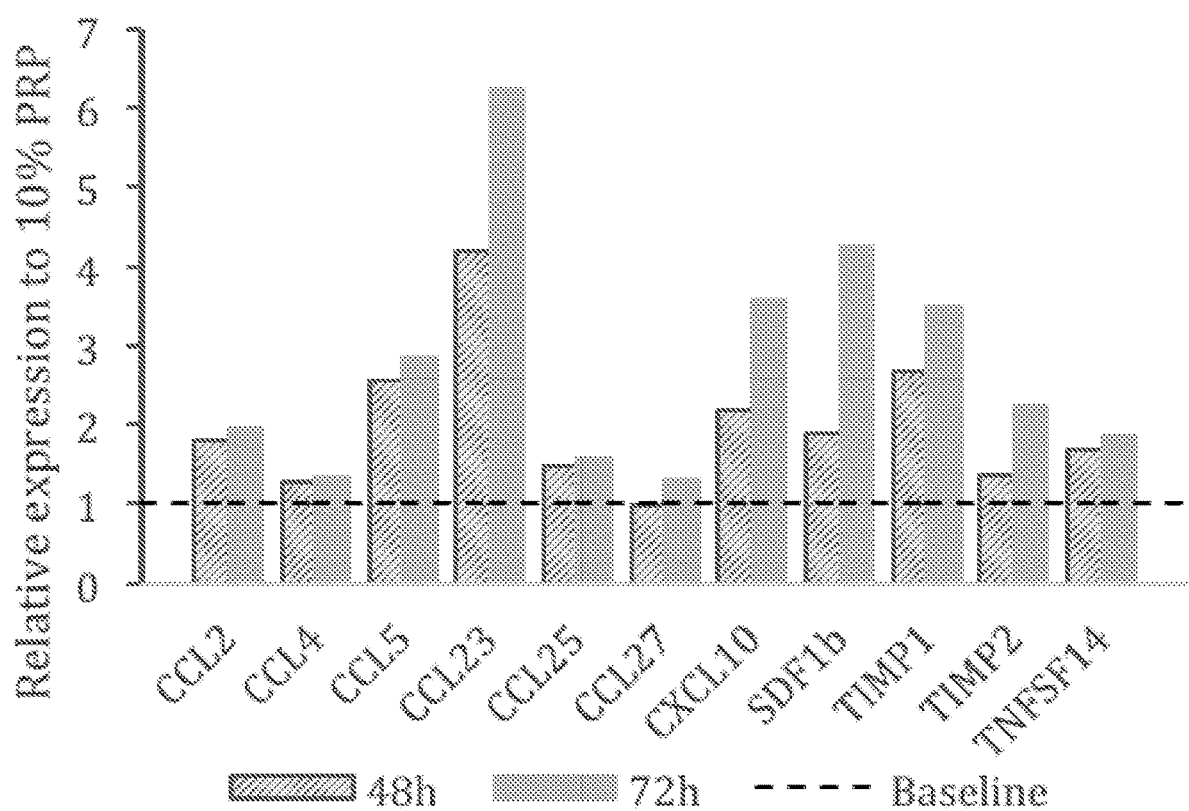

FIGS. 88-89 show the increase in secretion of the below named proteins (factors) from SEN-hADSCs maintained in a factor production unit of the invention, 72 hours post stimulation with IL-2. Secretion levels are shown relative to the amount of the corresponding protein present at basal levels in the 10% PRP containing media, used for hADSC support. FIG. 88 shows the increase in secretion of Adiponectin (Acrp30), Agouti-related protein (AgRP), ANGPT2 (Angiopoietin 2), basic-Fibroblast Growth Factor (bFGF), Probetacellulin (BTC), Interleukin-13 receptor subunit alpha-2 (IL13Ra2), Leptin (LEP), Neurotrophin 4 (NT4), and Stromal Cell-Derived Factor-1 alpha (SDF1a). FIG. 89 shows the increase in secretion of Chemokine (C-C motif) ligand 2 (CCL2), CCL4, CCL5, CCL23, CCL25, CCL27, CXC Chemokine ligand 10 (CXCL10), Stromal Cell-Derived Factor-1 beta (SDF1b), Metalloproteinase inhibitors 1 (TIMP1), TIMP2, and tumor necrosis factor superfamily member 14 (TNFSF14).

Figure 90:
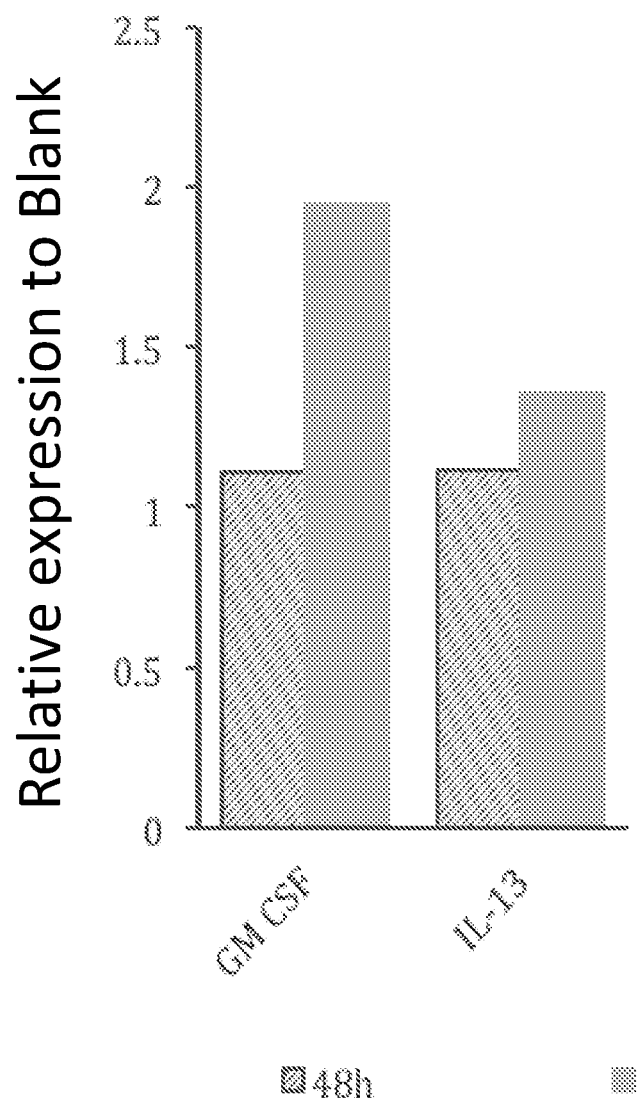
Figure 94:
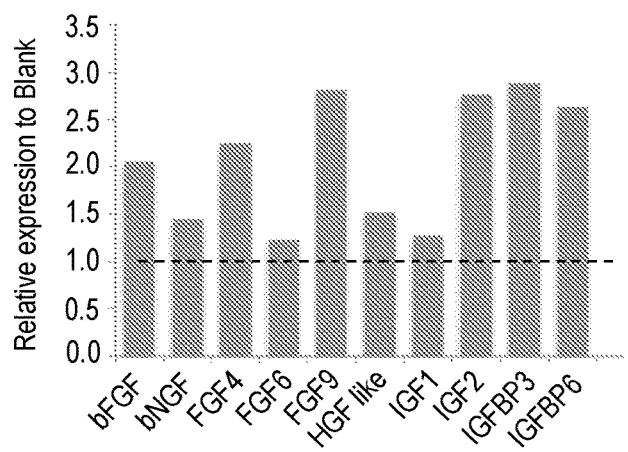

FIG. 90 shows the increase in secretion of Granulocyte-macrophage colony-stimulating factor (GM-CSF) and IL13 from SEN-hADSCs maintained in a factor production unit of the invention, 72 hours post stimulation with IL-2. These factors were found to not be present in PRP.

In general, the input cells and systems provided herein can produce factors including, but not limited to, HB-EGF; FGFs 1, 2, and 4; PDGF; IGF-1; TGF-ß1 and ß2; TGF-ß3; IL-1α and -ß; IL-10; IL-4; IL-2, IL-12; IL-6, IL-8, IL-17a; LEP and LEPR; Endoglin; Adipoq; IGFBP1, IGFPB3; CSF1, CSF3 and receptor CSFR1; PPBP/NAP-2; HGF; NGRF; EGF; TNF-α; and combinations thereof.

Exemplary interleukins produced using the input cells and systems provided herein involved in skin regeneration pathways include without limitation, IL 1b (interleukin 1ß), IL 2b (interleukin 2ß), IL 3 (interleukin 3), IL 6 (interleukin 6), IL6ST (interleukin 6ST), IL 9 (interleukin 9), IL 11 (interleukin 11), IL12a (interleukin 12α), IL 12b (interleukin 12ß), IL 13 (interleukin 13), and IL 17 (interleukin 17).

Exemplary interleukin receptors and binding proteins produced using the input cells and systems provided herein include without limitation, IL1Ra (interleukin 1 receptor α), IL 1R1 (interleukin 1 receptor type 1), IL 1R2 (interleukin 1 receptor type 2), IL 1R4 (interleukin 1 receptor 4), IL 2Ra (interleukin 2 receptor α), IL 2Rg (interleukin 2 receptor γ), IL 5Ra (interleukin 5 receptor α), IL 6R (interleukin 6 receptor), IL 10Rb (interleukin 10 receptor ß), IL 13Ra (interleukin 13 receptor α), IL 18 Rb (interleukin receptor ß), IL 18 BP (interleukin 18 binding protein), IL 21 R (interleukin 21 receptor).

Exemplary growth factors produced using the input cells and systems provided herein include without limitation, bFGF2 (basic fibroblast growth factor 2), bNGF (beta-nerve growth factor), FGF4 (fibroblast growth factor 4), FGF6 (fibroblast growth factor 6), FGF 9 (fibroblast growth factor 9), Fas ligand, IGFBP1 (insulin growth factor binding protein 1), IGFBP3 (insulin growth factor binding protein 3), IGFBP6 (insulin growth factor binding protein 6), LAP (transforming growth factor like), IGF-1 (insulin-like growth factor 1), IGF-2 (insulin-like growth factor 2), PDGF (platelet-derived growth factor), PDGFAA (platelet-derived growth factor Aα), PDGFAB (platelet-derived growth factor Aβ), PDGFBB (platelet-derived growth factor Bβ), TGFB1 (transforming growth factor β1), ANG (angiogenin), BDNF (brain-derived neurotrophic factor), BMP4 (bone morphogenic protein 4), BMP 6 (bone morphogenic protein 6), bNGF (beta-nerve growth factor), BTC (probetacellulin), CNTF (ciliary neurotrophic factor), EGF (epidermal growth factor), HGF (hepatocyte growth factor), hepatocyte-like growth factor, NT3 (neurotrophin 3), NT4 (neurotrophin 4), OPG (osteoprotegerin), Siglec5 (sialic acid binding If-like lectin 5), and TGF A (transforming growth factor alpha), TGF b1 (transforming growth factor beta 1), TGF b 2 (transforming growth factor beta 3), VEGF (vascular endothelial growth factor), VEGFD (vascular endothelial growth factor D), and PLGF (placental growth factor).

Exemplary growth factors receptors produced using the input cells and systems provided herein include without limitation, PDGFRA (platelet-derived growth factor receptor α), VEGFR2 (vascular endothelial growth factor receptor 2), VEGFR3 (vascular endothelial growth factor receptor 3), NGFR (nerve growth factor receptor), EGFR (epithelial growth factor receptor), and TNFRSF 10D (tumor necrosis factor receptor 10D).

Exemplary chemokines produced using the input cells and systems provided herein include without limitation, CCL 2 (chemokine ligand 2), CCL 3 (chemokine ligand 3), CCL 4 (chemokine ligand 4), CCL 5 (chemokine ligand 5), CCL 7 (chemokine ligand 7), CCL 8 (chemokine ligand 8), CCL 13 (chemokine ligand 13), CCL 15 (chemokine ligand 16), CCL 17 (chemokine ligand 17), CCL 18 (chemokine ligand 18), CCL 19 (chemokine ligand 19), CCL 20 (chemokine ligand 20), CCL 22 (chemokine ligand 22), CCL 23 (chemokine ligand 23), CCL 24 (chemokine ligand 24), CCL25 (chemokine ligand 25), CCL 26 (chemokine ligand 26), CCL 27 (chemokine ligand 27), CCL 28 (chemokine ligand 28), CXC L1 (chemokine ligand 1), CXCL1/2/3 (chemokine ligand 1/2/3), CXCL5 (CX chemokine ligand 5), CXCL9 (CX chemokine ligand 9), CXCL 10 (CX chemokine ligand 10), CXCL 13 (CX chemokine ligand 13), and CXCL 16 (CX chemokine ligand 16).

Exemplary molecules that provide cell adhesion signaling produced using the input cells and systems provided herein include without limitation, ALCAM (cell adhesion molecule), E-selectin, and VE cadherin.

Exemplary factors that may promote cell proliferation produced using the input cells and systems provided herein include without limitation, BMP4 (bone morphogenic protein 4), BMP5 (bone morphogenic protein 5), BMP6 (bone morphogenic protein 6), BMP7 (bone morphogenic protein 7), CSF 1R (colony stimulating factor 1 receptor), ICAM2 (intercellular adhesion molecule 2), MMP 1 (matrix metallopeptidase 1), MMP3 (matrix metallopeptidase 3), MMP 9 (matrix metallopeptidase 9), and TIMP4 (metalloproteinase inhibitor 4).

Dermatological aging and the physiological changes associated with aging of the skin include xerosis, loss of barrier function, loss elasticity due to damage to collagen and elastin fibers, modification of rhytides, and loss of efficient turnover of epidermal cells, ultimately resulting in thinning of the skin, malar fat atrophy, and pigmentary changes. Although aging is inevitable, in some variations of the compositions described herein may be used to combat these physiological and anatomic changes. Exemplary factor that may promote skin regeneration produced using the input cells and systems provided herein include without limitation, CXCL 16 (chemokine ligand 16), IGF-2 (insulin-like growth factor 2), and TIE2 (tyrosine kinase with immuno-globin/EGF like domain).

Exemplary factors that may promote wound healing produced using the input cells and systems provided herein include without limitation, Activin A, IGF-2 (insulin-like growth factor 2), and LEPR (leptin receptor).

Exemplary factors that may promote hyaluronic acid synthesis in the skin produced using the input cells and systems provided herein include without limitation, Activin A, LEPR (leptin receptor, TGFB1 (transforming growth factor ß1), EGF (epidermal growth factor), HGF (hepatocyte growth factor), and PDGF (platelet-derived growth factor).

Exemplary factors that may promote skin elasticity produced using the input cells and systems provided herein include without limitation, IGFBP1 (insulin-like growth factor binding protein 1), IGFBP2 (insulin-like growth factor binding protein 2), IGFBP4 (insulin-like growth factor binding protein 4), TIMP1 (metalloproteinase inhibitor 1), and TIMP2 (metalloproteinase inhibitor 2).

Exemplary factors for suppression of malignancies and UV-induced skin aging produced using the input cells and systems provided herein include without limitation, endoglin and SCFR (c-KIT stem cell factor receptor.

Exemplary factors for suppressing wound healing or the inflammatory response produced using the input cells and systems provided herein include without limitation, CD14 (cell differentiation antigen 14), CD 80 (cell differentiation antigen 80), IFNγ (interferon gamma), and LIF (leukemia inhibitory factor).

In an exemplary variation, NGF (nerve growth factor receptor) is produced using the input cells and systems provided herein may be a beneficial factor for the treatment of hair loss.

Other factors capable of being produced using the input cells and systems provided herein include without limitation, Adipoq (adiponectin), AgRP (agouti related protein), ANGPT2 (Angiopoietin 2), AREG (amphiregulin), Ax1 (tyrosine-protein kinase receptor UFO), BTC (betacellulin), CD 14 (cell differentiation antigen 14), CD 80 (cell differentiation antigen 80), CT-1 (cardiotropin-1), Dtk (tyrosine-protein kinase receptor TYRO3), ErbB3 (receptor tyrosine-protein kinase erB-3), OPG (osteoprotegerin), OSM (oncostatin M), PPBP (platelet basic protein), PRL (prolactin), THPO (thrombopoietin), and TIE-1 (angiopoietin 1 receptor).

In one exemplary variation, SR-hADSCs are stimulated with an IL-2 induction agent for 24 hours, and allowed to produce factors for 24 hours. FIG. 43 shows the collection of factors produced 24 hours post induction with IL-2.

In another exemplary variation, SR-hADSCs are stimulated with an IL-2 induction agent for 24 hours, and allowed to produce factors for 48 hours. FIGS. 43-57 show the collection of factors produced 48 hours post induction with IL-2.

In another exemplary variation, SR-hADSCs are stimulated with an IL-2 induction agent for 24 hours, and allowed to produce factors for 72 hours. FIGS. 43-58 show the collection of factors produced 72 hours post induction with IL-2.

In another exemplary variation, SR-hADSCs are media alone for 24 hours, and allowed to produce factors for 24 hours. FIGS. 11-19 show the collection of factors produced 24 hours post induction with media alone.

In another exemplary variation, SR-hADSCs are media alone for 24 hours, and allowed to produce factors for 48 hours FIGS. 11-42 show the collection of factors produced 48 hours post induction with media alone.

In another exemplary variation, SR-hADSCs are media alone for 24 hours, and allowed to produce factors for 72 hours. FIGS. 20-42 show the collection of factors produced 72 hours post induction with media alone.

In one exemplary variation, SEN-hADSCs are stimulated with an IL-2 induction agent for 24 hours, and allowed to produce factors for 24 hours. FIG. 75 show the collection of factors produced 24 hours post induction with IL-2.

In another exemplary variation, SEN-hADSCs are stimulated with an IL-2 induction agent for 24 hours, and allowed to produce factors for 48 hours. FIGS. 75-90 show the collection of factors produced 48 hours post induction with IL-2.

In another exemplary variation, SEN-hADSCs are stimulated with an IL-2 induction agent for 24 hours, and allowed to produce factors for 72 hours. FIGS. 75-90 show the collection of factors produced 72 hours post induction with IL-2.

In another exemplary variation, SEN-hADSCs are stimulated with media alone for 24 hours, and allowed to produce factors for 24 hours. FIGS. 59-60 show the collection of factors produced 24 hours post induction with media alone.

In another exemplary variation, SEN-hADSCs are stimulated with media alone for 24 hours, and allowed to produce factors for 48 hours. FIGS. 59-74 show the collection of factors produced 48 hours post induction with media alone.

In another exemplary variation, SEN-hADSCs are stimulated with media alone for 24 hours, and allowed to produce factors for 72 hours. FIGS. 59-74 show the collection of factors produced 72 hours post induction with media alone.

In an exemplary variation, the method for producing one or more factors in a factor production unit, the method comprises using input cells that comprise at least 50% SEN-hADSCs, adding an IL-2 inducing agent to the population of cells to promote production of the factors; and collecting the factors.

3. Exemplary Methods of Induction

FIG. 1A depicts an exemplary method for practicing an aspect of the invention described herein.

In general there may be multiple classes of stem cells and sub-combinations of them that are used as described herein, based on the SEN state of the cells. Each population and subcombination may produce different trophic factors. For example, a population of cells may be complete SR, completely SEN or (more likely) a mixed population of SR and SEN cells. A population of completely SR cells may be induced to produce particular factors, as described herein, and may produce a first profile of trophic factors (FIG. 1A "phenotype 3"). A population of just SEN cells may be rejuvenated as described herein and may produce factors either without induction ("phenotype 1") or with induction ("phenotype 2"). A fourth phenotype could be isolated SR cells that are not induced to produce factors ("phenotype 4"). These different populations (rejuvenated, formerly SEN cells, induced and not induced, and induced/induced SR cells) may be used alone or in various subcombinations to treat any of the diseases/disorders described herein.

FIG. 1A generically illustrates a method for modifying the properties of an exemplary input cell of the invention, a human adipose-derived mesenchymal stem cell (hADSC) to produce any of the phenotypes 1-3 just mentioned. As shown in FIG. 1A, an extract of mesenchymal stem cells (MSC) may be taken adipose tissue or a sample of cryopreserved cells may be used 101. The adipose tissue (and thus the MSC) may be derived from an autologous or heterologous source (e.g., from the same patient to be treated with the rejuvenated and/or induced hADSC and/or extract, or from a donor MSC). Adipose tissue may be harvested according to any appropriate procedure. The MSCs may be amplified and/or isolated from the adipose tissue, but in general the MSC is cultured 103. Optionally, either as a separate step of as part of the culturing step, the cells may be examined (QC) to determine the presence and/or identity of SEN cells. Thereafter, any SEN-hADSCs may be rejuvenated as described herein, so that all of the cells are in a SR state (which includes the formerly SEN cells, now rejuvenated), and not in a SEN state.

In some variations, only the identified SEN cells are rejuvenated either in a population of just SEN cells or in a mixed population of SEN and SR cells. For example, if rejuvenating only SEN cells, the SEN cells may first be isolated from the SR cells. Alternatively, all of the cells of a mixed population that may include both SEN and SR cells are rejuvenated.

For example, in FIG. 1A, the QC step may identify a population of just SEN cells 113, a mixed population of SEN/SR cells 115, and a population of just SR cells 117, or the method may include a cell sorting step for separating SEN and SR cells during the procedure. Thereafter, the cells may be allowed to produce trophic factors either with or without induction. For example, all or some of the cells can be "induced" (e.g., made ready to reliably and effectively produce a desired sub-set of factors) by exposing them to, in this example, IL-2 107, 107', 107". Cells can be induced with IL-2 with or without rejuvenation for therapeutic end-points, as illustrated in FIG. 1. As shown in FIG. 1A, each subpopulation (rejuvenated SEN only 113, SR-only 117, and mixed rejuvenated SEN and SR 115, may be optionally induced, and may produce different sets of trophic factors. These different populations may be combined in any subcombination (including with un-induced SR cells or trophic factors from them) for use in any of the therapeutic methods described and indicated herein. For example, rejuvenated SEN cells that are not induced may produce a beneficial set of trophic factors (phenotype 1), and induced rejuvenated SEN cells may produce a beneficial set of trophic factors (phenotype 2), and induced SR cells may produce a beneficial set of trophic factors (phenotype 3). As already described, any combination of these may be combined to form a set of therapeutic cells (hADSCs) and/or extracts therefrom.

In another variation, as illustrated in FIGS. 1A, 1B, 2A, and 2B, the production of one or more factors (or factor compositions as in FIG. 2A) using a factor production unit can be controlled or tailored. Upon induction/stimulation of the cell population, e.g., with IL-2, one or more factors is produced by the cell population. The one or more factors can then be collected at predetermined time points, e.g., at 24 hours, 48 hours, or 72 hours, as shown in the figures, depending on the factor desired to be collected. For example, if interleukins are produced at 24 hours, growth factors at 48 hours, and chemokines at 72 hours post induction, and growth factors are needed for formulation into a skin rejuvenation cream, the factor production unit can be cultured and factors collected at 48 hours post induction. Control of factor production can also be controlled by the type of cells and type of substrate included in the factor production unit. It is understood that time points for factor collection can be earlier than 24 hours and later than 72 hours.

FIG. 2B is a schematic showing five exemplary factor production units (A-E) populated with an individual's hAD-SCs for controlled production of factors. In this exemplary aspect, each factor production unit contains an ECM-like 3-D scaffold that mimics the natural growth environment for the stem cells. All five factor production units contain stem cells in a suitable media, e.g. 10% PRP containing StemPro MSC SFM Xeno-free medium (except for factor production unit A which represents a no cell control factor production unit. The factor production units are populated with SR or SEN cells, and either stimulated, or not stimulated with IL-2 for 24 hours.

D. Factor Compositions

The factors produced, as described herein, may be formulated into any suitable composition. The compositions can be tailored to the particular indication of use, for any of the diseases and disorders described herein.

The factors may be formulated with any suitable carrier and/or excipient(s) into a topical composition, an oral dosage form, an implant, an injectable composition, or an intravenous composition. In some instances, additional agents are included to enhance skin penetration or bioavailability of the factors, or other ingredients that enhance skin appearance. One or more factors may be included in the compositions. The compositions may be formulated for immediate, sustained, or controlled release of the one or more factors.

The amount of factor incorporated into the compositions will typically be in a range that constitutes an effective amount of the desired amount of factor, to induce the desired biological response.

In one variation the composition comprises factors produced from SR stem cells (e.g. SR-hADSCs) induced with IL-2 for 24 hours, wherein the factors are collected 24 hours post completion of the induction.

In one variation the composition comprises factors produced from SR stem cells (e.g. SR-hADSCs) induced with IL-2 for 24 hours, wherein the factors are collected 48 hours post completion of the induction.

In one variation the composition comprises factors produced from SR stem cells (e.g. SR-hADSCs) induced with IL-2 for 24 hours, wherein the factors are collected 72 hours post completion of the induction.

In one variation the composition comprises factors produced from SEN stem cells (e.g. SEN-hADSCs) induced with IL-2 for 24 hours, wherein the factors are collected 24 hours post completion of the induction.

In one variation the composition comprises factors produced from SEN stem cells (e.g. SEN-hADSCs) induced with IL-2 for 24 hours, wherein the factors are collected 48 hours post completion of the induction.

In one variation the composition comprises factors produced from SEN stem cells (e.g. SEN-hADSCs) induced with IL-2 for 24 hours, wherein the factors are collected 72 hours post completion of the induction.

In one variation the composition comprises factors produced from SR stem cells (e.g. SR-hADSCs) not induced with any inducing agent.

In one variation the composition comprises factors produced from SEN stem cells (e.g. SEN-hADSCs) not induced with any inducing agent.

E. Treatment of Diseases and Disorders

One or more induced factors, the conditioned media comprising the one or more induced factors, or compositions comprising the one or more factors, as provided herein, may be used for the treatment of a variety of diseases and disorders.

A non-limited list of diseases and disorders that can be treated comprise cancer, an autoimmune disease, a cardiovascular disease, diabetes, a skin disease, a neurodegenerative disease, osteoporosis, osteoarthritis, a spinal cord injury, a disease of the liver, a disease of the kidney, an age-related pathology, hair loss, a burn, a condition in need of a skin graft, and a skin lesion.

A beneficial aspect of the factor production methods is that therapy can be customized according to the particular disease, disorder, or condition to be treated. The population of cells and substrate can be selected depending on the desired factors to be produced. Furthermore, the produced factors can be collected at predetermined times. Factors produced by the selected cell population at a particular time point may be more beneficial in treating certain diseases, disorders, or conditions than others.

Particular modes of use and delivery of factors, for treatment, are discussed in more detail below.

As described in greater detail herein, factors may be produced and directly delivered to an individual in need using any appropriate method (e.g. a cream composition, injected, implanted, via plasmapheresis, etc.).

Alternatively factors may be produced using an exemplary factor production unit of the invention and may be used for modulation of immune cells from the individual. In this variation, the factors can come in contact with immune cells in a sample (e.g. blood or plasma) from the individual, effect modulation (immunomodulation) of the immune cells (e.g. induce production/differentiation of Tregs), after which the sample is delivered back to the individual. In this variation, the factors themselves are only optionally delivered. Rather, their use takes place ex vivo. In one variation, contemplated herein is a combination therapy using the immunomodulated cells produced herein (e.g. the Tregs produced as described) in combination with other factor compositions produced using the methods described herein, other active agents or treatment modalities. These other agents or treatments may include known drugs and therapies for the treatment of such disorders such as but not limited to corticosteroids and non-steroidal anti-inflammatory compounds and stimulatory drugs.

Factors used to treat other diseases or disorders described herein may be accomplished according to a treatment schedule, at home or at a doctor's office.

Figure 1B:
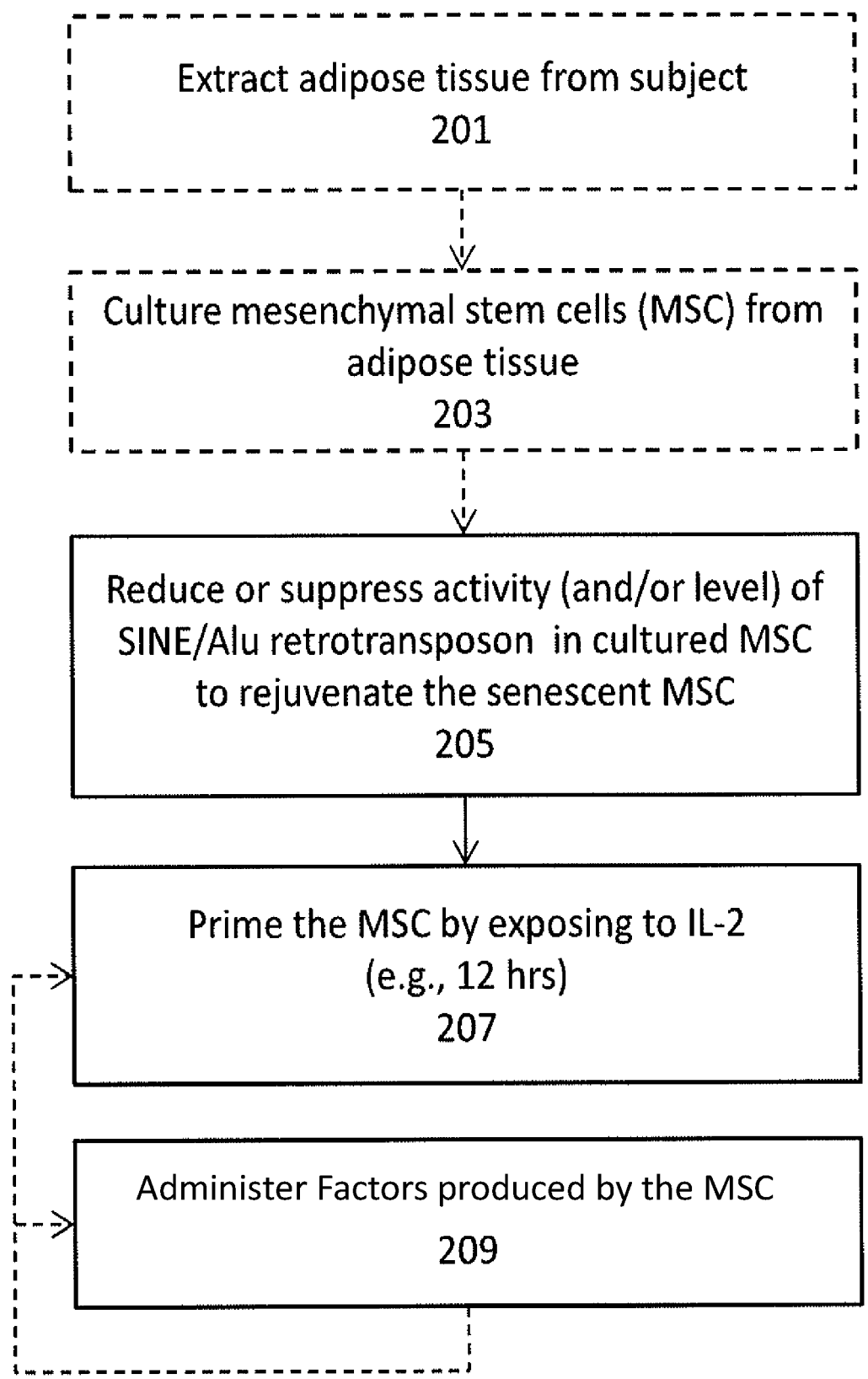
FIG. 1B illustrates an exemplary method of treating an individual using a composition of hADSCs (interchangeably referred to herein as hADMCs as described herein).
Figure 1C:
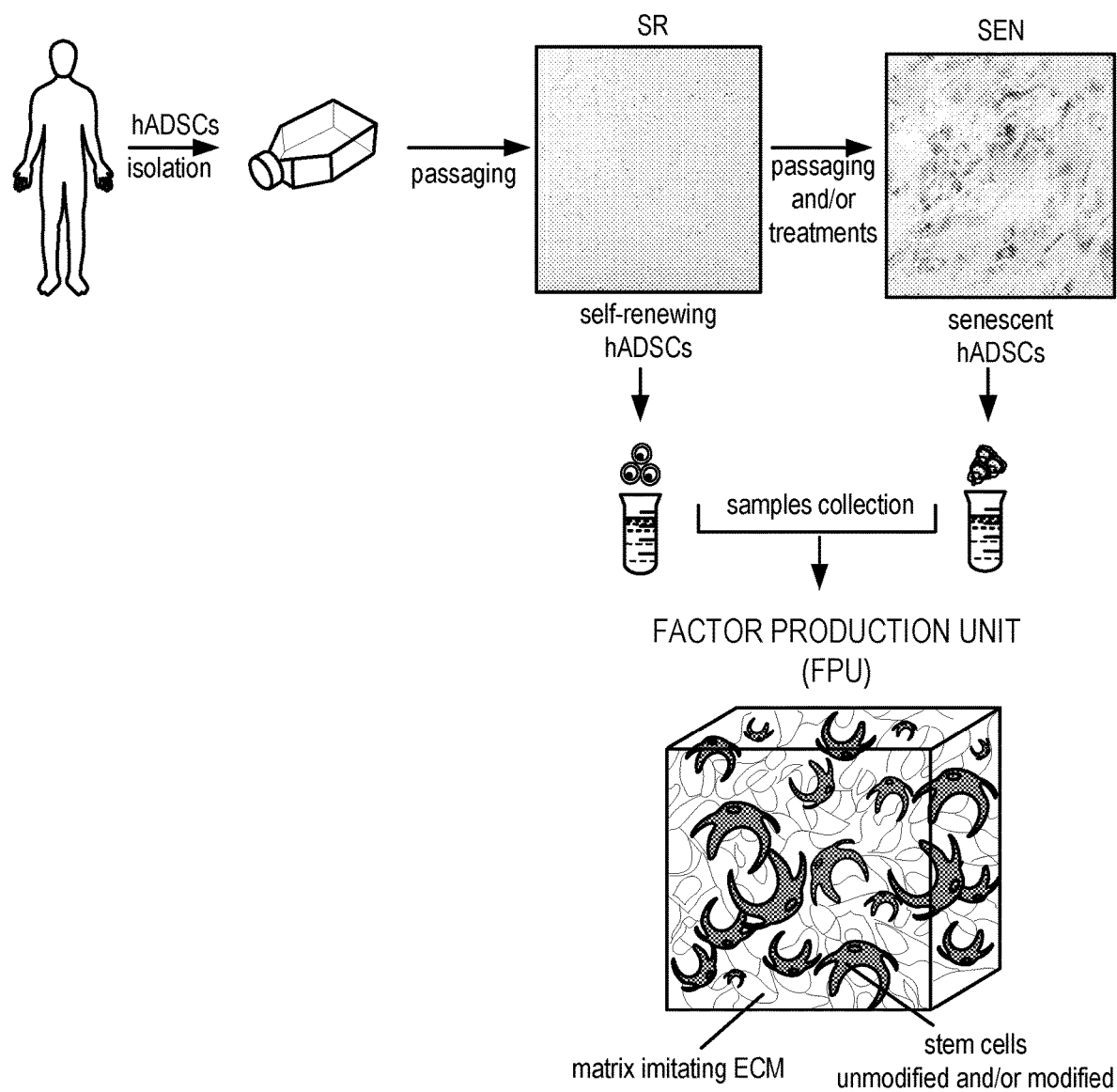
FIG. 1C illustrates an exemplary method of the invention starting from the isolation of hADSCs from an individual, to placement in an exemplary factor production unit described herein.

FIG. 1B illustrates a general method for treating a subject with, for example rejuvenated and induced hADSCs. In this exemplary method, the method may include an initial step (e.g., when performing an autologous procedure) of extracting adipose tissue from the subject 201 to be treated, and then culturing the MSCs from this adipose tissue 203 (as shown and described above in FIG. 1A). The use of the subject's own cells is optional (as indicated by the dashed lines around 201, 203), as heterologous cells may be used (e.g., from a donor) instead or in addition, which may be particularly useful when using extracts of the treated hADSC that do not include intact hADSC.

The cultured MSCs (e.g., hADSC) may then be treated as described above in FIG. 1A to rejuvenate them by reducing or suppressing activity (and/or level) of the SINE/ALU retrotransposon 205, and/or then inducing them (e.g., by exposing them to IL-2) 207. When inducing the cells by exposure to an inducing agent such as IL-2, the concentration and duration of the exposure may be selected to evoke a robust induction response. Examples of such treatment are described in examples below.

Once rejuvenated and induced, factors or extracts from the hADSC may be used to treat the patient, as described in 209 of FIG. 1B. In this example, extracts from the MSCs may be administered by any appropriate mechanism, including locally or systemically, e.g., by injection. As used herein administering the rejuvenated and induced MSC/hADSC may include administering the actual cells, and/or an extract of the cells.

1. Derma-Cosmetic and Skin Applications

In some variations, the induced factors, the conditioned media comprising the one or more induced factors, or compositions comprising the one or more factors may be used in compositions for application to the skin, e.g., cosmetic applications, for skin regeneration, for skin rejuvenation, for wound healing, or for aesthetic treatments. The factors can be used to treat cosmetic conditions such as, but not limited to, wrinkles, fine lines, scars (including acne scars), skin discoloration, age spots, decreased skin elasticity, sun damage, and hair loss. These cosmetic conditions can be treated by factors secreted from a factor production unit containing ADSCs in 10% PRP alone (no inducing agent). In some variations, the factors can be used in combination with microneedling applications to imitate light wounding to facilitate delivery of factors and physiological benefits.

Factors produced by a factor production unit in the presence of 10% PRP alone, collected at different time points (e.g. 24, 48, 72 hrs) may be used to effectively combat dermal aging on cellular level, to address both extrinsic and intrinsic aging.

In one variation, factors are produced by a factor production unit containing SR ADSCs in 10% PRP alone after 24 hours, and a composition comprising these factors may be used to achieve a balance between development of inflammation and its rapid resolution (a derma-cosmetic composition for a stage 1 dermal rejuvenation therapy). In this variation, an exemplary composition of factors, collected at 24 hours, comprises Interleukin 5 (IL5), Interleukin 6 (IL6), Interleukin 4 (ILA), Interleukin 1 receptor 4 (IL1R4), Neurotrophin 3 (NT3), platelet derived growth factor A alpha (PDGF AA), platelet derived growth factor A beta (PDGF AB), and pro-platelet basic protein (PPBP) Chemokine (C-C motif) ligand 18 (CCL18), Chemokine (C-Cmotif) ligand 25 (CCL25), Chemokine (C-C motif) ligand 27 (CCL27), and CXC chemokine ligand 11 (CXCL11), (ICAM-1), Metalloproteinase inhibitor 2 (TIMP-2), Metalloproteinase inhibitor 1 (TIMP-1), Vascular epithelium (VE) Cadherin (calcium dependent cell adhesion protein), and insulin-like growth factor-binding protein-1 (IGFBP1).

In another variation, factors are produced by a factor production unit containing SR ADSCs in 10% PRP alone after 48 hours, and a composition comprising these factors (a derma-cosmetic composition for a stage 2 dermal rejuvenation therapy) may be used to facilitate the transition from an inflammatory phase of wound healing to a granulation phase (proliferative). In this variation, an exemplary composition of factors, collected at 48 hours, comprises Interleukin 9 (IL9), Interleukin 18 binding protein alpha (IL18BPa), Interleukin 1 receptor type II (IL1R2), Interleukin 2 receptor beta (IL-2Rb), Interleukin 2 receptor gamma (IL-2Rg), Interleukin 5 receptor alpha (IL5Ra), Interleukin 10 receptor beta (IL10Rb), Interleukin 18 receptor accessory protein (IL18Rb), and Interleukin 21 receptor (IL-21R), Insulin-like growth factor 2 (IGF2), Transforming growth factor alpha (TGFa), Transforming growth factor beta 1/latency-associated peptide (LAP), Transforming growth factor beta 1 (TGFb1), Transforming growth factor beta 2 (TGFb2), Receptor tyrosine-protein kinase ErbB-3 (ErbB3), Fas ligand (Fas LG), Leukemia inhibitory factor (LIF), Prolactin (PRL) factor, platelet-derived growth factor receptor alpha (PDGFRa), platelet-derived growth factor receptor beta (PDGFRb), Stem cell factor kit receptor (SCFR), and Sialic acid-binding Ig-like Lectin 5 (Siglec 5), CXC chemokine ligand 16 (CXCL16), Activated leukocyte cell adhesion molecule (ALCAM), E selectin (cell surface glycoprotein in immune-adhesion), Intercellular adhesion molecule 2 (ICAM2), L selectin (Lymphocyte adhesion molecule), Platelet endothelial cell adhesion molecule (PECAM 1), Activin A (INHBA), Insulin-like growth factor 2 (IGF-2), and Leptin Receptor (LEPR), Bone morphogenetic protein 5 (BMP5), Bone morphogenetic protein 7 (BMP7), Macrophage colony-stimulating factor 1 receptor (MCSFR), matrix metalloproteinase 1 (MMP1), matrix metalloproteinase 3 (MMP3), matrix metalloproteinase 9 (MMP9), and matrix metalloproteinase 13 (MMP13), monocyte differentiation antigen (CD14), cell differentiation antigen (CD80), Cardiotrophin-1 (CT-1), and Leukemia inhibitory factor (LIF), Endoglin (ENG), Tyrosine kinase with immunoglobulin-like and EGF-like domains 1 (TIE1) and Tyrosine kinase with immunoglobulin-like and EGF-like domains 2 (TIE2), Leptin Receptor (Leptin R), and Nerve growth factor receptor (NGFR).

In another variation, factors are produced by a factor production unit containing SR ADSCs in 10% PRP alone after 72 hours, and a composition comprising these factors (a derma-cosmetic composition for a stage 3 dermal rejuvenation therapy) may be used to facilitate the transition from granulation to wound re-epithelialization (peeling of skin, which is the beginning of dermal tissue remodeling). During this stage low strength, unorganized type III collagen and elastin structures produced during the ECM production phase are replaced by stronger type III collagen and structured elastin fibers to provide strength and resiliency to the dermis. In this variation, an exemplary composition of factors, collected at 72 hours, comprises such as Interleukin 1 beta (IL1b), Interleukin 3 (IL3), Interleukin-13 Receptor subunit alpha-2 (IL13Rα2), Interleukin 1 receptor alpha (IL1Rα), Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, platelet-derived growth factor B beta (PDGF BB), Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), insulin-like growth factor-binding protein-4 (IGFBP4), Stem cell factor/c-kit ligand (SCF), Stromal Cell-Derived Factor-1 alpha (SDF1a), Stromal Cell-Derived Factor-1 beta (SDF1b), Angiotensin (ANG), colony stimulating factor 2 (CSF2), Transforming growth factor beta 1 (TGFb1), Transforming growth factor beta 3 (TGFb3), tumor necrosis factor superfamily member 14 (TNFSF14), Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), Chemokine (C-C motif) ligand 11 (CCL11), Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), CXC Chemokine ligand 10 (CXCL10), Chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1).

In another variation, combinations of derma-cosmetic compositions described above can be used to promote wound healing, e.g., healing of cuts and scrapes, burns, skin grafts, and pressure ulcers.

In another variation, any skin disorder may be treated by a composition of factors produced by the factor production units of the invention. Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis. photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis. In one variation, any of these conditions can be treated by factors produced by a factor production unit using SR hADSCs, for 72 hours. In this variation, the composition comprises Interleukin 1 beta (IL1b), Interleukin 3 (IL3), Interleukin-13 Receptor subunit alpha-2 (IL13Rα2), Interleukin 1 receptor alpha (IL1Rα), Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, platelet-derived growth factor B beta (PDGF BB), Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), insulin-like growth factor-binding protein-4 (IGFBP4), Stem cell factor/c-kit ligand (SCF), Stromal Cell-Derived Factor-1 alpha (SDF1a), Stromal Cell-Derived Factor-1 beta (SDF1b), Angiotensin (ANG), colony stimulating factor 2 (CSF2), Transforming growth factor beta 1 (TGFb1), Transforming growth factor beta 3 (TGFb3), tumor necrosis factor superfamily member 14 (TNFSF14), Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), Chemokine (C-C motif) ligand 11 (CCL11), Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), CXC Chemokine ligand 10 (CXCL10), Chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1).

These factors can be delivered alone, or in combination with factors produced at different time points, for example factors produced by SR cells in 10% PRP (24, 48, or 72 hours post incubation with PRP alone) can be combined with factors produced by SR cells+with IL-2 (72 hours post induction).

In some variations, step-wise doses of factors can be delivered for the treatment of a skin related condition.

In some variations step-wise doses of factors can be delivered in combination with immunomodulatory compositions described below.

Exemplary factors that may promote skin regeneration produced using the input cells and systems provided herein include without limitation, CXCL 16 (chemokine ligand 16), IGF-2 (insulin-like growth factor 2), and TIE2 (tyrosine kinase with immunoglobin/EGF like domain).

Exemplary factors that may promote wound healing produced using the input cells and systems provided herein include without limitation, Activin A, IGF-2 (insulin-like growth factor 2), and LEPR (leptin receptor).

Exemplary factors that may promote hyaluronic acid synthesis in the skin produced using the input cells and systems provided herein include without limitation, Activin A, LEPR (leptin receptor, TGFB1 (transforming growth factor ß1), EGF (epidermal growth factor), HGF (hepatocyte growth factor), and PDGF (platelet-derived growth factor).

Exemplary factors that may promote skin elasticity produced using the input cells and systems provided herein include without limitation, IGFBP1 (insulin-like growth factor binding protein 1), IGFBP2 (insulin-like growth factor binding protein 2), IGFBP4 (insulin-like growth factor binding protein 4), TIMP1 (metalloproteinase inhibitor 1), and TIMP2 (metalloproteinase inhibitor 2).

Exemplary factors for suppression of malignancies and UV-induced skin aging produced using the input cells and systems provided herein include without limitation, endoglin and SCFR (c-KIT stem cell factor receptor.

Exemplary factors for suppressing wound healing or the inflammatory response produced using the input cells and systems provided herein include without limitation, CD 14 (cell differentiation antigen 14), CD 80 (cell differentiation antigen 80), IFNγ (interferon gamma), and LIF (leukemia inhibitory factor).

When used as a cosmetic product (to treat a cosmetic or skin condition), the factors may be delivered according to a treatment schedule. Depending on the mode of factor delivery, treatments may be completed at home or at a doctor's office. Delivery of factors after a microneedling (described below) procedure or other skin surface procedure may be part of the treatment schedule.

2. Oncology Applications

In some variations, the produced/secreted factors, the conditioned media comprising the one or more factors, compositions comprising the one or more factors, or the immunomodulated immune cells (e.g the Tregs produced herein) can be used to treat a disease or disorder related to abnormal cell differentiation such as cancer. Examples of cellular proliferative and/or differentiation disorders include any type of cancer (e.g., carcinoma, sarcoma, metastatic disorders or hematopoietic neoplastic disorders, e.g., leukemias). As contemplated herein, the cancer may be cancer of the lung, breast, thyroid, lymph glands and lymphoid tissue, gastrointestinal organs, and the genitourinary tract. The cancer may be an adenocarcinoma which is generally considered to include malignancies such as most colon cancers, renal-cell carcinoma, prostate cancer and/or testicular tumors, non-small cell carcinoma of the lung, cancer of the small intestine and cancer of the esophagus.

In one variation of the invention, a composition of factors produced by SR cells, stimulated with IL-2, and collected 72 hours post stimulation, can be administered to an individual for treatment of cancer. Use of the factors for adoptive T cell therapy is also contemplated herein, when ex vivo immunomodulated T cells are produced using factors produced by SR cells, stimulated with IL-2, and collected 72 hours post stimulation and contacted with blood or plasma.

3. Autoimmune Diseases

In some variations, the produced/secreted factors, the conditioned media comprising the one or more factors, compositions comprising the one or more factors, or the immunomodulated immune cells (e.g the Tregs produced herein) may be used for the treatment of, or for the reduction of signs and symptoms of autoimmune diseases.

In one variation of the invention, a composition of factors produced by SR cells, stimulated with IL-2, and collected 72 hours post stimulation, can be administered to an individual for treatment of an autoimmune disease. Such compositions comprise cytokines and prostaglandins and with the use of the devices described in this invention, such factors upon delivery to an individual can be released into the blood or affected tissues.

In one variation, provided herein are factors, which upon administration may be used to reset the effector T cell/Treg cell balance to treat T cell-dependent inflammatory autoimmune diseases, where there is often an imbalance between effector T cells (increase in number in certain autoimmune diseases) and functional Treg (decrease in number in certain autoimmune diseases) cells. Thus provided herein are methods and factor production units useful to reset the effector T cell/Treg balance without delivery of IL-2 drug itself. This approach is suitable for any autoimmune disease listed herein, including, but not limited to, autoimmune vasculitis, alopecia areata, diabetes, chronic graft-versus-host disease, Alzheimer's disease and age-related neurodegeneration, encephalomyelitis, multiple sclerosis, ALS, periodontal infections, rheumatoid arthritis, autoimmune inflammation of variable severity associated with cancer immunotherapies such as CAR-T, lupus, and ankylosing spondylitis (Smigiel et al, *Immunol Rev.* 2014:40-59). Such production may also be useful for wound healing and wound repair.

In one variation, the factors for the production of Tregs are produced in SR cells (or SEN cells rejuvenated to be SR), wherein the SR cells are induced to produce factors with IL-2 (combined with IL-2 for a period of about 24 hours). Factors produced under these conditions can boost Treg production (e.g. increase Tregs that are CD4+ CD25+ FoxP3+ and/or CD4+ CD25-FoxP3+). In one variation, the SR cells are incubated with IL-2 for about 24 hours, following which the conditioned media from the SR cells is brought into contact with blood, plasma, or peripheral blood mononuclear cells (PBMCs) of the blood for a period of about 72 hours, thus immunomodulating the naïve T cells in the blood, plasma, or PBMCs.

FIG. 2C shows an exemplary aspect of the invention which includes production and testing of factors useful for immunomodulation and exemplifies the production of Tregs.

4. Neurodegenerative Diseases and Stroke

In some variations, the produced/secreted factors, the conditioned media comprising the one or more factors, compositions comprising the one or more factors, or the immunomodulated immune cells (e.g the Tregs produced herein) may be used for the treatment of, or for the reduction of signs and symptoms of, neurodegenerative diseases, including but not limited to Alzheimer's disease, multiple sclerosis, Parkinson's disease, amyolateral sclerosis (ALS), and Huntington's disease as well to prevent neuronal death upon injury. Exemplary factors that may aid in the treatment of neurodegenerative diseases using the input cells and systems provided herein include factors produced by SEN hADSCs+IL-2, collected at 24-72 hrs post induction; or factors produced by SR hADSCs+IL-2 at 48 hrs post induction. The factors obtained from a factor production unit using SEN ADSCs+IL-2 collected 48 hours after stimulation can be delivered to achieve therapeutic effects for cellular migration and enhancement of enhancement of revascularization and prevention of apoptosis as required. In some variations factors from these two conditions are combined and delivered to an individual in need.

5. Age-Related Diseases

In some variations, the produced/secreted factors, the conditioned media comprising the one or more factors, compositions comprising the one or more factors, or the immunomodulated immune cells (e.g the Tregs produced herein) may be used for the treatment of, or for the reduction of signs and symptoms of age-related diseases. Such age-related diseases include, without limitation, osteoporosis, osteoarthritis, and arthritis. Exemplary factors that may aid in the treatment of age-related diseases using the input cells and systems provided herein include without limitation Interleukin 9 (IL9), Interleukin 18 binding protein alpha (IL18BPa), Interleukin 1 receptor type II (IL1R2), Interleukin 2 receptor beta (IL-2Rb), Interleukin 2 receptor gamma (IL-2Rg), Interleukin 5 receptor alpha (IL5Ra), Interleukin 10 receptor beta (IL10Rb), Interleukin 18 receptor accessory protein (IL18Rb), and Interleukin 21 receptor (IL-21R), Insulin-like growth factor 2 (IGF2), Transforming growth factor alpha (TGFa), Transforming growth factor beta 1/latency-associated peptide (LAP), Transforming growth factor beta 1 (TGFb1), Transforming growth factor beta 2 (TGFb2), Receptor tyrosine-protein kinase ErbB-3 (ErbB3), Fas ligand (Fas LG), Leukemia inhibitory factor (LIF), Prolactin (PRL) factor, platelet-derived growth factor receptor alpha (PDGFRa), platelet-derived growth factor receptor beta (PDGFRb), Stem cell factor kit receptor (SCFR), and Sialic acid-binding Ig-like Lectin 5 (Siglec 5), CXC chemokine ligand 16 (CXCL16), Activated leukocyte cell adhesion molecule (ALCAM), E selectin (cell surface glycoprotein in immune-adhesion), Intercellular adhesion molecule 2 (ICAM2), L selectin (Lymphocyte adhesion molecule), and Platelet endothelial cell adhesion molecule (PECAM 1), Activin A (INHBA), Insulin-like growth factor 2 (IGF-2), Leptin Receptor (LEPR), Bone morphogenetic protein 5 (BMP5), Bone morphogenetic protein 7 (BMP7), Macrophage colony-stimulating factor 1 receptor (MCSFR), matrix metalloproteinase 1 (MMP1), matrix metalloproteinase 3 (MMP3), matrix metalloproteinase 9 (MMP9), and matrix metalloproteinase 13 (MMP13), monocyte differentiation antigen (CD 14), cell differentiation antigen (CD80), Cardiotrophin-1 (CT-1), and Leukemia inhibitory factor (LIF), Endoglin (ENG), Tyrosine kinase with immunoglobulin-like and EGF-like domains 1 (TIE1) and Tyrosine kinase with immunoglobulin-like and EGF-like domains 2 (TIE2), Leptin Receptor (Leptin R), and Nerve growth factor receptor (NGFR).

In an exemplary variation, when factors for the treatment of age-related diseases is desired, a population of SR stem cells (e.g. hADSCs) can be placed in a factor production unit in media containing 10% PRP and factors can be collected at 48 hrs.

6. Cardiovascular Diseases

In some variations, the produced/secreted factors, the conditioned media comprising the one or more factors, compositions comprising the one or more factors, or the immunomodulated immune cells (e.g the Tregs produced herein) may be used for the treatment of, or for the reduction of signs and symptoms of, cardiovascular diseases. Such cardiovascular diseases include, without limitation, myocardial infarction, and enhancement of stem cells related therapies. The factors obtained from the factor production unit comprising SR ADSCs at 48 hrs after placement in 10% PRP alone or in combination with factors obtained from a factor production unit using SEN ADSCs+IL-2 collected 48 hours after stimulation can be delivered to achieve therapeutic effects for myocyte differentiation, cellular migration and enhancement of angiogenesis. A similar composition of factors can be used for treatment of the conditions when enhancement of revascularization and prevention of apoptosis is required.

In some variations when enhanced cell survival and paracrine stimulation by HGF is required to promote cardioprotection in myocardial infarction, an factor production unit containing SEN ADSCs without IL-2 stimulation (in PRP alone) may be used to produce factors, with factors collected 72 hrs after placement in the PRP.

7. Other Diseases

In some variations, the produced/secreted factors, the conditioned media comprising the one or more factors, compositions comprising the one or more factors, or the immunomodulated immune cells (e.g the Tregs produced herein) may be used for the treatment of, or for the reduction of signs and symptoms of, other diseases including without limitation diabetes, spinal cord injury, Crohn's disease, aplastic anemia, rheumatoid arthritis, brain injury, graft versus host disease (GVHD), kidney diseases, liver cirrhosis, and stroke, diseases of the nervous system, and spinal cord injury.

II. Factor Production Units

Described herein are systems for producing various factors, beneficial for a variety of diseases and disorders as discussed above. The systems may include a factor production unit comprising a population of input stem cells and a substrate that provides support for the cell population. Upon contact with an appropriate induction agent, the cell population of the factor production units is stimulated to produce/secrete one or more factors. The production of a particular type of factor may be tailored by the choice of induction agent, choice of cell, choice of substrate, and/or duration of cell culture post-stimulation/induction.

Figure 2D:
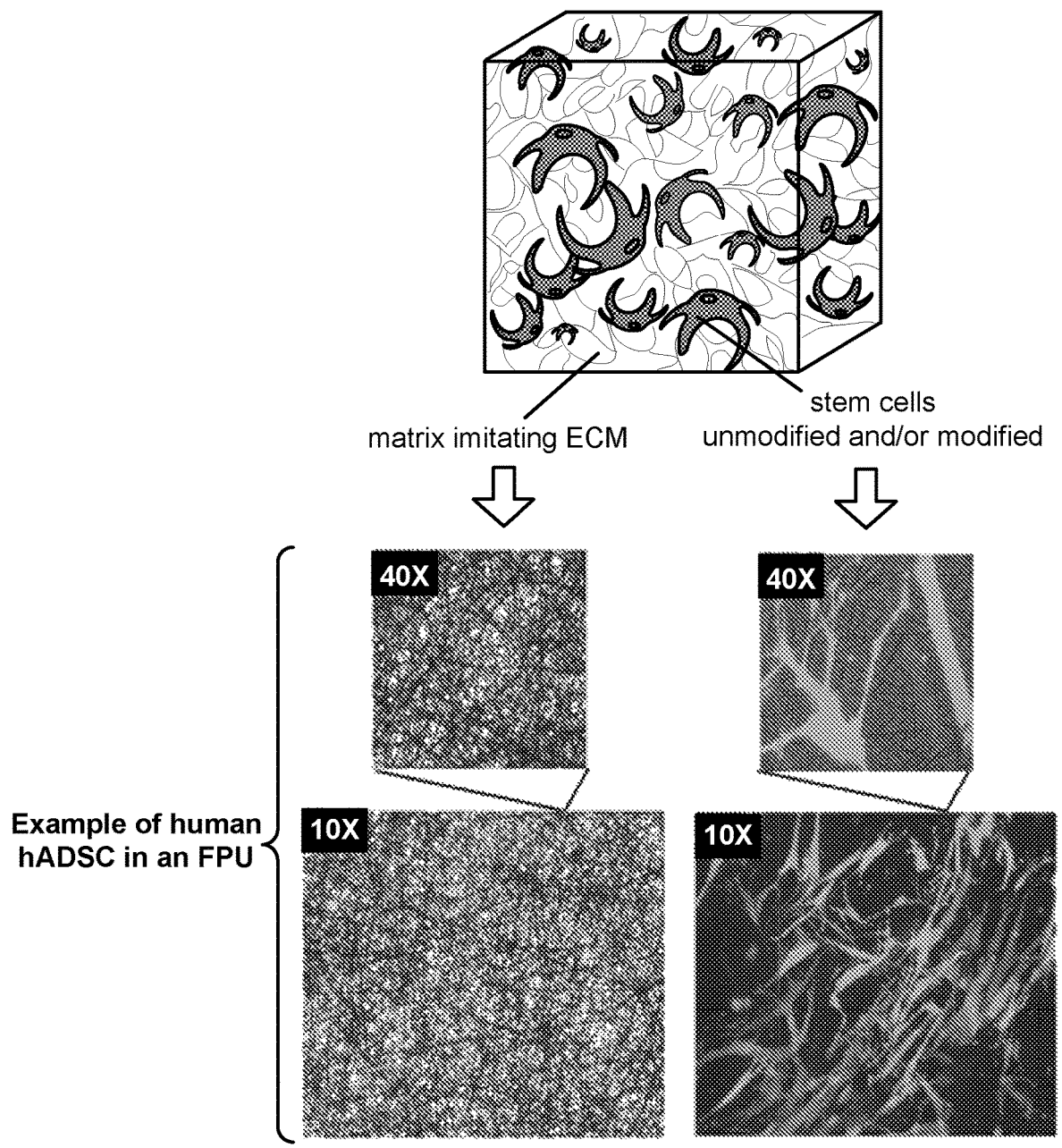
FIG. 2D pictorially illustrates hADSCs in a factor production unit of the invention, as described herein.

FIG. 2D pictorially illustrates hADSCs in an exemplary factor production unit of the invention, as described herein. The factor production unit illustrate contains 3-D scaffolds made from polymeric matrix/fibers that mimic the 3-D extracellular matrix (ECM) in which stem cells (e.g. MSCs) naturally reside. The factor production unit allows the cells to be maintained in their natural environment thereby maintaining the morphology and secretory properties of the stem cells. The stem cells produce growth factors, cytokines and other trophic factors important in the maintenance and regulation of local environment of the factor production unit, as well as secretion of bioactive molecules outside of the factor production unit space. The bottom left two panels are shown with the 3-D scaffolds without the cells the bottom right two panels show GFP-expressing hADSCs cells from a healthy 49 year old patient at 10× and 40× magnification (PD 8). GFP-expressing ADSCs were generated by lenti-viral transduction of the patient ADSCs for visualization of the cells in the matrix. GFP-expressing hADSCs were maintained in a factor production unit in 10% PRP in StemPro MSC SFM Xeno-free medium (ThermoFisher Scientific) for 12 days. GFP demonstrates the cell morphology and cell viability in the factor production unit.

A. Cells

As provided herein, the input cell populations may include any suitable type of stem cell that can be induced to produce/secrete a factor. The factors that are produced may be used for the treatment of, or for the reduction in signs and symptoms of, a variety of diseases and disorders.

The factor production unit can comprise a population of input cells, which are induced to produce factors, for delivery to an individual. The input cells may be autologous (cells from the individual who receives the factors) or allogeneic (cells not from the individual who receives the factors).

The factor production unit can comprise SR cells (including SEN cells that are rejuvenated to be SR) SEN cells (including SR cells that are induced to be SEN), only SR cells, only SEN cells, a mixture of SR and SEN cells, and any variations thereof.

B. Substrates

In addition to the cell population, the factor production units also comprise a substrate that provides support for the cell population.

Any suitable structure capable of being a matrix or scaffold for the cell population, or that can hold or carry the cell population can be employed as a substrate. For example, cells of the population can be placed and supported upon the surface of substrates such as films, membranes, sheets, meshes, discs, rods, fibers, nanofibers, etc., or can be disposed within the substrate material itself (e.g., encapsulated or embedded within the material).

Factor production units can hold cells within a volume, e.g., a multi-well plate, a tube, a chamber, or other container. In some variations, the factor production unit is an assembly that includes various compartments and/or filtering mechanisms. In further variations, the factor production unit is an implant that can be placed within a body tissue or lumen. Alternatively, the factor production unit may comprise a coating disposed upon or layered upon another structure, e.g., upon the well of a multi-well plate.

In some variations, the factor production unit is part of an apheresis system. The term "apheresis" is a general term given to a process or system that removes a component of blood. The process or system is more specifically defined by the particular blood component that is removed. For example, if plasma is removed, the process or system is referred to as "plasmapheresis" or a "plasmapheresis type system." Apheresis systems can be used to exchange cells types (e.g., erythrocytapheresis performed for sickle cell disease), treat plasma (e.g., to remove antibodies, paraproteins, cholesterol) or blood (to remove a component thought to contribute to a disease state), or modify blood components (e.g., photopheresis).

Polymers used to form the substrates are biocompatible, and can be biodegradable or non-biodegradable. Exemplary polymers include without limitation, polyamides, poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) poly(acrylic acid), poly(vinyl acetate), polyacrylamide, poly(ethylene-co-vinyl acetate), poly(ethylene glycol), poly(methacrylic acid), polylactides, polyglycolides, poly(lactide-co-glycolides), polyanhydrides, polyorthoesters, poly(carbonate), poly(acrylo nitrile), poly(ethylene oxide), polyaniline, polyvinyl carbazole, polystyrene, poly(vinyl phenol), polyhydroxyacids, poly(caprolactone), polyanhydrides, polyhydroxyalkanoates, polyurethanes, collagen, albumin, alginate, chitosan, fibronectin, gelatin, starch, hyaluronic acid, and blends and copolymers thereof.

The substrate may comprise one or more fibers. Fibers may be in the millimeter, micrometer, or nanometer range. As used herein, "fiber" refers to a fiber having any diameter, including nanofibers (diameter less than 1000 nanometers (nm)) and microfibers (diameter less than 50 micrometers ($\mu$m)). The diameter of the fibers used to make the substrates described herein may range from about 50 nm to about 20 $\mu$m. For example, the fiber diameter may be about 50 nm, about 100 nm, about 200 nm, about 300 nm, about 400 nm, about 500 nm, about 600 nm, about 700 nm, about 800 nm, about 900 nm, about 1 $\mu$m, about 2 $\mu$m, about 5 $\mu$m, about 6 $\mu$m, about 7 $\mu$m, about 8 $\mu$m, about 9 $\mu$m, about 10 $\mu$m, about 15 $\mu$m, about 20 $\mu$m, about 25 $\mu$m, about 30 $\mu$m, about 35 $\mu$m, about 40 $\mu$m, about 45 $\mu$m, or about 50 $\mu$m.

It may be beneficial in some instances for the substrate to comprise one or more nanofibers. These nanofibers can be configured to form two-dimensional (2D) or three-dimensional (3D) substrates of various size, shape, and geometry. In one variation, the nanofibers are used to construct an artificial extracellular matrix (ECM). The nanofibers may or may not be hollow. Additionally, the nanofibers may include pores of various shape, diameter, and/or distribution on or within the nanofibers.

When used to construct an appropriate ECM environment, choosing a material that accurately mimics the mechanical properties of the native ECM may provide an optimal environment for the maintenance of the cell population and for the production of factors. Included materials may be non-biodegradable polymers or polymers designed to slowly degrade. Non-biodegradable polymers may comprise polyurethane, polycarbonate, or polyester terephthalate. Biodegradable polymers may comprise polycaprolactone, polylactic acid, polyglycolic acid, gelatin, collagen, or fibronectin.

C. Formation of Substrates

The substrates may be formed by any suitable process. For example, they may be formed by extrusion, injection molding, vacuum thermoforming, or embossing the polymer material. When composed of fibers, the fibers can be also be formed by extrusion and injection molding. However, the fabrication of nanofibers can be challenging due to their minute diameters. Traditional methods, such as formation in porous solids or at the step-edges of laminated crystals, are often ineffective and costly. An alternative method is electrostatic fiber formation or electrospinning or 3-D laser printing.

In electrospinning, a high voltage (e.g., about 0.3 to about 0.50 kV) is typically applied between a target (or collector) and a conducting capillary into which a polymer solution or melt is injected. The high voltage can also be applied to the solution or melt through a wire if the capillary is a nonconductor such as a glass pipette. The collector may be a metal plate or screen, a rotating drum, or even a liquid bath if the capillary is vertical. Initially the solution at the open tip of the capillary is pulled into a conical shape (the so-called "Taylor cone") through the interplay of electrical force and surface tension. At a certain voltage range, a fine jet of polymer solution (or melt) forms at the tip of the Taylor cone and shoots toward the target. Forces from the electric field accelerate and stretch the jet. This stretching, together with evaporation of solvent molecules, causes the jet diameter to become smaller. As the jet diameter decreases, the charge density increases until electrostatic forces within the polymer overcome the cohesive forces holding the jet together (e.g., surface tension), causing the jet to split or "splay" into a multifilament of polymer fibers. The fibers continue to splay until they reach the collector, where they are collected as nonwoven fibers, and are optionally dried. A rapidly rotating collector collects aligned fibers while stationary collectors collect randomly oriented fiber mats. These fibers and mats can then be formed, shaped, etc. into various 2D or 3D structures. In one variation, the fibers are formed to resemble the structure of extracellular matrix.

Various parameters of the electrospinning process can be adjusted to modify fiber morphology. For example, solution parameters, processing parameters, and parameters such a temperature and humidity can affect fiber morphology, e.g., fiber diameter and/or porosity of the fiber. More specifically, solution parameters such as polymer concentration, polymer molecular weight, and solution viscosity; and processing parameters such as applied voltage, flow rate of the solution, and distance of between the collector and the nozzle can be adjusted.

In some variations, blends of different polymers may be electrospun together and one polymer preferentially dissolved to increase scaffold porosity.

Polymers that may be useful in making the polymer solutions for electrospinning may include without limitation, a polyethylene terephthalate, a polyester, a polymethylmethacrylate, polyacrylonitrile, a silicone, a polyurethane, a polycarbonate, a polyether ketone ketone, a polyether ether ketone, a polyether imide, a polyamide, a polystyrene, a polyether sulfone, a polysulfone, a polycaprolactone (PCL), a polylactic acid (PLA), a polyglycolic acid (PGA), a polyetherketoneketone (PEKK), a polyglycerol sebacic, a polydiol citrate, a polyhydroxy butyrate, a polyether amide, a polydiaxanone, and combinations, blends, or copolymers thereof. Alternative polymer solutions used for electrospinning may include natural polymers such as fibronectin, collagen, gelatin, hyaluronic acid, chitosan, or combinations thereof. In an exemplary variation the polymer is polycaprolactone.

It is understood that electrospinning solutions may include any polymer or combination of polymers in any compositional ratio. The concentration range of polymer or polymers in solvent or solvents may be, without limitation, about 5 wt % to about 50 wt %. Some non-limiting examples of polymer concentration in solution may include about 5 wt %, about 10 wt %, about 15 wt %, about 20 wt %, about 25 wt %, about 30 wt %, about 35 wt %, about 40 wt %, about 45 wt %, or about 50 wt %, or concentrations between any two of these values.

In some non-limiting examples, the polymer solution may comprise a weight percent ratio of polyethylene terephthalate to polyurethane of about 10% to about 90%. For example, the weight percent ratios may be about 10%, about 25%, about 33%, about 50%, about 66%, about 75%, about 90%, or a weight percent ratio between any two of these values.

The polymer solutions may also include one or more solvents such as acetone, dimethylformamide, dimethylsulfoxide, N-methylpyrrolidone, acetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof.

The polymer solutions may also include additional materials. Non-limiting examples of such additional materials may include radiopaque materials, electrically conductive materials, fluorescent materials, luminescent materials, antibiotics, growth factors, vitamins, cytokines, steroids, anti-inflammatory drugs, small molecules, sugars, lipids, salts, peptides, proteins, cell factors, or any combination thereof.

Particles such as salt or sucrose may be included in the electrospinning process and deposited throughout the scaffold. These particles may later be dissolved for increasing scaffold porosity. The properties of the fibers can be controlled to optimize the fiber diameter, the fiber spacing or porosity, the morphology of each fiber such as the porosity of the fibers or the aspect ratio, varying the shape from round to ribbon-like. Solution parameters may be controlled to customize the modulus or other mechanical properties of each fiber, the fiber composition, and/or the degradation rate. The fibers may also be formed as drug eluting fibers, anti-bacterial fibers, or radiopaque fibers to aid in positioning or locating the fibers in an x-ray, CT, or other scan.

An exemplary scaffold can be made by first preparing a polymer nanofiber precursor solution by dissolving 2-30 wt % polyethylene terephthalate (PET) in a mixture of 1,1,1, 3,3,3-hexafluoroisopropanol (HFIP) and trifluoroacetic acid, and then heating the solution to 60° C. followed by continuous stirring to dissolve the PET. The solution may be cooled to room temperature and the solution placed in a syringe (e.g., 60 cc) with a blunt tip needle (e.g., 20 gauge). The nanofibers can be formed by electrospinning using a high voltage DC power supply (Glassman High Voltage, Inc., High Bridge, N.J.) set to 1 kV-40 kV (e.g., +15 kV) positive or negative polarity, a 5-30 cm (e.g., 15 cm) tip-to-substrate distance, and a 1 µl/hr to 100 mL/hr (e.g., 10 ml/hr) flow rate. It is also possible to use a needle array including a large number of needles (e.g., >1000) to increase system output. Fiber diameter may be controlled by the viscosity of the precursor solution and the solvent used and suitable exemplary fibers are in the range of 100 nanometer 30 microns. Approximately 0.2-3 mm (e.g., 1 mm) thickness of randomly oriented and/or highly-aligned fibers may be deposited onto the form, and polymer rings added, followed by an additional approximately 0.2-3.0 mm (e.g., 2 mm) of fiber added while the form is rotated. The scaffold may be placed in a vacuum overnight to ensure removal of residual solvent (typically less than 10 ppm) and treated using a radiofrequency gas plasma for 1 minute to make the fibers more hydrophilic and promote cell attachment. Samples may be stored in re-closeable polyethylene bags, or the like.

Alternatively, the substrate fibers may be formed from a ceramic material. Exemplary ceramic materials include without limitation, titanium dioxide (TiO2), silicon dioxide (SiO2), zirconium dioxide (ZrO2), aluminum oxide (Al2O$_3$), lithium titanate (Li$_4$Ti$_5$O$_{12}$), titanium nitride (TiN), and platinum (Pt). In some variations, the nanofiber is made from a ceramic material provided as particles mixed with a polymer.

When the cell population is to be contained within the substrate material, e.g., in the material of the nanofiber, it can be added to the polymer solution which is then electrospun into nanofibers. Alternatively, the cell population can be sprayed (e.g., electrosprayed) via a separate nozzle (fiberization tip) while the nanofibers are electrospun so that the cells become embedded, encapsulated, or otherwise contained within the nanofibers before they dry.

Once made, the nanofibers can be configured to form two-dimensional (2D) or three-dimensional (3D) substrates of various size, shape, and geometry. For example, the nanofibers can be used to construct an artificial tissue such as ECM. The nanofibers can also be used to form meshes or fiber mats. The meshes, fiber mats, or collection of nanofibers may be incorporated into bandages, wound dressings, pads, wipes, etc. Alternatively, the nanofibers may be used to construct a filter or component of the factor production unit, as further described below.

In certain variations, the substrates are formed by electrospinning nanofibers onto a pre-shaped mandrel (preform) with the desired substrate shape. The mandrel may be coated with Teflon or similar material to facilitate removal of the substrate after deposition. In one variation, the mandrel shape is based on a native tissue or organ. The fibers are typically formed by extruding a polymer and/or ceramic solution from a fiberization tip, creating an electronic field proximate to the fiberization tip, and positioning a ground or opposite polarity within the mandrel. The mandrel may be rotated to align the fibers on the mandrel or a second ground or polarity may be placed in the mandrel so that rapid switching of the electric field can be done to align the fibers. The nanoscale polymer fibers may be randomly aligned or maybe substantially parallel or both.

The nanofiber structures, as well as other substrates described herein (e.g., films, membranes, meshes, sheets, implants, etc.), may be seeded with a cell population comprising one or more cell types to form a factor production unit. Seeding to apply the cells on the substrate surface may be accomplished by such known methods as spraying, electrospraying, pipetting, and printing. In some variations, the cells are electrosprayed onto the substrate. In other variations, electrospraying of cells occurs simultaneously with electrospinning of the nanofibers to seed the cells on the nanofiber or to encapsulate (or distribute) the cells within the nanofiber material. In yet further variations, the cells may be mixed with a polymer and/or ceramic material, and then extruded or injection molded into a substrate of desired size, shape, or geometry. The cells may be seeded or distributed on or within the substrate in any suitable manner. For example, the cells may be provided in a pattern on the substrate (e.g., symmetric or asymmetric pattern), or homogenously or heterogeneously distributed within the substrate material.

The substrates or nanofibers may also be coated or otherwise treated with at least one compound that is operative to promote cellular attachment to the substrate. The at least one compound may be selected from the group consisting of proteins, peptides, cytokines, growth factors, antibiotic compounds, lipids, anti-inflammatory compounds, and combinations thereof.

Hollow fibers/nanofibers can also be made by electrospinning. Here a single nozzle system may be used to electrospin two solutions, typically two different polymer solutions. The first polymer is considered the core of the fiber and the second polymer the shell of the fiber. The core material is generally a sacrificial polymer configured to be removed (e.g., by heating) after electrospinning to leave behind a hollow fiber.

D. Disposition of Cells on Substrates

The cell population may be disposed on a surface of the substrate or within the material of the substrate (e.g., the body of the substrate). In variations where the substrate comprises fibers or nanofibers, the cell population can be disposed on the surface of the fibers or nanofibers and/or a surface of the structure formed by the fibers or nanofibers, or within the material of the fiber or nanofiber itself. The cell populations can be placed on substrate surfaces by pipetting, spraying (including electrospraying), printing, or embossing the cells onto the substrate surface, or by extruding, injection molding, or thermoforming polymer-cell suspensions. Other ways of including a cell population on or within the substrate can be employed. In some variations, a cell population may be added to a polymer composition, and the resulting polymer-cell suspension electrospun so that the cells are disposed within the polymer material of the fiber. The type of substrate and/or fiber used, as well as the type of cell included on or within the substrate and/or fiber may be manipulated so that factor production by the factor production unit can be customized for the particular indication of use. For example, when the factors are to be used for cosmetic use, the substrate may comprise a plurality of nanofibers arranged as an artificial extracellular matrix, e.g., adipose extracellular matrix, and the cell population may comprise mesenchymal stem cells. In another variation, factors are produced by a factor production unit comprising a plurality of nanofibers arranged as an artificial extracellular matrix and hADSCs.

E. Exemplary Factor Production Units

In one exemplary variation, the factor production unit comprises a 3D substrate comprising nanofibers that are formed to substantially mimic the structure of extracellular matrix found within adipose tissue. A stromal vascular fraction containing MSCs, as well as endothelial cells, macrophages, monocytes, pericytes, fibroblasts, mast cells, and immune cells may be placed on this particular substrate and cultured and induced to produce one or more factors. The conditioned media containing the one or more factors may be used in any one or more of the applications provided herein (e.g. cosmetic compositions, e.g., for skin rejuvenation, wound healing, or for treating medical conditions such as an oncologic, cardiovascular, autoimmune, neurodegenerative, inflammatory or age-related diseases such as osteoporosis and arthritis).

Figure 107:
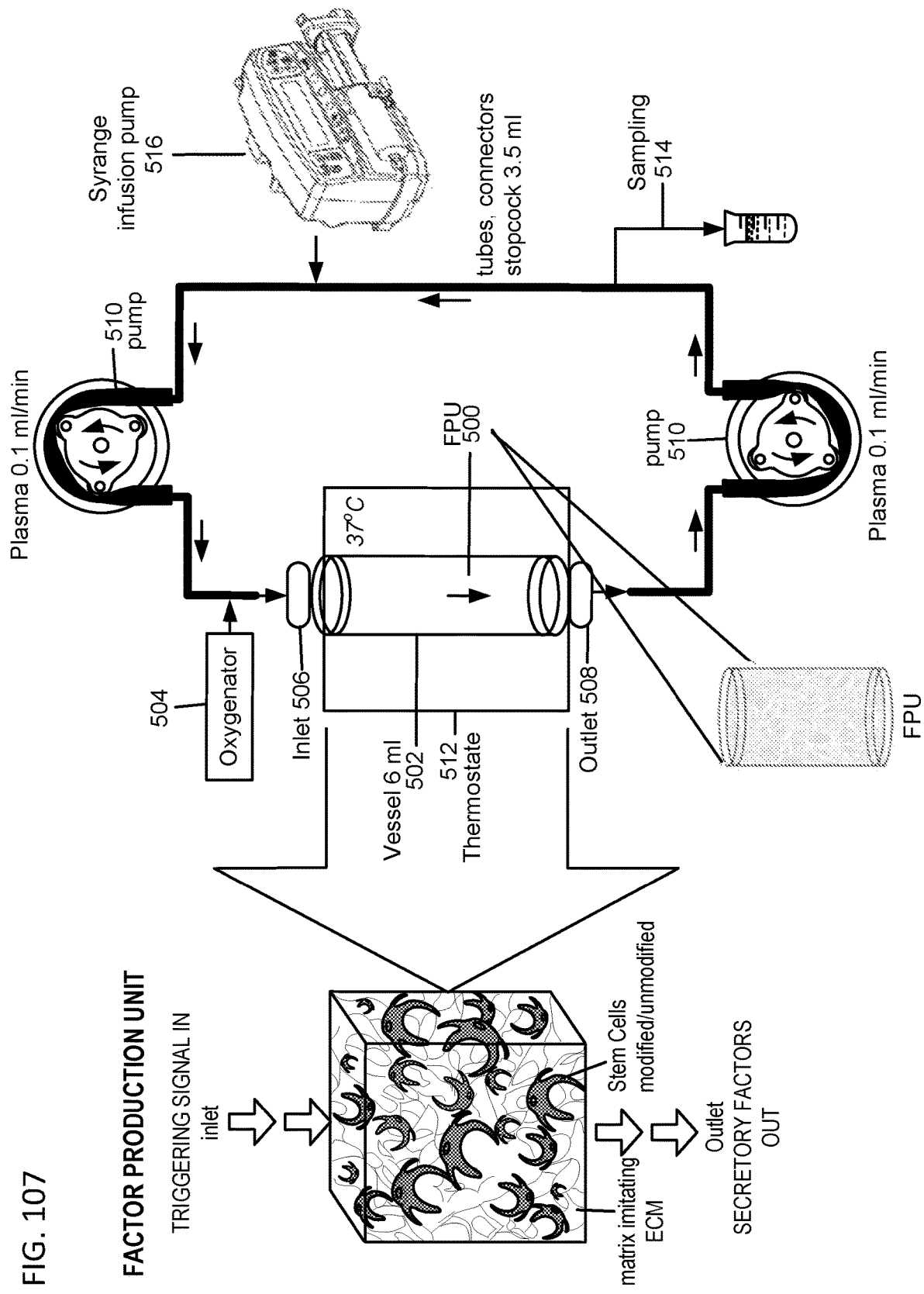
FIG. 107 shows an exemplary factor production unit within an enclosed system.

The factor production units of the invention can be stand-alone, or can be a part of a larger system, for example part of any one of the apheresis or plasmapheresis systems described herein. Referring to FIG. 107, the factor production unit can be part of an enclosed system. In FIG. 107, the factor production unit (500) is configured to connect to an individual's circulatory system to expose the individual to factors released therefrom. Any suitable factor unit described herein may be included as part of the enclosed system. Here the enclosed system comprises a vessel (502), a factor production unit (500) within the vessel (502), a fluid oxygenation device (504), an oxygenated fluid inlet (506) for introducing fluid, e.g., blood or plasma, into the factor production unit (500), a fluid outlet (508) for removing fluid from the factor production unit (500), a temperature support chamber (512), a sample collection outlet (514), and an infusion pump (516) for administration of heparin or other drugs. Peristaltic pumps (510) drive fluid flow through the enclosed system. Fluid flow through the factor production unit (500) may range from about 50 ml/min to about 500 ml/min with a plasma viscosity of about 1.10-1.30 mPA at 37° C. In some instances, fluid flow through the enclosed system ranges from about 0.1 ml/min to about 50 ml/min. The factor production unit (500) is generally configured to tolerate temperatures between about 37° C. to about 40° C. Temperature support chamber (512) generally maintains the temperature of the factor production unit (500) at 37° C.

Specifically, the enclosed system in FIG. 107 comprises a vessel (502) that accommodates a fluid volume of at least 6 ml. It is understood that the vessel can accommodate other fluid volumes. The factor production unit (500) is generally formed with a medical grade polymer that is non-heparin binding (e.g., at a heparin concentration of about 41.5 U/ml) and that tolerates DMSO (e.g., about 7-13% by weight); and cells, e.g., mesenchymal stem cells. The factor production unit (500) may be configured to be permeable to factors with a molecular weight ranging from about 1-3 kD, ranging from about 3-6 kD, or ranging from 6-50 kD. The factor production unit may also be permeable to factors having molecular weights of 50 kD and above. Fluid flowing through the fluid inlet (506) may first pass through an oxygenation device (504) that provides, e.g., about 21% $O_2$, about 5% $CO_2$, and about 74% $N_2$ to the factor production unit (500) to support cell viability. Factors that are collected at sample station (514) are typically collected at volumes of ranging from about 0.2 ml to about 1 ml.

Figure 105:
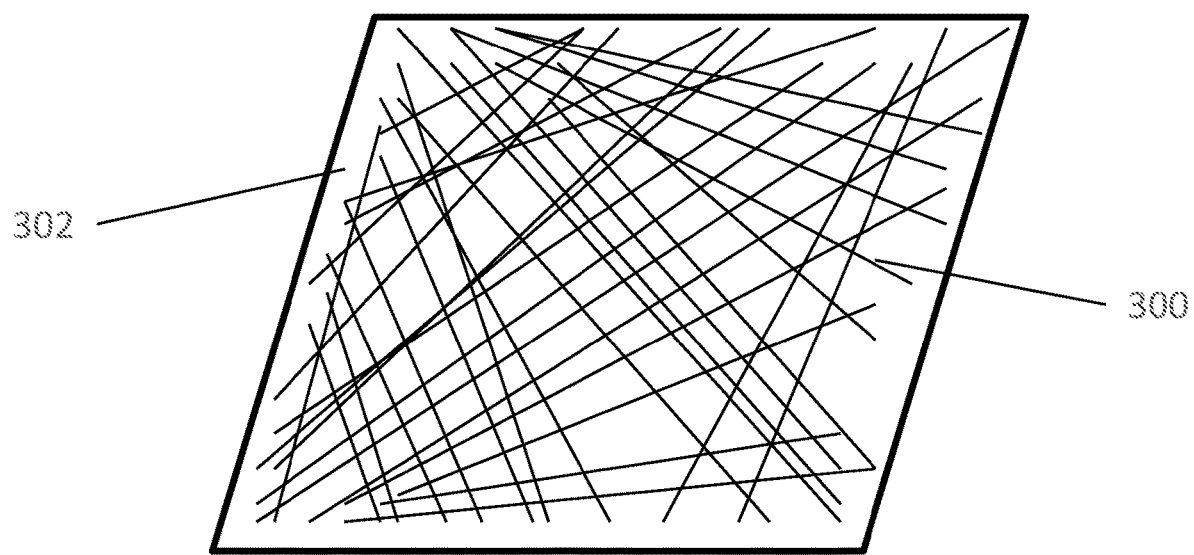
FIG. 105 depicts another exemplary factor production unit comprising electrospun polymer fibers formed as a membrane or fiber mat.

In some variations, the factor production unit is a membrane or mat formed from electrospun polymer fibers, for example, as disclosed in PCT Publication No. WO 2015/153011. For example, and as shown in FIG. 105, the factor production unit can comprise electrospun polymer fibers (300) formed as a membrane or fiber mat (substrate) (302). The fibers contain stem cells (not shown) for the training of patient-specific immune cells (e.g., T-cells) via release of instructive cytokines, matrikines, trophic factors, mediators, hormones, and/or trans-membrane and immune-cell docking receptors, from the stem cells. This exemplary variation can be used for immunomodulation applications, for example to increase the production of Tregs, for example for the treatment of autoimmune diseases, as described above. For example, when the fiber mat (factor production unit) is part of an enclosed system such as a plasmapheresis system, the fiber mat may be contacted or placed in proximity to plasma containing immune cells. The cells within the fiber mat may secrete factors into the plasma useful for modulating the immune cells or effecting a change in the immune cells. The stem cells and/or immune cells may also produce factors for collection and later use.

Factor production units comprising fiber mats and stem cells may be useful immunomodulation treatments, as noted above. Here circulating cells, pooled by apheresis immune cell populations (e.g., T-cells, B-cells, macrophages, NK cells, dendritic cells, or antigen presenting cells, etc.), or cryopreserved or isolated cells, are placed within provided media and attached to the fiber mat or placed in close proximity to the fiber mat and exposed to factors secreted from the fiber mat ex-vivo to effect a change in the cells (effect immunomodulation in the cells). These enhanced immune cells can then be released from the mat into the plasma, and the plasma containing the changed cells, e.g., mature T-cells, activated macrophages, dendritic cells, NK cells, etc., can be delivered back to the individual in a dose dependent manner. Delivery back to the individual can be by injection of the immunomodulatory cells, as well as in combination with medicaments and pharmaceutical compositions delivered into the blood circulation.

The immunomodulatory cells, as well as the factor-containing compositions described herein may be delivered into the lymphatics (intralymphatic administration), or by other routes, such as but not limited to, subcutaneous administration or sublingual administration, orally, transcutaneously (topical vaccination), intradermally, intramedullary, intrathecal, intraventricular, intranasally, conjunctival, intrabronchial, transdermally, intrarectally, intraperitoneally, intramuscularly, intrapulmonary, vaginally, rectally, and intraocularly. The immunomodulatory cells and factor-containing compositions may also be delivered by an implantable device.

In some variations, a factor production unit may be used to deliver factors for the production of Tregs.

Figures 106A, 106B:
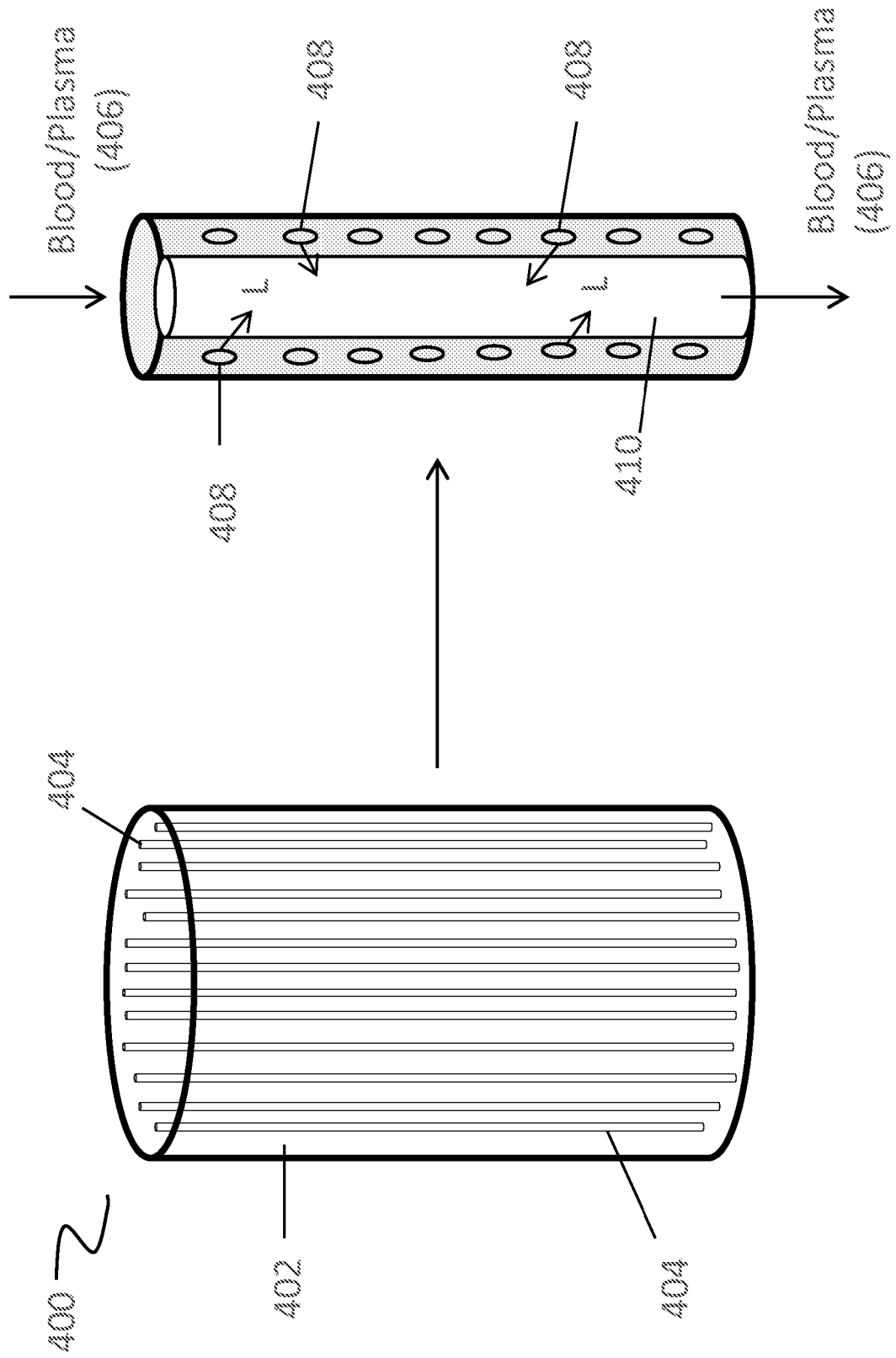
FIGS. 106A-B show an exemplary factor production unit that can be part of a reverse dialysis system or apheresis system. Specifically.

In other variations, the factor production unit can be part of a reverse dialysis type system comprising at least one cartridge formed by hollow polymeric fibers (tubes) that contain stem cells entrapped within the fiber walls. The stem cells may be autologous or allogeneic. Referring to FIG. 106A, an exemplary system includes a factor production unit (400) comprising a cartridge (402) that includes plurality of polymeric tubes (404) that run in parallel. In an exemplary variation, the system first takes a subject's blood and for circulation through a cartridge (402). As shown in FIG. 106B, which is a cross-sectional view of one of the polymeric tubes (404) in FIG. 106A, blood (406) passing through the hollow tubes (404) of the cartridge (402) permeate the tube wall (410) to contact the entrapped stem cells (408) therein, which enables the release of factors into the lumen (L) of the tube (404) and back into the blood (406). The blood with factors can then be given back to the patient. This cycle would be repeated until the desired factor dosage is achieved. These types of cartridges may also be used in plasmapheresis type systems, as further described below, where cells are removed from the blood to form plasma, and the plasma circulated through the cartridge. Factors released into the plasma can be recombined with the cells prior to introduction back into the patient. A similar type of hollow fiber cartridge is disclosed in U.S. Pat. No. 8,172,784. The hollow tubes can include pores within their walls that allow the release of factors from the stem cells. The pores may be arranged in any suitable fashion in the tube walls, e.g., homogeneously throughout, or in a symmetric or asymmetric pattern. Any suitable pore diameter may also be used. In other instances, the hollow fiber walls are made from a material permeable to the factors. Similar to the pores, the entire tube wall could be permeable or only portions thereof. Instead of being entrapped within the fiber walls, the stem cells can also be seeded and/or adhered to the inner and/or outer surfaces of the fiber walls.

In some variations, the factor production unit can comprise a cartridge that includes a pleated cylindrical membrane, as disclosed in U.S. Pat. No. 4,929,354. The factor production unit can include membranes having other suitable geometries.

Alternatively, the factor production unit may comprise a substrate, where the substrate is a single or multi-well plate having at least one layer of polymer fibers deposited on a surface of the well(s), as disclosed in U.S. Pat. No. 9,074,172. The polymer fibers may be conducive to the growth of biological cells thereon, and thus may be used for cell culture. The polymer fibers may be deposited on a surface of the well(s) by electrospinning, or 3D-printing.

In some variations, the factor production unit is a component of a plasmapheresis type system where blood is removed from an individual, separated into plasma and blood cells outside the body (extracorporeal), and one or more factors produced/secreted from the factor production unit into the plasma before return of the plasma and cells to the individual. Here the separated plasma can be circulated through various factor production units, e.g., filters comprising a plurality of fibers, to incorporate the one or more factors into the plasma for delivery back to the individual. Delivery of the factors may also be combined with drugs or genetically engineered biologics.

In one variation, the apparatus for extracorporeal circulation includes a factor production unit in the form of a cartridge or vessel comprising one or more compartments, and has at least a perfusion inlet and a perfusion outlet. A cell population can be supported on a matrix within a compartment of the cartridge, which provides a suitable environment for living cells while allowing perfusion of the cells with suitable media for maintaining the cells. Such cell compartments can be, e.g., hollow fibers, with circulation of blood or plasma outside the fibers, or flat plates; see, e.g., U.S. Pat. No. 6,759,245.

When the factor production unit is used for immunomodulation treatments, it may be disposed upstream to a cell collecting unit. In this variation, circulating cells or plasma, pooled by apheresis immune cell populations (e.g., T-cells, B-cells, macrophages, NK cells, dendritic cells, or antigen presenting cells, etc.), or cryopreserved or isolated cells, are exposed to factors secreted by the factor production unit in vitro to effect a change in the cells. These enhanced immune cells can then be collected and delivered back to the subject.

The factor production unit described herein may comprise any type of stem cell. In some variations, the factor production unit includes modified hADMSCs. Methods of treating an individual may be accomplished by connecting their circulatory system to these factor production units, thereby exposing the individual (through the blood) to factors produced by the input cells.

Apparatuses comprising factor production units may also continuously separate plasma from cellular components of blood using an ultrafiltrate generator. The ultrafiltrate (e.g., plasma) may be circulated through the cartridge containing cultured stem cells, e.g., hADSCs. Alternatively, whole blood can be treated in the factor production unit.

Factor production units may generally contain a semipermeable barrier made of a material that allows the passage of macromolecules and other cell derived products to and from the individual's plasma. In many variations cells themselves do not leave the factor production unit, however the invention is not so limited. After circulation and one or multiple passes through the factor production unit, the treated blood or ultrafiltrate (e.g., plasma, which may be recombined with the cellular components of the individual's blood) may be returned to the individual via venous access. The individual's blood or plasma may be supplemented with heparin to prevent clotting. This circulation may be maintained continuously for, e.g., a 2 hour, 3 hour, 4 hour, 5 hour, 6 hour, 7 hour, 8 hour, 9 hour, 10 hour, etc. period of therapy. Blood or plasma may carry factors to the individual from the stem cells in the factor production unit.

The factor production units may also include a fluid treatment compartment and a cell compartment, and optionally a selectively permeable barrier separating the fluid treatment compartment and the cell compartment. The cell reservoir can be in fluid communication with the cell compartment of the factor production unit, wherein the cell reservoir comprises a population of stem cells, e.g., hADSCs. Blood or ultrafiltrate from an individual can be passed into the fluid treatment compartment, where agents secreted by the stem cells pass into the blood or ultrafiltrate, either by direct contact between the stem cells and the blood or ultrafiltrate, or by passage of the agents across the optional selectively permeable barrier, when present.

Figure 100:
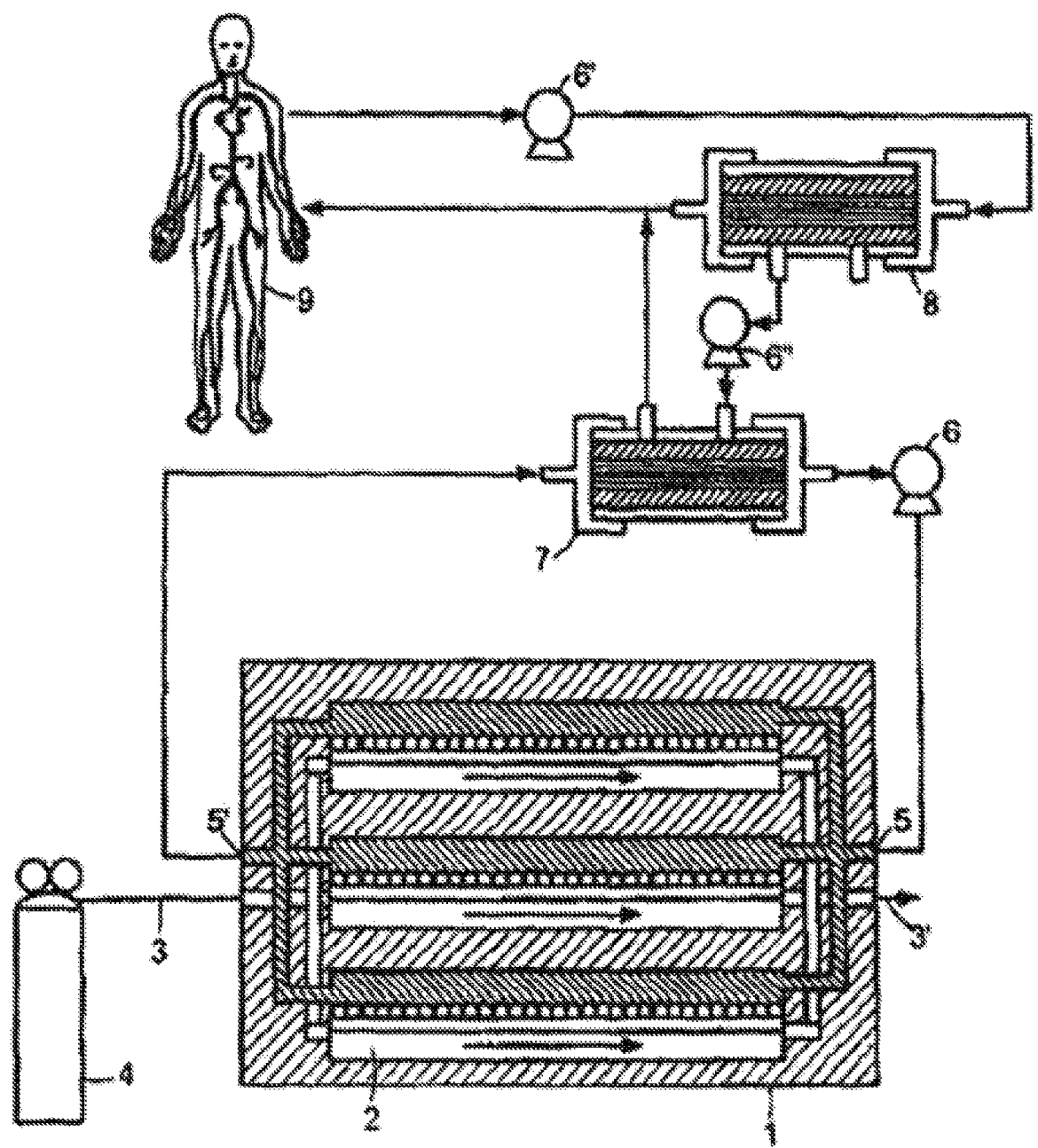
FIG. 100 shows a schematic diagram of an exemplary factor production unit.

FIG. 100 FIG. 100 illustrates a schematic diagram of an exemplary factor production unit. The factor production unit (1) which may have multiple cartridges and (2) contain modified (e.g., rejuvenated and induced) hADSCs as described herein. In this example, the factor production unit (1) includes an oxygenated fluid inlet (3) for introducing an oxygenated fluid from an oxygenated fluid supply (4), an oxygenated fluid outlet (3'), a liquid inlet (5) for introducing a biological liquid, supplied by pump (6) from immunoisolation unit (7), into the factor production unit and a liquid outlet (5') for removing the biological liquid containing one or more factors from the factor production unit for return to the immunoisolation unit (7). Blood from an individual (9) flows via pump (6') into a plasmapheresis unit (8), from which a portion of the plasma then flows into the immunoisolation unit (7), via pump (6''). Treated plasma (with the one or more factors) flows from the immunoisolation unit (7) and is mixed with blood from the plasmapheresis unit (8) prior to flowing back into the individual (9).

Figure 101:
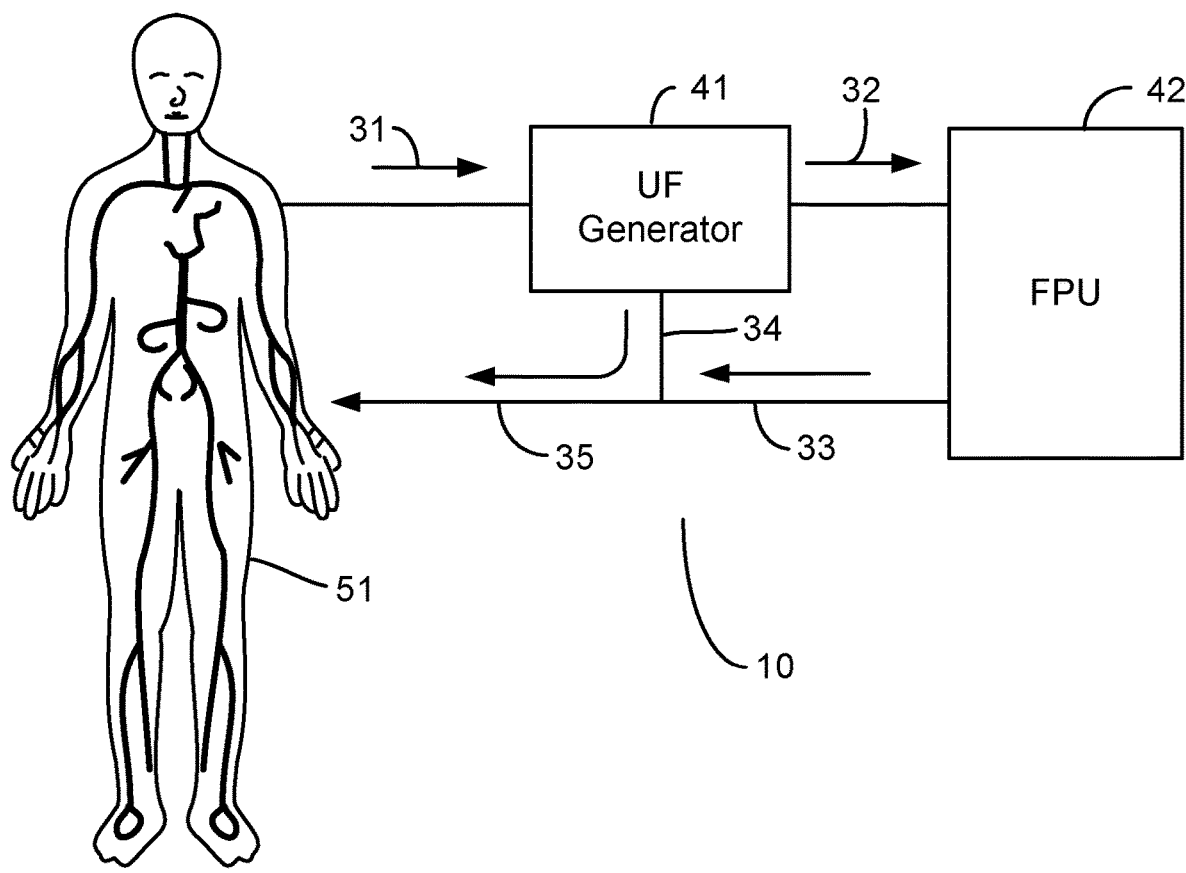
FIG. 101 shows an exemplary factor production unit in schematic form.

Referring to FIG. 101, another example of a factor production unit is shown in schematic form (see U.S. Pat. Nos. 7,160,719 and 8,172,784). System (10) is represented by and external factor production unit (FPU) (42) that includes modified hADSCs for the production of one or more factors. Blood or plasma can flow through the factor production unit (42) via biological fluid inlet pathway (32) and after the introduction of one or more factors, can exit via biological fluid outlet pathway (33). For example, a catheter can be used to place a mammal's bloodstream in fluid communication with EB (42) via biological fluid inlet path (32). In some variations, the apparatus includes an ultrafiltrate (UF) generator (41). In those cases, blood from the mammal (51) flows along blood path (31) into UF generator (41), where the cellular components are separated from plasma. The ultrafiltered plasma then flows along path (32) into EB (42), while the cellular components rejoin the treated UF via path (34). The biological fluid then returns to mammal (51) or to the biological fluid reservoir via path (35).

Although FIGS. 100 and 101 depict the various components of a factor production unit in a specific orientation and having similar dimensions, the components can be in any orientation, size, or shape.

The flow rate of an individual's plasma through a reverse dialysis system or plasmapheresis system can be adjusted as needed, e.g., to a rate of about 50-500 ml/minute, e.g., 50, 100, 200, 300, 400, and 500 ml/minute. In some variations, the flow rate will be adjusted to optimize passage of secreted factors from the stem cells (e.g., hADSCs) to the ultrafiltrate. In some variations, the target flow rate will be 175 ml/minute. Treatment of the individual (e.g., circulation of the individual's plasma through a factor production unit) can continue for a therapeutically effective time, e.g., between 1 hour and 72 hours, e.g., about 2, 3, 4, 5, 10, 12, 15, 18, 20, or 23 hours. Individuals can undergo multiple rounds of modified hADSC therapy with each round lasting for, e.g., between 1 hour and 24 hours. This therapy can be continued, e.g., until a desired therapeutic factor dose or effect has been achieved, as decided by the individual or the individual's healthcare provider.

The factors can be collected at other predetermined time points post induction. Alternatively, a predetermined duration of time for circulation of plasma or blood through a factor production unit, e.g., a hollow fiber cartridge, or the number of flow cycles through the factor production unit can be predetermined in order to customize the amount (dose) of factors received by an individual.

Factors generated by the cells can be released into the blood, plasma or culture media. The factors can be released into the blood, plasma or culture media flowing through the factor production unit, e.g., a hollow fiber cartridge or released into a media in which the factor production unit, e.g., an electrospun nanofiber extracellular matrix, is being cultured. Depending on the duration of factor production unit culturing or exposure of the factor production unit to flowing blood/plasma/media, and type of cell included in the factor production unit, different factors and/or different amounts (doses) of factors may be produced. Accordingly, the manufacture of factors can be controlled or tailored based upon the particular composition of the factor production unit and its duration of culturing or exposure to flowing plasma/media. When the factor production unit is exposed to flowing blood/plasma/media, the production and dosing of factors can also be tailored based on the number of flow cycles.

In other variations, the factor production unit may be integrated (e.g., with an integrated cell chamber) or may be configured to use one or more removable cartridges for holding/culturing the stem cells. The cartridges can be configured for single use (disposable) or repeated use. A number of suitable configurations of cartridges are known in the art, see, e.g., U.S. Pat. Nos. 5,270,192; 7,160,719; 6,858,146; 6,582,955; 6,759,245; 8,172,784; Dixit and Gitnick, Eur. J. Surg. Suppl. (582):71-6 (1998); and Legallais et al., J. Memb. Sci. 181:81-95 (2001). Such cartridges can include, e.g., hollow fibers or flat plates. A semi-permeable membrane can be used to separate the biological fluid to be treated from the cells, and such a membrane can form part of the cartridges, e.g., an exterior wall of the cartridge. The cartridges may be configured to be inserted into an factor production unit, e.g., as part of the factor production unit or as an entire factor production unit. Accordingly, the factor production unit may be part of a larger system.

Figure 102:
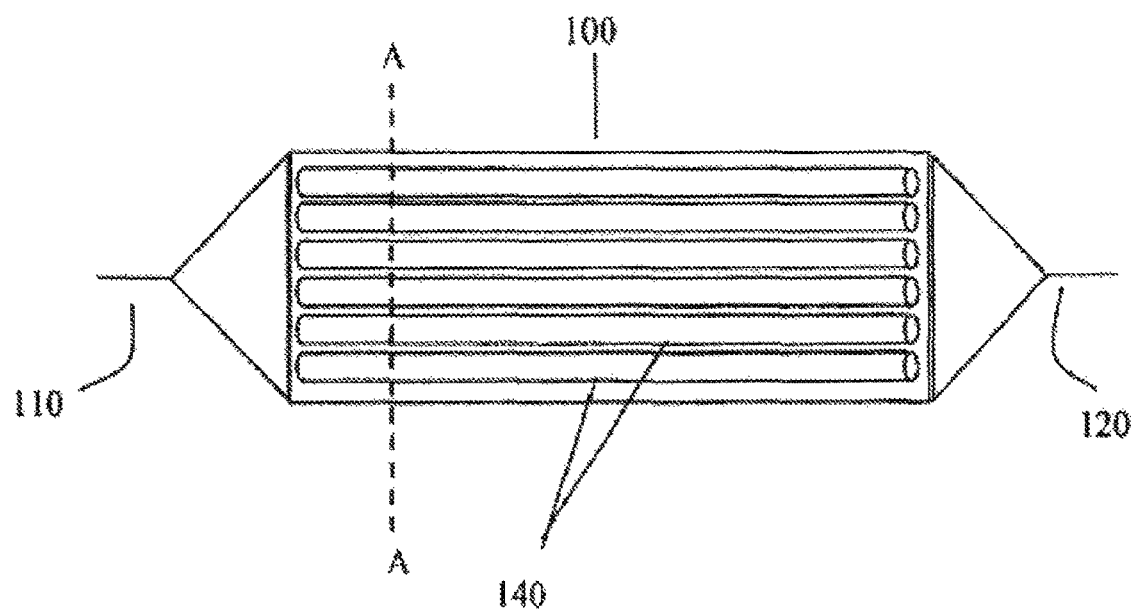
FIG. 102 shows an exemplary factor production unit in schematic form comprising a plurality of hollow fibers.

FIG. 102 is a schematic illustration of an exemplary factor production unit represented by hollow fiber cartridge (100), containing a number of hollow fibers (140), and an inlet (110) and outlet (120). The hollow fibers are semi-permeable, allowing passage of the factors secreted by the stem cells, e.g., hADSCs, into the blood or plasma.

Figure 103:
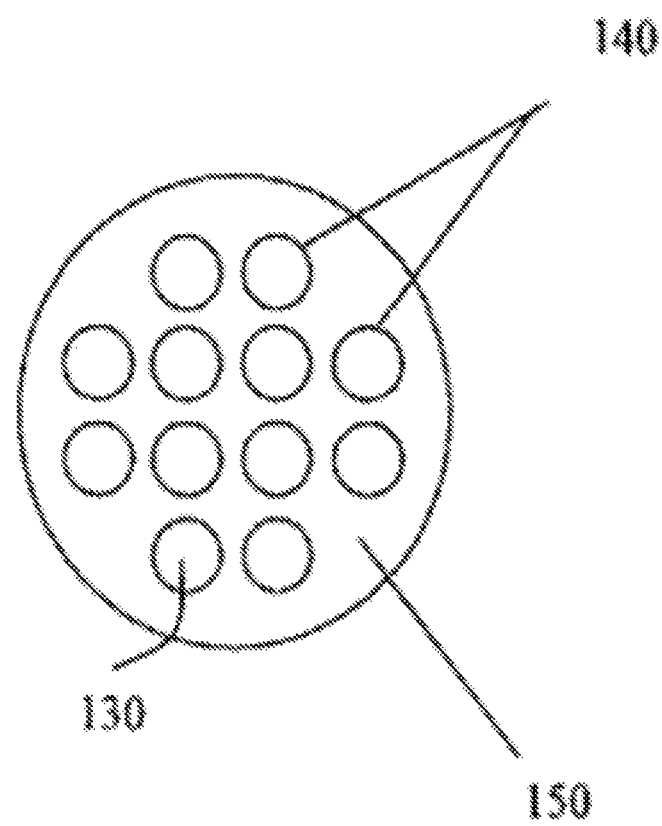
FIG. 103 is a cross-sectional view of the factor production unit provided in FIG. 102 taken at line A-A.

FIG. 103 is a cross-sectional view of a factor production unit (100) at line A-A in FIG. 102, illustrating the hollow fibers (140), which have an interior capillary lumen (130) surrounded by an extracapillary space (150). In hollow fiber factor production unit, the stem cells can be either in the lumen (130), while the blood or plasma flows through the extracapillary space (150), or vice-versa.

Figure 104:
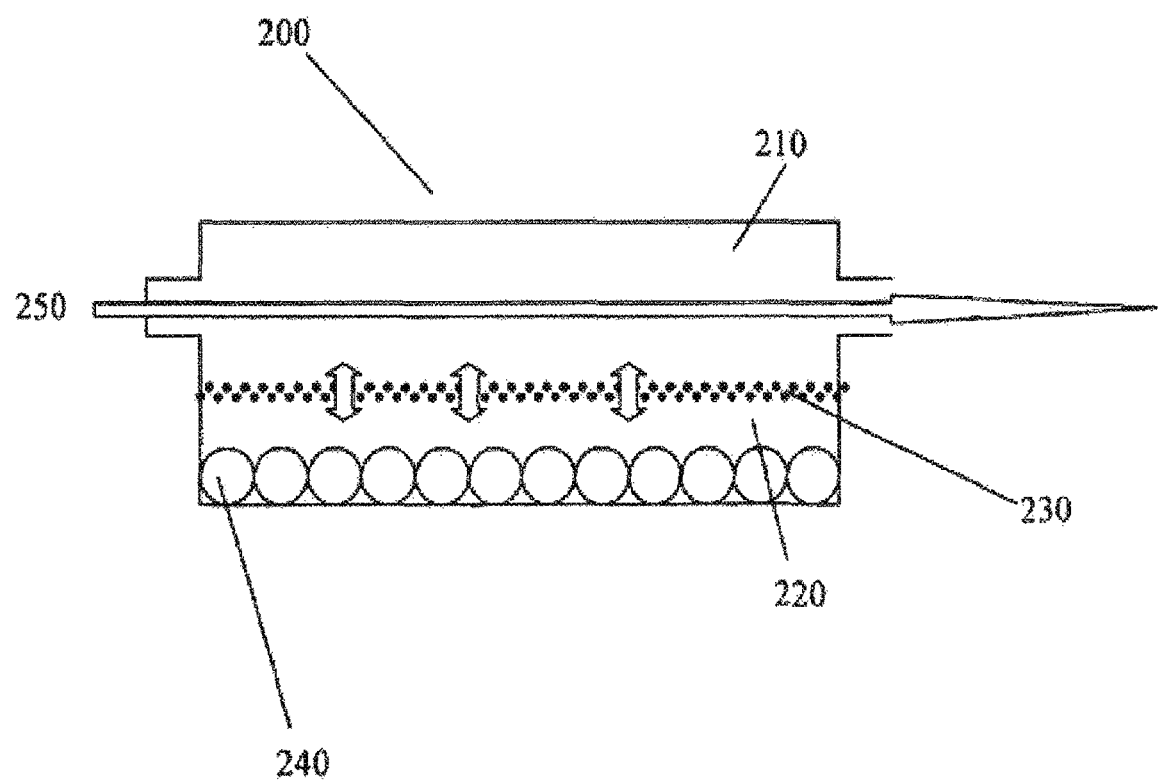
FIG. 104 shows another exemplary factor production unit in schematic form comprising a fluid treatment compartment and a cell compartment.

FIG. 104 is a schematic illustration of another exemplary factor production unit, represented by a flat-plate or two-compartment factor production unit (200), including a fluid treatment compartment (210) and a cell compartment (220), separated by a semi-permeable membrane (230). Blood or plasma flows through fluid treatment compartment (210) along path (250). Cell compartment (220) includes stem cells, e.g., rejuvenated and induced hADSCs (240). A similar type of unit is described in further detail in U.S. Pat. No. 6,759,254.

In one exemplary variation, the factor production unit comprises an apparatus configured to deliver factors derived from modified hADSCs, the apparatus comprising: a first compartment; a second compartment; a selectively permeable barrier separating the first compartment and the second compartment; a population of hADSC within the second compartment, wherein the level or activity of SINE/ALU retrotransposon transcripts in the hADSCs is reduced to an amount sufficient to induce or restore proliferative capacity and/or pluripotency to said hADSCs, further wherein the hADSCs have been induced by exposing the hADSCs to interleukin-2 (IL-2) so that the production of factors in the cells is enhanced; and a fluid inlet and a fluid outlet connected to the first compartment, wherein the fluid inlet and outlet permit fluid communication between the first compartment and the bloodstream of an individual.

The selectively permeable barrier may comprise a bundle of hollow fibers. Alternatively or additionally, the apparatus may include one or more filters for filtering the blood (or plasma) and/or for filtering fluid from the second compartment before it communicates with the first compartment. The second compartment may be configured as a cartridge that can be removably connected to the apparatus. The cartridge may be snap-connected to the rest of the apparatus, which may also include support for maintaining the hADSC alive and healthy before and during the treatments described herein.

Any of these apparatuses may also include fluidic handling components, including pumps, channels, filters, etc.; for example, any of these apparatuses may include a pump configured to circulate blood or plasma through the first compartment. Any of these apparatuses may include a filter in fluid communication with the first compartment.

Alternatively, the factor production unit may include a substrate comprising a plurality of polymer fibers contained within. These polymer fibers may be made by electrospinning. The fiber substrates of the present invention may be used with factor production units of different sizes and shapes, as well as those that are disposable or permanent (i.e., reusable). The polymer fibers in these substrates may also be randomly arranged relative to one another or may be aligned with one another. Depending on the factor production unit geometry, the fiber substrates may be adhered to the factor production unit walls or other surfaces or may be dispersed, individual fibers that are free-floating in the cell culture media contained in a factor production unit. To adhere polymer fibers to a factor production unit, the fiber may be deposited directly onto a surface by placing a negatively charged substrate behind the factor production unit. This technique permits uniform deposition of positively charged fibers onto the factor production unit surface. Alternatively, the fibers may be attached to the factor production unit walls with adhesives, heat, laser welding, ultrasonic welding, or other methods.

In an exemplary variation, methods of treatment include using hADSCs, using any of the factor production units described herein. For example, a method of treatment may include: reducing the level or activity of SINE/Alu retrotransposon transcripts in extracted hADSC in an amount sufficient to induce or restore proliferative capacity and/or pluripotency to said hADSC; and inducing the hADSC (either or both rejuvenated, formerly SEN-hADSC or SR-hADSC) by exposing the hADSC to interleukin-2 (IL-2) to enhance the production of factors; and induction the hADSC (either or both rejuvenated, formerly SEN-hADSC or SR-hADSC) by exposing the hADSC to interleukin-2 (IL-2) to enhance the production of factors; and connecting an factor production unit apparatus to the individual, wherein the factor production unit apparatus comprises a first compartment and a second compartment separated by a selectively permeable membrane, wherein the second compartment comprises the hADSC; and passing an individual's blood or plasma through the first compartment to expose the blood or plasma to factors produced by the hADSC in the second compartment. Connecting the apparatus to the individual may include connecting the apparatus to the individual's circulatory system through an inlet and an outlet of the factor production unit apparatus.

In yet further variations, the treatment method may include: connecting an factor production unit to the individual, wherein the factor production unit comprises a first compartment and a second compartment separated by a selectively permeable membrane, wherein the second compartment comprises a population of hADSC that have been rejuvenated by reducing the level or activity of SINE/Alu retrotransposon transcripts in the hADSC in an amount sufficient to induce or restore proliferative capacity and/or pluripotency to said hADSC, and further wherein the hADSC have been induced by exposure to interleukin-2 (IL-2) to enhance the production of factors; and passing the individual's blood or plasma through the first compartment to expose the blood or plasma to the hADSC in the second compartment.

Any of these methods may include a extracting the hADSC from an individual or obtaining or reviving of the hADSC after cryopreservation. The individual may be the same individual that the hADSC or an extract of the hADSC are administered to (e.g., autologous treatment).

Other methods may include identifying an individual having a disease (e.g., any of the disease discussed above which may benefit from MSC treatment), and providing an factor production unit for treating blood or plasma from the individual that includes a fluid treatment compartment and a cell compartment, and a selectively permeable barrier separating the fluid treatment compartment and the cell compartment, wherein the cell compartment includes a population of rejuvenated and induced hADSCs and exposing the individual's plasma or blood to the hADSCs in the factor production unit.

III. Use and Delivery of Factors

Methods of delivering the factors are also described herein. Once the factors are produced by the input cells, for example in the factor production units provided herein, they may be delivered to an individual in a variety of ways. The method of delivery is generally dependent on the type of composition that has been formulated with the factor. One or more factors may be delivered by conventional routes like sublingual administration, orally, intravenously, via injection, topically, transdermally, transcutaneously (topical vaccination), intradermally, intramedullary, intrathecal, intraventricular, intranasally, conjunctival, intrabronchial, transdermally, intrarectally, intraperitoneally, intramuscularly, intrapulmonary, vaginally, rectally, or intraocularly or through the CSF or intralymphatic administration.

In an exemplary variation, one or more factors are delivered using an apheresis-type delivery such as plasmapheresis. When plasmapheresis is performed, blood is removed from an individual, separated into plasma and blood cells outside the body (extracorporeal), and one or more factors are added into the plasma before return of the plasma and cells to the individual. Here, the separated plasma can be circulated through the factor production unit as described herein to incorporate the one or more factors into the plasma for delivery back to the individual. Delivery of the factors may also be combined with drugs or biologics.

When the factors are formulated into oral dosage forms, they may be delivered orally as a tablet, capsule, or as a coating thereon; as a dissolvable film; as an oral spray; etc.

When the factors are formulated into an intravenous dosage form, the factors can be delivered intravenously as a solution. Injectable compositions may be delivered via a syringe, image-guided needle, or other needled device (e.g., microneedle patch) for local administration of factors, e.g., into a wrinkle, a particular skin layer, or tumor mass. In some variations, instead of being delivered through the needle lumen, the factors are coated on a needle(s), and are released when the needle(s) is placed into tissue.

In some variations, the factors are provided in conjunction with an implant. If the composition is an implant, the composition may be implanted/placed within a particular body site or tissue. Sustained release of the factors may be achieved with implantable compositions, as well as other compositions described herein.

Alternatively, the factors may be formulated into compositions that are topically applied onto the skin or a mucosal surface, and include without limitation, water based gels or pastes, ointments, creams for dermatological use (anhydrous or hydrous), serums, lotions (anhydrous or hydrous), emulsions, sprays, solutions, aerosols, sticks (solid cream), films, bandages, towellettes, powders, skin sprays, nasal or throat sprays, oral drops, eye drops, ear drops, spreadable film-forming compositions, and transdermal patches.

When topically applied, delivery of the factors into the skin may be enhanced or assisted by various skin surface treatments preformed beforehand. The skin surface treatment may be performed prior to factor application. For example, the skin surface treatment may be performed up to two (2) hours before, up to one (1) hour before, up to 30 minutes before, up to 15 minutes before, up to 10 minutes before, or up to 5 minutes before factor application. The skin surface treatment can include without limitation, dermabrasion, laser resurfacing, and chemical peels. In some variations, the skin surface treatment includes micro-needling. Microneedling may be accomplished with any suitable derma roller. Derma rollers are commercially available devices that generally comprise a drum-shaped roller studded with microneedles arranged in rows around the roller, where the microneedles are about 0.5-1.5 mm in length and 0.1 mm in diameter. When rolled over the skin, the derma roller creates openings in the skin that allow for better penetration of the topically applied compositions. Here, microneedling with a derma roller can be performed prior to topical application of a factor composition to enhance penetration of the factors into the skin, and to also create micro-injuries, which trigger the inflammatory/healing process to produce collagen and other substances beneficial in rejuvenating the skin and improving skin appearance. In turn, the delivered factors can induce keratinocytes to produce growth factors including, but not limited to, PDGF, IL-1, TGF-α, and TGF-β, which have been shown to exert a paracrine effect on proliferation and activation of dermal fibroblasts, leading to skin regeneration and remodeling of dermal extracellular matrix.

The factor composition may be a topical composition, as previously stated. Exemplary topical compositions include, but are not limited to, water based gels or pastes, ointments, creams (anhydrous or hydrous), serums, lotions (anhydrous or hydrous), emulsions, sprays, solutions, aerosols, sticks (solid cream), films, bandages, towellettes, powders, skin sprays, nasal or throat sprays, oral drops, eye drops, ear drops, spreadable film-forming compositions, and transdermal patches.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (e.g., factor(s) or conditioned media) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (e.g., factor(s) or conditioned media) is added to the formulation at the desired concentration at a point preceding addition of the gelling agent.

Ointments generally are prepared using either (1) an oleaginous base, i.e., one consisting of fixed oils or hydrocarbons, such as white petrolatum or mineral oil, or (2) an absorbant base, i.e., one consisting of an anhydrous substance or substances which can absorb water, for example, anhydrous lanolin. Customarily, following formation of the base, whether oleaginous or absorbent, the active ingredient (e.g., factor(s) or conditioned media) is added in an amount affording the desired concentration.

Serums may be watery or thicker liquids, often clear in color. Serums are water based making them light in consistency. Serums may be layered under other serums as well as creams or lotions making them a very flexible product to incorporate into skin care regimens. Serums are tolerated well by all skin types as long as the individual is not sensitive to any of the ingredients. Serums may include glycerol or glycerine.

Some compositions of the invention can be applied as a thin homogeneous film, which does not require occlusion, bioadhesives, or other additives or devices to effect pharmacological action. The formulation may be applied through physical mechanical means including swab, applicator pad, syringe spreader, or like devices intended to apply liquids in a thin film.

The compositions may be formulated as desired with additives used commonly in the pharmaceutical sciences, such as penetration enhancers, surfactants, oils and fats, polyhydric alcohols, lower alcohols, thickening agents, UV absorbents, light scattering agents, preservatives, antioxidants, antibiotics, chelating agents, pH regulators, flavoring agents, pigments, and water.

Penetration enhancers suitable for use in the factor compositions include, but are not limited to, enhancers from any of the following classes: fatty alcohols, fatty acids (linear or branched); terpenes (e.g., mono, di and sequiterpenes; hydrocarbons, alcohols, ketones); fatty acid esters, organic acids, ethers, amides, amines, hydrocarbons, alcohols, phenols, polyols, surfactants (anionic, cationic, nonionic, bile salts).

Non limiting examples of surfactants include polyoxyethylene (hereinafter abbreviated as POE-branched alkyl ethers such as POE-octyldodecyl alcohol and POE-2-decyltetradecyl alcohol, POE-alkyl ethers such as POE-oleyl alcohol ether and POE-cetyl alcohol ether, sorbitan esters such as sorbitan monooleate, sorbitan monoisostearate and sorbitan monolaurate, POE-sorbitan esters such as POE-sorbitan monooleate, POE-sorbitan monoisostearate and POE-sorbitan monolaurate, fatty acid esters of glycerol such as glyceryl monooleate, glyceryl monostearate and glyceryl monomyristate, POE-fatty acid esters of glycerol such as POE-glyceryl monooleate, POE-glyceryl monostearate and POE-glyceryl monomyristate, POE-dihydrocholesterol ester, POE-hardened castor oil, POE-hardened castor oil fatty acid esters such as POE-hardened castor oil isostearate, POE-alkylaryl ethers such as POE-octylphenol ether, glycerol esters such as glycerol monoisostearate and glycerol monomyristate, POE-glycerol ethers such as POE-glycerol monoisostearate and POE-glycerol monomyristate, polyglycerol fatty acid esters such as diglyceryl monostearate, decaglyceryl decastearate, decaglyceryl decaisostearate and diglyceryl diisostearate and other nonionic surfactants; potassium salts, sodium salts, diethanolamine salts, triethanolamine salts, amino acid salts and other salts of higher fatty acids such as myristic acid, stearic acid, palmitic acid, behenic acid, isostearic acid and oleic acid, the above alkali salts of ether carboxylic acids, salts of N-acylamino acids, N-acylsalconates, higher alkylsulfonates and other anionic surfactants; alkylamine salts, polyamine, aminoalcohol fatty acids, organic silicone resin, alkyl quaternary ammonium salts and other cationic surfactants; and lecithin, betaine derivatives, and other amphoteric surfactants.

Examples of oils and fats include vegetable oils and fats such as castor-oil, olive oil, cacao oil, camellia oil, coconut oil, wood wax, jojoba oil, grape seed oil and avocado oil; animal oils and fats such as mink oil and egg yolk oil; waxes such as beeswax, whale wax, lanolin, carnauba wax and candelilla wax; hydrocarbons such as liquid paraffin, squalene, microcrystalline wax, ceresine wax, paraffin wax and vaseline; natural or synthetic fatty acids such as lauric acid, myristic acid, stearic acid, oleic acid, isostearic acid and behenic acid; natural or higher alcohols such as cetanol, stearyl alcohol, hexyldecanol, octyldecanol and lauryl alcohol; and esters such as isopropyl myristate, isopropyl palmitate, octyldodecyl myristate, octyldodecyl oleate, and cholesterol oleate.

Examples of polyhydric alcohols include ethylene glycol, polyethylene glycol, propylene glycol, 1,3-butyrene glycol, 1,4-butyrene glycol, dipropylene glycol, glycerol, diglycerol, triglycerol, tetraglycerol and other polyglycerols, glucose, maltose, maltitose, sucrose, fructose, xylitose, sorbitol, maltotriose, threitol, and erythritol.

Examples of thickening agents include naturally-occurring high molecular substances such as sodium alginate, xanthene gum, aluminum silicate, quince seed extract, gum tragacanth, starch, collagen and sodium hyaluronate; semi-synthetic high molecular substances such as methyl cellulose, hydroxyethyl cellulose, carboxymethyl cellulose, soluble starch and cationized cellulose; and synthetic high molecular substances such as carboxyvinyl polymer, and polyvinyl alcohol.

Examples of UV absorbents include p-aminobenzoic acid, 2-ethoxyethyl p-methoxycinnamate, isopropyl p-methoxycinnamate, butylmethoxybenzoylmethane, glyceryl-mono-2-ethylhexanoyl-di-p-methoxybenzophenone, digalloyl trioleate, 2,2'-dihydroxy-4-methoxybenzophenone, ethyl-4-bishydroxypropylaminobenzoate, 2-ethylhexyl-2-cyano-3,3'-diphenyl acrylate, ethylhexyl p-methoxycinnamate, 2-ethylhexyl salicylate, glyceryl p-aminobenzoate, homomethyl salicylate, methyl o-aminobenzoate, 2-hydroxy-4-methoxybenzophenone, amyl p-dimethylaminobenzoate, 2-phenylbenzoimidazole-5-sulfonic acid, and 2-hydroxy-4-methoxybenzophenone-5-sulfonic acid.

Examples of preservatives include benzoates, salicylates, sorbates, dehydroacetates, p-oxybenzoates, 2,4,4'-trichloro-2'-hydroxydiphenyl ether, 3,4,4'-trichlorocarbanilide, benzalkonium chloride, hinokitiol, resorcinol, and ethanol.

Examples of antioxidants include tocopherol, ascorbic acid, butylhydroxyanisole, dibutylhydroxytoluene, nordihydroguaiaretic acid and propyl gallate.

Examples of chelating agents include sodium edetate and sodium citrate.

In addition to those stated above, suitable vehicles, carriers, and adjuvants include water, vaseline, petrolatum, mineral oil, vegetable oil, animal oil, organic and inorganic waxes, polymers such as xanthanes, gelatin, cellulose, collagen, starch, kaolin, carrageenan, gum arabic, synthetic polymers, alcohols, polyols, and the like. The carrier can also include sustained release carrier such as lypizomes, microsponges, microspheres, or microcapsules, aqueous base ointments, water in oil or oil in water emulsions, gels or the like.

Additional agents that may be included in the factor compositions are vitamins, antioxidants, minerals, extracts, coenzyme Q10, caviar extract, shiitake extract, tripeptide (SYN-AKE), Matrixyl 3000 (palmitoyl oligopeptide and palmitoyl-tetrapeptide-7) (Sederma, Inc., Edison, N.J.), and other compounds such as alpha-tocopherol (vitamin E), melanin, vitamin C, vitamin A, retinyl proprionate, retinoic acid, vitamin D3, nicotinamide (vitamin B), niacinaminde (Vit B3), d-panthenol, hyaluronic acid, ceramides, or seaweed (algae) extracts.

In some instances, the factors are unstable when combined with substances such as surfactants, oils, and/or other excipients. In these instances, the factors can be formulated into a composition that can be lyophilized and dissolved in 10% hyaluronic acid before use.

IV. Articles of Manufacture

The present application also provides articles of manufacture comprising any one of the devices or compositions described herein.

An exemplary kit can contain one or more of the following in a package or container: (1) an factor production unit cartridge; (2) one or more pharmaceutically acceptable buffers; and (3) instructions for installing the factor production unit cartridge, including instructions for modifying and/or adding the stem cells such as hADSCs.

Also provided herein are dermarollers, microneedles, creams, and transdermal patches for use with delivery of the any of the factor compositions provided herein.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Example 1: Materials and Methods

This example provides the materials and methods subsequently used in Examples 2-9.

Isolation, Culture and Characterization of MSCs

MSCs used in this research were isolated from human adipose tissues obtained from healthy adult female donors age 32 and 49 undergoing routine liposuction procedures at the UCSD medical center, San Diego, Calif. The MSC isolation protocol was approved by the local ethics committee and performed as previously described. Isolated adipose-derived stem cell lines were grown in DMEM/F12 medium (Life Technologies). In accordance with the MSC minimal definition criteria set by the International Society for Cellular Therapy, flow cytometric analysis showed that hADSCs express CD29, CD73, CD90 and CD105 but do not express CD11b, CD14, CD19, CD34, CD45, CD80, CD86 (antibodies from eBiosciense, USA). Morphological analysis showed that the cells present a fibroblast-like morphology, were plastic adherent and capable of adipogenic, chondrogenic and osteogenic differentiation under in vitro conditions using commercially available differentiation mediums (Invitrogen, USA). Cumulative population doublings (PD) were calculated as PD=log(N/NO)×3.33 across the multiple passages as a function of the number of days of growth in culture, where NO is the number of cells plated in the flask and N is the number of cells harvested at this passage. hADSCs PD 4 or PD 6 SR populations and PD 41 and 45 for SEN populations were used in all experiments. Treatment with recombinant IL-2 (Peprotech, USA) was performed as described in Deenick E K, Gett A V, Hodgkin P D (2003) Stochastic model of T cell proliferation: a calculus revealing IL-2 regulation of precursor frequencies, cell cycle time, and survival. J Immunol 170: 4963-4972. 20 U/ml of IL-2 was added to the culturing media for 24 hours at 37° C.

Senescence—Associated SA-β Galactosidase Assay

The assay for monitoring the expression of pH-dependent senescence-associated (3-galactosidase activity (SA-βGal) was performed as described in manufacturer's kit (BioVision) and previously published in Wang J, Geesman G J, Hostikka S L, Atallah M, Blackwell B, et al. (2011) Inhibition of activated pericentromeric SINE/ALU repeat transcription in SEN human adult stem cells reinstates self-renewal. Cell cycle 10: 3016-3030. The cultured hADSCs were washed with PBS for 15 minutes at room temperature, washed twice with PBS and stained with X-Gal containing supplement overnight at 37° C. The cells were washed twice with PBS, and the images were captured using a microscope (Nikons, TE300, DXM1200 Digital Camera, Japan).

Migration and Invasion Assay

Transwell filters were from Corning Incorporated (Acton, Mass., USA) and all the cytokines in use were obtained from Peprotech Inc. (Rocky Hill, N.J., USA). The migration assay was performed as described in Perez L M, Bernal A, San Martin N, Galvez B G (2013), Arch Physiol Biochem 119: 195-201 using 8 mm thick Transwell chambers. For the Transwell migration assay, $1.0 \times 10^4$ cells were suspended in 80 ul of serum-free alpha-MEM and seeded in the upper chamber of 24-well Transwell plates containing 8 mm pore size filters (Corning, Costar, USA). In the lower chamber, 600 ul of DMEM or medium containing cytokines: IL-2, IL-6, IL-8, TNF-α, HMGβ1 was added. The concentrations in used were: 50 ng/ml IL-2, IL-6, IL-8 and HMGβ1; 30 ng/ml TNF-α as described in (Perez et al., 2013, Arch Physiol Biochem 119: 195-201). hADSCs were incubated at 37° C. for 16 h. The cells retained in the upper chamber were removed by swab and those that had migrated through the filter were fixed with 4% paraformaldehyde for 20 minutes at room temperature and stained overnight with 5% toluidine blue. The cells were counted at the lower side; in five different randomly selected 10× fields using a bright-field microscope (Nikons, TE300, DXM1200 Digital Camera, Japan). These experiments were done with hADSCs of two donors age 32 and 41, ether SR or SEN populations, with each donor sampled more than three times.

Enzyme-Linked Immunosorbent Assays (ELISA)

hADSCs (SR or SEN) were plated at a density of $10^5$ cells per 10 $cm^2$ dish and treated with 20 U/mL of IL-2 for 24 hour, with untreated controls as previously described in Deenick E K, Gett A V, Hodgkin P D (2003) Stochastic model of T cell proliferation: a calculus revealing IL-2 regulation of precursor frequencies, cell cycle time, and survival. J Immunol 170: 4963-4972. Then, cell membrane-associated protein fractions were prepared using MemPER Plus #89842 (ThermoFisher Scientific) following the manufacturer's protocol. Measurements of the concentrations of IL-2 receptors alpha and beta were obtained using human IL-2R alpha and human IL-2R beta ELISA kits #ELH-IL-2Ra and #ELH-IL-2Rb (RayBiotech, Inc) respectively. The optical densities for the standards (recombinant IL-2 receptors alpha and beta) as well as the experimental samples were measured at 450 nm by SPECTRA Max Plus (Molecular Devices) and concentrations were calculated as described in the manufacturer's protocol.

Real-Time Quantitative Polymerase Chain Reaction

Total RNA was isolated from hADSCs using the RNeasy Mini Kit (Qiagen, Germany). cDNA was then synthesized using the RevertAid First Strand cDNA Synthesis Kit (Fermentas, USA). Real-time quantitative polymerase chain reaction (qPCR) was performed using TaqMan instrument. The expression levels were calculated as $2^{-\Delta\Delta Ct}$, where relative expression was determined by normalization to beta-actin gene expression. All assays were conducted in triplicates and negative control samples without cDNA were used. Primers for the qPCR were as follows:

```
IL-2 Receptor Alpha chain (IL-2Rα)
For:
                              (SEQ ID NO: 1)
5'-CTGCCACTCGGAACACAAC-3'
and Rev:
                              (SEQ ID NO: 2)
5'-TGGTCCACTGGCTGCATT-3'.

IL-2 Receptor Beta chain (IL-2Rβ)
For:
                              (SEQ ID NO: 3)
5'-ACTCGAGAGCCAACATCTCC-3'
and Rev:
                              (SEQ ID NO: 4)
5'-TCCGAGGATCAGGTTGCAG-3'.

IL-2 Receptor Gamma 1 chain (IL-2Rγ1)
For:
                              (SEQ ID NO: 5)
5'-TGGATGGGCAGAAACGCTA-3'
and Rev:
                              (SEQ ID NO: 6)
5'-GGCTTCCAATGCAAACAGGA-3'.

STAT 5A
For:
                              (SEQ ID NO: 7)
5'-ACGCAGGACACAGAGAATGA-3'
and Rev:
                              (SEQ ID NO: 8)
5'-CTGGGCAAACTGAGCTTGG-3'.

STAT 5B
For:
                              (SEQ ID NO: 9)
5'-ACACAGCTCCAGAACACGT-3'
and Rev:
                              (SEQ ID NO: 10)
5'-TGTTGGCTTCTCGGACCAA-3'.

VEGF A
For:
                              (SEQ ID NO: 11)
5'-GGAGGAGGGCAGAATCATCA-3'
and Rev:
                              (SEQ ID NO: 12)
5'-ATCAGGGGCACACAGGATG-3'.
```

Transcriptomic Analysis

Transcriptomic analysis was performed with IL-2 treated and untreated (control group) SR and SEN-hADSCs as previously described in Deenick E K, Gett A V, Hodgkin P D (2003) Stochastic model of T cell proliferation: a calculus revealing IL-2 regulation of precursor frequencies, cell cycle time, and survival. J Immunol 170: 4963-4972. The two genotypes shown in FIG. 3A were used for the analysis of four different conditions: SR or SEN cells, with or without IL-2 stimulation, respectively. The same amount ($10^6$) cells was seeded in DMEM F12 media for each experimental condition, and IL-2 treatment was performed by adding 20 U/ml of recombinant IL-2 (Peprotech, USA) directly into the media for 24 hours as previously described in Deernick et al. 2003. Total RNA was isolated from samples using TRIzol reagent (Invitrogen, USA) according to the manufacturer's instructions. Samples from two different patients were combined together for the relevant conditions and RNA concentrations were measured with the Qubit 2.0 fluorimeter using the RNA HS Assay kit (Invitrogen, Life technologies, USA).

100 ng of total RNA of each sample was used to construct the libraries for sequencing on the Ion Proton™ System (Life technologies, USA) following the manufacturer's instructions. Prior to rRNA depletion and RNA-seq library construction, the ERCC RNA Spike-In Control mix (Ambion, Life Technologies) was added to total RNA for quality control analysis. The ERCC RNA Spike-In control mix contains 92 transcripts 250-2000 nt in length that mimic natural eukaryotic mRNAs. According to the protocol provided by manufacturer for 100 ng of total RNA was added to 2 ul of Mix1 in dilution 1:1000 of spike-in. Afterwards, rRNA depletion was performed with the Low Input Ribominus Eukaryote System v2 (Ambion, Life technologies, USA). cDNA libraries were constructed with Ion total RNA-seq kit v2 (Ambion, Life technologies, USA), and barcoded with Ion Xpress RNA-seq barcode (Ambion, Life technologies). The size distribution and quantification of the libraries were performed on a Bioanalyzer 2100 (Agilent technologies, USA). Library sequencing was performed on the Ion Proton™ System with P1 chip, and each library was sequenced 3 times.

RNA-Seq Data Analysis

RNA-seq reads from individual Ion Proton™ System sequencing runs were combined for each of the four conditions. Sequence reads were mapped to the reference human genome assembly hg19 (GRCh37) using the Torrent Mapping Alignment Program (TMAP, Life technologies). The quality of the four condition-specific combined RNA-seq runs was evaluated by comparing the expected counts of ERCC spike-in RNA sequences, obtained from the manufacturer's website, against the observed counts of RNA-seq tags that map to the same sequences. Initial gene expression levels were taken as the sum of exon-mapped reads for individual NCBI RefSeq gene models (c), and lowly expressed genes (read counts per million<1) were removed from subsequent analyses. For each library, individual gene expression levels were normalized using the beta-actin (ACTB) expression levels (cACTB) and the total exon length 1 of each gene. For library j, the beta-acting normalization factor $s_j$ was calculated as $$\frac{\frac{1}{n}\sum_{k=1}^{n} c_{ACTB,k}}{c_{ACTB,j}}$$

and the final normalized expression value for gene i in library j was calculated as as $$e_{i,j} = \frac{c_{i,j} \times s_j}{l_i}.$$

Differential gene expression analysis between pairs of libraries was performed using the program GFOLD v1.1.3, Feng J, Meyer C A, Wang Q, Liu J S, Shirley Liu X, et al. (2012) GFOLD: a generalized fold change for ranking differentially expressed genes from RNA-seq data. Bioinformatics 28: 2782-2788. GFOLD was chosen based on its demonstrated superior performance in characterizing differentially expressed genes in the absence of replicate data sets. GFOLD analysis yields a score that measures the extent of differential gene expression between conditions; the recommended GFOLD score cut-off of ±0.01 was used to define differentially expressed genes here. Functional enrichment analysis for differentially expressed genes between pairs of libraries was performed using the program GSEA v2.1.0. Specifically, individual pathways containing multiple genes that are up-regulated or down-regulated upon IL-2 treatment in SR, SEN or both were identified in this way. Individual pathways for specific sets of differentially regulated genes (IL-2+ up-regulated in SR and/or SEN and IL-2+ down-regulated in SR and/or SEN) were related using networks where the nodes correspond to pathways and the edges correspond to the presence of shared genes between pathways.

Figure 9:
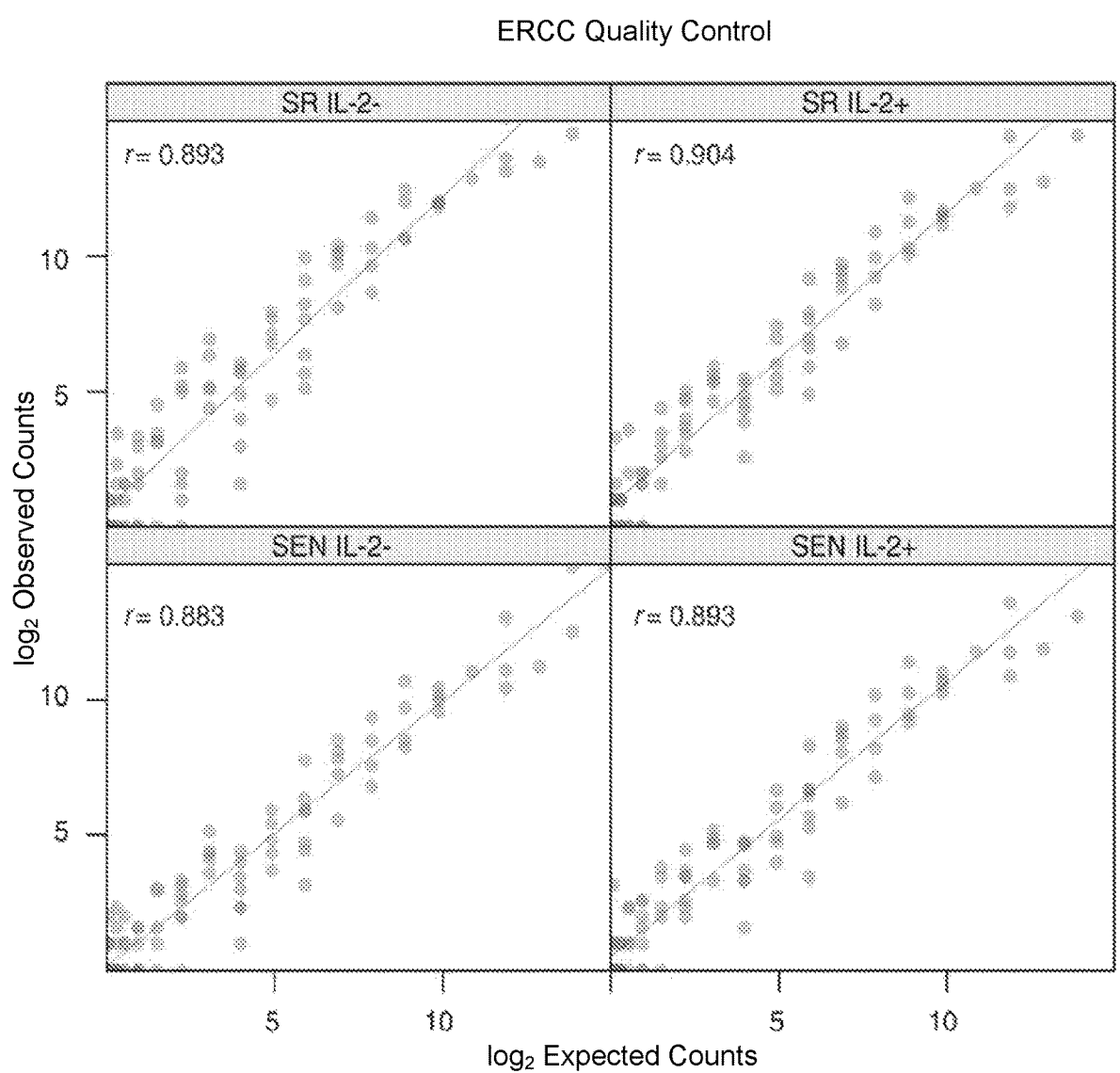
FIG. 9 shows External RNA Controls Consortium (ERCC, a common set of external RNA controls) dose response used for quality control of RNA-seq experiments.

FIG. 9 shows External RNA Controls Consortium (ERCC, a common set of external RNA controls) dose response used for quality control of RNA-seq experiments. For each of the four condition-specific RNA-seq pools, the expected counts of ERCC spike-in RNA sequences were regressed against the observed counts of RNA-seq tags that map to the same sequences. Observed versus expected counts were highly correlated, as indicated by the shape of the regression and the Pearson correlation r-values, consistent with high quality RNA-seq results.

Example 2: Characterization of the MSC Senescent Phenotype

Described in this example is a study that was conducted to evaluate the impact of replicative senescence on the transcriptional activity of human adipose-derived MSCs (hADSCs) in response to IL-2 signaling.

Figure 3A:
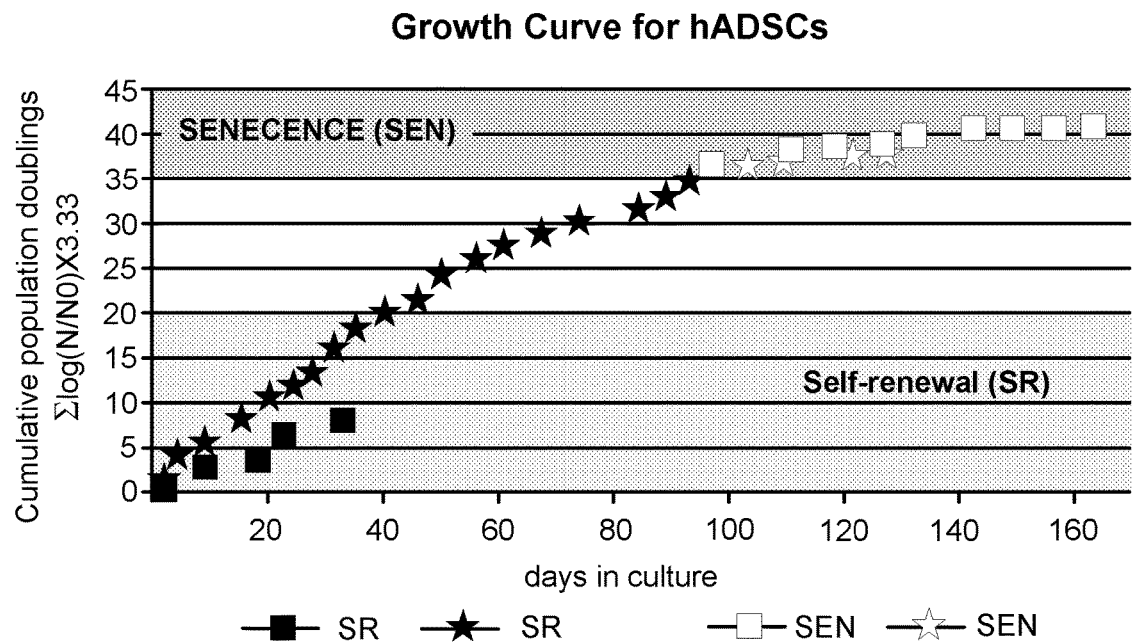
Figure 3B:
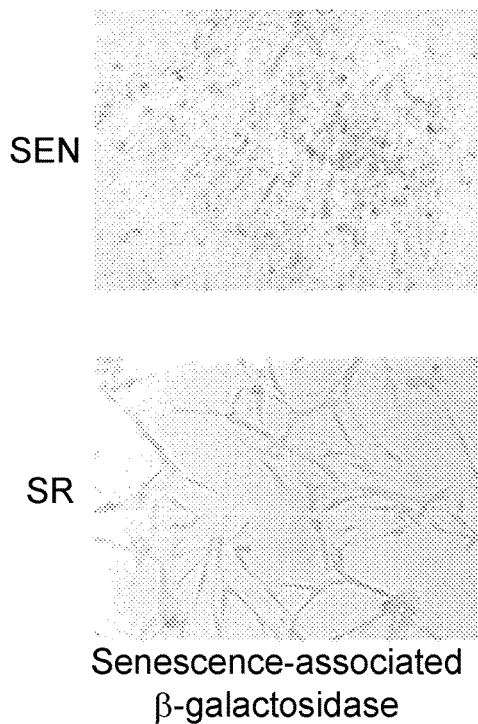

IL-2 signals via specific receptors, with three classes of cell surface receptors formed by various combinations of three IL-2R subunits: IL-2Ra (CD25), IL-2Rβ (CD 122) and IL-2Rg (CD 132). The experimental results indicate that hADSCs transcriptionally express all three receptors, however protein expression of the IL-2Ra in hADSCs is lower than seen for IL-2Rβ. These observations indicate that an IL-2 receptor composition consisting of IL-2Rβ and IL-2Rγ isoforms may mediate the predominant form of IL-2 cytokine recognition by hADSCs. The receptor composition changes only slightly upon replicative aging of the hADSCs, indicating that responsiveness of hADSCs to IL-2 does not change upon their senescence.

hADSCs were isolated and cultured as described above. Ex vivo replicative senescence led to decreased proliferation, accumulation of DNA damage and morphological changes: hADSCs became much larger with an irregular and flat shape, and nuclei became more circumscribed in phase contrast microscopy with the granular cytoplasm appearance of many inclusions and aggradations. The growth curve of hADSCs obtained from two different patients are shown in FIG. 3A. Typical staining for senescence-associated SA-β galactosidase activity for either hADSCs in linear growth rate, SR, or when cell lines cease their proliferation, SEN, is shown in FIG. 3B.

Example 3: SEN-MSCs Demonstrate a Higher Propensity for Migration

Figure 3C:
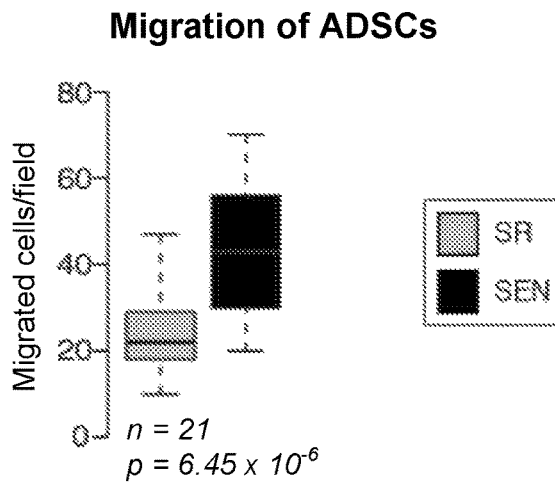

Migration assays were performed, using a set of cytokines and growth factors using the Transwell system as described in the Materials and Methods section, below. It was observed that adipose-derived MSCs undergoing replicative senescence demonstrated a higher propensity for migration. It was observed that SEN-hADSCs showed significantly higher basal migration capacity then their SR counterparts (FIG. 3C). FIG. 3C shows ex vivo migration assays for SR (left) and SEN (right) hADSCs. The black lines indicate the median values, and the whiskers indicate the range of values. Statistical differences were evaluated by a T-test with the p-value (p) as depicted.

In addition, the response of SEN-hADSCs to different cytokine chemo-attractants was measured. It was observed that hADSCs have an increased ability to migrate for late passages in comparison to early passages (FIG. 3D), indicating that replicative senescence increases the migratory properties of hADSCs in response to the tested chemo-attractants. IL-2 was the most potent chemo-taxis stimulant on SEN-MSCs, whereas the TNF-α was less potent among the tested chemo-attractants in these experiments (FIG. 3D). FIG. 3D shows the migration of self-renewing SR (on left) and senescence SEN (right) hADSCs. hADSCs were induced to migrate in the presence of different cytokines (50 ng/ml IL-2, IL-6, IL-8, HMGB1; 30 ng/ml TNF). The graphic represents the mean of ten independent experiments (n=10). P-values (p) related to experimental measurements are listed under the graphs.

Collectively, these data indicated that replicative senescence modifies the migratory properties of hADSCs and may influence the response of MSCs to the inflammatory environment and influence their immunomodulation output.

Figure 4A:
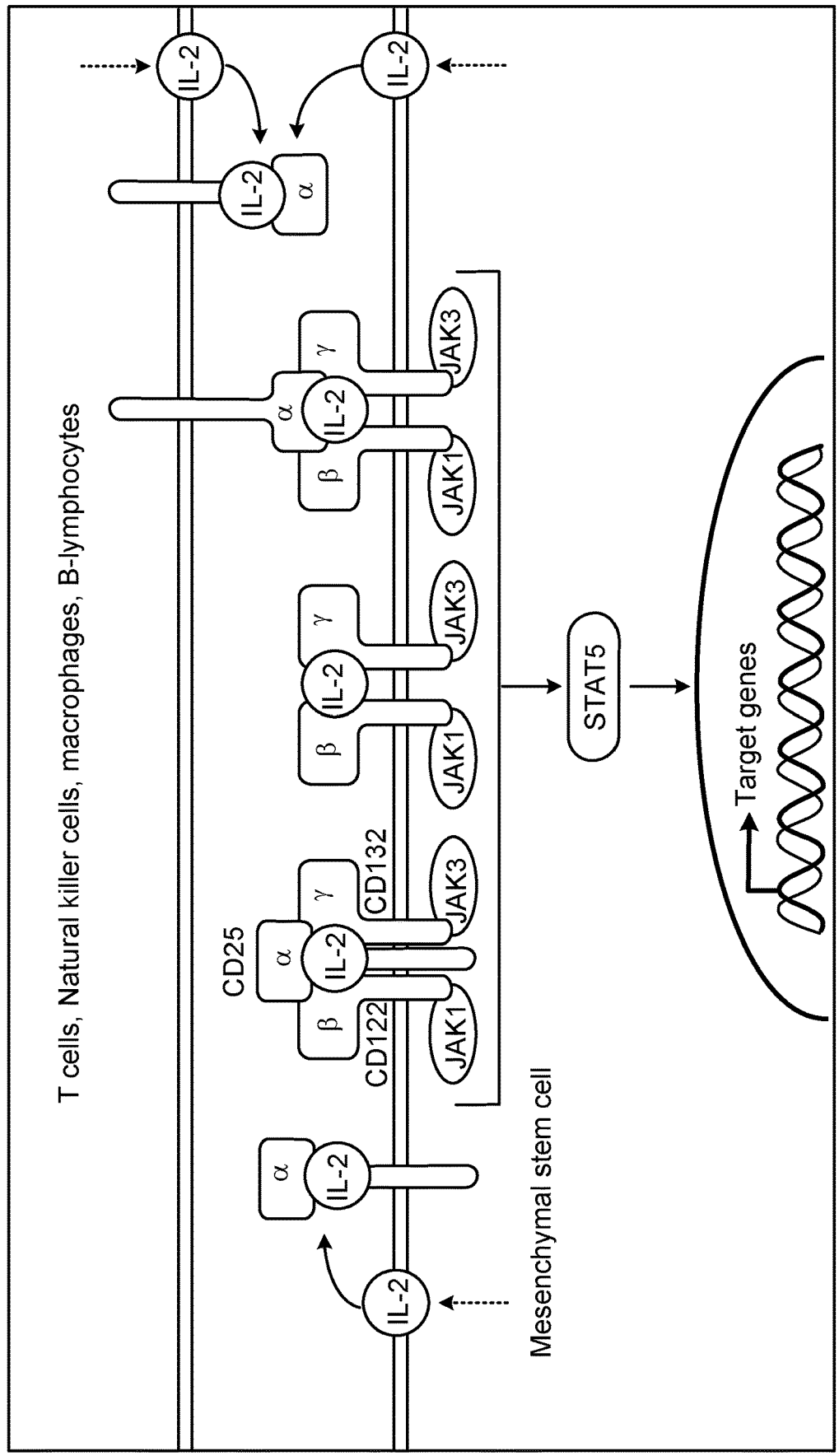

Example 4: Differential Response to Il-2 Stimulation in Human Adipose-Derived MSCs Upon Replicative Senescence Assessment of the IL-2 receptor isoforms expression, by qPCR, demonstrated significant changes in expression of the IL-2Rα isoform in comparison to IL-2Rg and IL-2Rβ upon replicative senescence ex vivo (FIG. 4B). FIG. 4B shows IL-2 receptors α, β, and γ assessed by quantitative PCR (qPCR) in un-stimulated (IL-2-)SR cells (first bar) and SEN cells (third bar) and upon stimulation with 20 ug/ml of recombinant IL-2 (IL-2+) (SR cells, second bar; SEN cells, fourth bar). Data shown as fold change (ΔΔCT). Mean±SD from three independent experiments is shown. Notably, the increased accumulation of the IL-2Rβ and IL-2Ra transcripts was recorded after IL-2 treatment in both SR and SEN-hADSCs, whereas IL-2Ra expression was abrogated when SEN cells were subjected to similar treatments (FIG. 4B).

However, the data indicated that protein level expression of the cellular membrane associated IL-2Rα receptor showed the opposite pattern (FIG. 4C). FIG. 4C shows the cellular membrane-associated levels of IL-2Rα and IL-2Rβ. The levels were quantified by ELISA in un-stimulated (IL-2-) SEN (third bar) and SR (first bar) hADSCs and upon stimulation with 20 ug/ml of recombinant IL-2(IL-2+) SEN (fourth bar) and SR (second bar). Data are expressed as pictogram per milliliter. Results are the mean of three independent experiments (mean±SD). Statistical significance was estimated by a t-test, where *p<0.001, p<0.01, *p<0.05.

Although the transcriptional status of IL-2 receptor isoforms does vary between the two different cell states (SR and SEN), it does not seem to be dependent upon IL-2 exposure (induction) as measured by the ELISA assay (described in the Materials and Methods, above). The data also demonstrated that protein encoding IL-2α receptor chain is less abundant than the IL-2Rβ isoform (compare 120 pg/ml of IL-2Rα to 350 pg/ml IL-2Rβ to 150 pg/ml of IL-2Rα and 440 pg/ml IL-2Rβ upon replicative senescence ex vivo) as shown in FIG. 4C. These data indicate that hADSCs response to IL-2 stimulation occurs through the intermediate-affinity receptor dimer composed of IL-2Rβ (CD 122) and the common IL-2Rg (CD 132).

Figure 7A:
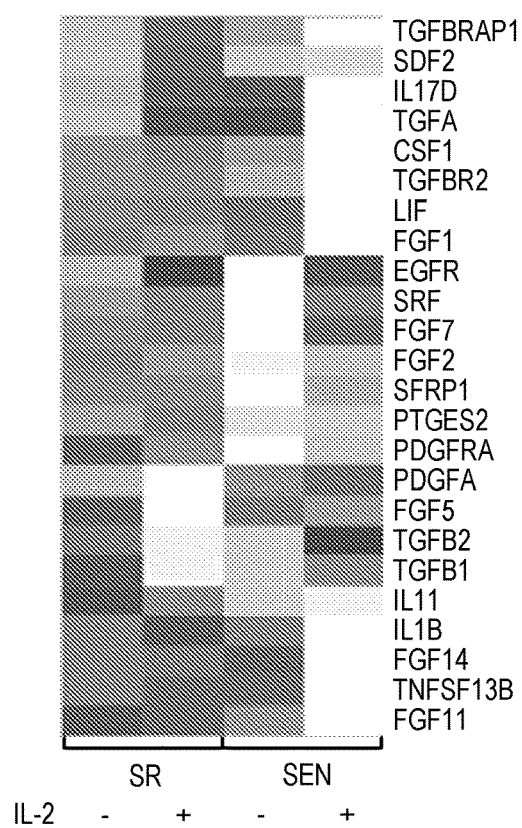
FIGS. 7A-7D illustrate gene expression levels for SR and SEN cells upon IL-2 treatment among functionally coherent sets of genes.
Figure 7B:
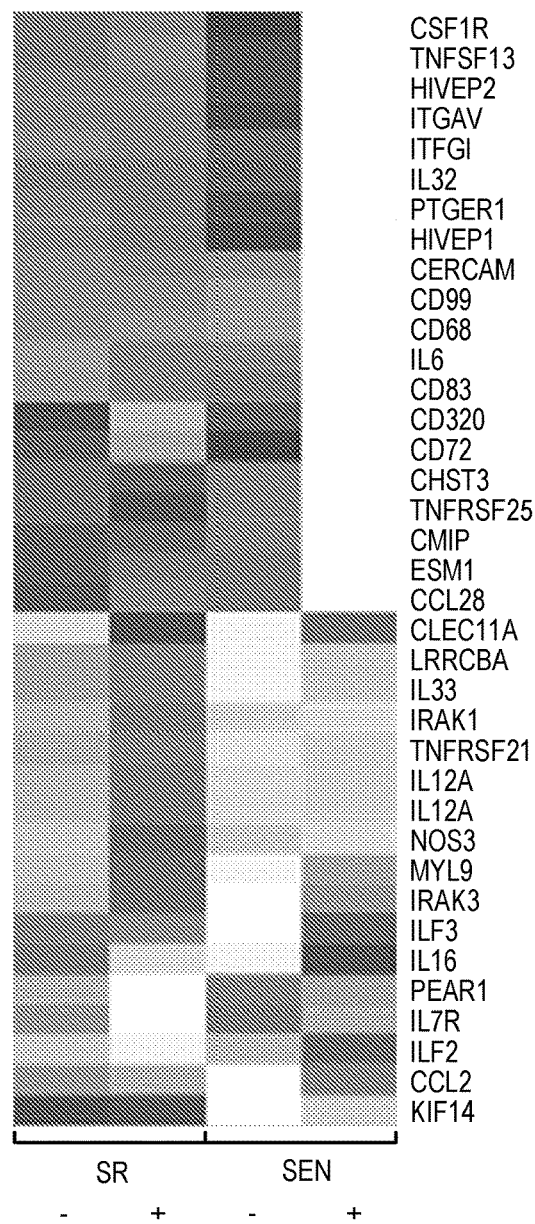

IL-2 signals via JAK1 and JAK3 to activate STAT5A and STAT5B, and additionally uses Ras-MAP kinase and phosphoinositol 3-kinase dependent signaling pathways. The expression of downstream target of IL-2, STAT5, is shown in FIGS. 5, 7A and 7B and the table of FIGS. 10A and 10B. In hADSCs, both STAT5A and STAT5B gene transcription follows the IL-2/STAT5 signaling axis.

FIG. 5 illustrates the effect of stimulation of the SR and SEN-hADSCs with IL-2. IL-2 upregulates mRNA of a mediator of IL-2 signaling STAT5 gene. STAT5A and STAT5B mRNA expression was assessed by quantitative RT-PCR in un-stimulated (IL-2−) SR (first bar) and SEN cells (third bar) and upon stimulation with 20 ug/ml of recombinant IL-2 (IL-2+) (SR+IL-2, second bar; SEN+IL-2, third bar). Data are shown as fold change (ΔΔCT). Mean±SD from three independent experiments is shown. The position of the qPCR primers is depicted graphically. Statistical significance was estimated by the t-test, where *$p<0.001$, $p<0.01$.

It was next investigated how IL-2 and its downstream target STAT5 affects transcriptional outcomes in hADSCs upon their replicative senescence ex vivo.

Figure 8A:
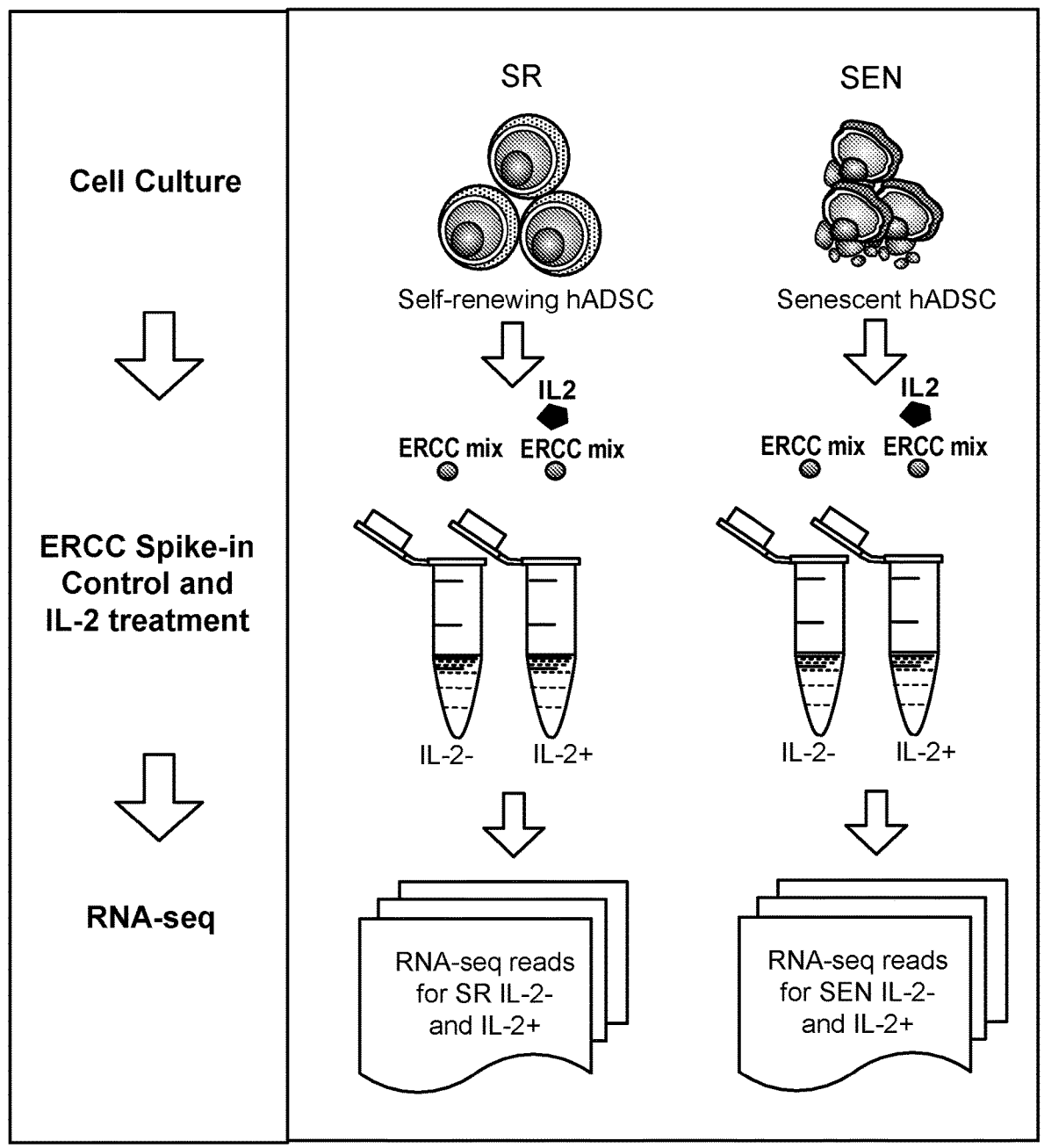
FIGS. 8A-8D illustrate the analysis for RNA-seq profiling of SR and SEN-hADSCs subjected to IL-2 treatment.
Figure 8B:
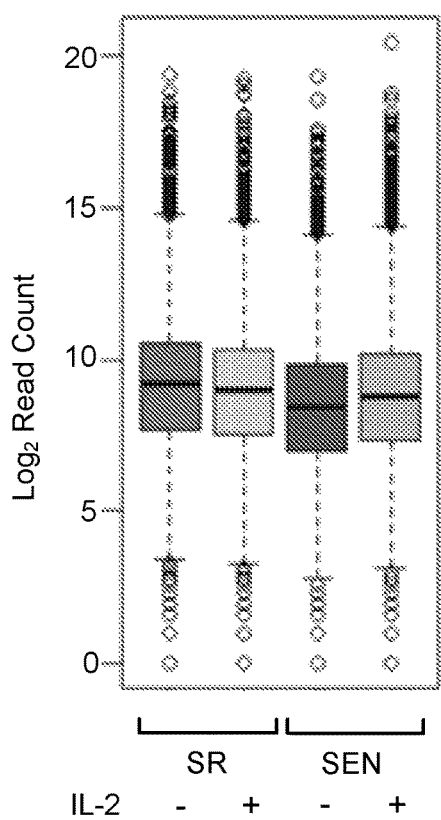
Figure 8C:
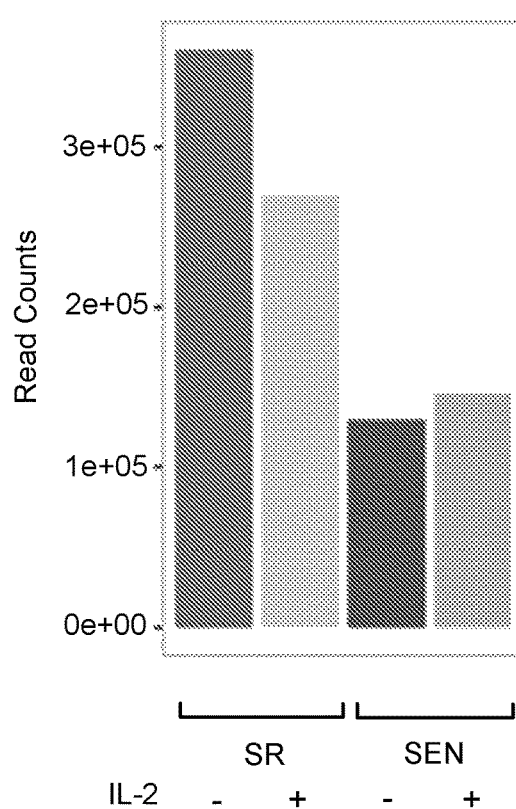

Exposure to IL-2 resulted in altered gene expression in human MCSs upon replicative senescence. To address how the transcriptional response to the IL-2/STAT5 axis changes upon replicative aging of hADSCs ex vivo, a RNA-seq transcriptome analysis was performed, using the Ion Proton™ System as described in Example 1 and shown in FIG. 8A. The gene expression levels in hADSCs across four conditions (libraries) was compared: self-renewal upon normal ex vivo culture (SR IL-2−), self-renewal upon 24 hrs recombinant IL-2 stimulation (SR IL-2+), replicative senescence upon normal ex vivo culture (SEN IL-2−), and replicative senescence upon 24 hrs recombinant IL-2 stimulation (SEN IL-2+). Distributions of the total read counts for the four conditions representing each condition are shown in FIG. 8B.

Figure 6A:
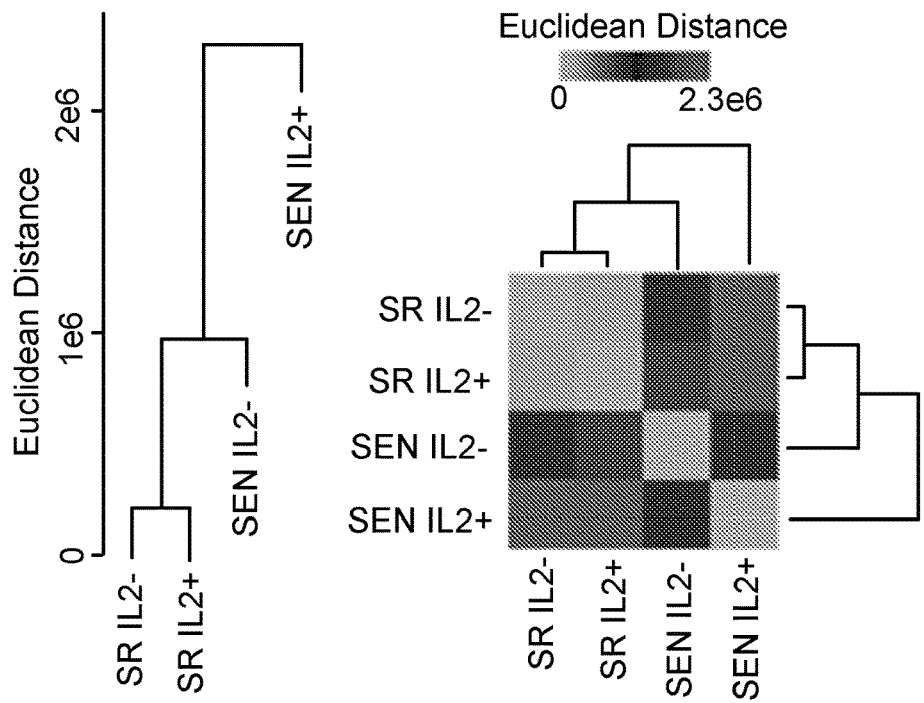
Figure 8D:
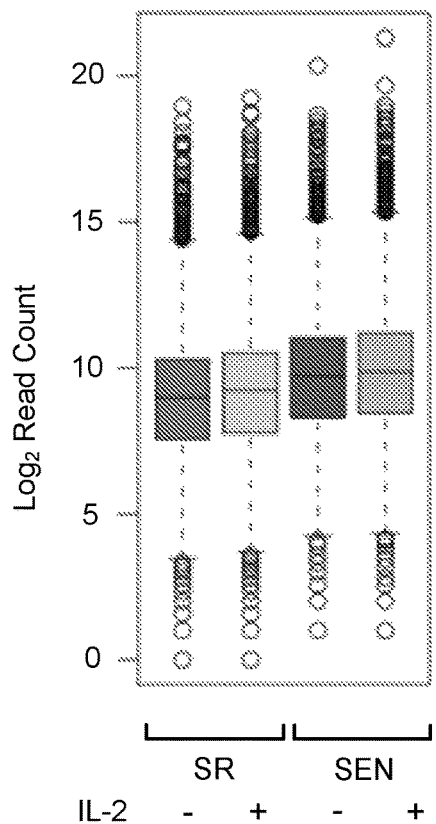

Beta-actin expression levels were used to normalize gene expression levels between conditions (as described in Example 1). This approach was taken to allow for the fact that overall gene expression levels may change upon IL-2 treatment. Beta-actin normalized gene expression distributions reveal overall up-regulation of gene expression upon IL-2 treatment in both SR and SEN states (FIG. 8D). However, comparison of individual gene expression levels among the four conditions indicates that IL-2 treatment more significantly affects SEN-compared to SR-hADSCs (FIG. 6A). FIG. 6A shows a hierarchical clustering showing the pairwise distance between conditions based on comparison of condition-specific gene expression profiles. The SR IL-2− and SR IL-2+ conditions group closely together when individual gene expression levels are compared followed by the SEN IL-2− condition. The SEN IL-2+ condition is an outlier amongst the four conditions showing a substantially divergent pattern of individual gene expression levels. This indicates that that the biological response to IL-2 treatment in hADSCs upon senescence may significantly impede MSC function via global transcriptional de-regulation in response to IL-2.

Figure 6B:
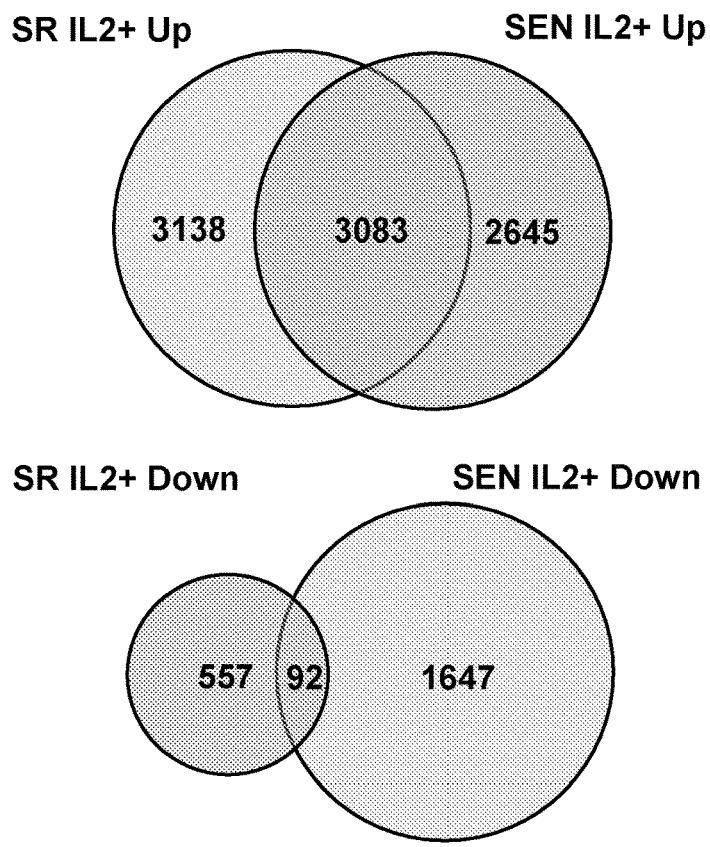

Expression levels were further compared between conditions in order to identify individual genes that are differentially expressed, up- and down-regulated, in response to IL-2 treatment in both SR and SEN states (FIG. 6B). FIG. 6B is a Venn diagram showing the numbers of genes, which are up-regulated and downregulated upon IL-2 treatment. There are several more genes that are up-regulated (8,866) compared to down-regulated (2,296) upon IL-2 treatment in both SR and SEN-hADSCs. There is also a substantially higher proportion of genes that are up-regulated in both SR and SEN-hADSCs (35%) compared to genes that are down-regulated in both states (4%). The greatest asymmetry is seen for genes that are down regulated in SEN-hADSCs upon IL-2 treatment (1,739); there are many more such genes than seen for the SR IL-2+ condition (649). This difference indicates that the overall divergence of the SEN IL-2+ condition is largely attributed to genes that are down-regulated upon IL-2 treatment, which is an unexpected result given the overall up-regulation across both SR and SEN upon IL-2 treatment (FIG. 6B and FIG. 8D).

FIGS. 6C-6D shows heat maps showing the expression levels of genes that are up-regulated (FIG. 6C) and down-regulated (FIG. 6D) upon IL-2 treatment. Normalized gene expression levels are shown as heat maps in grayscale. Groups correspond to genes that are up- or down-regulated in SR-only, SEN-only or both conditions.

Taken together, these data show that SEN-hADSCs have lost the ability to generate coordinated regulatory changes in response to IL-2 treatment to the same extent that exists for actively proliferating SR cells. The greater number of up-regulated genes seen for SR IL-2+, compared to SEN IL-2−, is consistent with this interpretation.

FIG. 10A shows a table (FIG. 10A) indicating biological pathways enriched for genes up-regulated upon IL-2 treatment in SR and SEN-hADSCs. In FIG. 10A, enriched pathways are shown along with the individual IL-2+ up-regulated genes belonging to the pathway and the pathway enrichment significance levels. Pathways with gene members up-regulated in SR are shown in the left column, and pathways with gene members up-regulated in SEN are shown in the right column. Pathways with gene members up-regulated in both SR and SEN are shown in the top row followed by pathways with gene members up-regulated only in SEN, and finally pathways with gene members up-regulated only in SR. Networks are shown relating pathways that are up-regulated in SR (left column) and pathways that are up-regulated in SEN (right column). The network nodes represent pathways, and the sizes of the nodes correspond to the number of up-regulated genes in that pathway. Pathway nodes are connected by edges if the pathways share up-regulated genes, and edge-weights correspond to the number of up-regulated genes shared between the pathways.

Figure 10B:
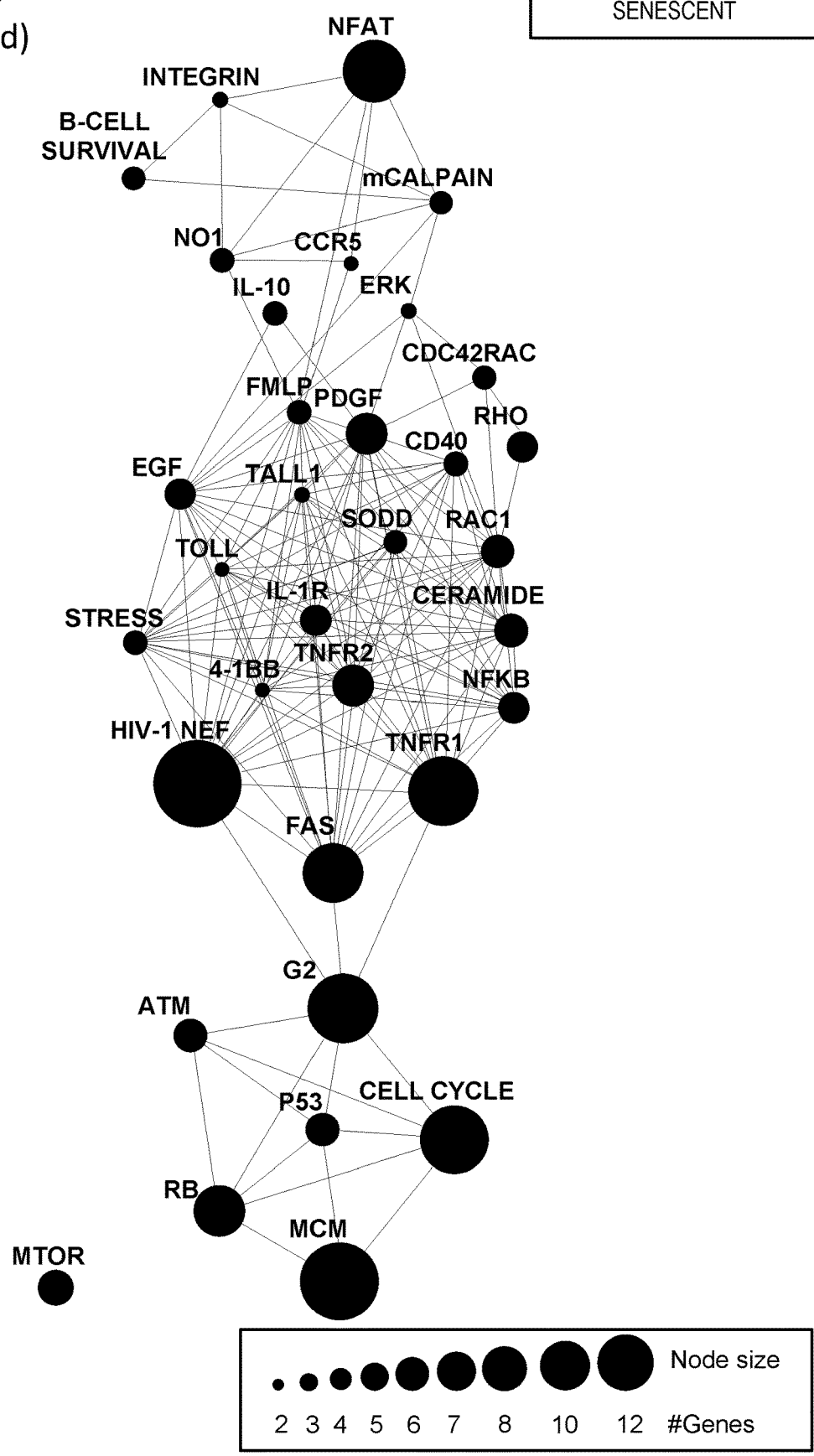

FIG. 10B illustrates biological pathways enriched for genes down-regulated upon IL-2 treatment in SR and SEN-hADSCs. Enriched pathways are shown along with the individual IL-2+ down-regulated genes belonging to the pathway and the pathway enrichment significance levels. Pathways with gene members down-regulated in SR are shown in the left column, and pathways with gene members down-regulated in SEN are shown in the right column. Pathways with gene members down-regulated in both SR and SEN are shown in the top row followed by pathways with gene members down-regulated only in SEN, and finally pathways with gene members down-regulated only in SR. A network is shown relating pathways that are down-regulated in SEN (left column). The network nodes represent pathways, and the sizes of the nodes correspond to the number of SEN down-regulated genes in that pathway. Pathway nodes are connected by edges if the pathways share SEN down-regulated genes, and edge-weights correspond to the number of down-regulated genes shared between the pathways.

Figure 7C:
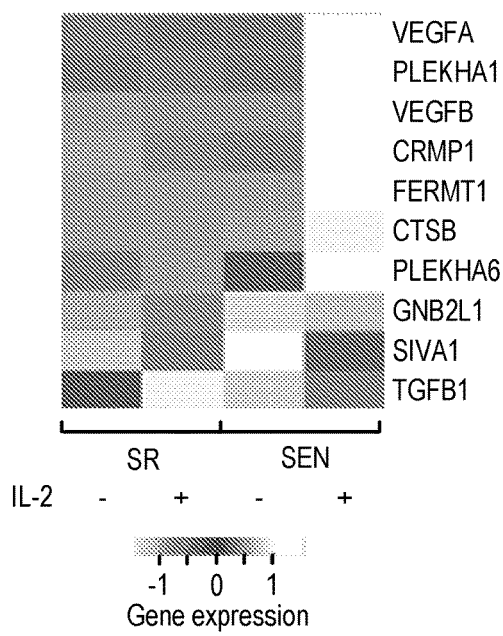
Figure 7D:
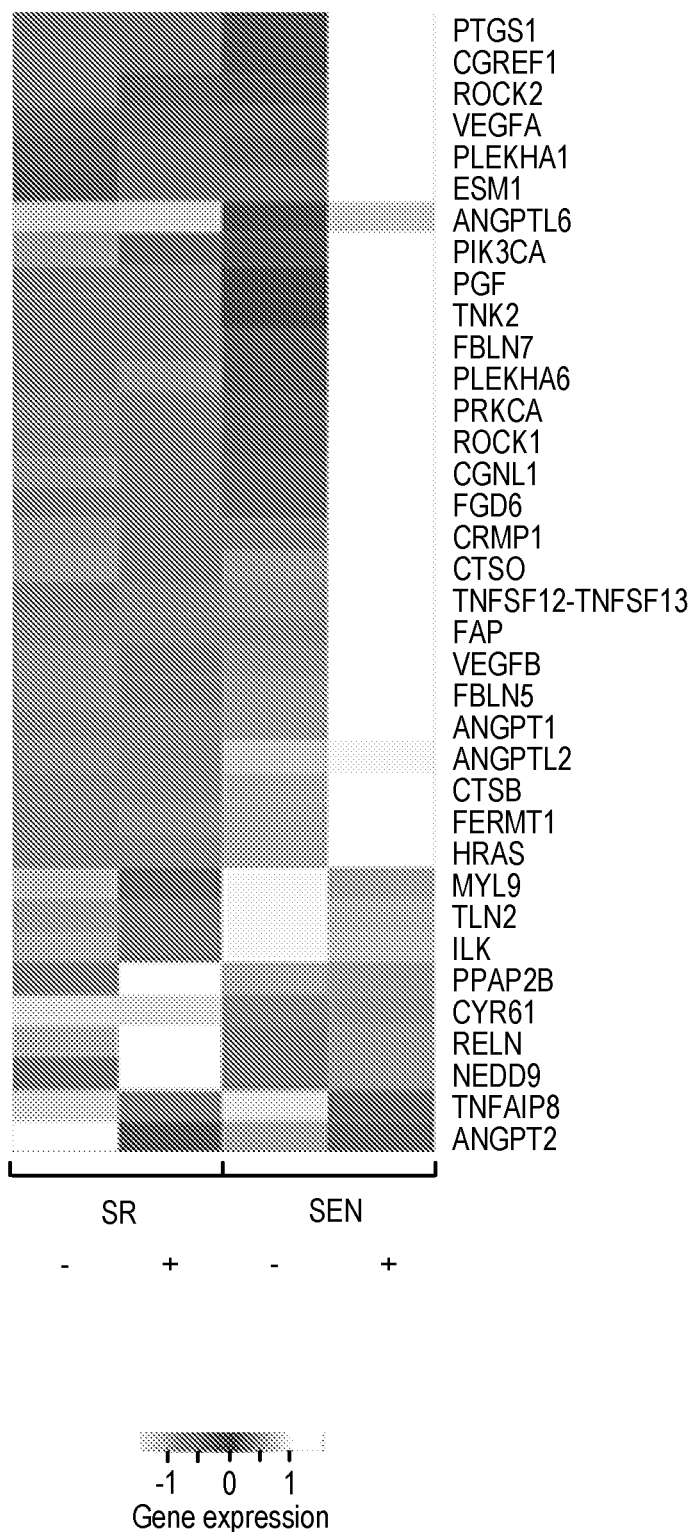

Example 5: Trophic Properties of the hADSCs after Il-2 Stimulation are Susceptible to Replicative Aging Ex Vivo FIGS. 7A-7D illustrate gene expression levels for SR and SEN cells upon IL-2 treatment among functionally coherent sets of genes. Expression levels are shown for sets of genes characterized as (in FIG. 7 A) trophic factors, (in FIG. 7B) anti-inflammatory and immunomodulatory, (as shown in FIG. 7C) anti-apoptotic and metastasis promoting, and (as shown in FIG. 7D) migration and angiogenesis promoting. Normalized gene expression levels are shown as heat maps in grayscale.

Table 1 shows the differential expression of trophic factors upon IL-2 treatment in SEN and SR cells. The SR GFold values represent the fold difference in SR cells treated with IL-2, relative to SR cells not treated with IL-2; the SEN GFold values represent the fold difference in SEN cells treated with IL-2, relative to SEN cells not treated with IL-2.

In addition, both SR and SEN IL-2 stimulated hADSCs were marked by up-regulation of colony stimulating factor 1 (CSF-1), LIF, IL-11, IL-17D, IL-3 and tumor necrosis factor (ligand) superfamily TNFSF13B, a cytokine encoding gene that stimulates B- and T-cell function (FIGS. 7A, 7B and FIGS. 10A-10B).

Taking into account that paracrine IL-17D induces expression of IL-6, IL-8, and GM-CSF genes in endothelial cells, and IL-1β stimulates fibroblast growth factor activity (TGFa, TGFβ1 and TGFβ2 genes are notably up-regulated in IL-2-exposed hADSCs) in autocrine and paracrine fashion, along with thymocyte and B-cell proliferation and maturation by inducing release of IL-2 from these cells, the data indicate that the transcriptional status of both SR and SEN-hADSCs may point to enhanced immunomodulatory properties of these cells after IL-2 exposure via a complex regulatory feed-back loop.

Both SR and SEN-hADSCs exposed to IL-2 are marked by significant increases in expression of transforming growth factors alpha and beta (TGFa, TGFβ1 and TGFβ2), transforming growth factor beta receptor TGFBR2 and transforming growth factor beta receptor-associated protein TGFBRAP1, as well as transforming growth factor beta-induced (TGFBI) genes (FIG. 7A).

TABLE 1

Differential Expression of Trophic Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| TGFBRAP1 | NM_001142621 | 941 | 1475 | 2242 | 2601 | 0.51 | 0.12 |
| SDF2 | NM_006923 | 685 | 992 | 1466 | 1516 | 0.37 | 0.00 |
| IL17D | NM_138284 | 9 | 49 | 69 | 124 | 0.97 | 0.34 |
| TGFA | NM_001099691 | 147 | 295 | 316 | 484 | 0.67 | 0.37 |
| CSF1 | NM_000757 | 1466 | 1691 | 3953 | 4906 | 0.09 | 0.24 |
| TGFBR2 | NM_001024847 | 3416 | 4028 | 20586 | 25244 | 0.16 | 0.26 |
| LIF | NM_002309 | 163 | 227 | 942 | 1652 | 0.13 | 0.67 |
| FGF1 | NM_001144892 | 287 | 237 | 524 | 741 | 0.00 | 0.31 |
| EGFR | NM_005228 | 4980 | 5431 | 5971 | 5368 | 0.06 | −0.09 |
| SRF | NM_003131 | 1689 | 1742 | 2132 | 1957 | 0.00 | −0.02 |
| FGF7 | NM_002009 | 756 | 766 | 1131 | 946 | 0.00 | −0.11 |
| FGF2 | NM_002006 | 5573 | 5301 | 8776 | 8185 | −0.01 | −0.05 |
| SFRP1 | NM_003012 | 1351 | 1346 | 4190 | 3575 | 0.00 | −0.15 |
| PTGES2 | NM_025072 | 521 | 746 | 1778 | 1699 | 0.33 | 0.00 |
| PDGFRA | NM_006206 | 3877 | 4533 | 5085 | 3109 | 0.15 | −0.63 |
| PDGFA | NM_002607 | 612 | 866 | 790 | 682 | 0.32 | −0.04 |
| FGF5 | NM_004464 | 4322 | 5738 | 3329 | 2895 | 0.34 | −0.12 |
| TGFB2 | NM_001135599 | 352 | 422 | 166 | 314 | 0.02 | 0.60 |
| TGFB1 | NM_000660 | 4834 | 6297 | 3413 | 5582 | 0.32 | 0.64 |
| IL11 | NM_000641 | 583 | 758 | 152 | 950 | 0.19 | 2.35 |
| IL1B | NM_000576 | 73 | 108 | 75 | 229 | 0.06 | 1.17 |
| FGF14 | NM_004115 | 61 | 69 | 89 | 255 | 0.00 | 1.11 |
| TNFSF13B | NM_001145645 | 0 | 12 | 10 | 104 | 0.65 | 2.12 |
| FGF11 | NM_004112 | 67 | 48 | 10 | 198 | 0.00 | 3.09 |

The data indicated that the expression of growth factors in hADSCs upon stimulation with IL-2 is subjected to significant changes upon replicative senescence ex vivo. While the exposure of actively proliferating (SR) hADSCs to IL-2 resulted in increased expression of mitogenic proteins such as stromal cell-derived factor 2 (SDF2) and SDFL2, and prostaglandin E synthetase 2 (PTGES2), both SR and SEN-hADSCs are marked by significant increases of transforming growth factors alpha and beta (TGFa, TGFβ1 and TGFβ2), transforming growth factor beta receptor TGFBR2 and transforming growth factor beta receptor-associated protein TGFBRAPI, as well as transforming growth factor beta-induced (TGFBI) (FIG. 7A and Tables 6A-6D).

In addition, essential differences in the IL-2 dependent expression of growth factors upon senescence of hADSCs that have not been observed in SR cells were also noted. This includes up-regulation of a subset of fibroblast growth factor family members (FGF 1, FGF 11, FGF 14) accompanied by down-regulation of other members, such as FGF2, FGF 5, FGF7, (FIG. 7 A, Table 1, and Tables 6A-6D).

IL-2 exposed SEN-hADSCs are marked by EGF mRNA up-regulation, but down-regulation of mRNA to its receptor EGFR, together a decrease in expression of the serum response factor SRF and the secreted modulator of WNT signaling SFRP1. The expression of both a potent mitogen for cells of mesenchymal origin that promotes wound healing, PDGFA, and its receptor, PDGFRA, is significantly suppressed in SEN-hADSCs in comparison to SR cells subjected to IL-2 exposure (FIG. 7A, FIG. 10A, Table 1, and Tables 6A-6D).

These data revealed senescence-related differences in the nature of IL-2 mediated transcriptional response in hADSCs that might impede these cells immunomodulatory properties ex vivo and, ultimately, in vivo.

A panel of anti-inflammatory and immunomodulatory markers for IL-2 treatment, IL-2 in combination with other drugs and IL-2 exposed human MSCs is shown (Table 2).

Differential gene expression analysis, comparing IL-2 treated versus untreated SR and SEN cells, allowed identification of individual genes that are up- or down-regulated upon IL-2 stimulation. Genes designated as up- or down-regulated in IL-2 treated SR and SEN-hADSCs were analyzed, using an integrated gene-set enrichment and pathway network approach in an attempt to capture the biological reality of coordinated cellular responses to IL-2 stimulation. To do this, pathways that were statistically enriched for up- or down-regulated genes were identified, and then chosen based on the differentially expressed genes that they have in common (FIGS. 10A-10B). The pathway network representation was weighted based on the numbers of differentially expressed genes in each pathway and the extent to which different pathways share sets of differentially expressed genes. This approach allowed identification of a highly connected network structure with numerous functionally related pathways as well as functionally relevant network substructures.

Upon senescence of hADSCs, IL-2 is less stimulatory for the gene pathways promoting proliferation (cell cycle pathway, q-value=1.54 e-5), imposing G2 checkpoint (G2 pathway, q-value=5.94e-4), p53 pathway (q-value=1.18e-2), major signal transduction MAPK pathway (MAPK, q-value=2.42e-4) and its major subgroup ERK pathway (ERK, q-value=2.62e-2), which regulate important cellular function such as survival, migration and proliferation. The analysis further corroborates the previous finding that PDGF-induced AKT and ERK pathways regulate opposing fate decisions of proliferation and differentiation in order to promote MSC self-renewal. Activation of the genes representing these pathways was observed only after ex vivo IL-2 exposure of actively SR-hADSCs but not their SEN counterparts (FIG. 10A, left side).

The data also provide information regarding the functionality of MSCs in carcinogenic settings. Both SR and SEN-hADSCs exposed to IL-2 are marked by significant increases in expression of transforming growth factors alpha and beta (TGF□, TGFβ1 and TGFβ2), transforming growth factor beta receptor TGFBR2 and transforming growth factor beta receptor-associated protein TGFBRAP1, as well as transforming growth factor beta-induced (TGFBI) genes (FIG. 7A). Secreted TGFP is believed to be important in regulation of the immune system by promoting differentiation of CD+4 T-cells and inhibiting immune-surveillance, thereby imposing immunosuppression. However, the higher level of TGFP expression in adipose-derived human MSCs after exposure to IL-2 might promote carcinogenesis. Since parts of the TGFP signaling pathway are shown to be mutated in cancer cells, this allows cancer cells to escape TGFP-induced cell cycle block, differentiation or apoptosis, while the surrounding stromal, immune, endothelial and smooth muscle cells still read the TGFP signaling as a potent suppressor of proliferation and trigger of differentiation causing immunosuppression and angiogenesis in the cancer cell microenvironment.

In IL-2 treated SEN-hADSCs prominent up-regulated genes are enriched for pathways associated with inflammation (IL-6 pathway, q-value=5.55e-3) and EGF signaling (q-value=2.33e-4) that have been proven to provide a survival advantages to MSCs. The SEN-hADSCs exposed to IL-2 are also marked by increased expression of IL-1 R, IL-6 and IL-12 (FIG. 7B), cytokines known to stimulate IL-17 from lymphocytes. The data also indicate that lymphocytes are the only source of IL-17 production, and those MSCs, particularly upon their senescence, display high transcriptional activity of IL-17 when subjected to a pro-inflammatory environment (FIG. 7 A).

The observed connection to the angiogenic VEGF pathway (q-value=5.24e-3) (FIG. 10A, right side and FIG. 7D) and the enhanced capacity of SEN-hADSC to migration (FIGS. 3A, 3B) may indicate that IL-2 exposed SEN-MSCs could acquire properties necessary to support a tumorigenic environment and metastasis. In addition, up-regulation of the genes included in nitric oxide synthase pathway (iNOS) NOS1 pathway (q-value=8.32e-2) in hADSC upon replicative senescence once again support that MSCs undergoing senescence can acquire metastasis-promoting properties via immunosuppression.

Pathways important for support of proliferation and DNA repair are down-regulated in hADCSs upon senescence: Cell Cycle pathway (q-value=2.52e-5), MCM pathway (q-value=1.62e-8), RB pathway (q-value=6.97e-5) ATM pathway (q-value=3.28e-2), p53 pathway (q-value=1.86 e-2) shown in FIG. 10 B. Overall, the data indicated that there are more biological pathways subjected to IL-2 triggered down-regulation in senescence then in self-renewal and these biological pathways are interconnected (FIG. 10B), further linking together a physiological impairment of IL-2 response upon replicative aging of hADSCs.

Table 2 shows the differential expression of anti-inflammatory and immunomodulatory factors upon IL-2 treatment in SEN and SR cells. The SR GFold values represent the fold difference in SR cells treated with IL-2, relative to SR cells not treated with IL-2; the SEN GFold values represent the fold difference in SEN cells treated with IL-2, relative to SEN cells not treated with IL-2.

TABLE 2

Differential Expression of Anti-Inflammatory and Immunomodulatory Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| CSF1R | NM_005211 | 80 | 43 | 189 | 455 | −0.27 | 0.98 |
| TNFSF13 | NM_003808 | 69 | 55 | 104 | 172 | 0.00 | 0.31 |
| HIVEP2 | NM_006734 | 2739 | 2790 | 3876 | 5495 | 0.00 | 0.43 |
| ITGAV | NM_002210 | 6797 | 7110 | 10656 | 17227 | 0.01 | 0.65 |
| ITFG1 | NM_030790 | 1067 | 1164 | 2398 | 3793 | 0.00 | 0.57 |

TABLE 2-continued

Differential Expression of Anti-Inflammatory and Immunomodulatory Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| IL32 | NM_001012631 | 404 | 422 | 526 | 1397 | 0.00 | 1.24 |
| PTGER1 | NM_000955 | 9 | 19 | 37 | 104 | 0.00 | 0.86 |
| HIVEP1 | NM_002114 | 1142 | 1217 | 1447 | 2046 | 0.00 | 0.38 |
| CERCAM | NM_016174 | 6943 | 7119 | 12879 | 16369 | 0.00 | 0.31 |
| CD99 | NM_001277710 | 6948 | 7069 | 13830 | 16928 | 0.00 | 0.25 |
| CD68 | NM_001251 | 3830 | 3590 | 9144 | 11331 | −0.02 | 0.26 |
| IL6 | NM_000600 | 434 | 502 | 782 | 996 | 0.00 | 0.19 |
| CD83 | NM_001040280 | 19 | 27 | 69 | 107 | 0.00 | 0.12 |
| CD320 | NM_016579 | 1068 | 782 | 990 | 1360 | −0.29 | 0.32 |
| CD72 | NM_001782 | 61 | 36 | 73 | 122 | −0.06 | 0.25 |
| CHST3 | NM_004273 | 2867 | 2935 | 2766 | 3706 | 0.00 | 0.34 |
| TNFRSF25 | NM_003790 | 61 | 68 | 56 | 98 | 0.00 | 0.25 |
| CMIP | NM_198390 | 1503 | 1435 | 1289 | 2460 | 0.00 | 0.82 |
| ESM1 | NM_007036 | 2562 | 1887 | 1863 | 7612 | −0.34 | 1.94 |
| CCL28 | NM_148672 | 68 | 37 | 44 | 170 | −0.20 | 1.39 |
| CLEC11A | NM_002975 | 1071 | 1403 | 1601 | 1449 | 0.25 | −0.02 |
| LRRC8A | NM_001127244 | 3710 | 4256 | 6709 | 6370 | 0.12 | −0.02 |
| IL33 | NM_033439 | 55 | 84 | 220 | 198 | 0.03 | 0.00 |
| IRAK1 | NM_001569 | 5587 | 6539 | 9009 | 9094 | 0.17 | 0.00 |
| TNFRSF21 | NM_014452 | 244 | 331 | 636 | 616 | 0.16 | 0.00 |
| IL12A | NM_000882 | 14 | 36 | 94 | 91 | 0.29 | 0.00 |
| NOS3 | NM_000603 | 48 | 83 | 137 | 142 | 0.19 | 0.00 |
| MYL9 | NM_006097 | 10584 | 19391 | 38407 | 32665 | 0.83 | −0.21 |
| IRAK3 | NM_007199 | 181 | 304 | 613 | 488 | 0.43 | −0.13 |
| ILF3 | NM_012218 | 5977 | 5913 | 6830 | 6368 | 0.00 | −0.04 |
| IL16 | NM_001172128 | 129 | 72 | 150 | 120 | −0.35 | 0.00 |
| PEAR1 | NM_001080471 | 1926 | 2387 | 510 | 187 | 0.21 | −1.16 |
| IL7R | NM_002185 | 831 | 954 | 634 | 545 | 0.04 | −0.02 |
| ILF2 | NM_001267809 | 1344 | 1961 | 1878 | 1580 | 0.43 | −0.13 |
| CCL2 | NM_002982 | 98 | 147 | 160 | 102 | 0.15 | −0.23 |
| KIF14 | NM_014875 | 329 | 331 | 381 | 251 | 0.00 | −0.33 |

Example 6: Anti-Inflammatory and Immunomodulatory Properties of IL-2 Stimulated Human MSCs Next, it was investigated how exposure to the IL-2 pro-inflammatory environment, when imposed on replicative aging, affects the expression of the genes assigned to provide immunomodulatory properties of hADSCs (e.g., the anti-inflammatory and immunomodulatory properties of IL-2 exposed human MSC). The data demonstrated that the capacity for immunomodulation is affected by replicative aging of the human adipose-derived MCS during ex vivo passaging (FIG. 7B and Table 2).

IL-2 exposure in SR-hADSCs activates distinct set of genes attributed to T cell regulation. IL-2 exposure of SR-hADSCs results in up-regulation of genes, such as TNFRSF21 (involved in T cells differentiation), IL12A (T-cell activator), ILF2 (potent regulator of transcription of the IL-2 gene during T-cell activation), IL33 (paracrine inducer of T-helper type 2 associated cytokines) and down-regulation of CCL28 (chemotactic factor for CD+4, CD+8 T-cells), CD320 (receptor molecule with autocrine and paracrine function to augment the proliferation of plasma cells) shown in FIG. 7B, Table 2, and Tables 6A-6D.

Contrary to that, IL-2 exposed SEN-hADSCs were characterized by significant transcriptional up-regulation of CD320, a number of integrins which could be involved in modulation of T-cell function (ITG 11, ITGA V, ITFG 1), and genes encoding important regulatory molecules such as: the T-cell adhesion receptor (CD99), a factor attributed to the maintenance of naïve T-cells (CHST3), T-cell activators (HIVEP1 and HIVEP2), a gene involved in T-cell signaling pathway (CMIP) and an autocrine/paracrine factor, PTGER1, involved in inhibition of CD+ cell proliferation (FIG. 7B, Table 2, and Tables 6A-6D).

The data also demonstrated that SR-hADSCs exposed to IL-2 trigger down-regulation of transcriptional activities of the genes encoding surface receptors that play a role in B-cell proliferation and differentiation (CD72) and homing macrophages (CD68). Both of these genes are significantly transcriptionally up-regulated in SEN cells upon similar treatment (FIG. 7B, Table 2, Tables 6A-6D). In addition, IL-2 treated SEN-hADSCs are set apart from similarly treated SR cells by transcriptional down-regulation of the genes required for pro-B to pre-B transitioning, the LRRC8A and PEAR1 genes, that regulate a number of non-adherent myeloid progenitors. In contrast, the genes involved in lymphocyte activation and homeostasis (CD83 and TNFRSF25) as well as leukocyte transmigration (CERCAM), and the genes responsible for endothelial cell-leukocyte interaction (ESM1), and a gene important for control monocytes/macrophage mediated immunological process (TNFSF 13), are up-regulated in SEN-hADSCs (FIG. 7B, Table 2, and Tables 6A-6D).

IL-2 exposure results in the differential expression of a number of cytokines and factors critical for chemotaxis (shown in FIG. 7B and Table 2).

SR-hADSCs are marked by up-regulation of IL-33, IL-12A, IL10RB, IL1RAP, IL7R, ILF2 and NOS3 genes, while IL-16 and CSF1R genes are down-regulated in these cells.

In SEN-hADSCs treated under similar conditions with IL-2, the genes encoding cytokines IL-32, IL-6, IL1RN, IL-20RB, IL-21R and inducers of inflammation TNFSF13 and TNFSF12, as well as the gene encoding extracellular matrix remodeler PLAU are up-regulated.

At the same time, several factors essential for cytokinesis such as MYL9, KIF14, IRAC3, as well as the genes encoding chemotactic factor that attracts monocytes and basophils (CCL2) and the CLEC11A gene regulating proliferation and differentiation of hematopoietic precursor cells, are down-regulated (FIG. 7B).

Similar down-regulation is also found for several interleukin receptor encoding genes IL7R, IL1R1, IL15RA, and interleukin enhancer binding factors ILF2 and ILF3.

These observations, together with IL-2 dependent differential transcriptional expression of cytokines in SEN-hADSCs (up-regulation of IL-32, IL-6, PLAU genes; down-regulation of CCL2, CLEC11A, ILF3, IRAK3, KIF14, MYL9 genes) and in SR-hADSCs (up-regulation of IL12A, IL7R, IRAK1, NOS3 genes; down-regulation of IL16, CSF1R genes), indicate that the immunomodulatory properties of hADSCs are susceptible to senescence imposed changes.

The observed connection to the angiogenic VEGF pathway (q-value=5.24e-3) (FIG. 10A, right side and FIG. 7D) and the enhanced capacity of SEN-hADSC to migration (FIGS. 4A,B) indicates that IL-2 exposed SEN-MSCs could acquire properties necessary to support a tumorigenic environment and metastasis. In addition, up-regulation of the genes included in nitric oxide synthase pathway (iNOS) NOS1 pathway (q-value=8.32e-2) in hADSC upon replicative senescence also indicate that MSCs undergoing senescence can acquire metastasis-promoting properties via immunosuppression.

Example 7: Anti-Apoptotic and Metastasis Promoting Properties of IL-2-Stimulated hADSCs Upon Replicative Senescence These experiments were also used to examine the anti-apoptotic and metastasis promoting properties of IL-2 exposed MSC upon replicative senescence.

The panel of anti-apoptotic and metastasis promoting markers for IL-2 treatment, IL-2 in combination with other drugs, or IL-2 in combination with MSC is shown in Table 3. The data provide a list of molecular marker targets important for assessment of anti-apoptotic and metastasis promoting events (e.g. for QC of SEN and SR stem cells for use in the invention).

Table 3 shows the differential expression of anti-apoptotic and metastasis factors upon IL-2 treatment in SEN and SR cells. The SR GFold values represent the fold difference in SR cells treated with IL-2, relative to SR cells not treated with IL-2; the SEN GFold values represent the fold difference in SEN cells treated with IL-2, relative to SEN cells not treated with IL-2.

TABLE 3

Differential Expression of Anti-Apoptotic and Metastasis Factors Upon IL-2 Treatment

| Gene Symbol | Gene ID | SR IL-2− | SR IL-2+ | SEN IL-2− | SEN IL-2+ | SR GFOLD | SEN GFOLD |
| --- | --- | --- | --- | --- | --- | --- | --- |
| VEGFA | NM_001025366 | 5690 | 5914 | 5781 | 20606 | 0.00 | 1.78 |
| PLEKHA1 | NM_001195608 | 716 | 676 | 713 | 1096 | 0.00 | 0.46 |
| VEGFB | NM_003377 | 989 | 1070 | 1832 | 2253 | 0.00 | 0.19 |
| CRMP1 | NM_001288661 | 168 | 209 | 401 | 547 | 0.00 | 0.23 |
| FERMT1 | NM_017671 | 76 | 70 | 264 | 325 | 0.00 | 0.02 |
| CTSB | NM_147780 | 28365 | 28109 | 115877 | 138711 | 0.00 | 0.25 |
| PLEKHA6 | NM_014935 | 78 | 57 | 150 | 251 | 0.00 | 0.40 |
| GNB2L1 | NM_006098 | 16273 | 18409 | 33137 | 32212 | 0.14 | −0.01 |
| SIVA1 | NM_006427 | 410 | 591 | 674 | 512 | 0.31 | −0.20 |
| TGFB1 | NM_000660 | 4834 | 6297 | 3413 | 5582 | 0.32 | 0.64 |

For example, MSCs have been proven to assist reversal of apoptosis in cardiomyoblasts after ischemia, as well as damaged neurons and lung fibroblasts. Stanniocalcini (STC1) has been identified as an essential factor capable of potent apoptotic reversal in fibroblasts damaged by UV and acidity.

The data indicate that IL-2 exposure transcriptionally upregulates both STC1 and STC2 genes, and such activation is not dependent on the replicative aging of hADSCs, at least ex vivo (Tables 6A-6D). In addition, paracrine effectors such as VEGF and TGFB1 have been implicated in the reversal of apoptosis in endothelial cells. The expression of genes encoding both of these factors is up-regulated in SR and SEN-hADSCs upon IL-2 treatment (FIG. 7C, FIG. 5, Table 3, and Tables 6A-6D).

The third graph of FIG. 5 shows that IL-2 upregulates transcription of the VEGFA gene upon replicative senescence of hADSCs. VEFGA gene expression was assessed by quantitative qPCR in unstimulated (IL-2-) SEN (dark) and SR (light) hADSCs and upon stimulation with 20 ug/ml of recombinant IL-2 (IL-2+). Data shown as fold change ΔΔCT Mean±SD from three independent experiments is shown. The position of the q-PCR primers are depicted graphically. Statistical significance was estimated by t—test, where *p<0.001, p<0.01.

However, transcriptional activity of VEGFA is notably higher in senescence than in actively proliferating cells as further verified by qPCR analysis shown in FIG. 7C. Notably, the SIVA1 gene encoding a pro-apoptotic factor and a potent inducer of T lymphocytes apoptosis is significantly down-regulated in SEN cells upon IL-2 treatment in comparison to proliferating hADSCs (FIG. 7C, Table 3, and Tables 6A-6D). SIVA1 is not a strictly pro-apoptotic factor, but also a potent suppressor of tumor metastasis. Importantly, a number of the factors responsible for invasive growth and metastasis are significantly up-regulated in SEN-hADSCs exposed to IL-2 in comparison with similarly treated SR cells (FIG. 7C and Table 3). This includes RACKI, PLEKHA1, PLEKHA6, CTSB, CRMP1, FERMT1 genes. These data indicated that pretreatment/exposure of hADSCs with IL-2 may enhance the antiapoptotic properties of these cells in general, and that such enhancement is affected by replicative senescence.

It was demonstrated that in IL-2 treated SEN-hADSCs, prominent up-regulated genes are enriched for pathways associated with inflammation (IL-6 pathway, q-value=5.55e-3) and EGF signaling (q-value=2.3 3 e-4) that have been proven to provide a survival advantages to MSCs. The SEN-hADSCs exposed to IL-2 are also marked by increased expression of IL-1β, IL-6 and IL-12 (FIG. 7B), cytokines known to stimulate IL-17 from lymphocytes.

The data also indicated that lymphocytes are the only source of IL-17 production, and those MSCs, particularly upon their senescence, display high transcriptional activity of IL-17 when subjected to a pro-inflammatory environment (FIG. 7A).

Example 8: Transcriptional Profiling Indicates Gene Targets Regulating Enhanced Migration and Angiogenesis in IL-2 Stimulated hADSCs Upon Replicative Senescence The panel of the markers indicating enhanced migration and angiogenesis in IL-2 treatments upon aging is shown (Table 4)

Transcriptional profiling indicates gene targets regulating enhanced migration and angiogenesis in IL-2 stimulated ADSCs upon replicative senescence. Further analysis of the transcriptional response indicates that IL-2 stimulation of SEN-hADSCs s enhances the expression of genes involved in vascular development and remodeling related to angiogenesis. It was observed significant up-regulation of the VEGFA, VEGFB, FBLN5, FBLN7, PGF, ANGPT1, ANGPT2, ANGPTL2, ANGPTL6, TNFSF12, PRKCA, PIK3CA, HRAS genes as well as a gene encoding a potent modulator of endothelial cell-leukocyte adhesion, ESM1 (FIG. 7D, FIGS. 10A-10B, Table 4, and Tables 6A-6D).

Table 4 shows the differential expression of migration and angiogenesis factors upon IL-2 treatment in SEN and SR cells. The SR GFold values represent the fold difference in SR cells treated with IL-2, relative to SR cells not treated with IL-2; the SEN GFold values represent the fold difference in SEN cells treated with IL-2, relative to SEN cells not treated with IL-2.

TABLE 4

Differential Expression of Migration and Angiogenesis Promoting Factors Upon IL-2 Treatment

| Gene Symbol | Gene ID | SR IL-2− | SR IL-2+ | SEN IL-2− | SEN IL-2+ | SR GFOLD | SEN GFOLD |
|---|---|---|---|---|---|---|---|
| PTGS1 | NM_000962 | 1202 | 1233 | 2595 | 8456 | 0.00 | 1.63 |
| CGREF1 | NM_001166239 | 60 | 77 | 137 | 384 | 0.00 | 1.15 |
| ROCK2 | NM_004850 | 2014 | 2149 | 2171 | 2737 | 0.00 | 0.24 |
| VEGFA | NM_001025366 | 5690 | 5914 | 5781 | 20606 | 0.00 | 1.78 |
| PLEKHA1 | NM_001195608 | 716 | 676 | 713 | 1096 | 0.00 | 0.46 |
| ESM1 | NM_007036 | 2562 | 1887 | 1863 | 7612 | −0.34 | 1.94 |
| ANGPTL6 | NM_031917 | 339 | 195 | 279 | 342 | −0.50 | 0.02 |
| PIK3CA | NM_006218 | 519 | 597 | 720 | 939 | 0.00 | 0.22 |
| PGF | NM_002632 | 471 | 471 | 842 | 1503 | 0.00 | 0.69 |
| TNK2 | NM_005781 | 582 | 624 | 813 | 1176 | 0.00 | 0.38 |
| FBLN7 | NM_153214 | 201 | 195 | 268 | 353 | 0.00 | 0.13 |
| PLEKHA6 | NM_014935 | 78 | 57 | 150 | 251 | 0.00 | 0.40 |
| PRKCA | NM_002737 | 3139 | 3258 | 4215 | 5298 | 0.00 | 0.26 |
| ROCK1 | NM_005406 | 2280 | 2326 | 2662 | 3068 | 0.00 | 0.12 |
| CGNL1 | NM_001252335 | 11 | 22 | 67 | 115 | 0.00 | 0.27 |
| FGD6 | NM_018351 | 419 | 411 | 749 | 1055 | 0.00 | 0.33 |
| CRMP1 | NM_001288661 | 168 | 209 | 401 | 547 | 0.00 | 0.23 |
| CTSO | NM_001334 | 222 | 275 | 499 | 617 | 0.01 | 0.10 |
| TNFSF12-TNFSF13 | NM_172089 | 268 | 259 | 464 | 577 | 0.00 | 0.11 |
| FAP | NM_004460 | 1810 | 1767 | 4594 | 6279 | 0.00 | 0.39 |
| VEGFB | NM_003377 | 989 | 1070 | 1832 | 2253 | 0.00 | 0.19 |
| FBLN5 | NM_006329 | 5879 | 6117 | 8801 | 10137 | 0.00 | 0.15 |
| ANGPT1 | NM_001146 | 386 | 406 | 1069 | 1346 | 0.00 | 0.20 |
| ANGPTL2 | NM_012098 | 1241 | 1362 | 4927 | 5560 | 0.00 | 0.11 |
| CTSB | NM_147780 | 28365 | 28109 | 115877 | 138711 | 0.00 | 0.25 |
| FERMT1 | NM_017671 | 76 | 70 | 264 | 325 | 0.00 | 0.02 |
| HRAS | NM_176795 | 604 | 604 | 996 | 1124 | 0.00 | 0.03 |
| MYL9 | NM_006097 | 10584 | 19391 | 38407 | 32665 | 0.83 | −0.21 |
| TLN2 | NM_015059 | 2058 | 2352 | 4839 | 4309 | 0.09 | −0.10 |
| ILK | NM_001014795 | 5437 | 6108 | 8647 | 8164 | 0.11 | −0.03 |
| PPAP2B | NM_003713 | 1703 | 2546 | 2327 | 1579 | 0.48 | −0.45 |
| CYR61 | NM_001554 | 31391 | 30861 | 12856 | 12074 | 0.00 | −0.05 |
| RELN | NM_005045 | 2490 | 2989 | 925 | 671 | 0.17 | −0.29 |
| NEDD9 | NM_006403 | 2617 | 3093 | 2123 | 1956 | 0.15 | −0.01 |
| TNFAIP8 | NM_001077654 | 109 | 101 | 67 | 100 | 0.00 | 0.05 |
| ANGPT2 | NM_001118887 | 430 | 259 | 89 | 179 | −0.47 | 0.58 |

The vascular endothelial growth factor, VEGF, released by MCSs, enables recruitment of endothelial lineage cells and initiation of vascularization as was previously reported. It is further demonstrated that up-regulation of VEGFA gene expression in SEN-hADSCs can be detected by quantitative RT-PCR analysis and IL-2 exposure results in a statistically significant increase of VEGFA gene transcription in SR and SEN-hADSCs (FIG. 7D and Table 4).

It was further observed that in response to IL-2 exposure, a group of genes responsible for cell motility, migration and invasive growth are significantly up-regulated only in the hADSCs undergoing replicative senescence: CGNL1, CGREF1, CRMP1, FGD6, TNK2, PTGS1, TNFAIP8, CTSB, CTSO, FAP, FERMT1, PLEKHA1, PLEKHA6, ROCK1, ROCK2. A set of genes promoting cell adhesion, such as CHD24, CYR61, ILK, NEDD9, MYL9, PPAP2B, RELN and TLN2 were down-regulated (FIG. 7D, Table 4, and Tables 6A-6D). These data further the support experimental evidence for the enhanced migration capacity of SEN-hADSCs shown in FIG. 3B.

Example 9: Proteomic Antibody Array Data

Table 7 provides the raw values for all proteomic antibody array data.

FIG. 2B shows the five factor production units used for collection of these data. All 5 factor production units contained stem cells from a 38 year old patient in 10% PRP containing StemPro MSC SFM Xeno-free medium except A (no cell control). Factor production units were populated with SR or SEN-hADSC 2500 cells/cm$^3$ in 700 ul/cm$^3$ of 10% PRP containing StemPro MSC SFM Xeno-free medium. Referring to FIG. 2B, factor production units C and E, the cells of the factor production units were stimulated with IL-2 for 24 hrs, after which media was exchanged to the 10% PRP containing StemPro MSC SFM Xeno-free medium. Factor production units were kept at 37° C. and 5% CO2 for 24, 48, and 72 hrs after which media was collected and analyzed.

Equal volumes of medium from the factor production units were analyzed on a RayBio C-Series Human Cytokine Antibody Array AAH-CYT-2000 (RayBiotech, Inc). The C-Series Human Cytokine Antibody Array AAH-CYT-2000 is based on chemiluminescence assay principle and contains antibodies to 174 protein of interest. Data were extracted from the membranes using LI-COR Biosciences densitometry software (Li-COR). The raw data were normalized by taking the ratio between Average Intensity of the given protein signal/to Average Intensity Negative Control, to account for differences in exposure and array to array variation.

The factor production unit represented as A contained no cells, as a control. This factor production unit was set-up with 700 ul/cm$^2$ of 10% PRP containing StemPro MSC SFM Xeno-free medium. The medium was collected at 24, 48 and 72 hrs and total protein was quantified by Qubit fluorimetric quantification using Qubit 2.0 (Thermofisher), applied on RayBio C-Series Human Cytokine Antibody Array AAH-CYT-2000 and data were extracted as described above and analyzed.

The factor production unit labeled as B contained SR-hADSCs not treated with IL-2. This factor production unit was populated with patient specific hADSC 2500 cells/cm$^3$ in 700 ul/cm$^3$ of 10% PRP containing StemPro MSC SFM Xeno-free medium. The samples were collected at 24 hr, 48 hr or 72 hrs.

The factor production unit labeled as C was a factor production unit containing SR-hADSCs treated with IL-2. This factor production unit contained 2500 cells/cm$^3$ of patient specific SR-hADSCs in 700 ul/cm$^3$ of 10% PRP containing StemPro MSC SFM Xeno-free medium. The cells in the factor production unit were treated with IL-2. For the IL-2 treatment, the factor production unit was treated with 20 U/ml IL-2 (Peprotech) in 10% PRP in StemPro MSC SFM Xeno-free medium at 37° C. for 24 h. IL-2 was removed post-treatment with 2 washes of PBS-cmf. Fresh medium was added at 700 ul/cm$^3$. The samples were collected 24 hr, 48 hr or 72 hr later.

The factor production unit labeled as D contained senescent hADSCs (SEN-hADSCs). This factor production unit contained SEN-hADSC at 2500 cells/cm$^3$ in 700 ul/cm$^3$ of 10% PRP containing StemPro MSC SFM Xeno-free medium. Samples were collected at 24 h, 48 h or 72 h.

The factor production unit labeled as E contained SEN-hADSCs treated with IL-2 as described above for the factor production unit labeled as C. Samples were collected at 24 h, 48 h or 72 h.

The factors collected from factor production units A-E represented in FIG. 2B are characterized in detail below.

FIGS. 11-17 show the increase in secretion of the below named proteins (factors) from SR-hADSCs maintained in a factor production unit of the invention, 24 hours post incubation with media containing 10% PRP (platelet-rich plasma) alone (no IL-2 stimulation). Secretion levels are shown relative to the amount of the corresponding protein present at basal levels in the 10% PRP containing media, used for hADSC support. FIG. 11 shows the increase in secretion of Interleukin 5 (IL5) and Interleukin 6 (IL6). FIG. 12 shows the increase in secretion of Interleukin 1 receptor 4 (IL1R4). FIG. 13 shows the increase in secretion of Neurotrophin 3 (NT3), platelet derived growth factor A alpha (PDGF AA), platelet derived growth factor A beta (PDGF AB), and pro-platelet basic protein (PPBP). FIG. 14 shows the increase in secretion of Chemokine (C-C motif) ligand 18 (CCL18), Chemokine (C-Cmotif) ligand 25 (CCL25), Chemokine (C-C motif) ligand 27 (CCL27), and CXC chemokine ligand 11 (CXCL 11). FIG. 15 shows the increase in secretion of Intercellular Adhesion Molecule 1 (ICAM-1) and Metalloproteinase inhibitor 2 (TIMP-2). FIG. 16 shows the increase in secretion of Metalloproteinase inhibitor 1 (TIMP-1). FIG. 17 shows the increase in secretion of vascular epithelium (VE) Cadherin (calcium dependent cell adhesion protein).

FIGS. 18-19 show the increase in secretion of the below named proteins (factors) from SR-hADSCs, 24 hours post incubation with 10% PRP alone (no IL-2 stimulation). These proteins were found to not be present in PRP. FIG. 18 shows the increase in secretion of Interleukin 4 (ILA). FIG. 19 shows the increase in secretion of insulin-like growth factor-binding protein-1 (IGFBP1).

FIGS. 20-31 show an increase in the below named proteins (factors) from SR-hADSCs maintained in a factor production unit of the invention, 48 hours post incubation with 10% PRP alone (no IL-2 stimulation). Secretion levels are shown relative to the amount of the corresponding protein present at basal levels in the 10% PRP containing media, used for hADSC support. FIG. 20 shows the increase in secretion of Interleukin 9 (IL9) and Interleukin 18 binding protein alpha (IL18BPa). FIG. 21 shows the increase in secretion of Interleukin 1 receptor type II (IL1R2), Interleukin 2 receptor beta (IL-2Rb), Interleukin 2 receptor gamma (IL-2Rg), Interleukin 5 receptor alpha (IL5Ra), Interleukin 10 receptor beta (IL10Rb), Interleukin 18 receptor accessory protein (IL18Rb), and Interleukin 21 receptor (IL-21R). FIG. 22 shows the increase in secretion of Insulin-like growth factor 2 (IGF2), Transforming growth factor alpha (TGFa), Transforming growth factor beta 1/latency-associated peptide (LAP) (TGFb1), and Transforming growth factor beta 2 (TGFb2). FIG. 23 shows the increase in secretion of Receptor tyrosine-protein kinase ErbB-3 (ErbB3), Fas ligand (Fas LG), Leukemia inhibitory factor (LIF), Prolactin (PRL) factor, platelet-derived growth factor receptor alpha (PDGFRa), platelet-derived growth factor receptor beta (PDGFRb), Stem cell factor kit receptor (SCFR), and Sialic acid-binding Ig-like Lectin 5 (Siglec 5). FIG. 24 shows the increase in secretion of CXC chemokine ligand 16 (CXCL16). FIG. 25 shows the increase in secretion of activated leukocyte cell adhesion molecule (ALCAM), E selectin (cell surface glycoprotein in immune-adhesion), Intercellular adhesion molecule 2 (ICAM2), L selectin (Lymphocyte adhesion molecule), and Platelet endothelial cell adhesion molecule (PECAM 1). FIG. 26 shows the increase in secretion of Activin A (INHBA), Insulin-like growth factor 2 (IGF-2), and Leptin Receptor (LEPR). FIG. 27 shows the increase in secretion of Bone morphogenetic protein 5 (BMP5), Bone morphogenetic protein 7 (BMP7), Macrophage colony-stimulating factor 1 receptor (MCSFR), matrix metalloproteinase 1 (MMP1), matrix metalloproteinase 3 (MMP3), matrix metalloproteinase 9 (MMP9), and matrix metalloproteinase 13 (MMP13). FIG. 28 shows the increase in secretion of monocyte differentiation antigen (CD14), cell differentiation antigen (CD80), Cardiotrophin-1 (CT-1), and Leukemia inhibitory factor (LIF). FIG. 29 shows the increase in secretion of Endoglin (ENG). FIG. 30 shows the increase in secretion of Tyrosine kinase with immunoglobulin-like and EGF-like domains 1 (TIE1) and Tyrosine kinase with immunoglobulin-like and EGF-like domains 2 (TIE2). FIG. 31 shows the increase in secretion of Activin A (Inhibin beta A, INHBA), Leptin Receptor (Leptin R), and Transforming growth factor beta 1 (TGFb1).

FIG. 32 shows the increase in secretion of Nerve growth factor receptor (NGFR) from SR-MSCs maintained in a factor production unit of the invention, 48 hours post incubation with 10% PRP alone (no IL-2 stimulation). NGFR was found to not be present in in PRP.

FIGS. 33-39 show the increase in secretion of the below named proteins (factors) from SR-hADSCs maintained in a factor production unit of the invention, 72 hours post incubation with 10% PRP alone (no IL-2 stimulation). Secretion levels are shown relative to the amount of the corresponding protein present at basal levels in the 10% PRP containing media, used for hADSC support. FIG. 33 shows the increase in secretion of Interleukin 1 beta (IL1b), Interleukin 3 (IL3), Interleukin-13 Receptor subunit alpha-2 (IL13Rα2), and Interleukin 1 receptor alpha (IL1Rα). FIG. 34 shows the increase in secretion of Probetacellulin (BTC), Colony stimulating factor (CSF1), Fibroblast growth factor 6 (FGF6), Glial cell line-derived neurotrophic factor (GDNF), insulin-like growth factor 1 (IGF-1), Leptin, and platelet-derived growth factor B beta (PDGF BB). FIG. 35 shows the increase in secretion of stem cell factor/c-kit ligand (SCF), Stromal Cell-Derived Factor-1 alpha (SDF1a), Stromal Cell-Derived Factor-1 beta (SDF1b), Transforming growth factor beta 1 (TGFb1), Transforming growth factor beta 3 (TGFb3), and tumor necrosis factor superfamily member 14 (TNFSF14). FIG. 36 shows the increase in secretion of Insulin-like growth factor 1 (IGF1). FIG. 37 shows the increase in secretion of Transforming growth factor beta 1 (TGFb1) and platelet-derived growth factor B beta (PDGF BB). FIG. 38 shows the increase in secretion of Chemokine (C-C motif) ligand 2 (CCL2), Chemokine (C-C motif) ligand 5 (CCL5), Chemokine (C-C motif) ligand 7 (CCL7), Chemokine (C-C motif) ligand 8 (CCL8), and Chemokine (C-C motif) ligand 11 (CCL11). FIG. 39 shows the increase in secretion of Chemokine (C-C motif) ligand 13 (CCL13), Chemokine (C-C motif) ligand 22 (CCL22), Chemokine (C-C motif) ligand 23 (CCL23), Chemokine (C-C motif) ligand 24 (CCL24), and CXC Chemokine ligand 10 (CXCL10).

FIGS. 40-42 show the increase in secretion of the below named proteins (factors) from SR-hADSCs maintained in a factor production unit of the invention, 72 hours post incubation with 10% PRP alone (no IL-2 stimulation). These factors were found to not be present in PRP. FIG. 40 shows the increase in secretion of Brain-derived neurotrophic factor (BDNF), Bone morphogenetic protein 4 (BMP4), Bone morphogenetic protein 6 (BMP6), Ciliary neurotrophic factor (CNTF), Epidermal growth factor (EGF), Fibroblast growth factor 7 (FGF7), and insulin-like growth factor-binding protein-4 (IGFBP4). FIG. 41 shows the increase in secretion of chemokine (C-X-C motif) ligand 13 (BLC), Chemokine (C-C motif) ligand 23 (CCL23), Chemokine (C-C motif) ligand 28 (CCL28), chemokine (C-C motif) ligand 11 (Eotaxin 1), Chemokine (C-X-C motif) ligand 6 (GCP-2), FLT3LG (Fms-Related Tyrosine Kinase 3 Ligand), and Fractalkine (CX3CL1). FIG. 42 shows the increase in secretion of Angiotensin (ANG) and colony stimulating factor 2 (CSF2).

FIG. 43 shows the increase in secretion of Chemokine (C-C motif) ligand 27 (CCL27) and TNFRSF1B (Tumor Necrosis Factor Receptor Superfamily, Member 1B) from SR-hADSCs maintained in a factor production unit of the invention, 24 hours post stimulation with IL-2. Secretion levels are shown relative to the amount of the corresponding protein present at basal levels in the 10% PRP containing media, used for hADSC support.

FIGS. 44-53 show the increase of the below named proteins (factors) from SR-hADSCs maintained in a factor production unit of the invention, 48 hours post stimulation with IL-2. Secretion levels are shown relative to the amount of the corresponding protein present at basal levels in the 10% PRP containing media, used for hADSC support. FIG. 44 shows the increase in secretion of Interleukin 9 (IL9), Interleukin 11 (IL11), Interleukin 12 alpha (IL12a), Interleukin 12 beta (IL12b), and Interleukin 18 binding protein alpha (IL18BPa). FIG. 45 shows the increase in secretion of Interleukin 1 receptor type I (IL1R1), Interleukin 1 receptor type II (IL1R2), Interleukin 1 receptor type IV (IL1R4), Interleukin 2 receptor beta (IL-2Rb), Interleukin 2 receptor gamma (IL-2Rg), Interleukin 5 receptor alpha (IL5Ra) Interleukin 10 receptor beta (IL10Rb), Interleukin 18 receptor beta (IL18Rb), and Interleukin 21 receptor (IL-21R). FIG. 46 shows the increase in secretion of Fibroblast growth factor 4 (FGF4), FGF9, MSP alpha/HGF like factor (HGF like), Insulin-like growth factor 1 (IGF1), IGF2, insulin-like growth factor-binding protein-6 (IGFBP6), LAP (TGF beta family), and platelet derived growth factor A alpha (PDGFAA). FIG. 47 shows the increase in secretion of platelet derived growth factor A beta (PDGFAB), platelet derived growth factor B beta (PDGFBB), Stromal Cell-Derived Factor-1 alpha (SDF1a), Sialic acid-binding Ig-like Lectin 5 (Siglec 5), Transforming growth factor alpha (TGFa), Transforming growth factor beta 2 (TGFb2), Vascular endothelial growth factor (VEGF), and Vascular endothelial growth factor D (VEGFD). FIG. 47 also shows the increase in secretion of DR6, Dtk, EGFR, Endoglin, ErbB3, Fas, Fas LG, and IGF1 sr. FIG. 48 shows the increase in secretion of Leptin (LEP), Leptin Receptor (LEPR), Macrophage colony-stimulating factor 1 receptor (MCSFR), Neurotrophin 4 (NT4), Osteoprotegerin (OPG), platelet-derived growth factor receptor alpha (PDGFRa), platelet-derived growth factor receptor beta (PDGFRb), and Prolactin (PRL). FIG. 49 shows the increase in secretion of Stem cell factor receptor (SCFR), Angiopoietin 1 receptor (TIE1), Angiopoietin 1 receptor (TIE2), TNF superfamily member 10C (TNFSF10C), TNF superfamily member 10D (TNFSF10D), TNF superfamily member 14 (TNFSF14), urokinase plasminogen activator receptor (uPAR), and Vascular endothelial growth factor receptor-2 (VEGFR2). FIG. 50 shows the increase in secretion of Chemokine (C-C motif) ligand 2 (CCL2), CCL3, CCL5, CCL8, CCL17, CCL20, CCL25, CXC chemokine ligand 5 (CXCL5), CXCL11, and CXCL16. FIG. 51 shows the increase in secretion of activated leukocyte cell adhesion molecule (ALCAM), Bone morphogenetic protein 5 (BMP5), BMP7, E selectin (endothelial cell adhesion molecule), Intercellular adhesion molecule 2 (ICAM2), ICAM3, L selectin (Lymphocyte adhesion molecule), and matrix metalloproteinase 1 (MMP1). FIG. 52 shows the increase in secretion of matrix metalloproteinase 13 (MMP13), MMP3, MMP9, Platelet endothelial cell adhesion molecule (PECAM 1), Metalloproteinase inhibitors TIMP 1, TIMP 2, TIMP 4, and vascular epithelium (VE) Cadherin (calcium dependent cell adhesion protein). FIG. 53 shows the increase in secretion of monocyte differentiation antigen (CD 14), cell differentiation antigen (CD80), Cardiotrophin-1 (CT-1), Leukemia inhibitory factor (LIF), Macrophage migration inhibitory factor (MIF), Thrombopoietin (THPO), and Lymphotactin (XCL1).

FIG. 54 shows the increase in secretion of Nerve growth factor receptor (NGFR) from SR-hADSCs maintained in a factor production unit of the invention, 48 hours post stimulation with IL-2. FIG. 54 also shows increase in the secretion of IL8 and TNFRSF1A with IL-2 at 24 h post-IL-2 stimulation. NGFR, IL8 and TNFRSF1A were found to not be present in PRP.

FIGS. 55-57 show the increase in the secretion of the below named proteins (factors) from SR-hADSCs maintained in a factor production unit of the invention, 72 hours post stimulation with IL-2. Secretion levels are shown relative to the amount of the corresponding protein present at basal levels in the 10% PRP containing media, used for hADSC support. FIG. 55 shows the increase in secretion of Interleukin 1 receptor alpha (IL1Rα), Interleukin 6 (IL6), and Interleukin-13 receptor subunit alpha-2 (IL13Rα2). FIG. 56 shows the increase in secretion of Fibroblast growth factor 6 (FGF6), pro-platelet basic protein (PPBP), stem cell factor (SCF), and Vascular endothelial growth factor receptor-3 (VEGFR3). FIG. 57 shows the increase in secretion of Chemokine (C-C motif) ligand 22 (CCL22), CCL23, CCL24, CCL26, and CXC chemokine ligand 10 (CXCL10).

FIG. 58 shows the increase in secretion of Angiotensin (ANG), Brain-derived neurotrophic factor (BDNF), Bone morphogenetic protein 4 (BMP4), colony stimulating factor 2 (CSF2), Epidermal growth factor (EGF), Fibroblast growth factor 7 (FGF-7), Interferon gamma (IFNγ), insulin-like growth factor-binding protein-1 (IGFBP 1), and IGFBP 2 from SR-hADSCs maintained in a factor production unit of the invention, 72 hours post stimulation with IL-2. These factors were found to not be present in PRP.

FIG. 59 shows the increase in secretion of Fibroblast growth factor 6 (FGF6), CXC chemokine ligand 16 (CXCL16), and Stromal Cell-Derived Factor-1 alpha (SDF1a) from SEN-hADSCs maintained in a factor production unit of the invention, 24 hours post incubation with 10% PRP alone (no IL-2 stimulation). Secretion levels are shown relative to the amount of the corresponding protein present at basal levels in the 10% PRP containing media, used for hADSC support.

FIG. 60 shows the increase in secretion of Brain-derived neurotrophic factor (BDNF), B lymphocyte chemokine (CXCL13; BLC), Chemokine (C-C motif) ligand 1 (CCL1), Flt-3 LG (Fms-Related Tyrosine Kinase 3 Ligand), Fractalkine (T-cell chemokine CX3CL1), granulocyte chemotactic protein 2 (GCP-2)/CXCL6, Interleukin 1 alpha (IL1a), Interleukin 4 (IL4), IL15, and Interferon gamma (IFNγ) from SEN-hADSCs maintained in a factor production unit of the invention, 24 hours post incubation with 10% PRP alone (no IL-2 stimulation). These factors were found to not be present in PRP.

FIGS. 61-70 show the increase in the secretion of the below named proteins (factors) from SEN-hADSCs maintained in a factor production unit of the invention, 48 hours post incubation with 10% PRP alone (no IL-2 stimulation). Secretion levels are shown relative to the amount of the corresponding protein present at basal levels in the 10% PRP containing media, used for hADSC support. FIG. 61 shows the increase in secretion of Interleukin 2 beta (IL-2b), IL3, IL5, and IL6. FIG. 62 shows the increase in secretion of Interleukin 1 receptor type II (IL1R2), Interleukin 2 receptor gamma (IL-2Rg), Interleukin 5 receptor alpha (IL5Ra), Interleukin 10 receptor beta (IL10Rb), Interleukin 18 receptor binding protein alpha (IL18BPa), Interleukin 18 receptor beta (IL18Rb), and Interleukin 21 receptor (IL-21R). FIG. 63 shows the increase in secretion of Insulin-like growth factor 1 (IGF1), IGF2, LAP (TGF beta family), Leptin (LEP), Leptin Receptor (LEPR), platelet derived growth factor A alpha (PDGFAA), platelet derived growth factor A beta (PDGFAB), and platelet derived growth factor B beta (PDGFBB). FIG. 64 shows the increase in secretion of platelet-derived growth factor receptor alpha (PDGFRa), Stem cell factor (SCF), Stem cell factor receptor (SCFR), Transforming growth factor beta 1 (TGF b1), Transforming growth factor beta 2 (TGF b2), Transforming growth factor alpha (TGFa), Vascular endothelial growth factor receptor-2 (VEGFR2), and VEGFR3. FIG. 65 shows the increase in secretion of Death receptor 6 (DR6; TNF receptor superfamily member 21), Glial cell line-derived neurotrophic factor (GDNF), Neurotrophin 3 (NT3), Tyrosine kinase with immunoglobulin-like and EGF-like domains 1 (TIE1), TIE2, and TNF superfamily member 14 (TNFSF14). FIG. 66 shows the increase in secretion of Chemokine (C-C motif) ligand 2 (CCL2), CCL5, CCL8, CCL17, CCL18, and CCL23. FIG. 67 shows the increase in secretion of Chemokine (C-C motif) ligand 24 (CCL24), CCL25, CCL26, CCL27, CXC Chemokine ligand 10 (CXCL10), and CXCL11. FIG. 68 shows the increase in secretion of activated leukocyte cell adhesion molecule (ALCAM), Bone morphogenetic protein 5 (BMP5), BMP7, E selectin (endothelial cell adhesion molecule), Intercellular adhesion molecule 1 (ICAM1), ICAM2, L selectin (Lymphocyte adhesion molecule), and matrix metalloproteinase 1 (MMP1). FIG. 69 shows the increase in secretion of matrix metalloproteinase 3 (MMP3), MMP9, MMP13, Platelet endothelial cell adhesion molecule (PECAM 1), Metalloproteinase inhibitors TIMP 1, TIMP 2, and TIMP 4. FIG. 70 shows the increase in secretion of monocyte differentiation antigen (CD14), monocyte differentiation antigen (CD80), Cardiotrophin-1 (CT-1), and Leukemia inhibitory factor (LIF).

FIGS. 71-72 show the increase in the secretion the below named proteins (factors) from SEN-hADSCs maintained in a factor production unit of the invention, 48 hours post incubation with 10% PRP alone (no IL-2 stimulation). These factors were found to not be present in PRP. FIG. 71 shows the increase in secretion of Bone morphogenetic protein 4 (BMP4), Chemokine (C-C motif) ligand 11 (CCL 11), CCL23, Ciliary neurotrophic factor (CNTF), Epidermal growth factor (EGF), Fibroblast growth factor 7 (FGF7), insulin-like growth factor-binding protein-1 (IGFBP1), IGFBP2, IGFBP4, and Nerve growth factor receptor (NGFR). FIG. 72 shows the increase in secretion of Interleukin 7 (IL7), IL10, IL13, and IL16.

FIG. 73 shows the increase in secretion of Probetacellulin (BTC), Interleukin-13 receptor subunit alpha-2 (IL13Ra2), and Stromal Cell-Derived Factor-1 beta (SDF1b) from SEN-hADSCs maintained in a factor production unit of the invention, 72 hours post incubation with 10% PRP alone (no IL-2 stimulation). Secretion levels are shown relative to the amount of the corresponding protein present at basal levels in the 10% PRP containing media, used for hADSC support.

FIG. 74 shows the increase in secretion of Hepatocyte growth factor (HGF), Interleukin 8 (IL8), and TNFRSF1A (Tumor Necrosis Factor Receptor Superfamily, member 1A) from SEN-hADSCs maintained in a factor production unit of the invention, 72 hours post incubation with 10% PRP alone (no IL-2 stimulation). These factors were found to not be present in PRP.

FIG. 75 shows the increase in secretion of Chemokine (C-C motif) ligand 23 (CCL23), Ciliary neurotrophic factor (CNTF), Epidermal growth factor (EGF), CCL11 (Eotaxin 1), IL4, and Nerve growth factor receptor (NGFR) from SEN-hADSCs maintained in a factor production unit of the invention, 24 hours post stimulation with IL-2. These factors were found to not be present in PRP. These factors were found to not be present in PRP.

FIG. 75 also shows the increase in secretion of CXCL16, HCC4, sgp130, and TNFRSF1B at 24 h post IL-2 stimulation. Secretion levels are shown relative to the amount of the corresponding protein present at basal levels in the 10% PRP containing media.

FIGS. 76-86 show the increase in the secretion of the below named proteins (factors) from SEN-hADSCs, 48 hours post stimulation with IL-2. Secretion levels are shown relative to the amount of the corresponding protein present at basal levels in the 10% PRP containing media, used for hADSC support. FIG. 76 shows the increase in secretion of Interleukin 1 beta (IL1b), IL3, IL5, IL6, IL9, IL10, IL12b, and Interleukin 18 binding protein alpha (IL18BPa). FIG. 77 shows the increase in secretion of Interleukin 1 receptor alpha (IL1Ra), IL1R4, IL10Rb, IL18Rb, IL1R2, IL-21R, IL-2Rb, IL-2Rg, and IL5Ra. FIG. 78 shows the increase in secretion of Fibroblast growth factor 6 (FGF6), insulin-like growth factors IGF1 and IGF2, LAP (TGF beta family), Neurotrophin 3 (NT3), platelet derived growth factor A alpha (PDGFAA), platelet derived growth factor A beta (PDGFAB), and platelet-derived growth factor receptor alpha (PDGFRa). FIG. 79 shows the increase in secretion of Stem cell factor (SCF), Transforming growth factor 2 (TGF2), TGFa, TGFb1, TGFb3, Tumor necrosis factor beta (TNFb), Vascular endothelial growth factor receptor-2 (VEGF R2), and VEGF R3. FIG. 80 shows the increase in secretion of DR6 (TNF receptor superfamily member 21), Endoglin (ENG), Receptor tyrosine-protein kinase erbB-3 (ErbB3), Fas ligand (Fas LG), Glial cell line-derived neurotrophic factor (GDNF), GITR ligand (GITR LG), and Leptin receptor (LEPR). FIG. 81 shows the increase in secretion of Prolactin (PRL), Stem cell factor receptor (SCFR), Sialic acid-binding Ig-like Lectin 5 (Siglec 5), Angiopoietin 1 receptor (TIE1), and Angiopoietin 1 receptor (TIE2). FIG. 82 shows the increase in secretion of Chemokine (C-C motif) ligand 8 (CCL8), CCL13, CCL15, CCL17, CCL18, and CCL20. FIG. 83 shows the increase in secretion of Chemokine (C-C motif) ligand 22 (CCL22), CCL24, CCL26, CXC chemokine ligand 9 (CXCL9), and CXCL11. FIG. 84 shows the increase in secretion of Activin A (INHBA), Bone morphogenetic protein 5 (BMP5), E selectin (endothelial cell adhesion molecule), Intercellular adhesion molecule 1 (ICAM 1), ICAM 2, L selectin (Lymphocyte adhesion molecule), and Macrophage colony-stimulating factor (MCSF). FIG. 85 shows the increase in secretion of matrix metalloproteinase 1 (MMP1), MMP13, MMP3, MMP9, Platelet endothelial cell adhesion molecule (PECAM 1), and Metalloproteinase inhibitor 4 (TIMP-4). FIG. 86 shows the increase in secretion of monocyte differentiation antigen (CD14), Lymphotactin (XCL1), Cardiotrophin-1 (CT-1), Leukemia inhibitory factor (LIF), Macrophage Migration Inhibitory Factor (MIF), and pro-platelet basic protein (PPBP).

FIG. 87 shows the increase in secretion of Brain-derived neurotrophic factor (BDNF), Bone morphogenetic protein 4 (BMP4), Fibroblast growth factor 7 (FGF7), insulin-like growth factor-binding protein-2 (IGFBP2), IL-2, IL16, and Interferon gamma (INF gamma) from SEN-hADSCs maintained in a factor production unit of the invention, 48 hours post stimulation with IL-2. These factors were found to not be present in PRP.

FIGS. 88-89 show the increase in secretion of the below named proteins (factors) from SEN-hADSCs maintained in a factor production unit of the invention, 72 hours post stimulation with IL-2. Secretion levels are shown relative to the amount of the corresponding protein present at basal levels in the 10% PRP containing media, used for hADSC support. FIG. 88 shows the increase in secretion of Adiponectin (Acrp30), Agouti-related protein (AgRP), ANGPT2 (Angiopoietin 2), basic-Fibroblast Growth Factor (bFGF), Probetacellulin (BTC), Interleukin-13 receptor subunit alpha-2 (IL13Ra2), Leptin (LEP), Neurotrophin 4 (NT4), and Stromal Cell-Derived Factor-1 alpha (SDF1a). FIG. 89 shows the increase in secretion of Chemokine (C-C motif) ligand 2 (CCL2), CCL4, CCL5, CCL23, CCL25, CCL27, CXC Chemokine ligand 10 (CXCL10), Stromal Cell-Derived Factor-1 beta (SDF1b), Metalloproteinase inhibitors 1 (TIMP1), TIMP2, and tumor necrosis factor superfamily member 14 (TNFSF14).

FIG. 90 shows the increase in secretion of Granulocyte-macrophage colony-stimulating factor (GM-CSF) and IL13 from SEN-hADSCs maintained in a factor production unit of the invention, 72 hours post stimulation with IL-2. These factors were found to not be present in PRP.

Example 10: Induction of Senescence Using microRNAs

The SEN phenotype can be achieved by transfection of a range of concentrations (1 pm to 1000 uM) of senescence-associated micro RNAs (SA-miRNAs) or SA-miRNA mimics.

This example shows that SA-miRNAs originating from MIRG17HG and MIR100HG clusters can coordinately regulate gene targets to induce senescence. Transient delivery of SA-miRNAs to SR-ADSCs is sufficient to induce SEN phenotypes. Delivery of the miRNA mimics of SAmiRNAs from either MIR100HG or MIR17HG clusters separately does not result in a SEN phenotype as detected by SA-βgal (FIG. 108, Panel A). When SA-miRNAs from both clusters were transfected into SR-hADSCs, about 40% of the cells became marked by expression of senescence-associated β-galactosidase (SA-βgal). FITC-labeled random RNAs were used as a control for the transfection efficiency in all of these experiments, which ranges from 50 to 60% (FIG. 108, Panel B). The SEN phenotype was achieved by a range of concentrations (5 pM or 10 pM combined with SA-miRNA mimics).

Cell Culture

SR-hADSCs are seeded on 4-well slides at a density of about $1 \times 10^4$ cells/well one day before transfection. Transfection is carried out with 5 pmol or 10 pmol of one or more senescence associated microRNA mimics using a transfection reagent such as Fugene 6 (Promega).

RT-PCR

Total cellular RNA was extracted from cells using the TRIzol Reagent™ (Life Technologies) according to manufacturer's instructions. The microRNA was isolated using a mirPremier microRNA isolation kit (Sigma-Aldrich), RNA and microRNA were quantified with a NanoDrop ND-2000 Spectrophotometer (Thermo Scientific). The cDNA was synthesized by adding the purified RNA and oligo (dT) primers by using superscript III reverse transcriptase (Life Technologies). Primers were designed by primer3 software and shown in Table S1. For miRNA cDNA synthesis, the Mystic microRNA cDNA synthesis Mix kit (Sigma-Aldrich) was used. All microRNA assay primers were bought from Sigma-Aldrich.

Real-Time Quantitative PCR

Quantification of mRNA and microRNA expression for candidate genes was performed by real-time quantitative PCR (qRT-PCR) using the LightCycler® 480 Real-Time PCR System (Roche). Total RNA and microRNA was reverse transcribed by using the high capacity superscript III reverse transcriptase (Life Technologies) and the Mystic microRNA cDNA synthesis Mix kit (Sigma-Aldrich), respectively. Primers were designed by primer3 software, and sequences are provided below in Table 5. All microRNA assay primers were bought from Sigma-Aldrich. qRT-PCR reactions were performed with the power SYBR® green PCR master mix and the mystic microRNA SYBR green qPCR ReadyMix in a MicroAmp optical 96-well reaction plate. The PCR amplification of total RNA was performed in a LightCycler® 480 Real-Time PCR System (Roche) using the following program: Cycle 1, 95° C. for 10 min. Cycle 2, 40 cycles of 95° C. for 15 sec, 60° C. for 60 sec. CT values were automatically obtained. Relative expression values of RNA were obtained by normalizing CT values of the mRNA genes in comparison with CT values of the endogenous control (beta-actin) using the CT method. The PCR amplification of microRNA was performed in a LightCycler® 480 Real-Time PCR System (Roche) using the following program: Cycle 1, 95° C. for 2 min. Cycle 2, 40 cycles of 95° C. for 5 sec, 60° C. for 30 sec. Relative expression values of microRNA were obtained by normalizing CT values of the microRNA genes in comparison with CT values of the endogenous control (U6) using the CT method.

TABLE 5 qPCR primers

| Gene | Forward Primer | Reverse Primer |
|---|---|---|
| NAP1L1 | 5' CTGGCTCCCC ATACTAGTCG 3' (SEQ ID NO: 13) | 5' CTTGAAGGGC TGCAAGAATC 3' (SEQ ID NO: 14) |
| USP6 | 5' ACCATCACAG GCTCTTCACC 3' (SEQ ID NO: 15) | 5' AACGATCAAT GCTGCTGTTG 3' (SEQ ID NO: 16) |
| SMARCD2 | 5' ACCCCATTGT CATCAACCAT 3' (SEQ ID NO: 17) | 5' TCTCTGGGTC TTCAGCTGGT 3' (SEQ ID NO: 18) |
| CHD2 | 5' GATGACGAAG CTCCCAAAG 3' (SEQ ID NO: 19) | 5' TAGATGCTCC AGTGGCTCCT 3' (SEQ ID NO: 20) |
| CHD4 | 5' CATCGATGGT GGAATCACTG 3' (SEQ ID NO: 21) | 5' ATCCGGTGAG CTCTGCTAAA 3' (SEQ ID NO: 22) |
| CHD8 | 5' ATGCGGATTG TGAAGAAGGA 3' (SEQ ID NO: 23) | 5' GGCTCTTCAT CCTCATGGAA 3' (SEQ ID NO: 24) |
| HDAC3 | 5' TGGCTTCTGC TATGTCAACG 3' (SEQ ID NO: 25) | 5' TCTCTGCCCC GACTTCATAC 3' (SEQ ID NO: 26) |
| HDAC5 | 5' TCTGAACCAC TGCATTTCCA 3' (SEQ ID NO: 27) | 5' GCCTGGACCG TAATTTCAGA 3' (SEQ ID NO: 28) |
| HDAC9 | 5' CAGGCGGAAG GATGGAAATG 3' (SEQ ID NO: 29) | 5' ATGCGTTGCT GTGAAACCAT 3' (SEQ ID NO: 30) |
| WDR44 | 5' TCTCTCCTAA CCGCAAGCAT 3' (SEQ ID NO: 31) | 5' AGCTCTCTCC CAGAGTTGGA 3' (SEQ ID NO: 32) |
| SAP18 | 5' CCACTGTTGC TACGGGTCTT 3' (SEQ ID NO: 33) | 5' CCACTGTTGC TACGGGTCTT 3' (SEQ ID NO: 34) |
| SUZ12 | 5' GCCTTTGAGA AGCCAACACA 3' (SEQ ID NO: 35) | 5' CTGCAAATGA GCTGACAAGC 3' (SEQ ID NO: 36) |
| SMARCA1 | 5' AGGGCGAGAA GAAGAAGGAG 3' (SEQ ID NO: 37) | 5' TCTGTGCTGA AGGCTGAATG 3' (SEQ ID NO: 38) |
| IGF2BP3 | 5' TCCAAGCAGA AACCATGTGA 3' (SEQ ID NO: 39) | 5' ACTTACAAGC CGCAGAGGTG 3' (SEQ ID NO: 40) |

Results

SA-miRNA mimics that can be used to induce senescence include mir-17-5p, mir-18a-5p, mir-19a-3p, mir-20a-5p and mir-92a1-5p, mir-125b1-5p, mir-1let7a-2-3p, and mir-100-5p (referred to in this Example as the set of SA-miRNA mimics).

FIG. 108 illustrates that senescence associated-miRNAs from oncogenic MIR17HG and tumori-suppressive MIR100HG clusters function to establish the hADSC SEN phenotype. Panel A shows the percentage of SA-D-Gal positive cells among the total amount of cells counted after transient transfection of mimics of SA-miRNA from either the MIR17HG (mir-17-5p, mir-18a-5p, mir-19a-3p, mir-20a-5p and mir-92a1-5p) or the MIR100HG (mir-125b1-5p, mir-1let7a-2-3p, mir-100-5p) clusters separately or after simultaneous transfection by the set of SA-miRNA mimics from both clusters in SR hADSCs. SA-miRNA mimics were transfected with FITC-labeled control to account for transfection efficiency as described in Experimental Procedures. Transfection efficiency for each combination is shown in (B) and expressed as a percentage of green cells among the total amount of cells (n) counted under the fluorescent microscope.

Figure 109:
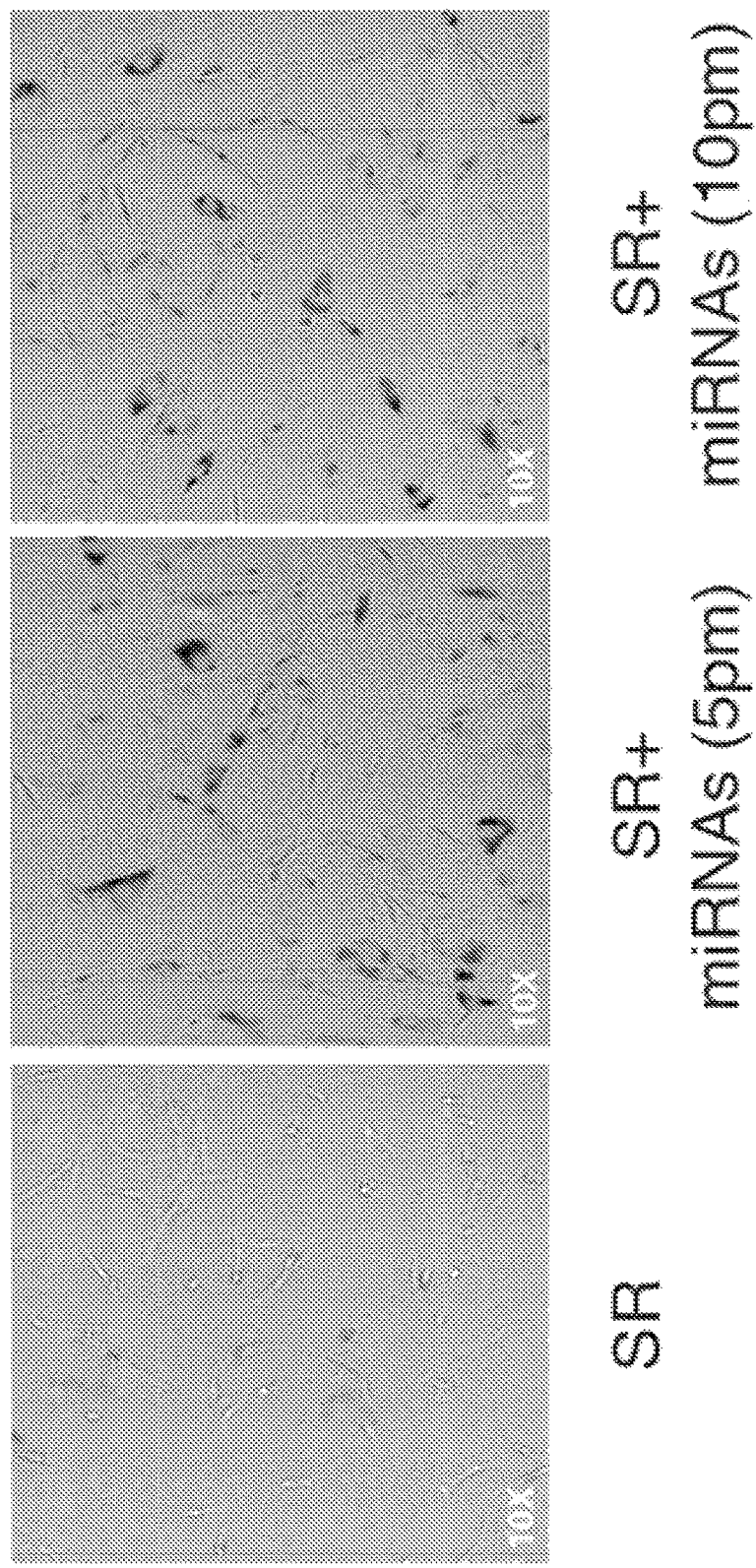
FIG. 109 illustrates a field depicting SA-β-Gal positivity and conversion of SR-hADSCs into SEN-hADSCs.

FIG. 109 illustrates a field depicting SA-β-Gal positivity and conversion of SR-hADSCs into SEN-hADSCs after transfection by 5 pM or 10 pM of mimics of SA-miRNAs into SR-hADSCs.

Figure 110:
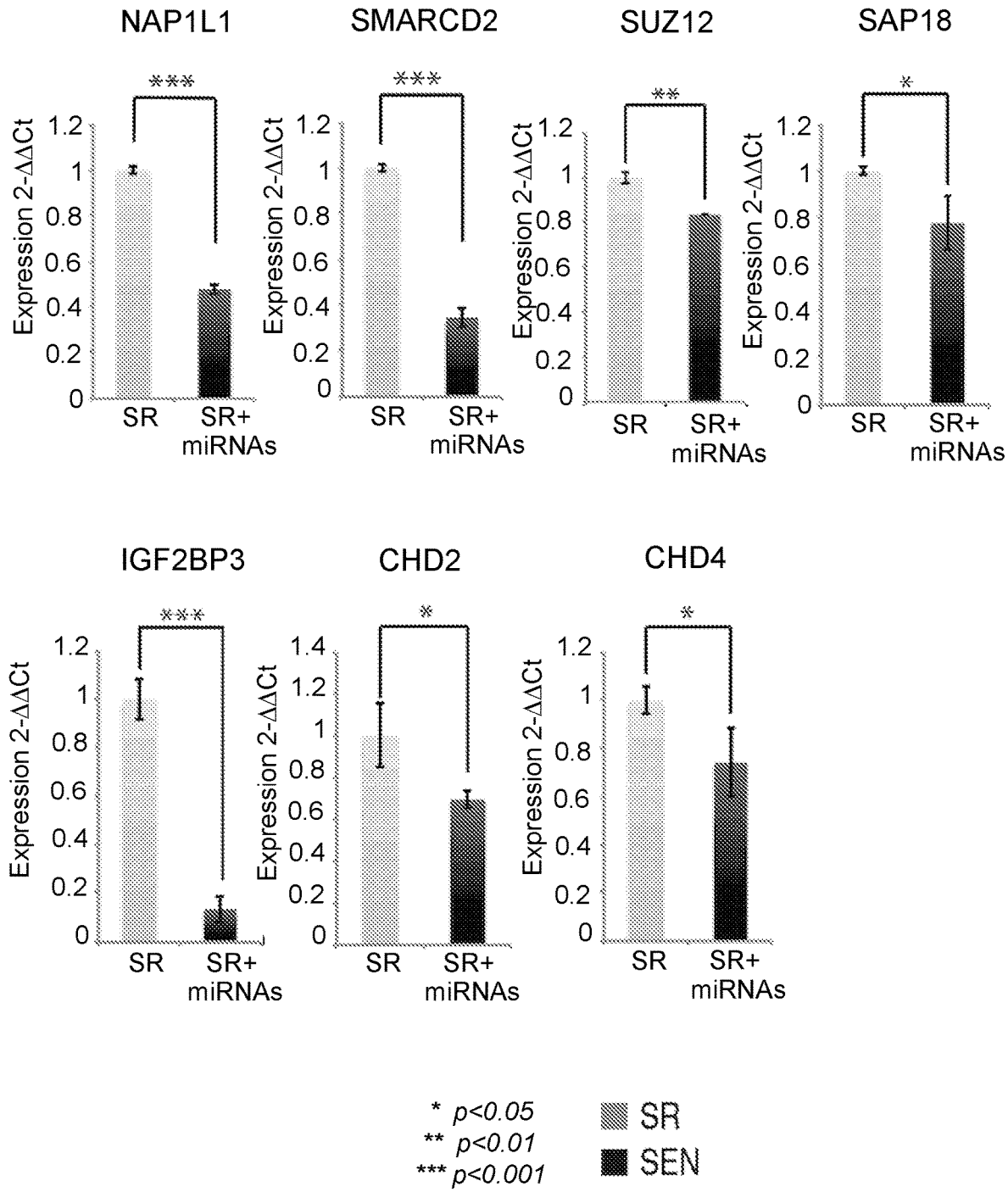
FIG. 110 demonstrates the direct influence of SA-miRNAs on gene transcription (on SA-miRNA target genes).
Figure 111:
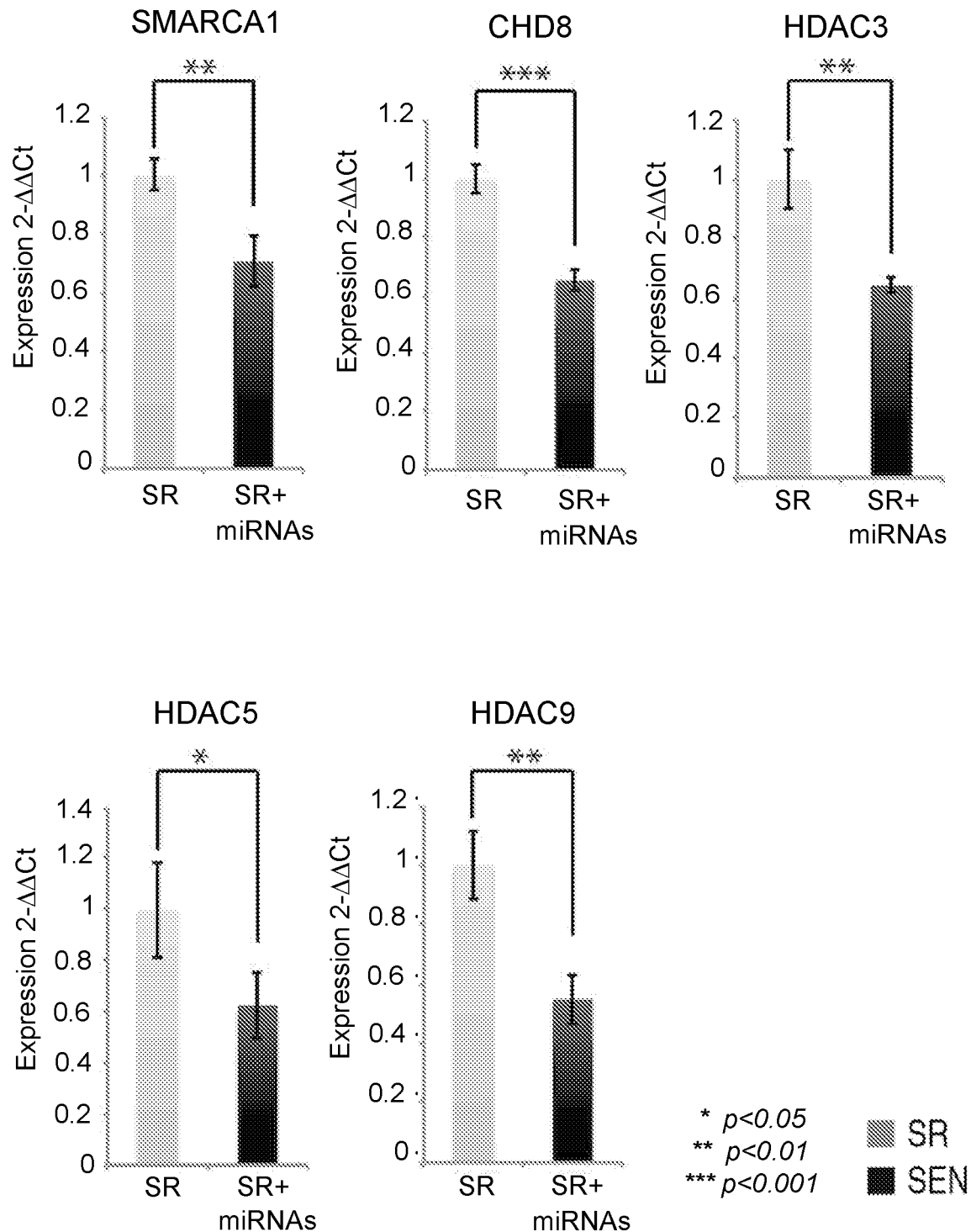
FIG. 111 demonstrates the indirect influence of SA-RNAs on gene transcription.
Figure 112:
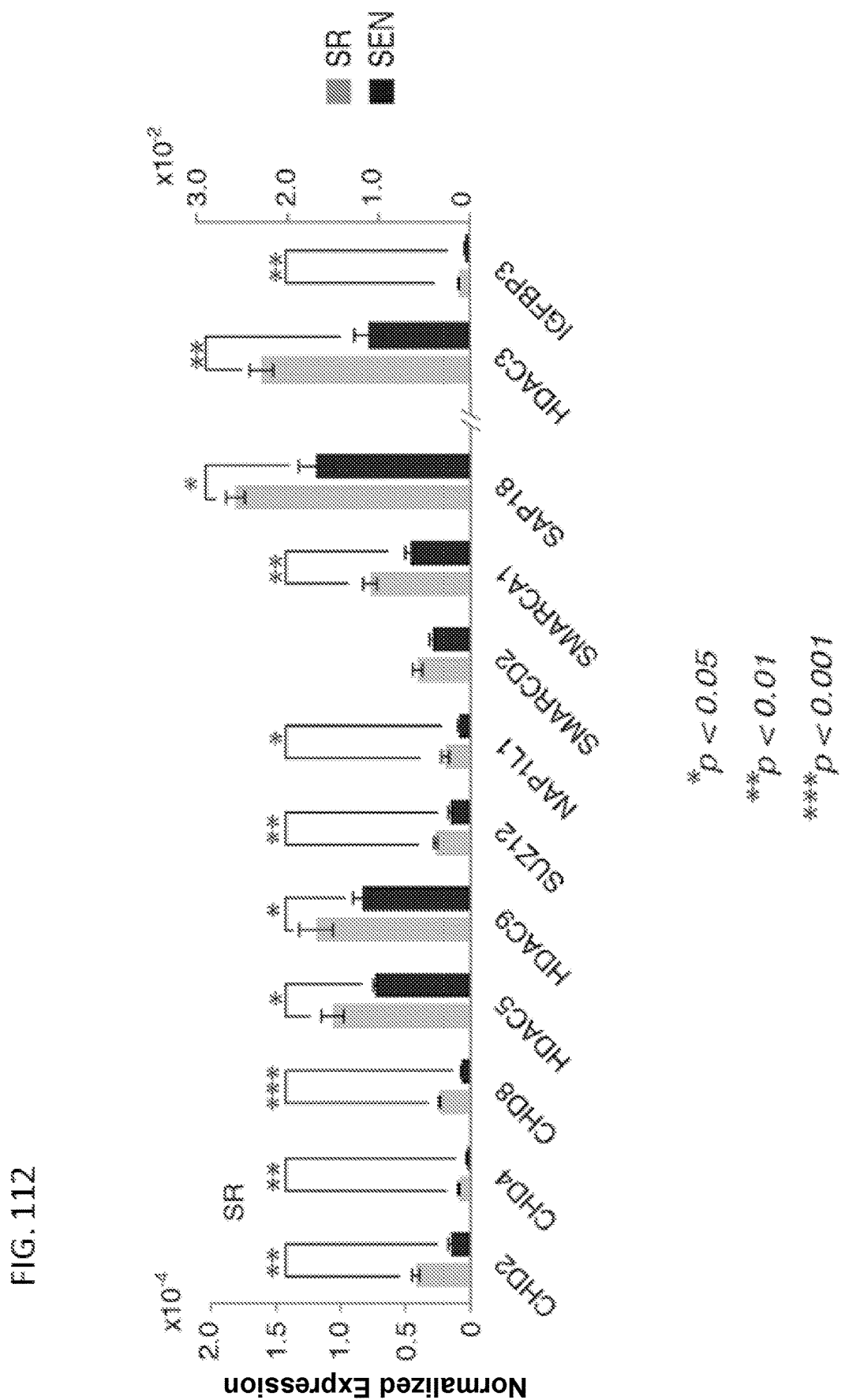
FIG. 112 shows the mean normalized protein expression levels in SR-hADSCs and SEN-hADSCs transfected with SA-miRNAs.

The SEN phenotype induced under these conditions is similar to replicative senescence as demonstrated by downregulation of a handful of selected genes (FIGS. 110-112). In SR-hADSCs transfected with a full set of SA-miRNA mimics, downregulation of endogenous mRNA from the enriched functional network that represents SA-miRNA target genes such as SUZ12, NAP1L1, SMARCD2, SAP18, IGF2BP3, CHD2, and CHD4 (FIG. 110 and FIG. 113), as well as a number of the genes not targeted by SA-miRNAs but, nevertheless, shown to be downregulated upon replicative senescence, such as SMARCA1, CHD8, HDAC3, HDAC5, and HDAC9 (FIG. 111 and FIG. 113) was observed.

FIG. 110 demonstrates the direct influence of SA-miRNAs on gene transcription. Expression of SA-miRNA target genes was measured by qPCR analysis in SR-hADSCs (SR, light bars) and in SR-hADSCs transiently transfected with the set of SA-miRNA mimics (SR+miRNA, dark bars).).

FIG. 111 demonstrates the indirect influence of SA-RNAs on gene transcription. Expression of genes previously shown to be downregulated in SEN-hADSCs but not identified as SA-miRNA targets was measured by qPCR analysis in SR-hADSCs (SR, light bars) and in SR-hADSCs transiently transfected with the set of SA-miRNA mimics (SR+miRNA, dark bars). RNA was isolated from the cells 48 h post transfection. Samples were normalized against β-actin. Mean expression levels±SEM (n=3) are shown as fold change (ΔΔCτ). Statistical differences were evaluated, where *$p<0.001$, $p<0.01$, *$p<0.05$.

FIG. 112 shows the mean normalized protein expression levels±SEM (n=3) in SR-hADSCs (light bars) and SEN-hADSCs (dark bars) transfected with SA-miRNAs. Results are shown for SA-miRNA direct and indirect target genes. Statistical differences were evaluated by Student's t-test, where *$p<0.001$, $p<0.01$, *$p<0.05$.

Figure 113:
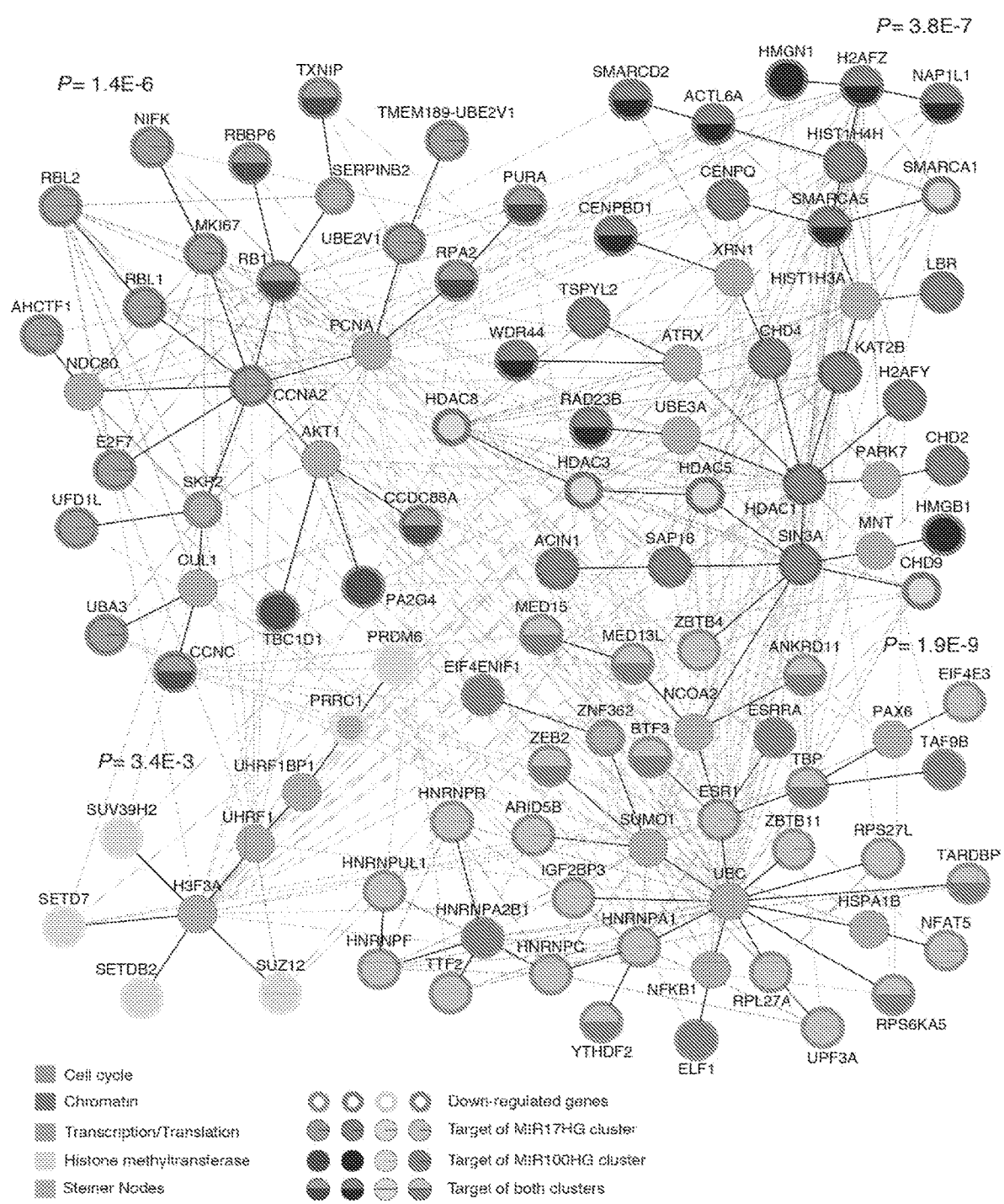
FIG. 113 illustrates the novel genes that are the targets of SA-miRNA in replicative senescence, and their functional relationships and enrichment.

FIG. 113 illustrates the novel genes that are the targets of SA-miRNA in replicative senescence, and their functional relationships and enrichment. Four functional categories of genes were evaluated for their relationships and functional enrichment using a network-based approach as described above. The network nodes represent genes and are categorized based on their functional category. Gene nodes are labeled in regards to targeted miRNA. Edges represent annotated protein relationships from the STRING database. Black solid edges represent connections of the sub-network minimal spanning trees (i.e. Steiner trees), dark gray dashed edges show additional sub-network connections, and light gray dashed edges represent connections between function-specific sub-networks. P-values indicate the extent to which each function-specific sub-network is enriched for genes from that particular functional category. Steiner nodes are shown in grey. Downregulated genes, which are not targeted by SA-miRNAs are shown based on their functional category.

Example 11: Factor-Dependent Immunostimulation of Human PBMCs to Increase Production of Treg Cells The inventors show here (in FIG. 98) that factors produced by SR MSCs+IL-2 in an exemplary factor production unit of the invention has the ability to modulate the production of Tregs cells. Treg cells are defined here by CD4+ CD25+ FoxP3+(Forkhead box P3 (FoxP3)+ expression) and CD4+ CD25-FoxP3+. CD4+ regulatory T cells (Treg cells) expressing the transcription factor FoxP3 are highly immune suppressive and play central roles in the maintenance of self-tolerance and immune homeostasis.

Described below are materials and methods for the production of factors that can influence Treg differentiation and production.

Isolation, Culture and Characterization of hADSCs

MSCs used in this example were isolated from human adipose tissues obtained from healthy adult female donors age 38, 45 and 49 undergoing routine liposuction procedures at the UCSD medical center, San Diego, Calif. The MSC isolation protocol was approved by the local ethics committee and performed as previously described (Wang et al., Cell Cycle, 2011). Isolated adipose-derived stem cell lines were grown in DMEM/F12 medium (Life Technologies). In accordance with the MSC minimal definition criteria set by the International Society for Cellular Therapy (Dominici et. al. 2006, Cytotherapy 8: 315-317), flow cytometric analysis showed that hADSCs expressed CD29, CD73, CD90 and CD105 but do not express CD11b, CD14, CD19, CD34, CD45, CD80, CD86 (antibodies from eBiosciense, USA). Morphological analysis showed that the cells present a fibroblast-like morphology, were plastic adherent and capable of adipogenic, chondrogenic and osteogenic differentiation under in vitro conditions using commercially available differentiation mediums (Invitrogen, USA). Cumulative population doublings (PD) were calculated as PD=log(N/N0)×3.33 across the multiple passages as a function of the number of days of growth in culture as described (Wang et al., Cell Cycle, 2011; Niu et al., 2015, Oncotarget), where N0 is the number of cells plated in the flask and N is the number of cells harvested at this passage. hADSCs PD 4 or PD 6 for SR populations.

Induction of Senescence Using a Genotoxic Agent

To induce genotoxic senescence, the cells were treated with a genotoxic agent, Bleomycin (Cayman chemical) an anticancer chemotherapy drug. The factor production unit (containing 3-D scaffolds made from polycaprolactone (PCL) matrix/fibers that mimic 3-D ECM), populated with patient hADSCs was treated with 50 ug/ml of bleomycin in 10% PRP containing StemPro MSC SFM xeno-free medium for 2 h at 37 C (Niu et al., Oncotarget, 2015). Following the genotoxic exposure, the factor production unit was washed twice with PBS-cmf and fresh medium was replaced. The factor production unit was maintained for 5 days to achieve complete genotoxic-induced senescence, then the factor production unit with SEN cells were either left untreated (SEN) or treated with 20 U/ml IL-2 for 24 h (SEN+IL-2) as described below. The assay for monitoring the expression of pH-dependent senescence-associated β-galactosidase activity (SA-βGal) was performed as described in manufacturer's kit (BioVision) and previously published in (Wang et al., 2011, Cell Cycle 10: 3016-3030). The cultured hADSCs were washed with PBS for 15 minutes at room temperature, and stained with X-Gal containing supplement overnight at 37° C. The cells were washed twice with PBS, and the images were captured using a microscope (Nikons, TE300, DXM1200 Digital Camera, Japan).

IL-2 Stimulation/Treatment

Stimulation with recombinant IL-2 (Peprotech, USA) was performed as described (Deenick et al., 2003, J Immunol 170: 4963-4972; Niu et al., 2015, Oncotarget). 20 U/ml of IL-2 was added to the culturing media for 24 hours at 37° C. For the IL-2 treatment, the factor production unit containing hADSCs was treated with 20 U/ml IL-2 (Peprotech) in 10% PRP in StemPro MSC SFM xeno-free medium at 37° C. for 24 h. IL-2 was removed post-treatment with 2 washes of PBS-cmf and cells were co-cultured with PBMCs in 10% PRP in StemPro MSC SFM xeno-free medium.

Co-Culture with PBMCs for Immunomodulation

Four factor production units were populated with cells for the four conditions and shown in FIG. 2C: untreated SR-hADSCs, untreated genotoxic-induced SEN-hADSCs, SR-hADSCs treated with 11-2, and SEN-hADSCs treated with IL-2. Factors produced by the cells were used to guide Treg production in PBMC population. For each condition, 50,000 hADSCs were co-cultured for 72 h with 500,000 viable Normal Peripheral Blood Mononuclear Cells (PBMCs). PBMCs from a single healthy 32 years old male donor were purchased from AllCells, Alameda, Calif. A fresh Vial was thawed for each experiment and viability and cell count was performed using a Biorad TC20 cell counter after staining with trypan blue. Controls were run with PBMCs alone (FIG. 2C). Cells were collected by trypsinization at 24 h or 72 h time points and Tregs were stained using anti-human-FoxP3 Staining kit (BD Biosciences) containing FoxP3 Alexa Fluor 647, PE Mouse Anti-Human CD25, FITC Mouse Anti-Human CD4, Isotype FITC-Mouse IgG1, Isotype PE-Mouse IgG1, Isotype Alexa 647-Mouse IgG1 k following maunfacturer's recommendations as demonstrated in FIG. 97 and FIG. 99.

FACS Data Analysis Strategy—Analysis for Treg Production

Cells were collected by trypsinization at 24 h and 72 h time points and Tregs were stained with anti-human-FoxP3 Staining kit (BD Biosciences) containing FoxP3 Alexa Fluor 647, PE Mouse Anti-Human CD25, FITC Mouse Anti-Human CD4, Isotype FITC-Mouse IgG1, Isotype PE-Mouse IgG1, Isotype Alexa 647-Mouse IgG1 k following manufacturer's recommendations. Briefly, the cells were incubated with human Fc-receptor block (BD Biosciences) diluted 1:50 in staining Buffer (BD Biosciences, CA) for 10 min on ice to block the non-specific receptor binding. The cells were incubated on ice, in dark for 30 min with 20 ul each surface antibody against CD4(FITC) or CD25(PE) or both and isotype-matched control antibodies. The cells were then washed with 1 ml staining buffer and fixed with fixation buffer that was supplied in the FoxP3 Staining kit (BD Biosciences) for 10 min at 4° C. in the dark. The cells were permeabilized using permeabilization buffer (BD Biosciences) for 30 min at room temperature and then washed with 1 ml staining buffer. After washing, the cells were incubated with 20 ul of FoxP3-Alexa Fluor 647 antibody for 30 min at room temperature in dark. At the end of the incubation period, the PBMCS were washed and resuspended into 500 ul of fixative buffer and flow cytometry was performed on a FACS Canto II flow cytometer (BD Biosciences.

Data were collected on a FACS Canto II flow cytometer (BD Biosciences) at UCSF core facility. Onecomp ebeads (eBioscience) were used for compensation following manufactures protocol. Briefly, 1 drop of beads was added to in a separate tube and a single antibody was added to each tube at a concentration that was used for PBMCs. The samples were incubated at 4 C for 15 min, then washed with 2 ml of staining buffer, resuspended in staining buffer and used to set-up the optimal fluorescence detector (PMT) voltages for PE, FITC and Alexa-647 fluorochromes used for PBMCs staining.

Figure 97:
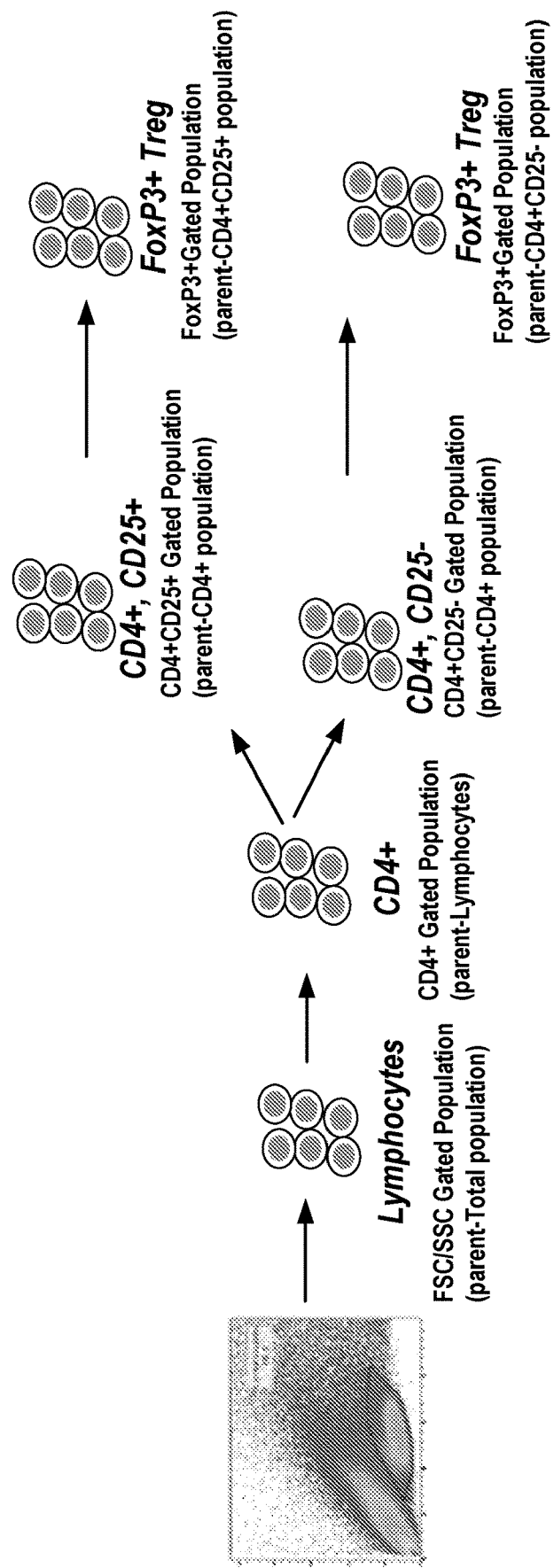
FIG. 97 illustrates a FACS analysis gating strategy to identify T cells (Tregs).

Analysis for Tregs was performed as outlined in the FACS analysis gating strategy in FIG. 97B using FlowJo software (Tree Star Inc). Lymphocytes were gated on forward and side scatter from the total PBMC population. Then, lymphocytes population expressing CD4-FITC population was gated to identify CD25-PE Tcells: CD4+ CD25+ Tcells or CD4+ CD25− T cells. The populations expressing FoxP3 protein were identified as Tregs (shown in FIG. 97). The Treg population can be defined as CD4+ CD25-FoxP3+ and triple positive CD4+CD25+ FoxP3+ lymphocytes.

Figure 98:
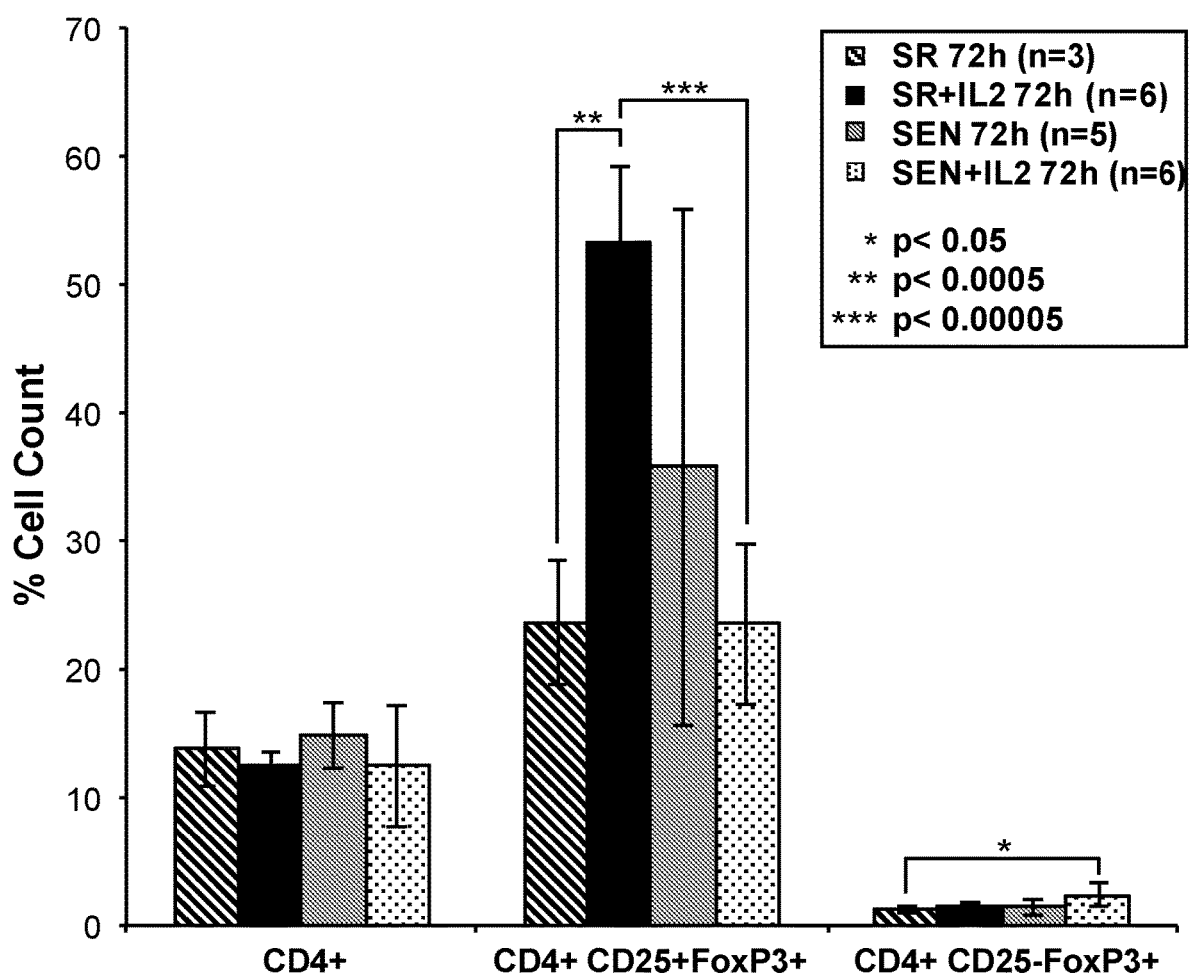
FIG. 98 illustrates that factors produced in an exemplary factor production unit of the invention influences production of Tregs.

FIG. 98 illustrates that factors produced in an exemplary factor production unit of the invention influences production of Tregs. This figure shows that factors collected from SR hADSCs 72 hours after stimulation with IL-2 (for 24 hours) were optimal for increased production of Tregs, out of the conditions tested.

Figure 99:
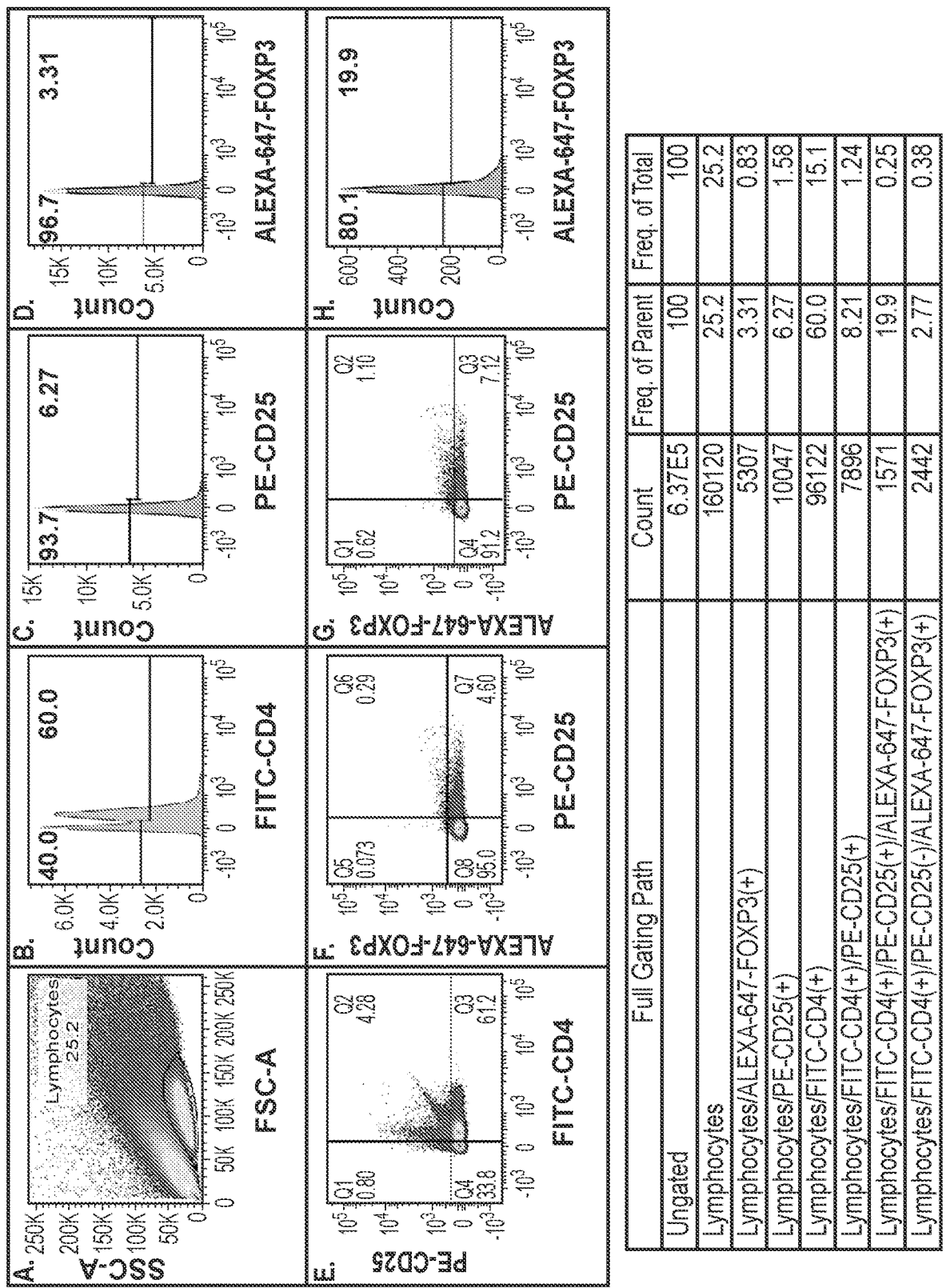
FIG. 99 illustrates an exemplary gating strategy, for the identification of Treg populations as described in FIG. 98.

FIG. 99 shows representative data from the FACS analysis. The numbers inside the plots represent the number of cells in the population expressing the marker. The table provides a summary of the number of cells expressing the marker on Panels A-D. In this gating, lymphocytes were gated based on the light scatter plot distribution (SSC-A vs. FSC-A) (A). The lymphocyte population from panel A was further analyzed for CD4+ lymphocytes based on bound CD4 FITC and is shown as a histogram plot (B). CD4+ Lymphocytes were then sequentially analyzed for CD25 expression (D) followed by analysis of Foxp3 expressing Tregs based on positive Alexa-Fluor 647 anti-FoxP3 antibody binding. Panels E-H show the dot plot for lymphocytes for the expression of 2 markers. CD4+ lymphocytes are shown on the x-axis and CD25 expression is on the y-axis (E). The CD4+ CD25+ lymphocytes are in Q2. Foxp3+ positive T-Regs expressing CD25+ or CD25 negative are represented (panels F and G). Total CD4+ CD25+ FoxP3+ Tregs are plotted in panel H.

Lengthy table referenced here

US11291689-20220405-T00001

Please refer to the end of the specification for access instructions.

Lengthy table referenced here

US11291689-20220405-T00002

Please refer to the end of the specification for access instructions.

Lengthy table referenced here

US11291689-20220405-T00003

Please refer to the end of the specification for access instructions.

Lengthy table referenced here

US11291689-20220405-T00004

Please refer to the end of the specification for access instructions.

Lengthy table referenced here

US11291689-20220405-T00005

Please refer to the end of the specification for access instructions.

From the foregoing it will be appreciated that, although specific variations of the invention have been described herein for purposes of illustration, various modifications may be made without deviating from the spirit and scope of the invention. Accordingly, the invention is not limited except as by the appended claims.

LENGTHY TABLES

The patent contains a lengthy table section. A copy of the table is available in electronic form from the USPTO web site (https://seqdata.uspto.gov/?pageRequest=docDetail&DocID=US11291689B2). An electronic copy of the table will also be available from the USPTO upon request and payment of the fee set forth in 37 CFR 1.19(b)(3).

What is claimed is:

1. A method of producing one or more factors in a factor production unit comprising adding an inducing agent comprising IL-2 to a population of human adipose derived stem cells (hADSCs) to induce the production of factors, wherein exposure to the inducing agent is for about 24 hours to produce the one or more factors, and wherein the one or more factors are obtained about 72 hours post-induction, wherein:
the population of hADSCs comprise at least 50% self-renewing (SR) cells or at least 50% senescent (SEN) cells.

2. The method of claim 1, wherein the hADSCs comprise self-renewing (SR) cells and senescent (SEN) cells.

3. The method of claim 1, wherein the factors are used in the treatment of cancer, an autoimmune disease, a cardiovascular disease, diabetes, a skin disease, a neurodegenerative disease, osteoporosis, osteoarthritis, a spinal cord injury, a disease of the liver, a disease of the kidney, an age-related pathology, hair loss, a burn, a condition in need of a skin graft, or a skin lesion.

* * * * *

```
                         SEQUENCE LISTING

<160> NUMBER OF SEQ ID NOS: 40

<210> SEQ ID NO 1
<211> LENGTH: 19
<212> TYPE: DNA
<213> ORGANISM: Artificial Sequence
<220> FEATURE:
<223> OTHER INFORMATION: synthetic construct

<400> SEQUENCE: 1
ctgccactcg gaacacaac                                               19

<210> SEQ ID NO 2
<211> LENGTH: 18
<212> TYPE: DNA
<213> ORGANISM: Artificial Sequence
<220> FEATURE:
<223> OTHER INFORMATION: synthetic construct

<400> SEQUENCE: 2
tggtccactg gctgcatt                                                18

<210> SEQ ID NO 3
<211> LENGTH: 20
<212> TYPE: DNA
<213> ORGANISM: Artificial Sequence
<220> FEATURE:
<223> OTHER INFORMATION: synthetic construct

<400> SEQUENCE: 3
actcgagagc caacatctcc                                              20

<210> SEQ ID NO 4
<211> LENGTH: 19
<212> TYPE: DNA
<213> ORGANISM: Artificial Sequence
<220> FEATURE:
<223> OTHER INFORMATION: synthetic construct

<400> SEQUENCE: 4
```
tccgaggatc aggttgcag                                                19

<210> SEQ ID NO 5
<211> LENGTH: 19
<212> TYPE: DNA
<213> ORGANISM: Artificial Sequence
<220> FEATURE:
<223> OTHER INFORMATION: synthetic construct

<400> SEQUENCE: 5
tggatgggca gaaacgcta                                                19

<210> SEQ ID NO 6
<211> LENGTH: 20
<212> TYPE: DNA
<213> ORGANISM: Artificial Sequence
<220> FEATURE:
<223> OTHER INFORMATION: synthetic construct

<400> SEQUENCE: 6
ggcttccaat gcaaacagga                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic construct

<400> SEQUENCE: 7
acgcaggaca cagagaatga                                               20

<210> SEQ ID NO 8
<211> LENGTH: 19
<212> TYPE: DNA
<213> ORGANISM: Artificial Sequence
<220> FEATURE:
<223> OTHER INFORMATION: synthetic construct

<400> SEQUENCE: 8
ctgggcaaac tgagcttgg                                                19

<210> SEQ ID NO 9
<211> LENGTH: 19
<212> TYPE: DNA
<213> ORGANISM: Artificial Sequence
<220> FEATURE:
<223> OTHER INFORMATION: synthetic construct

<400> SEQUENCE: 9
acacagctcc agaacacgt                                                19

<210> SEQ ID NO 10
<211> LENGTH: 19
<212> TYPE: DNA
<213> ORGANISM: Artificial Sequence
<220> FEATURE:
<223> OTHER INFORMATION: synthetic construct

<400> SEQUENCE: 10
tgttggcttc tcggaccaa                                                19

<210> SEQ ID NO 11
<211> LENGTH: 20
<212> TYPE: DNA

```
<213> ORGANISM: Artificial Sequence
<220> FEATURE:
<223> OTHER INFORMATION: synthetic construct

<400> SEQUENCE: 11
ggaggagggc agaatcatca                                              20

<210> SEQ ID NO 12
<211> LENGTH: 19
<212> TYPE: DNA
<213> ORGANISM: Artificial Sequence
<220> FEATURE:
<223> OTHER INFORMATION: synthetic construct

<400> SEQUENCE: 12
atcaggggca cacaggatg                                               19

<210> SEQ ID NO 13
<211> LENGTH: 20
<212> TYPE: DNA
<213> ORGANISM: Artificial Sequence
<220> FEATURE:
<223> OTHER INFORMATION: synthetic construct

<400> SEQUENCE: 13
ctggctcccc atactagtcg                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14
cttgaagggc tgcaagaatc                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic construct

<400> SEQUENCE: 15
accatcacag gctcttcacc                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic construct

<400> SEQUENCE: 16
aacgatcaat gctgctgttg                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
accccattgt catcaaccat                                              20
```

<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
tctctgggtc ttcagctggt                                          20

<210> SEQ ID NO 19
<211> LENGTH: 19
<212> TYPE: DNA
<213> ORGANISM: Artificial Sequence
<220> FEATURE:
<223> OTHER INFORMATION: synthetic construct

<400> SEQUENCE: 19
gatgacgaag ctcccaaag                                           19

<210> SEQ ID NO 20
<211> LENGTH: 20
<212> TYPE: DNA
<213> ORGANISM: Artificial Sequence
<220> FEATURE:
<223> OTHER INFORMATION: synthetic construct

<400> SEQUENCE: 20
tagatgctcc agtggctcct                                          20

<210> SEQ ID NO 21
<211> LENGTH: 20
<212> TYPE: DNA
<213> ORGANISM: Artificial Sequence
<220> FEATURE:
<223> OTHER INFORMATION: synthetic construct

<400> SEQUENCE: 21
catcgatggt ggaatcactg                                          20

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
atccggtgag ctctgctaaa                                          20

<210> SEQ ID NO 23
<211> LENGTH: 20
<212> TYPE: DNA
<213> ORGANISM: Artificial Sequence
<220> FEATURE:
<223> OTHER INFORMATION: synthetic construct

<400> SEQUENCE: 23
atgcggattg tgaagaagga                                          20

<210> SEQ ID NO 24
<211> LENGTH: 20
<212> TYPE: DNA
<213> ORGANISM: Artificial Sequence
<220> FEATURE:

<223> OTHER INFORMATION: synthetic construct

<400> SEQUENCE: 24
ggctcttcat cctcatggaa                                               20

<210> SEQ ID NO 25
<211> LENGTH: 20
<212> TYPE: DNA
<213> ORGANISM: Artificial Sequence
<220> FEATURE:
<223> OTHER INFORMATION: synthetic construct

<400> SEQUENCE: 25
tggcttctgc tatgtcaacg                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic construct

<400> SEQUENCE: 26
tctctgcccc gacttcatac                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic construct

<400> SEQUENCE: 27
tctgaaccac tgcatttcca                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic construct

<400> SEQUENCE: 28
gcctggaccg taatttcaga                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic construct

<400> SEQUENCE: 29
caggcggaag gatggaaatg                                               20

<210> SEQ ID NO 30
<211> LENGTH: 19
<212> TYPE: DNA
<213> ORGANISM: Artificial Sequence
<220> FEATURE:
<223> OTHER INFORMATION: synthetic construct

<400> SEQUENCE: 30
atgcgttgct gtgaaacca                                                19

```
<210> SEQ ID NO 31
<211> LENGTH: 20
<212> TYPE: DNA
<213> ORGANISM: Artificial Sequence
<220> FEATURE:
<223> OTHER INFORMATION: synthetic construct

<400> SEQUENCE: 31
tctctcctaa ccgcaagcat                                              20

<210> SEQ ID NO 32
<211> LENGTH: 20
<212> TYPE: DNA
<213> ORGANISM: Artificial Sequence
<220> FEATURE:
<223> OTHER INFORMATION: synthetic construct

<400> SEQUENCE: 32
agctctctcc cagagttgga                                              20

<210> SEQ ID NO 33
<211> LENGTH: 20
<212> TYPE: DNA
<213> ORGANISM: Artificial Sequence
<220> FEATURE:
<223> OTHER INFORMATION: synthetic construct

<400> SEQUENCE: 33
ccactgttgc tacgggtctt                                              20

<210> SEQ ID NO 34
<211> LENGTH: 20
<212> TYPE: DNA
<213> ORGANISM: Artificial Sequence
<220> FEATURE:
<223> OTHER INFORMATION: synthetic construct

<400> SEQUENCE: 34
ccactgttgc tacgggtctt                                              20

<210> SEQ ID NO 35
<211> LENGTH: 20
<212> TYPE: DNA
<213> ORGANISM: Artificial Sequence
<220> FEATURE:
<223> OTHER INFORMATION: synthetic construct

<400> SEQUENCE: 35
gcctttgaga agccaacaca                                              20

<210> SEQ ID NO 36
<211> LENGTH: 20
<212> TYPE: DNA
<213> ORGANISM: Artificial Sequence
<220> FEATURE:
<223> OTHER INFORMATION: synthetic construct

<400> SEQUENCE: 36
ctgcaaatga gctgacaagc                                              20

<210> SEQ ID NO 37
<211> LENGTH: 20
<212> TYPE: DNA
<213> ORGANISM: Artificial Sequence
<220> FEATURE:
<223> OTHER INFORMATION: synthetic construct
```

```
<400> SEQUENCE: 37
agggcgagaa gaagaaggag                                               20

<210> SEQ ID NO 38
<211> LENGTH: 20
<212> TYPE: DNA
<213> ORGANISM: Artificial Sequence
<220> FEATURE:
<223> OTHER INFORMATION: synthetic construct

<400> SEQUENCE: 38
tctgtgctga aggctgaatg                                               20

<210> SEQ ID NO 39
<211> LENGTH: 20
<212> TYPE: DNA
<213> ORGANISM: Artificial Sequence
<220> FEATURE:
<223> OTHER INFORMATION: synthetic construct

<400> SEQUENCE: 39
tccaagcaga aaccatgtga                                               20

<210> SEQ ID NO 40
<211> LENGTH: 20
<212> TYPE: DNA
<213> ORGANISM: Artificial Sequence
<220> FEATURE:
<223> OTHER INFORMATION: synthetic construct

<400> SEQUENCE: 40
acttacaagc cgcagaggtg                                               20
```